(12) United States Patent
Jadhav et al.

(10) Patent No.: US 11,053,495 B2
(45) Date of Patent: Jul. 6, 2021

(54) MULTI-TARGETED SINGLE ENTITY CONJUGATES

(71) Applicant: ALNYLAM PHARMACEUTICALS, INC., Cambridge, MA (US)

(72) Inventors: Vasant Jadhav, Cambridge, MA (US); Martin Maier, Cambridge, MA (US); Ivan Zlatev, Cambridge, MA (US); Akin Akinc, Cambridge, MA (US); Kallanthottathil G. Rajeev, Cambridge, MA (US); Jayaprakash K. Nair, Cambridge, MA (US); Pachamuthu Kandasamy, Cambridge, MA (US); Muthiah Manoharan, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/745,591

(22) PCT Filed: Jul. 15, 2016

(86) PCT No.: PCT/US2016/042498
§ 371 (c)(1),
(2) Date: Jan. 17, 2018

(87) PCT Pub. No.: WO2017/015109
PCT Pub. Date: Jan. 26, 2017

(65) Prior Publication Data
US 2018/0208927 A1 Jul. 26, 2018

Related U.S. Application Data

(60) Provisional application No. 62/194,003, filed on Jul. 17, 2015.

(51) Int. Cl.
*C12N 15/113* (2010.01)
*C12N 15/11* (2006.01)
*C07H 21/00* (2006.01)
*A61K 47/55* (2017.01)
*A61K 47/54* (2017.01)

(52) U.S. Cl.
CPC .......... *C12N 15/113* (2013.01); *A61K 47/549* (2017.08); *A61K 47/55* (2017.08); *C07H 21/00* (2013.01); *C12N 15/111* (2013.01); *C12N 2310/14* (2013.01); *C12N 2310/20* (2017.05); *C12N 2310/351* (2013.01); *C12N 2310/3519* (2013.01); *C12N 2310/51* (2013.01); *C12N 2320/31* (2013.01)

(58) Field of Classification Search
USPC ........................................................ 536/24.5
See application file for complete search history.

(56) References Cited

U.S. PATENT DOCUMENTS

| 8,546,350 B2 * | 10/2013 | Bennett | C12N 15/111 514/44 A |
|---|---|---|---|
| 2007/0032441 A1 * | 2/2007 | McSwiggen | C12N 15/111 514/44 A |
| 2010/0267805 A1 | 10/2010 | McCallus et al. | |
| 2011/0118335 A1 * | 5/2011 | Jadhav | C12N 15/1131 514/44 A |
| 2013/0158097 A1 | 6/2013 | Hinkle et al. | |
| 2015/0119445 A1 | 4/2015 | Manoharan et al. | |

FOREIGN PATENT DOCUMENTS

| WO | 2008109105 A2 | 9/2008 |
|---|---|---|
| WO | 2010093788 A2 | 8/2010 |
| WO | 2011038031 A1 | 3/2011 |
| WO | 2013074974 A2 | 5/2013 |

\* cited by examiner

*Primary Examiner* — Kimberly Chong
(74) *Attorney, Agent, or Firm* — Nixon Peabody LLP; David S. Resnick; Raviriderjit Braich

(57) ABSTRACT

The present invention relates, in general to, compounds, compositions and methods useful for modulating gene expression of multiple target nucleic acids by a single chemical entity.

13 Claims, 36 Drawing Sheets

Specification includes a Sequence Listing.

Dose
- 1 mg/kg or 3 mg/kg
- Doses normalized on molar basis to match with the mg/kg dose of parent siRNAs

N=3 mice/group

Readout
- Serum TTR or Factor VII levels @ day -7 (pre-dose), 7 d, 14 d, 21, 28 d
- Liver [mRNA] and [siRNA] at harvest (day 28)

Monomers

Q51

$C_{12}H_{26}O_4PS_2$
Exact Mass: 329.1010
Mol. Wt.: 329.4362

Q173

Chemical Formula: $C_{18}H_{31}N_2O_{11}P$
Exact Mass: 482.17
Molecular Weight: 482.42

MULTI-TARGETED SINGLE ENTITY CONJUGATES

CROSS REFERENCE TO RELATED APPLICATIONS

This application is a 371 National Phase Entry of International Patent Application No. PCT/US2016/042498 filed on Jul. 15, 2016 which claims benefit under 35 U.S.C. § 119(e) of the U.S. Provisional Application No. 62/194,003, filed Jul. 17, 2015, the contents of which are incorporated herein by reference in there entirety.

SEQUENCE LISTING

The sequence listing of the present application has been submitted electronically via EFS-Web as an ASCII formatted sequence listing with a file name "051058-085082-PCT_SL", creation date of Jan. 12, 2018 and a size of 22,851 bytes. The sequence listing submitted via EFS-Web is part of the specification and is herein incorporated by reference in its entirety.

TECHNICAL FIELD

The present disclosure relates generally to compounds, compositions and methods useful for modulating gene expression of multiple targets.

BACKGROUND

There is need in the art for molecules that can target more than one target. This disclosure provides some answers to that need.

SUMMARY OF THE INVENTION

In one aspect, provided herein are multi-targeted molecules. Generally, the multi-targeted molecules comprise at least two nucleic acid based effector molecules, wherein said at least two nucleic acid based effector molecules are covalently or non-covalently linked to each other. Without limitations, any nucleic acid based effector molecule capable of modulating gene expression of a target can be comprised in the multi-targeted molecules disclosed herein.

By a "nucleic acid based effector molecule" is meant a modified or unmodified single-stranded or double-stranded nucleic acid molecule capable of modulating gene expression of a target gene. Exemplary nucleic acid based effector molecules capable of modulating gene expression of a target gene include, but are not limited to, double-stranded and single-stranded RNA interference agents (such as siRNA and shRNA, and also referred to as dsRNA agents herein), antisense oligonucleotides, microRNAs, anti-microRNAs or antimirs, supermirs, antagomirs, ribozymes, triplex-forming oligonucleotides, decoy oligonucleotides, RNA activators, U1 adaptors, guide RNA (gRNA) of CRISPR Cas and the like.

It is noted that said at least two effector molecules are two separate effector molecules. In other words, the at least two effector molecules do not overlap with each other. As such, the multi-targeted molecules disclosed herein differ from molecules where one effector molecule is directed to two different targets, for example, double-stranded effector molecules where each strand is directed to a different target or an effector molecule comprising a sequence, wherein at least a portion of the sequence is complementary to or can hybridize with two different target sequences.

In some embodiments, the multi-targeted molecule or an effector molecule in the multi-targeted molecule does not modulate unspecific gene expression by two different mechanisms. For example, the multi-targeted molecule or an effector molecule in the multi-targeted molecule does not modulate gene expression via RNA interference and targeting a seed region of a microRNA.

In some embodiments, each nucleic acid based effector molecule in the multi-targeted molecule can modulate gene expression of a target nucleic acid. Without limitations, each effector molecule in the multi-targeted molecule can be directed to the same target gene, different target genes, different positions with the same target gene, or different transcripts of the same target gene. Further, it is noted that said effector molecules comprised in the multi-targeted molecules disclosed herein can comprise any of the nucleic acid modifications, motifs or structures described herein.

Moreover, the effector molecules comprised in the multi-targeted molecules described herein have comparable gene expression modulating activity compared to the gene expression modulating activity when said effector molecules are not part of a multi-targeted molecule. In other words, an effector molecule has similar gene expression modulating activity when it is part of a multi-targeted molecule disclosed herein relative to when it is not part of a multi-targeted molecule. In some embodiments, the effector molecules comprised in the multi-targeted molecule described herein can independently modulate gene expression of their respective target nucleic acids by at least 50% (e.g., 50%, 60%, 70%, 75%, 80%, 85%, 90%, 95% or more) relative to their modulation of gene expression when not part of a multi-targeted molecule. In some embodiments, one of the effector molecules in the multi-targeted molecule modulates gene expression at a higher level relative to the other effector molecule in said multi-targeted molecule. In some embodiments, said at least two effector molecules in multi-targeted molecule modulate gene expression at similar levels (e.g., within 10%, 7.5%, 5%, 2.5% or less of each other).

The inventors have found that multi-targeted molecules conjugated with a ligand are particularly effective in modulating gene expression. Accordingly, in some embodiments, at least one ligand is conjugated with the multi-targeted molecule. As such, multi-targeted molecules conjugated with at least one ligand are also referred to as "conjugated multi-targeted molecule" herein. Without limitation, the ligand can be present in any of the effector molecules in the multi-targeted molecule. Further, the ligand can be present at any position of the effector molecule and/or the multi-targeted molecule. For example, the ligand can be conjugated at the 5'-end, 3'-end an internal position of an effector molecule, or combinations thereof in the multi-targeted molecule. In some embodiments, at least two ligands are conjugated with the multi-targeted molecule. The said at least two ligands can be the same, different or any combinations of same and different. The two ligands can be conjugated at independently at any position in the multi-targeted molecule. In some embodiments, at least two effector molecules in the multi-targeted molecule have at least one ligand attached thereto. Without wishing to be bound by a theory, a ligand can improve delivery or pharmacokinetic profile of the conjugated multi-targeted molecule.

At least two effector molecules in the multi-targeted molecules disclosed herein can be covalently linked to each other via nucleotide-based linkers or non-nucleotide based linkers as generally known in the art and as described herein.

Accordingly, in some embodiments, the two effector molecules are linked to each other via a nucleotide-based linker. In some other embodiments, the two effector molecules are linked to each other via a non-nucleotide based linker.

As disclosed herein, at least two effector molecules in a multi-targeted described herein can be linked to each other non-covalently. Thus, in some embodiments, the multi-targeted molecule is assembled from two effector molecules, wherein each effector molecule has at least one ligand attached thereto. In some embodiments of this, the multi-targeted molecule is assembled from two siRNAs, wherein at least one ligand is conjugated with each siRNA.

As disclosed herein, at least two effector molecules in a multi-targeted described herein can be linked to each other covalently via a nucleotide-based linker. Without limitation, a nucleotide-based linker connecting the effector molecules can be all DNA, all RNA or a mixture of DNA and RNA. In some embodiments, the nucleotide-based linker connecting the two effector molecules is all DNA. The RNA and DNA can be natural and modified. Further, the nucleotide-based linker connecting the two effector molecules can be unmodified or comprise one or more nucleic acid modifications described in the present disclosure. Accordingly, in some embodiments, the nucleotide-based linker connecting the effector molecules comprises at least one modification selected from the group consisting of modified internucleoside linkage, modified nucleobase, modified sugar, and any combinations thereof.

The nucleotide-based linker connecting the effector molecules can comprise one or two nucleic acid strands and can be single stranded, double-stranded, or comprise single-stranded and double-stranded regions. In some embodiments, the nucleotide-based linker connecting the effector molecules comprises two nucleic acid strands that do not form a double-stranded structure. In other words, the nucleotide-based linker comprises two strands that do not hybridize with each other. In some embodiments, the nucleotide-based linker connecting the effector molecules comprises two nucleic acid strands and wherein one of the strands comprises all DNA and the other strand comprises a mixture of DNA and 2'-Oalkyl modifications. In some embodiments, the linker connecting the effector molecules comprises the nucleotide sequence uuu or (dT)n, where n is 1-20. In some embodiments, the linker connecting the effector molecules comprises a molecule selected from the group consisting of —(CH$_2$)$_{12}$— (C12 linker or Q50), —(CH$_2$)$_6$—S—S—(CH$_2$)$_6$— (C6-S—S—C6 linker or Q51), Q151, Q173, —CH$_2$CH$_2$O—(CH$_2$CH$_2$)$_n$—CH$_2$CH$_2$O—CH$_2$CH$_2$O—, where n is 0 or 1-20; —(CH$_2$)$_9$—(CH$_2$)$_n$—CH$_2$—, where n is 0 or 1-20; mono-, di-, tri-, tetra-, penta- or polyprolinol, optionally conjugated with a ligand; mono-, di-, tri-, tetra-, penta- or polyhydroxyprolinol, optionally conjugated with a ligand. In some embodiments, the linker connecting the effector molecules comprises a molecule selected from those shown in FIGS. 16-23 and 26. In some embodiments, the linker comprises a monomer selected from the monomers described below in the section titled "Exemplary ligand monomers." For example, MONOMERS 1-30 described below. Exemplary linkers are also described in the Examples section of the disclosure, e.g., Examples 1-23.

DETAILED DESCRIPTION OF THE INVENTION

Figure 1:
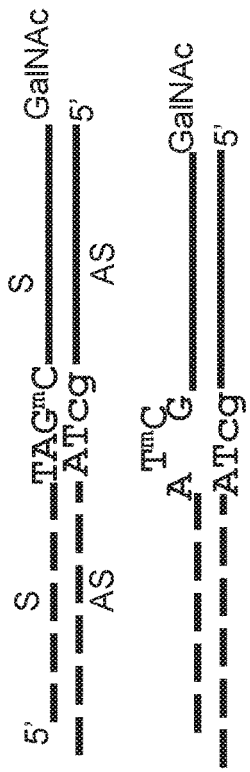
FIG. 1 shows designs of multi-targeted single entity conjugates according to some embodiments of the invention.
Figure 1:
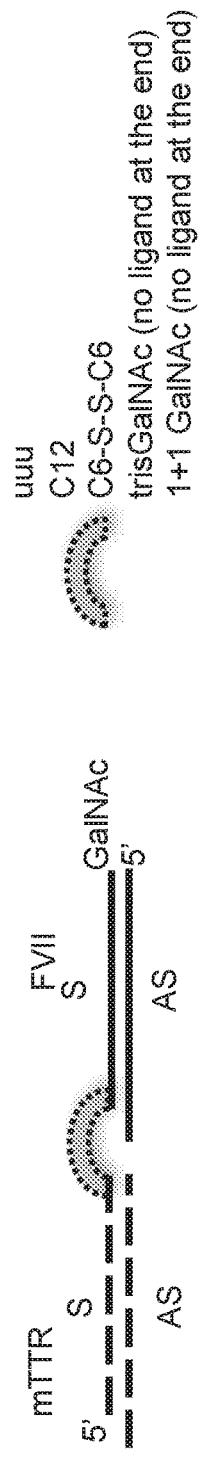
Figure 1:
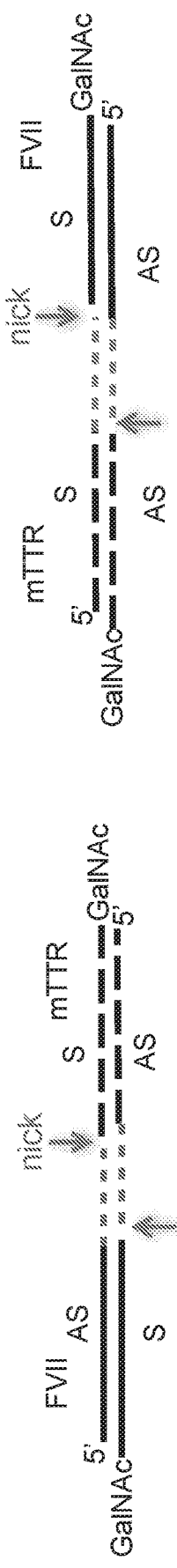
Figure 2:
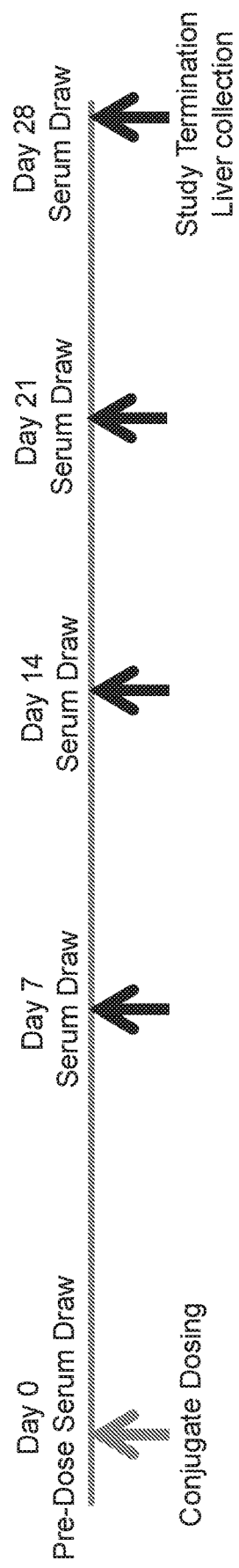
FIG. 2 is a schematic representation of an exemplary study design.
Figure 3A:
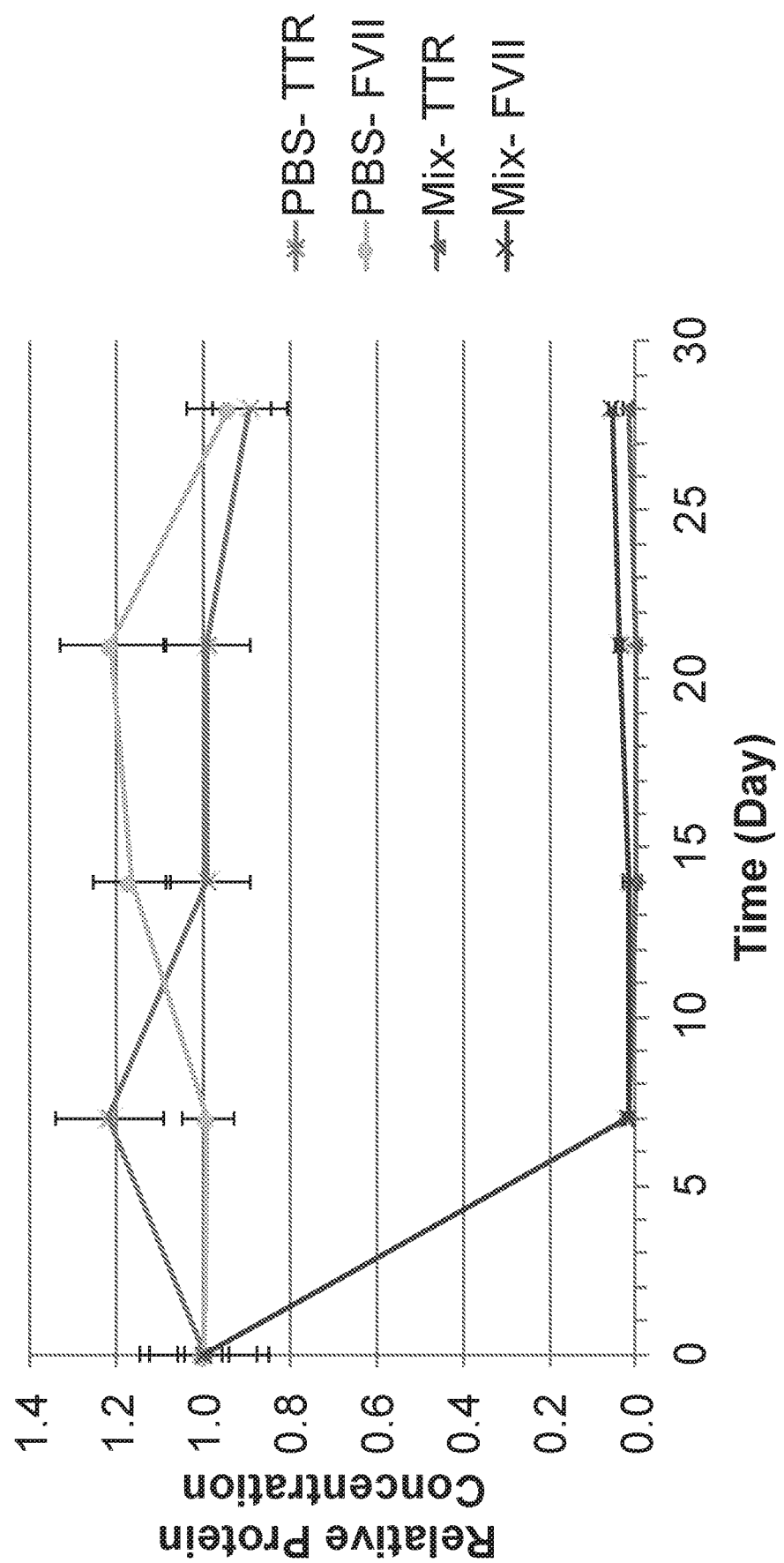
FIGS. 3A and 3B show in vivo activity of mixture of two siRNAs directed against two different targets.
Figure 3B:
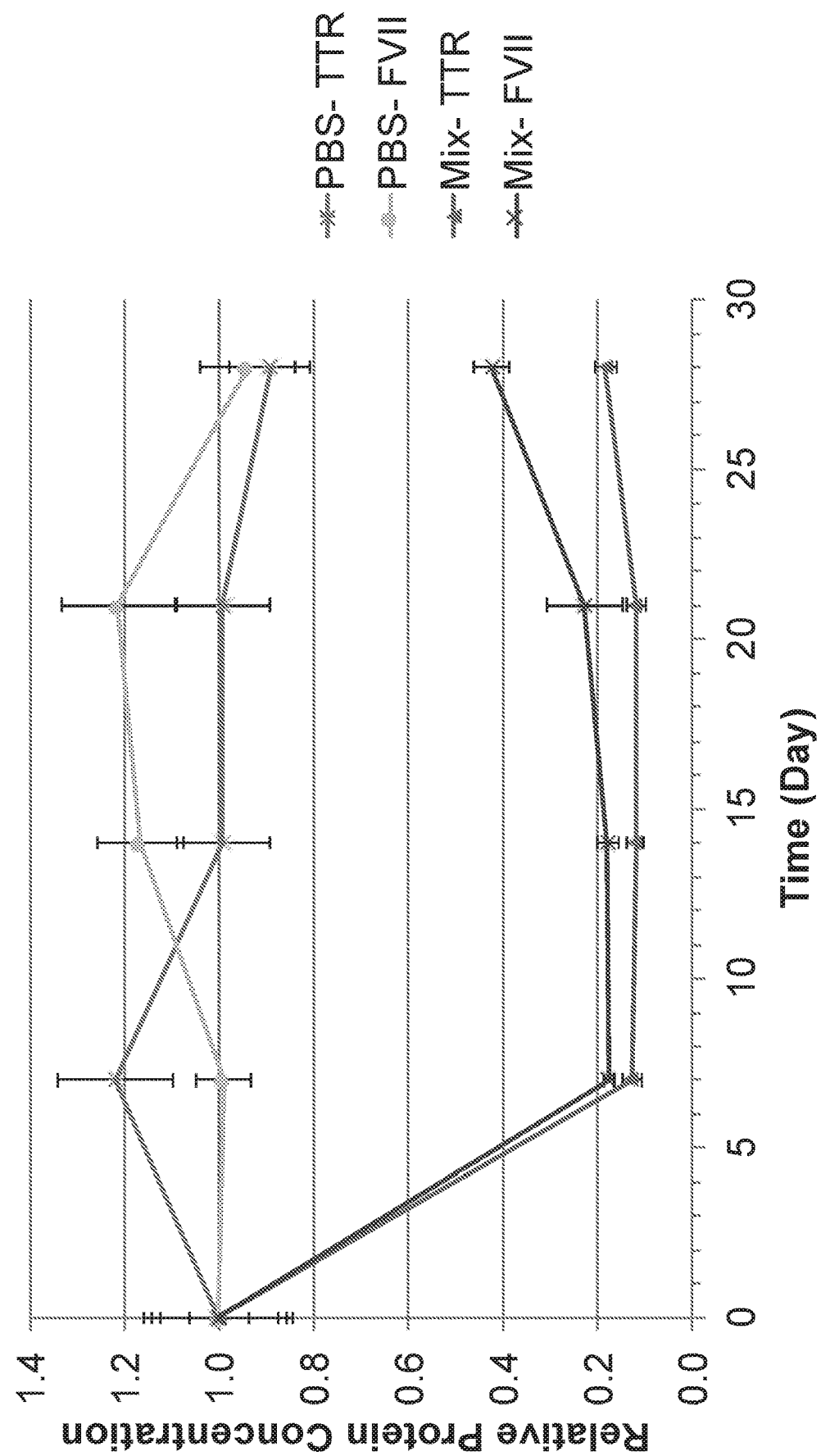
Figure 4:
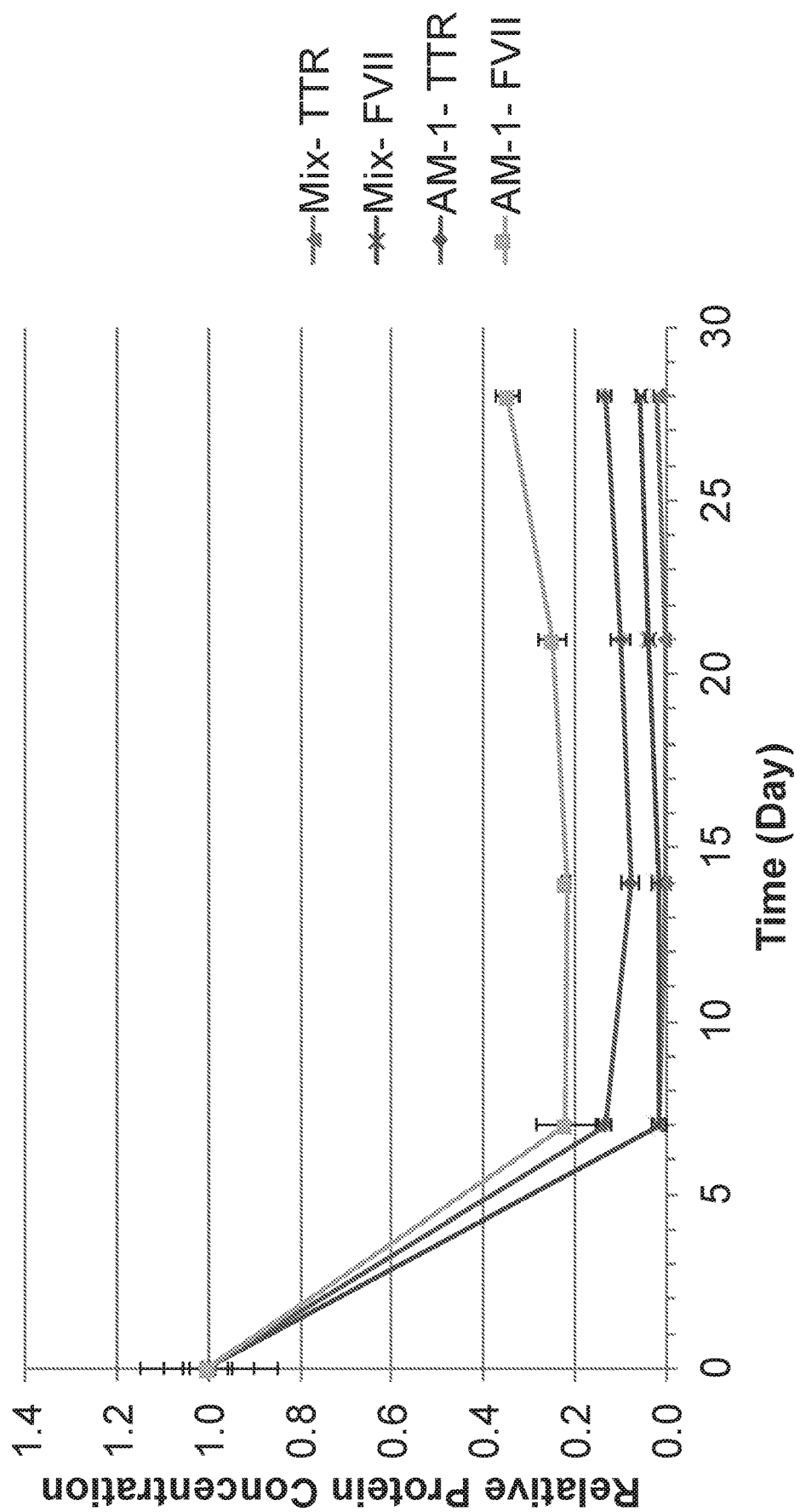
FIGS. 4-12 show in vivo activity of exemplary embodiments of multi-targeted molecules.
Figure 5:
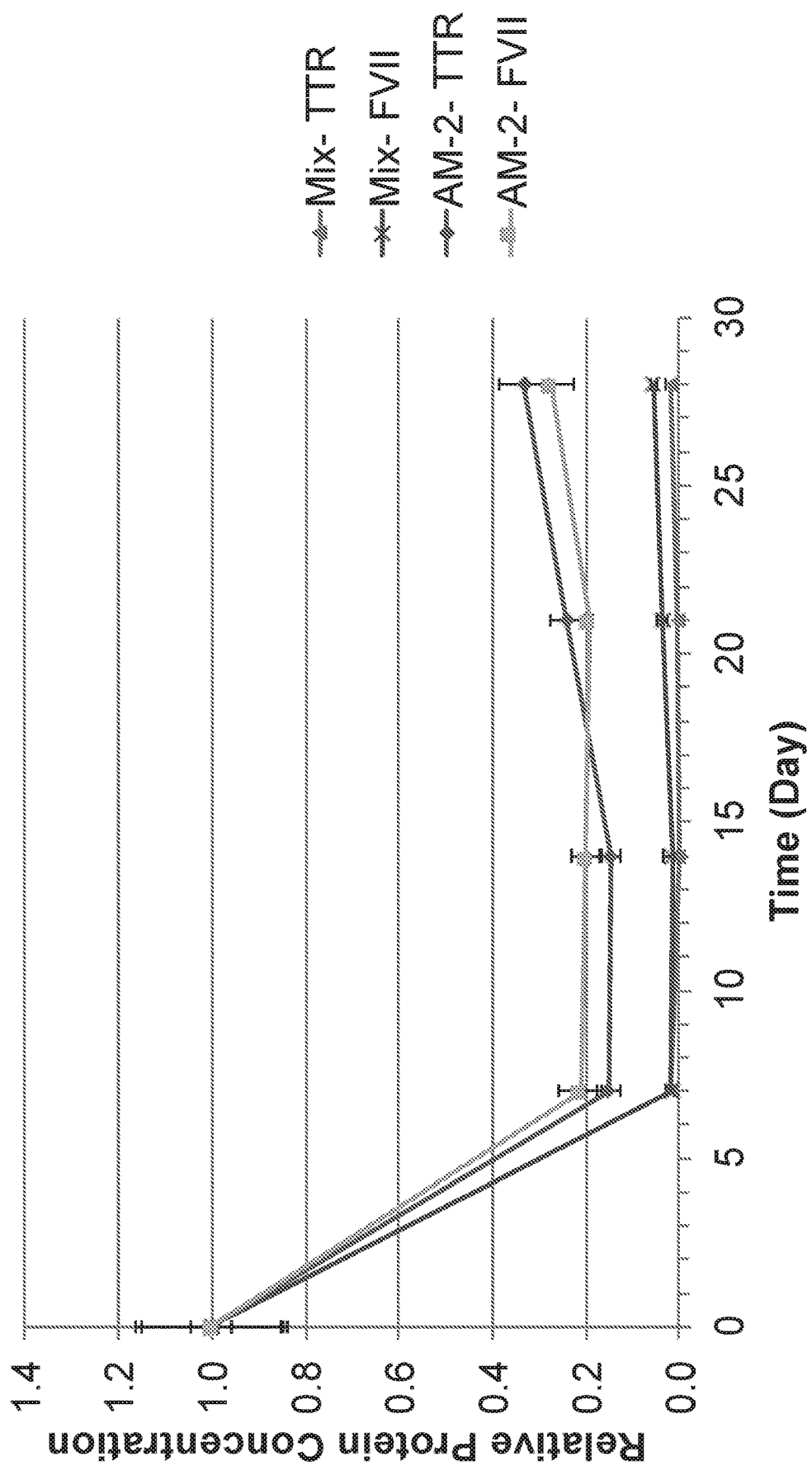
Figure 6:
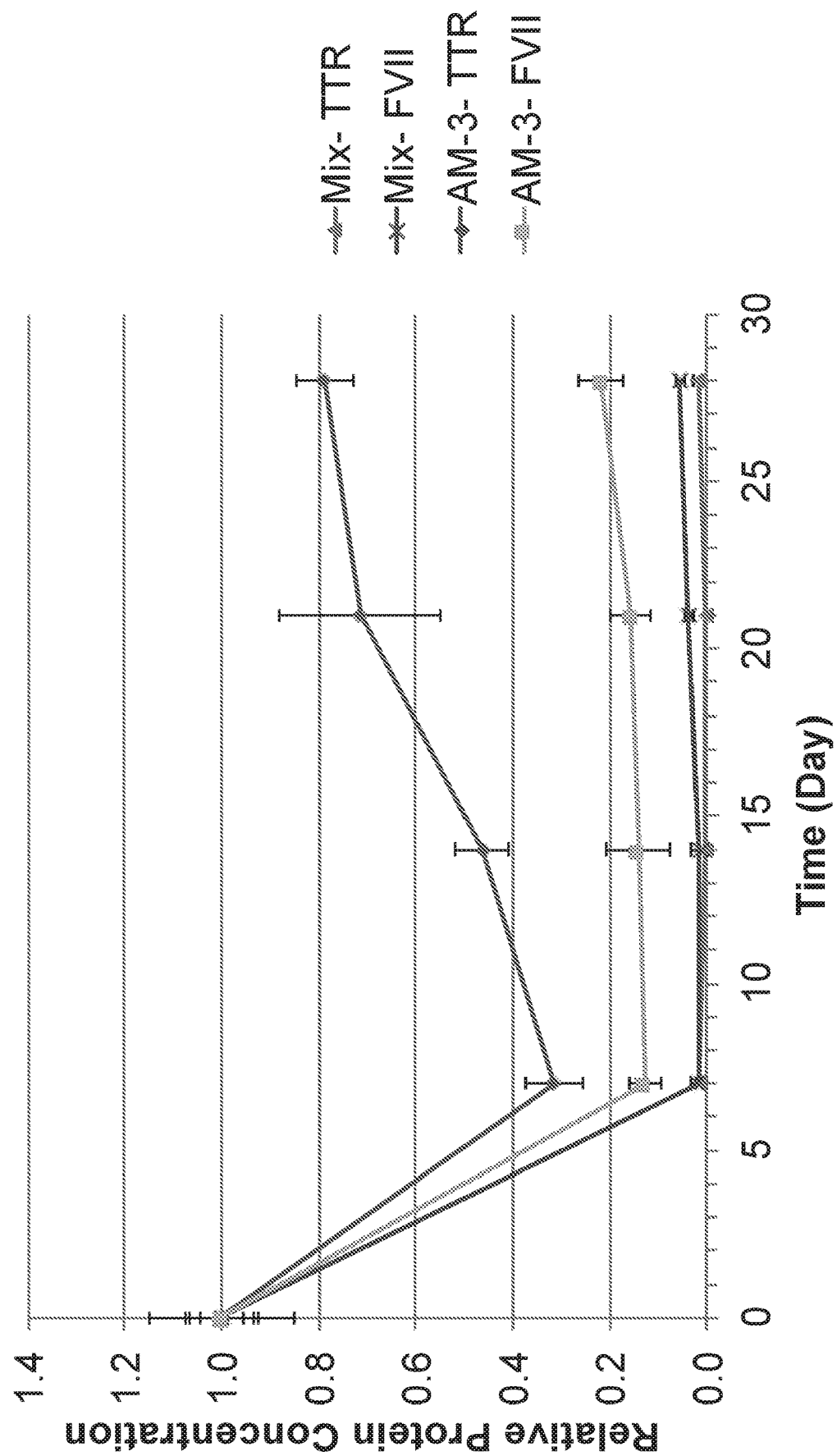
Figure 7:
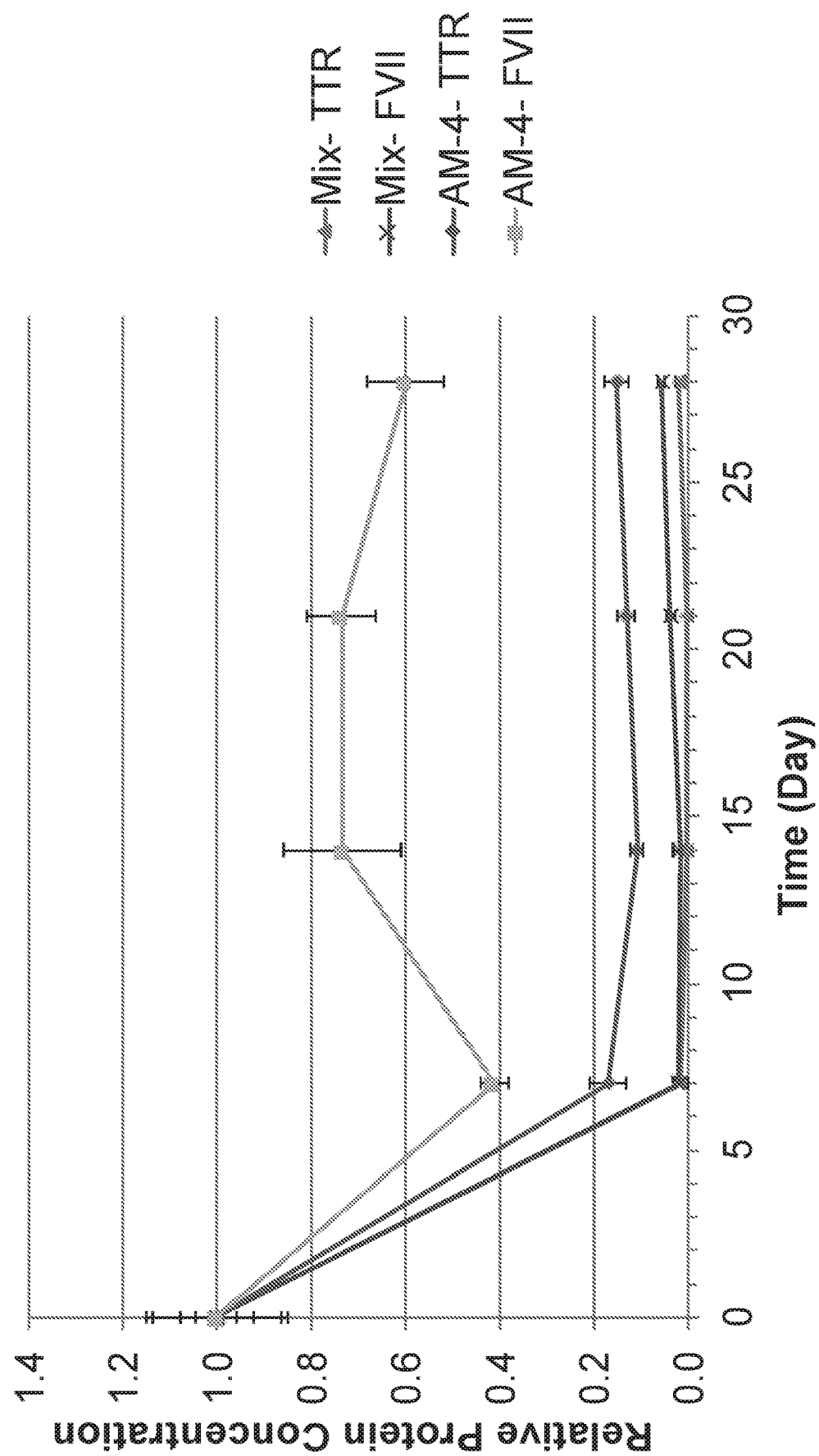
Figure 8:
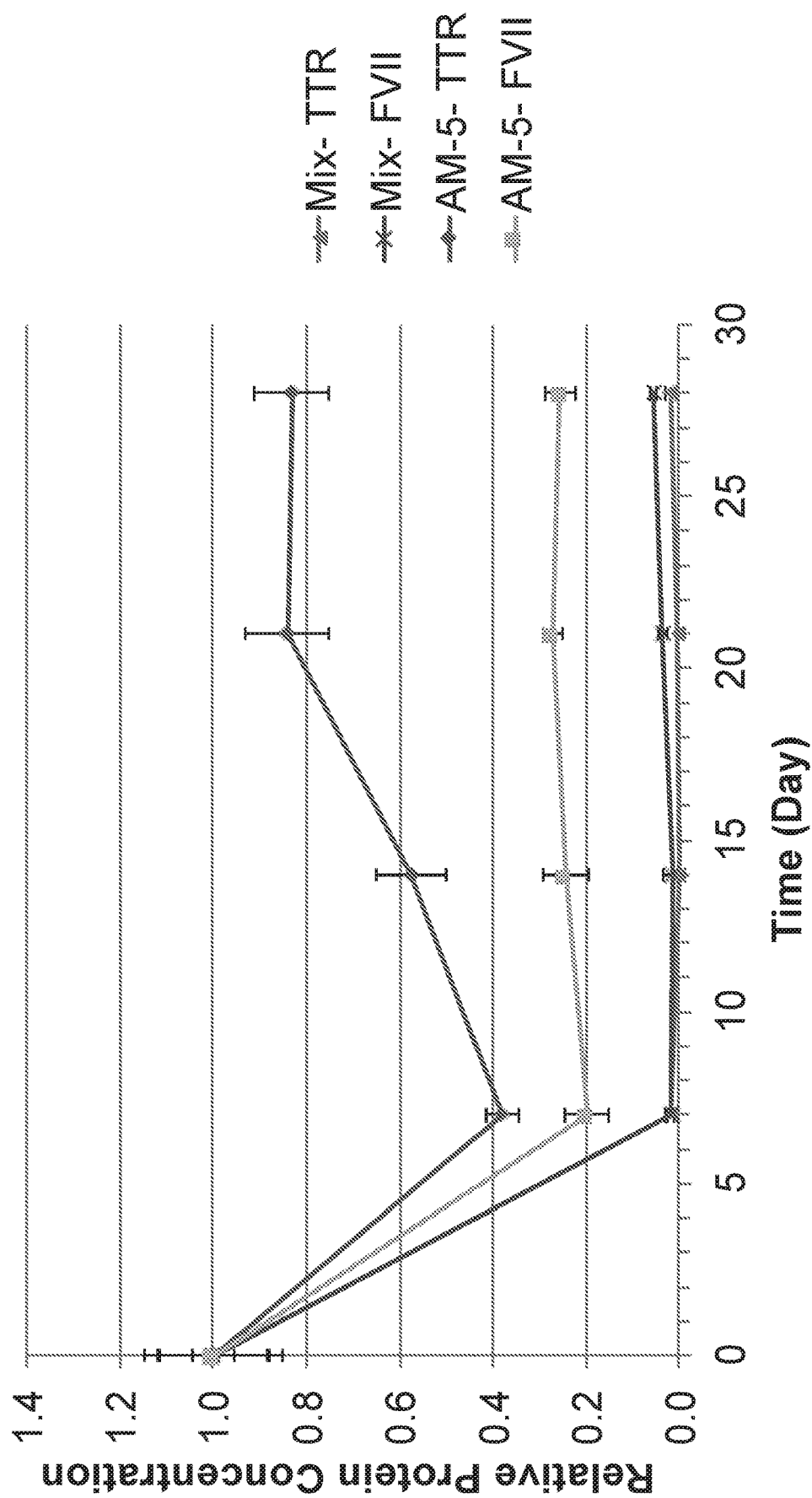
Figure 9:
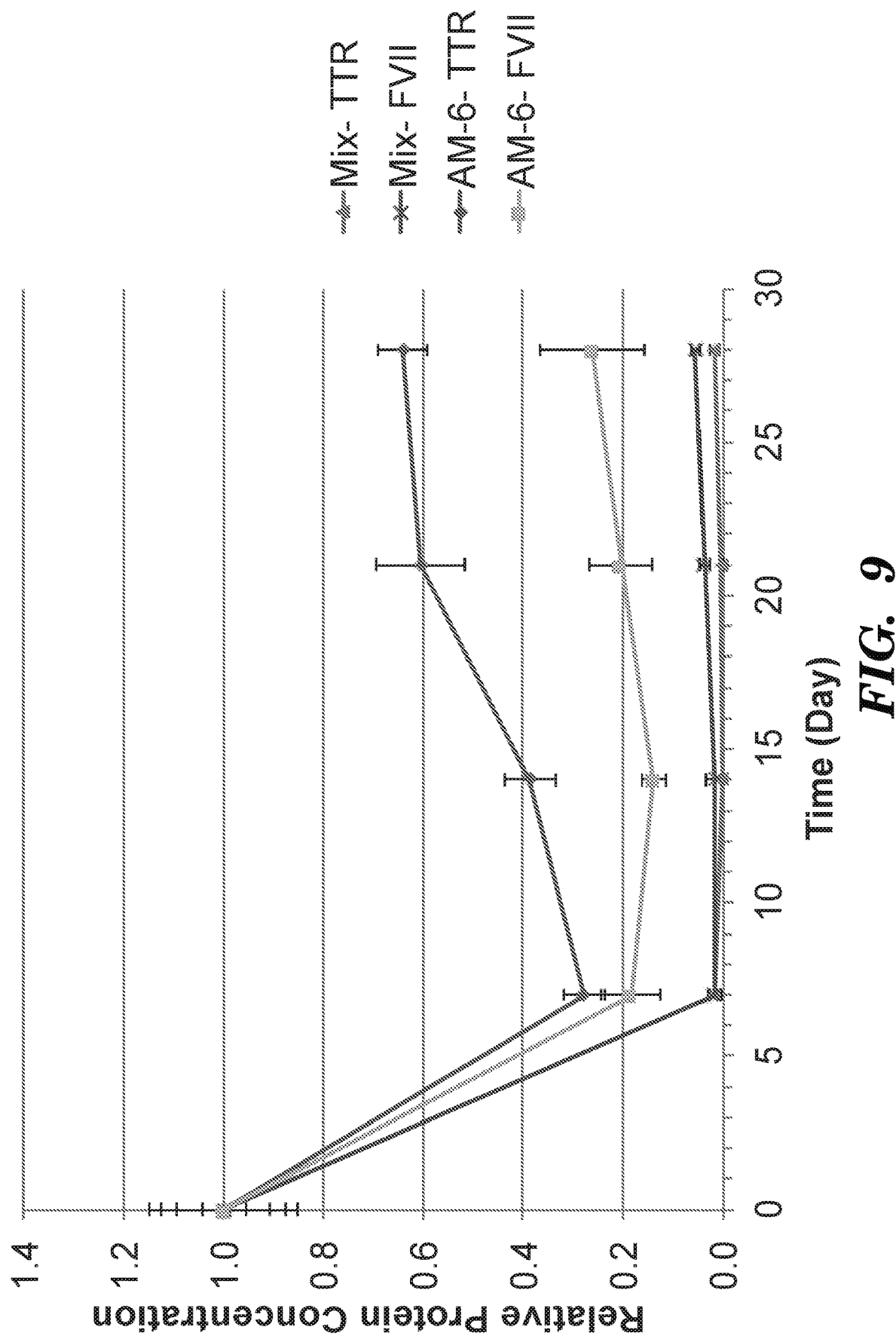
Figure 10:
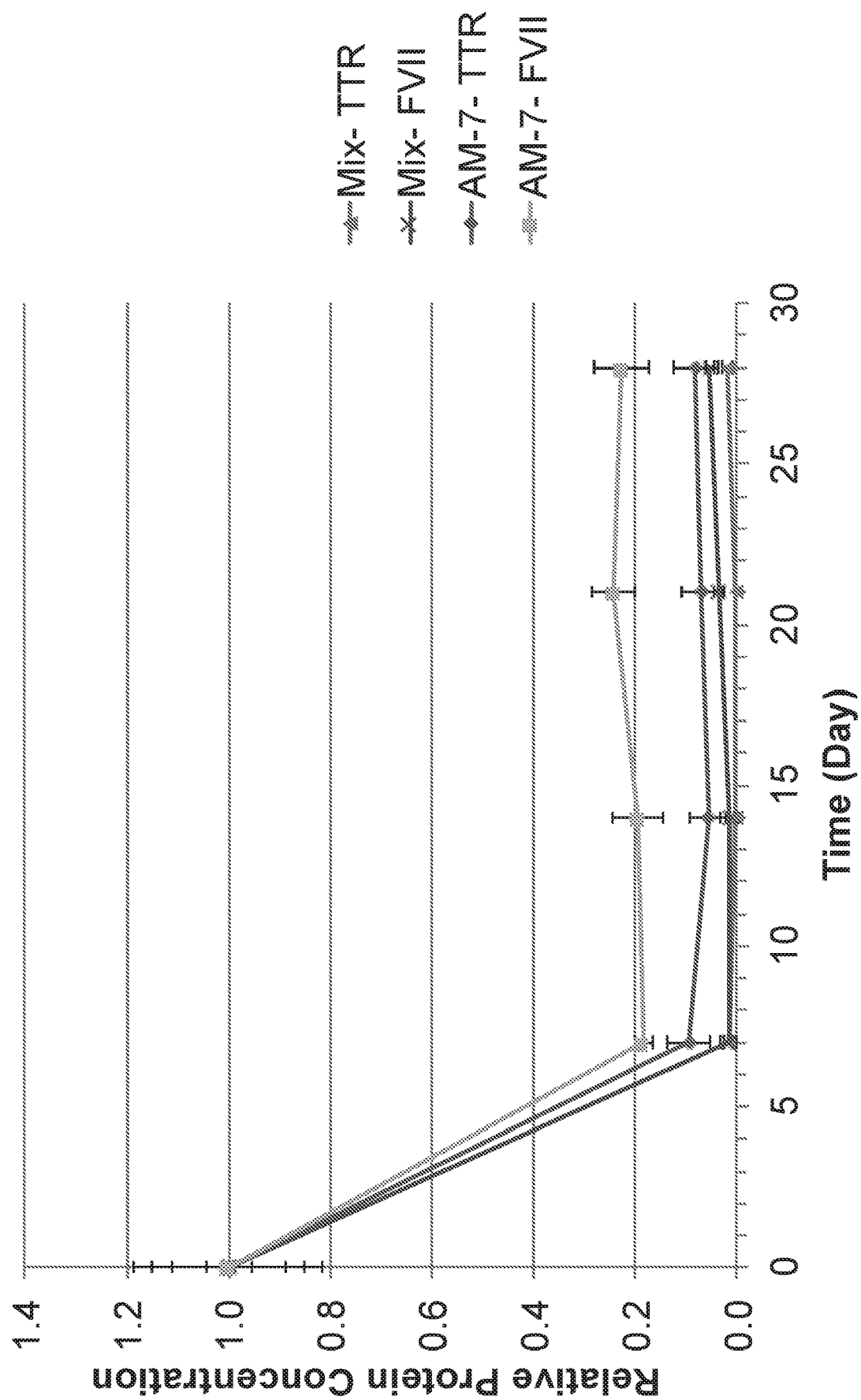
Figure 11:
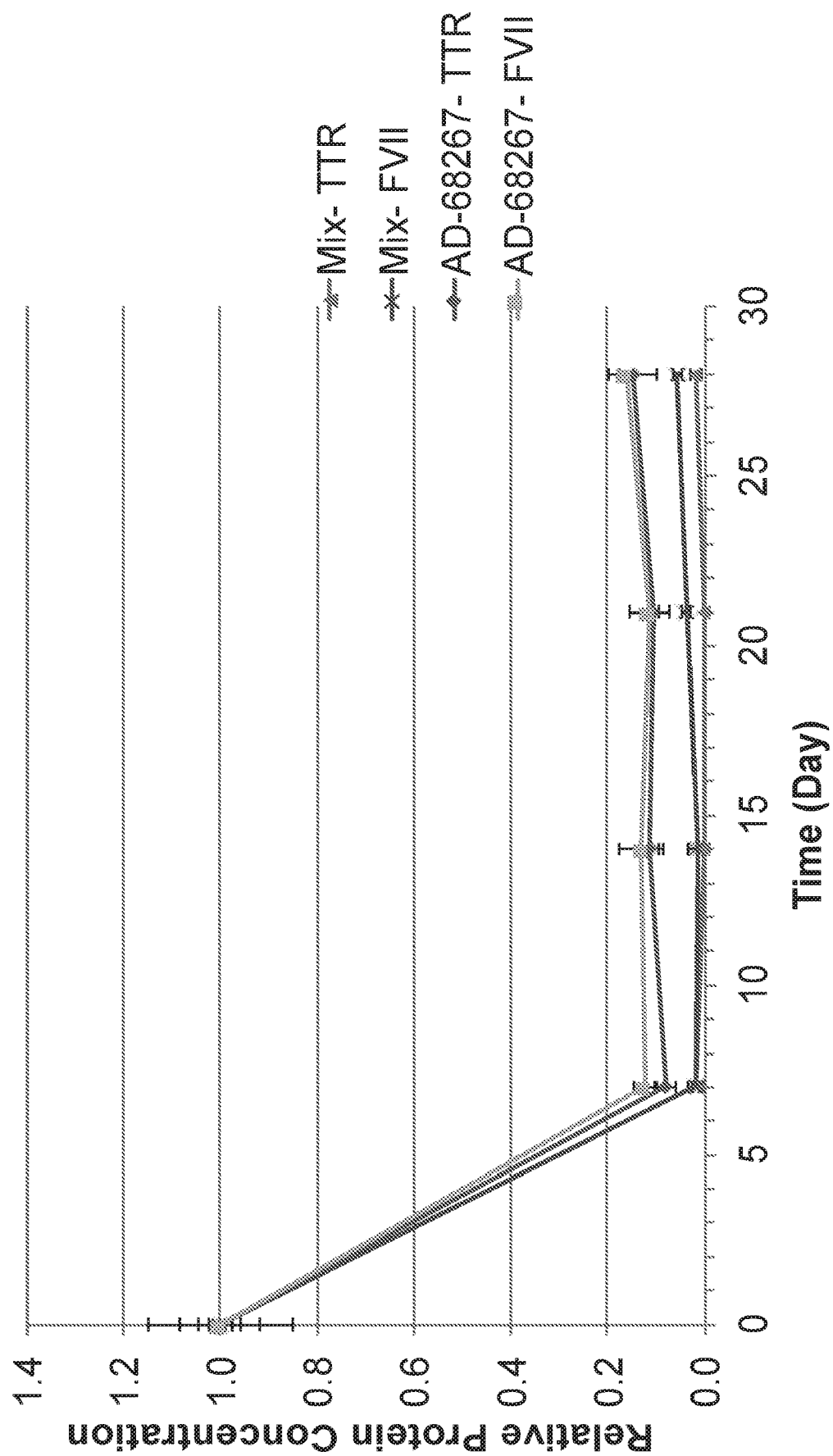
Figure 12:
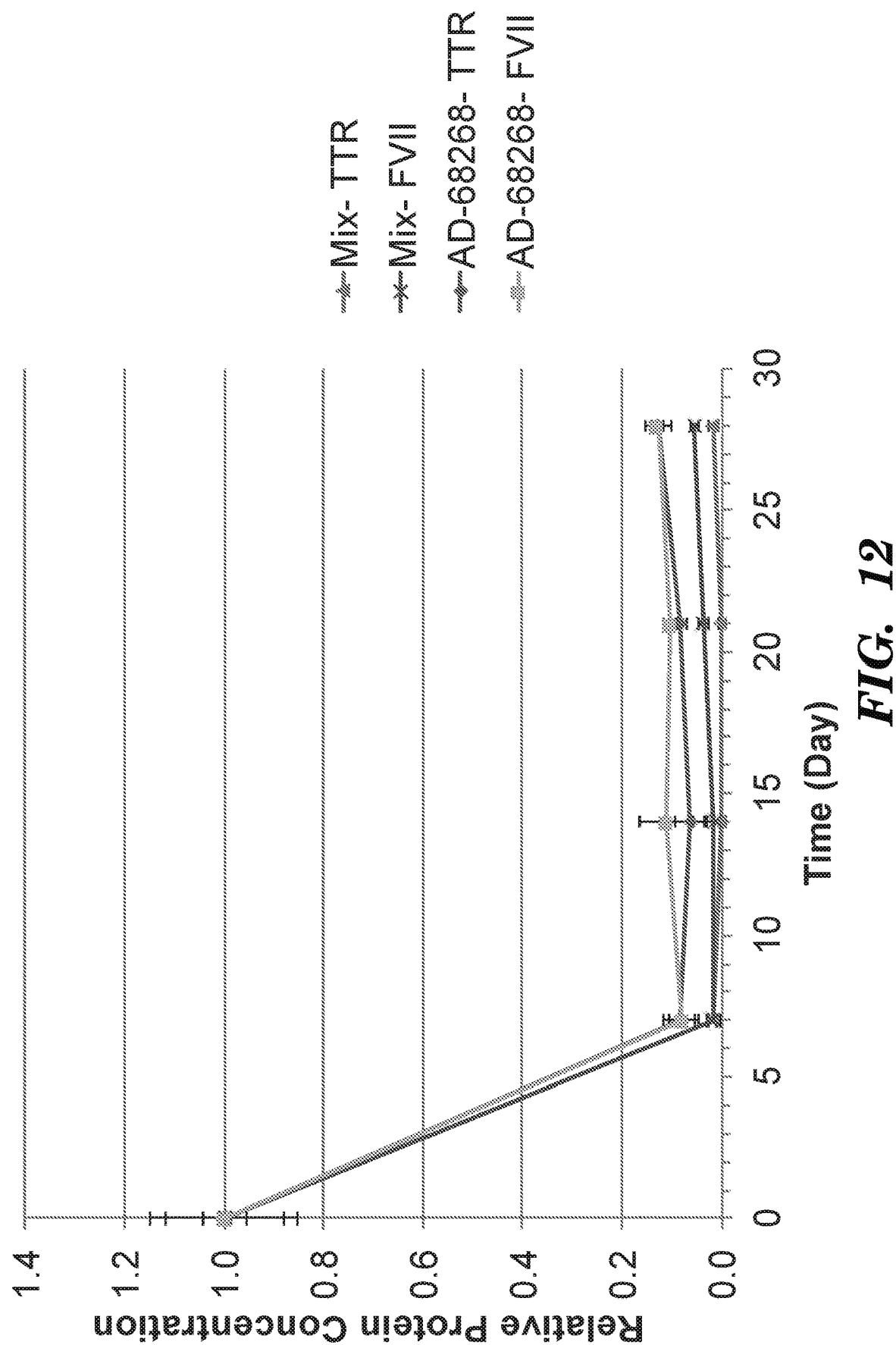
Figure 13:
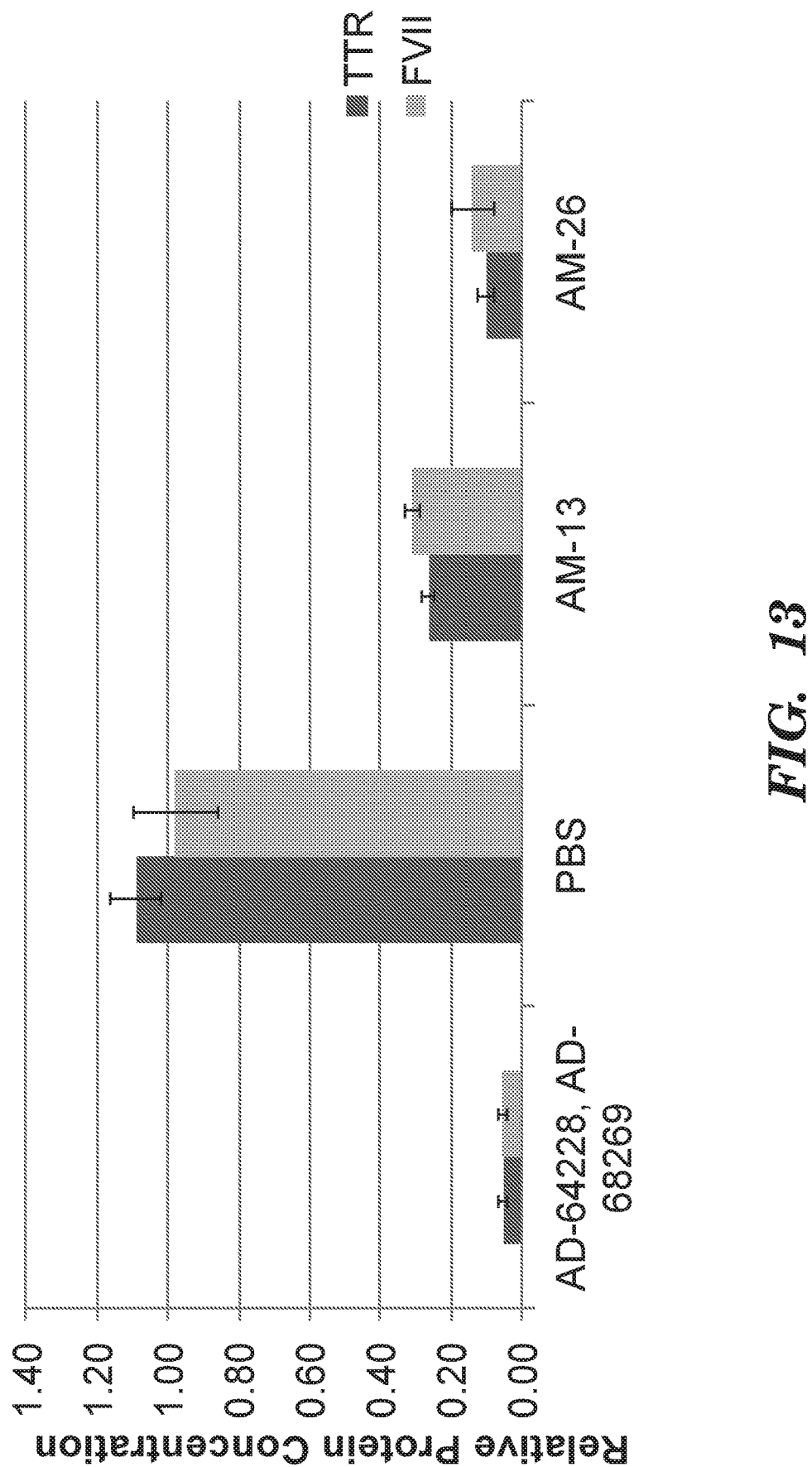
FIG. 13 shows activity of exemplary embodiments of multi-targeted molecules as measured by relative protein concentrations.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

Various aspects described herein are based on multi-targeted molecule comprising at least two nucleic acid based effector molecules that each can modulate gene expression of a target gene. Without limitations, each effector molecule in the multi-targeted molecule can be directed to the same target gene, different target genes, or different positions with the same target gene. Generally, the multi-targeted molecules comprise at least two effector molecules.

Sticky Ends

As disclosed herein, in some embodiments, at least two effector molecules in the multi-targeted molecule are non-covalently linked to each other via hybridization of nucleotides between the effector molecules and each effector molecule is conjugated with at least one ligand each. For example, a portion of an oligonucleotide strand of a first effector molecule hybridizes with a portion of an oligonucleotide strand of a second effector molecule.

In some embodiments, the multi-targeted molecule is assembled from two siRNAs, wherein the two siRNAs can be linked to each other non-covalently and wherein each siRNA has at least one ligand attached thereto. Accordingly, in some embodiments, the multi-targeted molecule comprises a first siRNA and a second siRNA, wherein a first ligand is conjugated with the first siRNA and a second ligand is conjugated with the second siRNA. Generally, a portion of the first siRNA hybridizes to a portion of the second siRNA molecule. Without limitations, either a portion at the 5'- or the 3'-end of the first siRNA can hybridize to a portion of the second siRNA, independent of the nature of the single strands (sense strand or antisense strand).

In some embodiments, the siRNA comprises a first strand and a second strand. Thus, in some embodiments, a portion of one of the strands in the first siRNA hybridizes to a portion of one of the strands in the second siRNA. The strands in the first and second siRNAs that hybridize can both be sense strands, both antisense strands or one sense strand and the other one antisense strand.

In some embodiments, the 3'-end of a strand in the first siRNA is at least 70% (e.g., 70%, 75%, 80%, 85%, 90%, 95% or more) complementary to 3'-end of a strand of the second siRNA molecule. In some embodiments, the 3'-end of the sense strand of the first siRNA is fully complementary to 3'-end of the antisense strand of the second siRNA molecule. In some other embodiments, the 3'-end of the antisense strand of the first siRNA is fully complementary to 3'-end of the sense strand of the second siRNA molecule. In some embodiments, the 3'-end of the sense strand of the first siRNA is fully complementary to 3'-end of the sense strand of the second siRNA molecule. In some other embodiments, the 3'-end of the antisense strand of the first siRNA is fully complementary to 3'-end of the antisense strand of the second siRNA molecule.

In some embodiments, the 3'-end of a strand in the first siRNA is at least 70% (e.g., 70%, 75%, 80%, 85%, 90%, 95% or more) complementary to 5'-end of a strand of the second siRNA molecule. In some embodiments, the 3'-end of the sense strand of the first siRNA is fully complementary to 5'-end of the antisense strand of the second siRNA molecule. In some other embodiments, the 3'-end of the antisense strand of the first siRNA is fully complementary to 5'-end of the sense strand of the second siRNA molecule. In some embodiments, the 3'-end of the sense strand of the first siRNA is fully complementary to 5'-end of the sense strand of the second siRNA molecule. In some other embodiments, the 3'-end of the antisense strand of the first siRNA is fully complementary to 5'-end of the antisense strand of the second siRNA molecule. In some embodiments, the 3'-end of a strand in the first siRNA is at least 70% (e.g., 70%, 75%, 80%, 85%, 90%, 95% or more) complementary to 5'-end of a strand of the second siRNA molecule. In some embodiments, the 5'-end of the sense strand of the first siRNA is fully complementary to 5'-end of the antisense strand of the second siRNA molecule. In some other embodiments, the 5'-end of the antisense strand of the first siRNA is fully complementary to 5'-end of the sense strand of the second siRNA molecule. In some embodiments, the 5'-end of the sense strand of the first siRNA is fully complementary to 5'-end of the sense strand of the second siRNA molecule. In some other embodiments, the 5'-end of the antisense strand of the first siRNA is fully complementary to 5'-end of the antisense strand of the second siRNA molecule.

Generally, the portion of the strand in the first siRNA that is complementary to a portion of the strand of the second siRNA can be 1, 2, 3, 4, 5, 6, 7, 8, 9, 10, 11, 12, 13, 14, 15, 16, 17, 18, 19, 20, 21, 22, 23, 24 or 25 nucleotides in length. Similarly, the portion of the strand in the second siRNA that is complementary to a portion of the strand of the first siRNA can be 1, 2, 3, 4, 5, 6, 7, 8, 9, 10, 11, 12, 13, 14, 15, 16, 17, 18, 19, 20, 21, 22, 23, 24 or 25 nucleotides in length. It is noted that two portions do not need to be of the same length. Thus, one can be shorter than the other.

Without limitations, the length of complementarity between the strands of the first siRNA and the second siRNA should be sufficient for hybridization under physiological conditions. Accordingly, the length of complementary sequence can range from about 1 nucleotide to about 25 nucleotides. For example, the length of complementary sequence can be 1, 2, 3, 4, 5, 6, 7, 8, 9, 10, 11, 12, 13, 14, 15, 16, 17, 18, 19, 20, 21, 22, 23, 24 or 25 nucleotides. As noted above, full complementarity between the strands of the first siRNA and the second siRNA may not be needed. Thus, the complementary portion can comprise one or more (e.g., one, two, three, four, five or more) nucleotide mismatches, bulges or loops.

The portion of the strand in the first siRNA having complementarity with the strand of the second siRNA can be all DNA, all RNA or a mixture of DNA and RNA. The RNA and DNA can be natural and modified. Accordingly, the portion of the strand in the first siRNA having complementarity with the strand of the second siRNA can be unmodified or comprise one or more nucleic acid modifications described herein.

Similarly, the portion of the strand in the second siRNA having complementarity with the strand of the first siRNA can be all DNA, all RNA or a mixture of DNA and RNA. The RNA and DNA can be natural and modified. Accordingly, the portion of the strand in the second siRNA having complementarity with the strand of the first siRNA can be unmodified or comprise one or more nucleic acid modifications described herein.

In some embodiments, the portion of the strand in the first siRNA that is complementary to a portion of the strand of the second siRNA is all RNA. In some embodiments, the portion of the strand in the first siRNA that is complementary to a portion of the strand of the second siRNA is all DNA. Further, said complementary region can be unmodified or comprise one or more nucleic acid modifications described in the present disclosure. Accordingly, in some embodiments, said complementary region comprises at least one modification selected from the group consisting of modified internucleoside linkage, modified nucleobase, modified sugar, and any combinations thereof.

In some embodiments, the portion of the strand in the first siRNA having complementarity with the strand of the second siRNA is all RNA and the portion of the strand in the second siRNA having complementarity with the strand of the first siRNA is all DNA.

In another embodiment, the portion of the strand in the first siRNA having complementarity with the strand of the second siRNA and the portion of the strand in the second siRNA having complementarity with the strand of the first siRNA are both DNA.

In some embodiments, the multi-targeted molecule is assembled from two separate siRNA molecules, wherein each siRNA has at least one ligand attached thereto and wherein a portion of sense strand of the first siRNA hybridizes to a portion of antisense strand of the second siRNA molecule. In some other embodiments, the multi-targeted molecule is assembled from two separate siRNA molecules, wherein each siRNA has at least one ligand attached thereto and wherein a portion of the antisense strand of the first siRNA hybridizes to a portion of sense strand of the second siRNA molecule. In yet other embodiments, the multi-targeted molecule is assembled from two separate siRNA molecules, wherein each siRNA has at least one ligand attached thereto and wherein a portion of antisense strand of the first siRNA hybridizes to a portion of antisense strand of the second siRNA molecule. In yet other embodiments, the multi-targeted molecule is assembled from two separate siRNA molecules, wherein each siRNA has at least one ligand attached thereto and wherein a portion of sense strand of the first siRNA hybridizes to a portion of sense strand of the second siRNA molecule.

In various embodiments of the multi-targeted molecule, where at least two siRNAs, each having at least one ligand, are linked non-covalently to each other, sense strand of a siRNA in the multi-targeted molecule can comprise a single-stranded overhang on it 3'-end with a ligand at the 3'-end of the antisense strand. By single-strand overhang in the present context is meant that the 3'-end of the sense strand extends beyond the 5'-end of its complementary antisense sequence. Without limitations, the overhang can comprise from about 1 nucleotide to about 25 nucleotides. For example, the single-stranded over hang can be 1, 2, 3, 4, 5, 6, 7, 8, 9, 10, 11, 12, 13, 14, 15, 16, 17, 18, 19, 20, 21, 22, 23, 24 or 25 nucleotides.

In various embodiments of the multi-targeted molecule, where at least two siRNAs, each having at least one ligand, are linked non-covalently to each other, antisense strand of a siRNA in the multi-targeted molecule can comprise a single-stranded overhang on it 3'-end with a ligand at the 3'-end of the sense strand. By single-strand overhang in the present context is meant that the 3'-end of the antisense strand extends beyond the 5'-end of its complementary sense sequence. Without limitations, the overhang can comprises from about 1 nucleotide to about 25 nucleotides. For example, the single-stranded over hang can be 1, 2, 3, 4, 5, 6, 7, 8, 9, 10, 11, 12, 13, 14, 15, 16, 17, 18, 19, 20, 21, 22, 23, 24 or 25 nucleotides.

Without limitations, the single-stranded overhang in the sense strand and/or the antisense strand can be an all DNA, all RNA or a mixture of DNA and RNA. In some embodiments, said single-stranded overhang is all RNA. In some embodiments, said single-stranded overhang is all DNA. Moreover, the single-stranded overhang can be unmodified or comprise one or more nucleic acid modifications described in the present disclosure. Accordingly, in some embodiments, said single-strand overhang comprises at least one modification selected from the group consisting of modified internucleoside linkage, modified nucleobase, modified sugar, and any combinations thereof.

In some embodiments, the single-stranded overhang in the sense strand of first siRNA is all RNA and the complementary single-strand in the antisense strand of the second siRNA is all DNA. In another embodiment, the single-strand overhang in the antisense strand of first siRNA is all RNA and the complementary single-strand in the antisense strand of the second siRNA is all DNA. In some embodiments, the single-stranded overhang in the first siRNA and the single-stranded overhang in the second siRNA both are DNA.

The single-strand overhang in the first siRNA can be of similar length as the single-strand overhang in its complementary strand of the second siRNA. Further, there can be zero, one, two, three, four, five or more nucleobases at the 5'-end of the single-strand overhang that have no complementary nucleobase in the single-stranded overhang of the other sequence. Thus, there can be a gap of zero (e.g., a nick), one, two, three, four, five or more nucleobases between the 3'-end of the single-strand overhang of sense strand of the first siRNA and sense strand of the second siRNA when the two siRNAs in the multi-targeted molecule are assembled together. Similarly, there can also be a gap of zero (e.g., a nick), one, two, three, four, five or more nucleobases between the 3'-end of the single-strand overhang of antisense strand of a first siRNA and sense strand of a second siRNA when the two siRNAs in the multi-targeted molecule are assembled together.

In various embodiments of the multi-targeted molecule, where at least two siRNAs, each having at least one ligand, are linked non-covalently to each other, said at least two ligands can be the same or they can be different. Further, the said at least ligands can be conjugated independently at any position of the respective siRNAs. For example, one ligand can be attached to the sense strand of the first siRNA and the other can be attached to the sense strand of the second siRNA, or one ligand can be attached to the sense strand of the first siRNA and the other can be attached to the antisense strand of the second siRNA, or one ligand can be attached to the antisense strand of the first siRNA and the other can be attached to the antisense strand of the second siRNA. Without limitations, the first ligand can be attached independently at the 5'-end, 3'-end or at an internal position of one strand (sense or antisense) of the first siRNA. Similarly, the second ligand can be attached independently at the 5'-end, 3'-end or at an internal position of one strand (sense or antisense) of the second siRNA.

In some embodiments, one ligand is conjugated to 3'-end of a sense strand of the first siRNA and the other ligand is conjugated to the 3'-end of an antisense strand of the second siRNA. In some embodiments, one ligand is conjugated to 5'-end of a sense strand of the first siRNA and the other ligand is conjugated to the 3'-end of an antisense strand of the second siRNA. In some embodiments, one ligand is conjugated to 3'-end of a sense strand of the first siRNA and the other ligand is conjugated to the 5'-end of an antisense strand of the second siRNA. In some embodiments, one ligand is conjugated to 5'-end of a sense strand of the first siRNA and the other ligand is conjugated to the 5'-end of an antisense strand of the second siRNA. In some embodiments, one ligand is conjugated to 3'-end of a sense strand first siRNA and the other ligand is conjugated at an internal position of an antisense strand of the second siRNA. In some embodiments, one ligand is conjugated to 5'-end of a sense strand of the first siRNA and the other ligand is conjugated at an internal position of an antisense strand of the second siRNA. In some embodiments, one ligand is conjugated to 3'-end of an antisense strand of the first siRNA and the other ligand is conjugated at an internal position of a sense strand of the second siRNA. In some embodiments, one ligand is conjugated to 5'-end of an antisense strand of the first siRNA and the other ligand is conjugated at an internal position of a sense strand of the second siRNA. In some embodiments, one ligand is conjugated at an internal position of an antisense strand of the first siRNA and the other ligand is conjugated at an internal position of a sense strand of the second siRNA.

In some embodiments, one ligand is conjugated to 3'-end of a first sense strand and the other ligand is conjugated to the 3'-end of a second sense strand. In some embodiments, one ligand is conjugated to 3'-end of a first sense strand and the other ligand is conjugated to the 5'-end of a second sense strand. In some embodiments, one ligand is conjugated to 5'-end of a first sense strand and the other ligand is conjugated to the 3'-end of a second sense strand. In some embodiments, one ligand is conjugated to 5'-end of a first sense strand and the other ligand is conjugated to the 5'-end of a second sense strand. In some embodiments, one ligand is conjugated to 3'-end of a first sense strand and the other ligand is conjugated at an internal position of a second sense strand. In some embodiments, one ligand is conjugated to 5'-end of a first sense strand and the other ligand is conjugated to an internal position of a second sense strand. In some embodiments, one ligand is conjugated at an internal position of a first sense strand and the other ligand is conjugated at an internal position of a second sense strand. In some embodiments, one ligand is conjugated to 3'-end of a first antisense strand and the other ligand is conjugated to the 3'-end of a second antisense strand. In some embodiments, one ligand is conjugated to 3'-end of a first antisense strand and the other ligand is conjugated to the 5'-end of a second antisense strand. In some embodiments, one ligand is conjugated to 5'-end of a first antisense strand and the other ligand is conjugated to the 3'-end of a second antisense strand. In some embodiments, one ligand is conjugated to 5'-end of a first antisense strand and the other ligand is conjugated to the 5'-end of a second antisense strand. In some embodiments, one ligand is conjugated to 3'-end of a first antisense strand and the other ligand is conjugated at an internal position of a second antisense strand. In some embodiments, one ligand is conjugated to 5'-end of a first antisense strand and the other ligand is conjugated to an internal position of a second antisense strand. In some embodiments, one ligand is conjugated at an internal position of a first antisense strand and the other ligand is conjugated at an internal position of a second antisense strand.

Covalently Linked

In some embodiments, at least two nucleic acid based effector molecules in the multi-targeted molecules can be covalently linked to each other via nucleotide-based linkers or non-nucleotide based linkers as generally known in the art and as described herein. Accordingly, in some embodiments, at least two effector molecules in the multi-targeted molecule are linked via a nucleotide-based linker. In some other embodiments, at least two effector molecules are linked via a non-nucleotide based linker.

It is noted that a nucleotide-based linker may form part of one or both the effector molecules being connected together. What is meant by this is that at least a portion of the nucleotide sequence of the linker is needed for functioning of one of the effector molecules. In preferred embodiments, the nucleotide sequence of the linker does not form part of the effector molecule. In other words, either of the effector molecules does not require any part of the nucleotide sequence of the linker modulating gene expression. For example, if the linker sequence is removed from the effector molecule, the effector molecule is still capable of modulating gene expression at a similar level (e.g., within 95%) relative to when the linker is present. Where the effector molecule needs complementarity with the target gene for activity, the linker may or may not be part of the effector molecule needed for complementarity to the target sequence. In some embodiments, the linker does not have complementarity (e.g., less than 5% complementarity) with or hybridizes to the target sequence.

In some embodiments, a first strand of double-stranded nucleotide-based linker connecting the two effector molecules comprises a nucleotide sequence substantially complementary to the second strand of said double-stranded nucleotide-based linker. In some embodiments, the first strand of the linker comprises a nucleobase sequence that is at least 75% (e.g., 75%, 80%, 85%, 90%, 95% or more) complementary to the nucleobase sequence of the second strand of the linker. In some embodiments, the first strand of the linker comprises a nucleobase sequence that is fully complementary to the nucleobase sequence of the second strand of the linker connecting the two effector molecules.

Without limitation, a nucleotide-based linker connecting the effector molecules can be all DNA, all RNA or a mixture of DNA and RNA. In some embodiments, the nucleotide-based linker connecting the two effector molecules is all DNA. The RNA and DNA can be natural and modified. Accordingly, in some embodiments, the nucleotide-based linker connecting the effector molecules comprises at least one modification selected from the group consisting of modified internucleoside linkage, modified nucleobase, modified sugar, and any combinations thereof. Exemplary modifications for the linker include, but are not limited to, locked nucleic acids (e.g., LNA, ENA and BNA), 2'-O-alkyl nucleosides, 2'-halo nucleosides (such as 2'-F nucleotides), 2'-amino nucleosides, 2'-S-alkyl nucleosides, abasic nucleosides, 2'-cyano nucleosides, 2'-mercapto nucleosides; 2'-MOE nucleosides, acyclic nucleosides, (S)-cEt monomers, and modified internucleotide linkages (such as phosphodiesters, phosphotriesters, hydrogen phosphonates, alkyl or aryl phosphonates, phosphoramidates, phosphorothioates, phosphorodithioates, methylenemethylimino, thiodiester, thionocarbamate, N,N'-dimethylhydrazine, phosphoroselenates, borano phosphates, borano phosphate esters, amides, hydroxylamino, siloxane, dialkylsiloxane, carboxamide, carbonate, carboxymethyl, carbamate, carboxylate ester, thioether, ethylene oxide linker, sulfide, sulfonate, sulfonamide, sulfonate ester, thioformacetal, formacetal, oxime, methyleneimino, methykenecarbonylamino, methyl-enemethylimino, methylenehydrazo, methylenedimethylhy-drazo, methyleneoxymethylimino, ethers, thioethers, and thioacetamido). Nucleic acid modifications are described in more detail below in the disclosure.

In some embodiments, at least one of the internucleoside linkages between the linker connecting the effector molecules and an effector molecule is a modified internucleoside linkage. In some embodiments, the internucleoside linkage connecting the 5'-end of the linker to the 3'-end of one of the effector molecule is a modified internucleoside linkage. In some embodiments, the internucleoside linkage connecting the 3'-end of the linker to the 5'-end of one of the effector molecules is a modified internucleoside linkage.

In some embodiments, first (e.g., first, second, third, fourth or fifth) internucleoside linkage at the 5'- and/or 3'-end of the linker connecting the effector molecules is a modified internucleoside linkage. In some embodiments, one, two, three, four, five or more internucleoside linkages from the 5'- and/or 3'-end of the linker are modified internucleoside linkages.

In some embodiments, the linker connecting the effector molecules comprises at least one (e.g., one, two, three, four, five, six or more) modified internucleoside linkages at an internal position of the linker.

Without limitations, the nucleotide-based linker connecting the effector molecules can be of any desired length. For example, the nucleotide-based linker connecting the effector molecules can be 1, 2, 3, 4, 5, 6, 7, 8, 9, 10, 11, 12, 13, 14, 15, 16, 17, 18, 19, 20 or more nucleotides in length. In some embodiments, the nucleotide-based linker connecting the effector molecules can range in length from 1 nucleotide to 5 nucleotides in length. In a particular embodiment, the nucleotide-based linker connecting the two effector molecules is 4 nucleotides in length.

When the nucleotide-based linker connecting the effector molecules comprises a nucleic acid modification, such modification can be located at any position in the linker. For example, the modification can be at the 5'-nucleotide, the 3'-nucleotide or at an internal nucleotide of the linker. In some embodiments, first (e.g., first, second, third, fourth or fifth) nucleotide at the 5'- and/or 3'-end of the linker comprises a nucleic acid modification. In some embodiments, one, two, three, four, five or more nucleotides from the 5'- and/or 3'-end of the linker comprise a nucleic acid modification. In some embodiments, one, two, three, four, five or more internal nucleotides of the linker comprise a nucleic acid modification. In some embodiments, internal nucleotides of the linker comprise all DNA on the sense strand. In another embodiment, the internal internal nucleotides of the linker comprise a mixture of DNA and 2'-OAlkyl modifications on the antisense strand.

The nucleotide-based linker connecting the effector molecules can comprise one or two nucleic acid strands and can be single stranded, double-stranded, or comprise single-stranded and double-stranded regions. In some embodiments, the nucleotide-based linker connecting the effector molecules comprises two nucleic acid strands that do not form a double-stranded structure. In other words, the nucleotide-based linker comprises two strands that do not hybridize with each other.

In some embodiments, the nucleotide-based linker connecting the effector molecules comprises two nucleic acid strands, wherein nucleotide sequence of the first strand of the linker comprises at least one (e.g., one, two, three, four, five or more) nucleotide mismatch with the nucleotide sequence of the second strand of the linker. In some embodiments, at least one of the strands of the linker comprises a bulge or a loop. For example, at least one of the linker strands comprises at least one (e.g., one, two, three, four, five or more consecutive or nonconsecutive) non-complementary nucleobase with the other linker strand.

Without limitations, the nucleotide-based linker connecting the effector molecules can comprise one or more nucleic acid modifications disclosed herein. When the nucleotide-based linker connecting the effector molecules comprises two nucleic acid strands, each strand can be independently unmodified or comprise one or more nucleic acid modifications disclosed herein. Accordingly, in some embodiments, the nucleotide-based linker connecting the effector molecules comprises two nucleic acid strands where each strand is unmodified. In some embodiments, the nucleotide-based linker connecting the effector molecules comprises two nucleic acid strands, wherein one strand is unmodified and the other strand comprises at least one modification selected from the group consisting of modified internucleoside linkage, modified nucleobase, modified sugar, and any combinations thereof. In some embodiments, the nucleotide-based linker connecting the effector molecules comprises two nucleic acid strands and both strands comprise at least one modification independently selected from the group consisting of modified internucleoside linkage, modified nucleobase, modified sugar, and any combinations thereof.

In some embodiments, the nucleotide-based linker connecting the effector molecules comprises two nucleic acid strands and wherein one of the strands comprises all DNA and the other strand comprises a mixture of DNA and 2'-Oalkyl modifications.

The nucleotide-based linker connecting the effector molecules can be resistant to degradation or cleavage by a single- or double-strand nuclease. Alternatively, nucleotide-based linker connecting the effector molecules can be a cleavable linker. For example, a linker connecting the effector molecules can undergo cleavage by a single- or double-strand nuclease.

As described herein, the linker connecting the effector molecules in a multi-targeted molecule can be a non-nucleotide based linker. In some embodiments, the non-nucleotide based linker connecting the two oligonucleotides comprises a cleavable group.

In some embodiments, the non-nucleotide based linker connecting the two oligonucleotides comprises at least one disulfide group.

As disclosed herein, in some embodiments, at least two effector molecules in the multi-targeted molecule are covalently linked to each other via a nucleotide-based or non-nucleotide based linker and the multi-targeted molecule is further conjugated with at least one ligand. Without limitations, the ligand can be present anywhere in the multi-targeted molecule. For example, the ligand can be present at one end of one of the at least two effector molecules covalently linked by the linker, at an internal position in one of the at least two effector molecules covalently linked by the linker, or at a position in the linker.

In some embodiments, the multi-targeted molecule comprising at least two effector molecules covalently linked together is conjugated with at least one ligand. Without limitations, the ligands can be the same or they can be different. The two ligands can be conjugated independently at any position in the multi-targeted molecule. For example, a first ligand can be present in the first effector molecule and the second ligand can be present in the linker connecting the first effector molecule to a second effector molecule or a first ligand can be present in the first effector molecule and the second ligand can be present in the second effector molecule covalently that is covalently linked to the first effector molecule; or both ligands can be present in the same effector molecule; or both ligands can be present in the linker connecting the effector molecules.

In some embodiment, the linker connecting the effector molecules comprises a monomer selected from the group consisting of Q151 (FIG. 26), Q173 (FIG. 26), the monomers shown in FIGS. 19-24 and the monomers described below in the section titled "Exemplary ligand monomers." For example, MONOMERS 1-30 described in below. 00365]. Without limitations, the ligand can be present at any position in the linker. For example, the ligand can be conjugated to the middle position or within 1, 2, or 3 monomers or units at middle of the linker. In some embodiments, the ligand carrying monomer acts as the linker.

In some embodiments, the multi-targeted molecule is assembled from two siRNAs, wherein the two siRNAs are linked to each other covalently via a nucleotide-based or non-nucleotide based linker. In some embodiments, the linker connecting the two siRNAs comprises the nucleotide sequence uuu or (dT)n, where n is 1-20. In some embodiments, the linker connecting the effector molecules comprises a molecule selected from the group consisting of —$(CH_2)_{12}$— (C12 linker or Q50), —$(CH_2)_6$—S—S—$(CH_2)_6$— (C6-S—S—C6 linker or Q51), Q151, Q173, —$CH_2CH_2O$—$(CH_2CH_2)_n$—$CH_2CH_2O$—$CH_2CH_2O$—, where n is 0 or 1-20; —$(CH_2)_9$—$(CH_2)_n$—$CH_2$—, where n is 0 or 1-20; mono-, di-, tri-, tetra-, penta- or polyprolinol, optionally conjugated with a ligand; mono-, di-, tri-, tetra-, penta- or polyhydroxyprolinol, optionally conjugated with a ligand. In some embodiments, the linker connecting the two siRNAs comprises a molecule selected from those shown in FIGS. 16-23 and 26. In some embodiments, the linker comprises a monomer selected from the monomers described below in the section titled "Exemplary ligand monomers." For example, MONOMERS 1-30 described in below. Exemplary linkers are also described in the Examples section of the disclosure, e.g., Examples 1-23.

In some embodiments, the multi-targeted molecule is assembled from two siRNAs wherein sense strand of the first siRNA is covalently linked to the sense strand of the second siRNA. Without limitations, the two sense strands can be linked to each other in any orientation. For example, 3'-end of the first sense strand can be linked to 5'-end of the second sense strand; 3'-end of the first sense strand can be linked to 3'-end of the second sense strand; or 5'-end of the first sense strand can be linked to 5'-end of the second sense strand.

In some embodiments, the multi-targeted molecule is assembled from two siRNAs wherein antisense strand of the first siRNA is covalently linked to the antisense strand of the second siRNA. Without limitations, the two antisense strands can be linked to each other in any orientation. For example, 3'-end of the first antisense strand can be linked to 5'-end of the second antisense strand; 3'-end of the first antisense strand can be linked to 3'-end of the second antisense strand; or 5'-end of the first antisense strand can be linked to 5'-end of the second antisense strand.

In some embodiments, the multi-targeted molecule is assembled from two siRNAs wherein sense strand of the first siRNA is covalently linked to the antisense strand of the second siRNA. Without limitations, the sense strand of the first siRNA can be linked to the antisense strand of the second siRNA in any orientation. For example, 3'-end of the sense strand can be linked to 5'-end of the antisense strand; 3'-end of the sense strand can be linked to 3'-end of the antisense strand; or 5'-end of the sense strand can be linked to 5'-end of the antisense strand.

In some embodiments, the multi-targeted molecule is assembled from two siRNAs wherein sense strand of the first siRNA is covalently linked to the sense strand of the second siRNA and antisense strand of the first siRNA is covalently linked to the antisense strand of the second siRNA. In some embodiments, the multi-targeted molecule is assembled from two siRNAs wherein antisense strand of the first siRNA is covalently linked to the sense strand of the second siRNA and sense strand of the first siRNA is covalently linked to the antisense strand of the second siRNA.

Effector Molecules

The skilled person is well aware that double-stranded oligonucleotides comprising a duplex structure of between 20 and 23, but specifically 21, base pairs have been hailed as particularly effective in inducing RNA interference (Elbashir et al., EMBO 2001, 20:6877-6888). However, others have found that shorter or longer double-stranded oligonucleotides can be effective as well.

In some embodiments, at least one effector molecule in the multi-targeted molecule is an siRNA. In some embodiments, the multi-targeted molecule comprises at least siR-NAs. As used herein, the term "siRNA" refers to an agent that mediates the targeted cleavage of an RNA transcript. These agents associate with a cytoplasmic multi-protein complex known as RNAi-induced silencing complex (RISC). Agents that are effective in inducing RNA interference are also referred to as siRNA, RNAi agent, or iRNA agent, herein. As used herein, the term siRNA includes microRNAs and pre-microRNAs. As used herein, the terms "siRNA activity" and "RNAi activity" refer to gene silencing by an siRNA.

The double-stranded oligonucleotides comprise two oligonucleotide strands that are sufficiently complementary to hybridize to form a duplex structure. Generally, the duplex structure is between 15 and 35, more generally between 18 and 25, yet more generally between 19 and 24, and most generally between 19 and 21 base pairs in length. In some embodiments, longer double-stranded oligonucleotides of between 25 and 30 base pairs in length are preferred. In some embodiments, shorter double-stranded oligonucleotides of between 10 and 15 base pairs in length are preferred. In another embodiment, the double-stranded oligonucleotide is at least 21 nucleotides long.

In some embodiments, the double-stranded oligonucleotide comprises a sense strand and an antisense strand, wherein the antisense RNA strand has a region of complementarity which is complementary to at least a part of a target sequence, and the duplex region is 14-30 nucleotides in length. Similarly, the region of complementarity to the target sequence is between 14 and 30, more generally between 18 and 25, yet more generally between 19 and 24, and most generally between 19 and 21 nucleotides in length.

The phrase "antisense strand" as used herein, refers to an oligomeric compound that is substantially or 100% complementary to a target sequence of interest. The phrase "antisense strand" includes the antisense region of both oligomeric compounds that are formed from two separate strands, as well as unimolecular oligomeric compounds that are capable of forming hairpin or dumbbell type structures. The terms "antisense strand" and "guide strand" are used interchangeably herein.

The phrase "sense strand" refers to an oligomeric compound that has the same nucleoside sequence, in whole or in part, as a target sequence such as a messenger RNA or a sequence of DNA. The terms "sense strand" and "passenger strand" are used interchangeably herein.

In some embodiments, the double-stranded region of a double-stranded oligonucleotide is equal to or at least, 10, 11, 12, 13, 14, 15, 16, 17, 18, 19, 20, 21, 22, 23, 23, 24, 25, 26, 27, 28, 29, 30, 31, 32, 33, 34, 35, 36, 37, 38, 39, 40 or more nucleotide pairs in length.

In some embodiments, the antisense strand of a double-stranded oligonucleotide is equal to or at least 14, 15, 16, 17, 18, 19, 20, 21, 22, 23, 23, 24, 25, 26, 27, 28, 29, 30, 31, 32, 33, 34, 35, 36, 37, 38, 39, or 40 or more nucleotides in length.

In some embodiments, the sense strand of a double-stranded oligonucleotide is equal to or at least 10, 11, 12, 13, 14, 15, 16, 17, 18, 19, 20, 21, 22, 23, 23, 24, 25, 26, 27, 28, 29, 30, 31, 32, 33, 34, 35, 36, 37, 38, 39, 40 or more nucleotides in length.

In some embodiments, one strand has at least one stretch of 1-10 single-stranded nucleotides in the double-stranded region. By "stretch of single-stranded nucleotides in the double-stranded region" is meant that there is present at least one nucleotide in the double-stranded region that is not basepaired with another nucleotide. When the stretch of single-stranded nucleotides is present internally in the double-stranded region, at least one nucleotide base pair can be present at both ends of the single-stranded stretch. When present at the end of a double-stranded region, the stretch of single-stranded nucleotides can be a singe-stranded overhang. The stretch of single-stranded nucleotides in the double-stranded region can be in the form of a bulge or one-or more mismatched nucleotides. In some embodiments, both strands have at least one stretch of 1-5 (e.g., 1, 2, 3, 4, or 5) single-stranded nucleotides in the double stranded region. When both strands have a stretch of 1-5 (e.g., 1, 2, 3, 4, or 5) single-stranded nucleotides in the double stranded region, such single-stranded nucleotides can be opposite to each other (e.g., a stretch of mismatches) or they can be located such that the second strand has no non-basepaired nucleotides opposite to the single-stranded oligonucleotides of the first strand and vice versa (e.g., a single-stranded loop). In some embodiments, the single-stranded nucleotides are present within 8 nucleotides from either end, for example 8, 7, 6, 5, 4, 3, or 2 nucleotide from either the 5' or 3' end of the region of complementarity between the two strands.

Hairpin and dumbbell type oligonucleotides will have a duplex region equal to or at least 14, 15, 15, 16, 17, 18, 19, 29, 21, 22, 23, 24, or 25 nucleotide pairs. The duplex region can be equal to or less than 200, 100, or 50, in length. In some embodiments, ranges for the duplex region are 15-30, 17 to 23, 19 to 23, and 19 to 21 nucleotides pairs in length.

In some embodiments, the nucleic acid based effector molecule is a hairpin oligonucleotides that can have a single strand overhang or terminal unpaired region, in some embodiments at the 3', and in some embodiments on the antisense side of the hairpin. In some embodiments, the overhangs are 1-4, more generally 2-3 nucleotides in length. The hairpin oligonucleotides that can induce RNA interference are also referred to as "shRNA" herein.

In certain embodiments, two oligonucleotide strands specifically hybridize when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated.

It is understood in the art that incorporation of nucleotide affinity modifications may allow for a greater number of mismatches compared to an unmodified compound. Similarly, certain oligonucleotide sequences may be more tolerant to mismatches than other oligonucleotide sequences. One of ordinary skill in the art is capable of determining an appropriate number of mismatches between oligonucleotides, or between an oligonucleotide and a target nucleic acid, such as by determining melting temperature (Tm). Tm or ΔTm can be calculated by techniques that are familiar to one of ordinary skill in the art. For example, techniques described in Freier et al. (Nucleic Acids Research, 1997, 25, 22: 4429-4443) allow one of ordinary skill in the art to evaluate nucleotide modifications for their ability to increase the melting temperature of an RNA:DNA and an RNA:RNA duplex.

In some embodiments, the effector molecule is a double-stranded RNA (dsRNA) agent, i.e., siRNA, for inhibiting the expression of a target gene. It is understood that dsRNA, siRNA, oligonucleotides can be used interchangeably unless otherwise stated. The dsRNA agent comprises a sense strand and an antisense: strand, each strand having 14 to 40 nucleotides. The dsRNA agent is represented by formula (I):

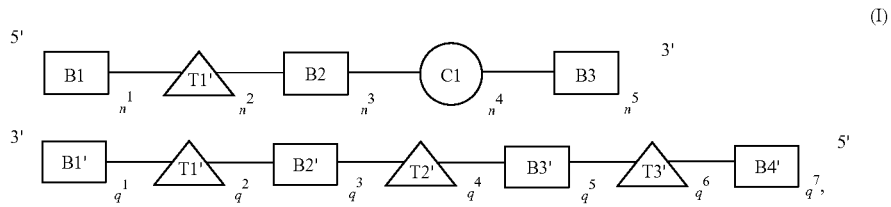

(I)

In formula (I), B1, B2, B3, B1', B2', B3', and B4' each are independently a nucleotide containing a modification selected from the group consisting of 2'-O-alkyl, 2'-substituted alkoxy, 2'-substituted alkyl, 2'-halo, ENA, and BNA/LNA. In some embodiments, B1, B2, B3, B1', B2', B3', and B4' each contain 2'-OMe modifications.

C1 is a thermally destabilizing nucleotide placed at a site opposite to the seed region of the antisense strand (i.e., at positions 2-8 of the 5'-end of the antisense strand). For example, C1 is at a position of the sense strand that pairs with a nucleotide at positions 2-8 of the 5'-end of the antisense strand. C1 nucleotide bears the thermally destabilizing modification which can include abasic modification; mismatch with the opposing nucleotide in the duplex; and sugar modification such as 2'-deoxy modification or acyclic nucleotide e.g., unlocked nucleic acids (UNA) or glycerol nucleic acid (GNA). In some embodiments, C1 has thermally destabilizing modification selected from the group consisting of: i) mismatch with the opposing nucleotide in the antisense strand; ii) abasic modification selected from the group consisting of:

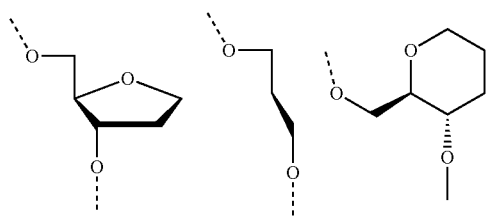

and iii) sugar modification selected from the group consisting of:

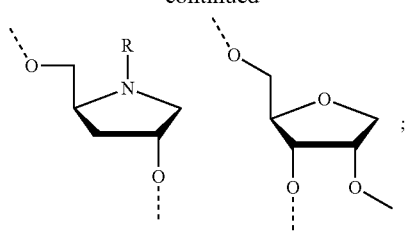

2'-deoxy

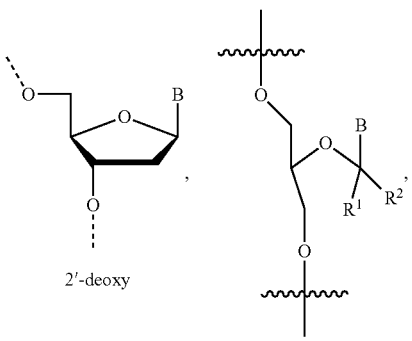

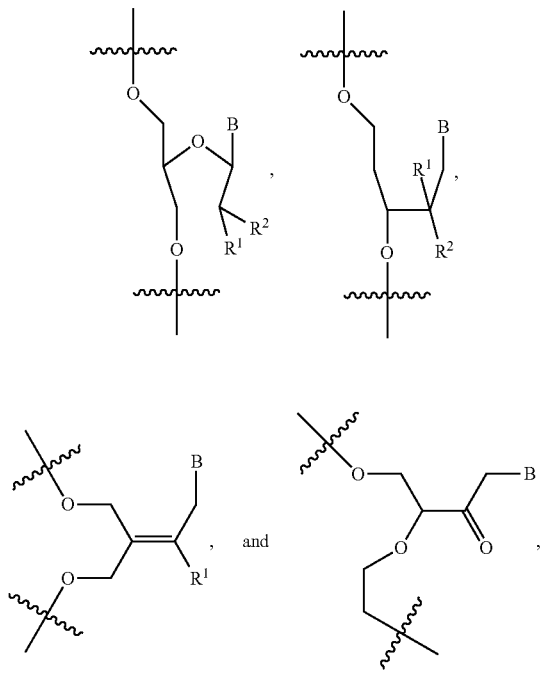

and wherein B is a modified or unmodified nucleobase, $R^1$ and $R^2$ independently are H, halogen, $OR_3$, or alkyl; and $R_3$ is H, alkyl, cycloalkyl, aryl, aralkyl, heteroaryl or sugar. In some embodiments, the thermally destabilizing modification in C1 is a mismatch selected from the group consisting of G:G, G:A, G:U, G:T, A:A, A:C, C:C, C:U, C:T, U:U, T:T, and U:T; and optionally, at least one nucleobase in the mismatch pair is a 2'-deoxy nucleobase. In one example, the thermally destabilizing modification in C1 is GNA or

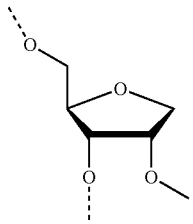

T1, T1', T2', and T3' each independently represent a nucleotide comprising a modification providing the nucleotide a steric bulk that is less or equal to the steric bulk of a 2'-OMe modification. The modification can be at the 2' position of a ribose sugar of the nucleotide, or a modification to a non-ribose nucleotide, acyclic nucleotide, or the backbone of the nucleotide that is similar or equivalent to the 2' position of the ribose sugar, and provides the nucleotide a steric bulk that is less than or equal to the steric bulk of a 2'-OMe modification. For example, T1, T1', T2', and T3' are each independently selected from DNA, RNA, LNA, 2'-F, and 2'-F-5'-methyl. In some embodiments, T1 is DNA. In some embodiments, T1' is DNA, RNA or LNA. In some embodiments, T2' is DNA or RNA. In some embodiments, T3' is DNA or RNA.

$n^1$, $n^3$, and $q^1$ are independently 4 to 15 nucleotides in length.

$n^5$, $q^3$, and $q^7$ are independently 1-6 nucleotide(s) in length.

$n^4$, $q^2$, and $q^6$ are independently 1-3 nucleotide(s) in length.

$q^5$ is independently 0-10 nucleotide(s) in length.

$n^2$ and $q^4$ are independently 0-3 nucleotide(s) in length. Alternatively, $n^4$ is 0-3 nucleotide(s) in length.

In some embodiments, $n^4$ can be 0. In one example, $n^4$ is 0, and $q^2$ and $q^6$ are 1. In another example, $n^4$ is 0, and $q^2$ and $q^6$ are 1, with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In some embodiments, $n^4$, $q^2$, and $q^6$ are each 1.

In some embodiments, $n^2$, $n^4$, $q^2$, $q^4$, and $q^6$ are each 1.

In some embodiments, C1 is at position 14-17 of the 5'-end of the sense strand, when the sense strand is 19-22 nucleotides in length, and $n^4$ is 1.

In some embodiments, T3' starts at position 2 from the 5' end of the antisense strand. In one example, T3' is at position 2 from the 5' end of the antisense strand and $q^6$ is equal to 1.

In some embodiments, T1' starts at position 14 from the 5' end of the antisense strand. In one example, T1' is at position 14 from the 5' end of the antisense strand and $q^2$ is equal to 1.

In some embodiments, T1' and T3' are separated by 11 nucleotides in length (i.e. not counting the T1' and T3' nucleotides.

In some embodiments, T1' is at position 14 from the 5' end of the antisense strand. In one example, T1' is at position 14 from the 5' end of the antisense strand and $q^2$ is equal to 1, and the modification at the 2' position or positions in a non-ribose, acyclic or backbone that provide less steric bulk than a 2'-OMe ribose.

In some embodiments, T3' is at position 2 from the 5' end of the antisense strand. In one example, T3' is at position 2 from the 5' end of the antisense strand and $q^6$ is equal to 1, and the modification at the 2' position or positions in a non-ribose, acyclic or backbone that provide less than or equal to steric bulk than a 2'-OMe ribose.

In some embodiments, T1 is at cleavage site of the sense strand. In one example, T1 is at position 11 from the 5' end of the sense strand, when the sense strand is 19-22 nucleotides in length, and $n^2$ is 1.

In some embodiments, T2' starts at position 6 from the 5' end of the antisense strand. In one example, T2' is at positions 6-10 from the 5' end of the antisense strand, and $q^4$ is 1.

In some embodiments, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1.

In some embodiments, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In some embodiments, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1.

In some embodiments, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1.

In some embodiments, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In some embodiments, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1.

In some embodiments, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In some embodiments, 100%, 95%, 90%, 85%, 80%, 75%, 70%, 65%, 60%, 55%, 50%, 45%, 40%, 35% or 30% of the dsRNA agent of the invention is modified.

In some embodiments, each of the sense and antisense strands of the dsRNA agent is independently modified with acyclic nucleotides, LNA, HNA, CeNA, 2'-methoxyethyl, 2'-O-methyl, 2'-O-allyl, 2'-C-allyl, 2'-deoxy, 2'-fluoro, 2'-O—N-methylacetamido (2'-O-NMA), a 2'-O-dimethylaminoethoxyethyl (2'-O-DMAEOE), 2'-O-aminopropyl (2'-O-AP), or 2'-ara-F.

In some embodiments, each of the sense and antisense strands of the dsRNA agent contains at least two different modifications.

In some embodiments, the dsRNA agent of Formula (I) further comprises 3' and/or 5' overhang(s) of 1-10 nucleotides in length. In one example, dsRNA agent of formula (I) comprises a 3' overhang at the 3'-end of the antisense strand and a blunt end at the 5'-end of the antisense strand. In another example, the dsRNA agent has a 5' overhang at the 5'-end of the sense strand.

In some embodiments, the dsRNA agent of the invention does not contain any 2'-F modification.

In some embodiments, the dsRNA agent of the invention contains one, two, three, four, five, six, seven, eight, nine, ten, eleven or twelve 2'-F modification(s). In one example, the effector molecule of the invention contains nine or ten 2'-F modifications.

In some embodiments, the sense strand and/or antisense strand of the dsRNA agent comprises one or more blocks of phosphorothioate or methylphosphonate internucleotide linkages. In one example, the sense strand comprises one block of two phosphorothioate or methylphosphonate internucleotide linkages. In one example, the antisense strand comprises two blocks of two phosphorothioate or methylphosphonate internucleotide linkages. For example, the two blocks of phosphorothioate or methylphosphonate internucleotide linkages are separated by 16-18 phosphate internucleotide linkages.

In some embodiments, each of the sense and antisense strands of the dsRNA agent has 15-30 nucleotides. In one example, the sense strand has 19-22 nucleotides, and the antisense strand has 19-25 nucleotides. In another example, the sense strand has 21 nucleotides, and the antisense strand has 23 nucleotides.

In some embodiments, the nucleotide at position 1 of the 5'-end of the antisense strand in the duplex is selected from the group consisting of A, dA, dU, U, and dT. In some embodiments, at least one of the first, second, and third base pair from the 5'-end of the antisense strand is an AU base pair.

In some embodiments, the antisense strand of the dsRNA agent of the invention is 100% complementary to a target RNA to hybridize thereto and inhibits its expression through RNA interference. In another embodiment, the antisense strand of the dsRNA agent of the invention is at least 95%, at least 90%, at least 85%, at least 80%, at least 75%, at least 70%, at least 65%, at least 60%, at least 55%, or at least 50% complementary to a target RNA.

In one aspect, the invention relates to a dsRNA agent capable of inhibiting the expression of a target gene. The dsRNA agent comprises a sense strand and an antisense strand, each strand having 14 to 40 nucleotides. The sense strand contains at least one thermally destabilizing nucleotide, wherein at at least one said thermally destabilizing nucleotide occurs at or near the site that is opposite to the seed region of the antisense strand (i.e. at position 2-8 of the 5'-end of the antisense strand), For example, the thermally destabilizing nucleotide occurs between positions 14-17 of the 5'-end of the sense strand when the sense strand is 21 nucleotides in length. The antisense strand contains at least two modified nucleic acids that are smaller than a sterically demanding 2'-OMe modification. Preferably, the two modified nucleic acids that is smaller than a sterically demanding 2'-OMe are separated by 11 nucleotides in length. For example, the two modified nucleic acids are at positions 2 and 14 of the 5' end of the antisense strand.

In some embodiments, the sense strand sequence of the dsRNA agent is represented by formula (Is):

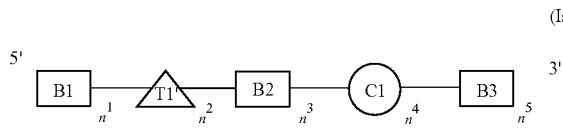

wherein:
B1, B2, and B3 each independently represent a nucleotide containing a modification selected from the group consisting of 2'-Oalkyl, 2'-substituted alkoxy, 2'-substituted alkyl, 2'-halo, ENA, and BNA/LNA;
C1 is a thermally destabilizing nucleotide (e.g., acyclic nucleotide such as UNA or GNA, mismatch, abasic, or DNA) placed at the opposite of the antisense seed region (i.e., positions 2-8 of the 5'-end of the antisense strand);
T1 represents a nucleotide comprising a chemical modification at the 2' position or equivalent position in a non-ribose, acyclic or backbone that provide the nucleotide a less steric bulk than a 2'-OMe modification; for example, T1 is selected from the group consisting of DNA, RNA, LNA, 2'-F, and 2'-F-5'-methyl;
$n^1$ or $n^3$ is independently 4 to 15 nucleotides in length;
$n^5$ is 1-6 nucleotide(s) in length;
$n^4$ is 1-3 nucleotide(s) in length; and
$n^2$ is 0-3 nucleotide(s) in length.

In some embodiments, the sense strand sequence having 19, 20, 21, or 22 nucleotides in length of the dsRNA agent is represented by formula (Is):

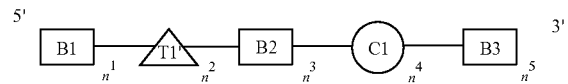

wherein:
B1, B2, and B3 each independently represent a nucleotide containing a modification selected from the group consisting of 2'-Oalkyl, 2'-substituted alkoxy, 2'-substituted alkyl, 2'-halo, ENA, and BNA/LNA;
C1 is a thermally destabilizing nucleotide (e.g., acyclic nucleotide such as UNA or GNA, mismatch, abasic, or DNA) placed at the opposite of the antisense seed region (i.e., positions 2-8 of the 5'-end of the antisense strand);
T1 represents a nucleotide comprising a chemical modification selected from the group consisting of DNA, RNA, LNA, 2'-F, and 2'-F-5'-methyl;
$n^1$ or $n^3$ is independently 4 to 15 nucleotides in length;
$n^5$ is 1-6 nucleotide(s) in length;
$n^4$ is 1-3 nucleotide(s) in length; and
$n^2$ is 0-3 nucleotide(s) in length.

In some embodiments, the dsRNA agent of formula (Is) further comprises 3' and/or 5' overhang(s) of 1-10 nucleotides in length. In one example, the dsRNA agent of formula (Is) comprises a 5' overhang.

In some embodiments, C1 comprises one thermally destabilizing nucleotide at position 14, 15, 16 or 17 from the 5'-end of the sense strand. For example, C1 is an acyclic nucleotide (e.g., UNA or GNA), mismatch, abasic, or DNA. In one specific example, C1 is a GNA.

In some embodiments, T1 comprises a DNA, RNA, LNA, 2'-F, or 2'-F-5'-methyl at position 11 from the 5'-end of the sense strand.

In some embodiments, the dsRNA agent of the invention comprises a sense strand (Is), wherein C1 is an acyclic nucleotide (e.g., UNA or GNA), mismatch, abasic, or DNA; and T1 comprises a DNA, RNA, LNA, 2'-F, or 2'-F-5'-methyl at position 11 from the 5'-end of the sense strand.

In some embodiments, the antisense strand sequence of the dsRNA agent is represented by formula (Ia):

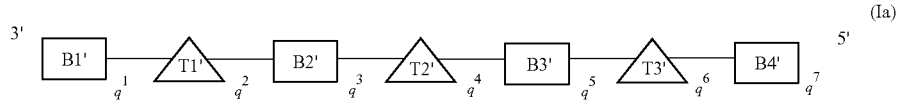

wherein:
B1', B2', B3', and B4' each independently represent a nucleotide containing a modification selected from the group consisting of 2'-Oalkyl, 2'-substituted alkoxy, 2'-substituted alkyl, 2'-halo, ENA, and BNA/LNA;
T1', T2', and T3' each independently represent a nucleotide comprising a chemical modification at the 2' position or equivalent position in a non-ribose, acyclic or backbone that provide the nucleotide a less steric bulk than a 2'-OMe modification; for example, T1', T2', and T3' each are independently selected from the group consisting of DNA, RNA, LNA, 2'-F, and 2'-F-5'-methyl;
$q^1$ is independently 4 to 15 nucleotides in length;
$q^3$ or $q^7$ is independently 1-6 nucleotide(s) in length;

$q^2$ or $q^6$ is independently 1-3 nucleotide(s) in length;
$q^4$ is independently 0-3 nucleotide(s) in length; and
$q^5$ is independently 0-10 nucleotide(s) in length.

In some embodiments, the antisense strand sequence having 19, 20, 21, 22, 23, 24, or 25 nucleotides in length of the dsRNA agent is represented by formula (Ia):

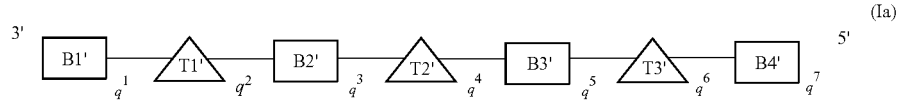

(Ia)

wherein:
B1', B2', B3', and B4' each independently represent a nucleotide containing a modification selected from the group consisting of 2'-Oalkyl, 2'-substituted alkoxy, 2'-substituted alkyl, 2'-halo, ENA, and BNA/LNA;
T1', T2', and T3' each independently represent a nucleotide comprising a chemical modification selected from the group consisting of DNA, RNA, LNA, 2'-F, and 2'-F-5'-methyl;
$q^1$ is independently 4 to 15 nucleotides in length;
$q^3$ or $q^7$ is independently 1-6 nucleotide(s) in length;
$q^2$ or $q^6$ is independently 1-3 nucleotide(s) in length;
$q^4$ is independently 0-3 nucleotide(s) in length; and
$q^5$ is independently 0-10 nucleotide(s) in length.

In some embodiments, dsRNA of formula (Ia) further comprises 3' and/or 5' overhang(s) of 1-10 nucleotides in length. In one example, dsRNA of formula (Ia) comprises a 3' overhang.

In some embodiments, the invention relates to a double-stranded RNA (dsRNA) agent for inhibiting the expression of a target gene. The dsRNA agent comprises a sense strand and an antisense strand, each strand having 14 to 40 nucleotides:

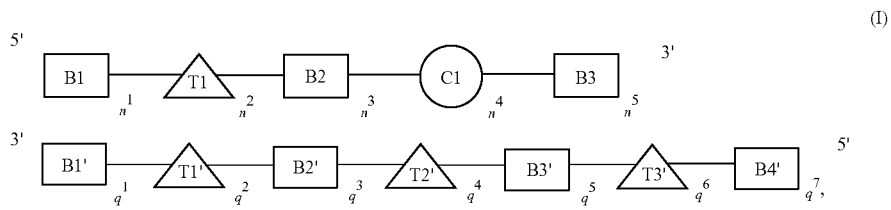

(I)

wherein:
B1, B2, B3, B1', B2', and B3' each independently represent a nucleotide containing a modification selected from the group consisting of 2'-Oalkyl, 2'-substituted alkoxy, 2'-substituted alkyl, 2'-halo, ENA, and BNA/LNA;
T1, T1', T2', and T3' each independently represent a nucleotide comprising a chemical modification selected from the group consisting of DNA, RNA, LNA, 2'-F, and 2'-F-5'-methyl;
$n^1$, $n^3$, or $q^1$ is independently 4 to 15 nucleotides in length;
$n^5$, $q^3$ or $q^7$ is independently 1-6 nucleotide(s) in length;
$n^4$, $q^2$ or $q^6$ is independently 1-3 nucleotide(s) in length;
$n^2$ or $q^4$ is independently 0-3 nucleotide(s) in length;
$q^5$ is independently 0-10 nucleotide(s) in length; and
wherein the dsRNA agent has 3' and/or 5' overhang(s) of 1-10 nucleotides in length of the antisense and/or sense strand(s).

In some embodiments, the invention relates to a double-stranded RNA (dsRNA) agent for inhibiting the expression of a target gene. The dsRNA agent comprises a sense strand and an antisense strand, each strand having 14 to 40 nucleotides:

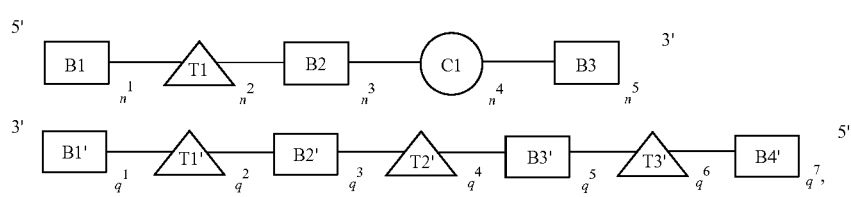

(I)

wherein:
B1, B2, B3, B1', B2', B3', and B4' each independently represent a nucleotide containing a modification selected from the group consisting of 2'-O-alkyl, 2'-substituted alkoxy, 2'-substituted alkyl, 2'-halo, ENA, and BNA/LNA;
C1 is an acyclic nucleotide (e.g., UNA or GNA);
T1, T1', T2', and T3' each independently represent a nucleotide comprising a chemical modification selected from the group consisting of DNA, RNA, LNA, 2'-F, and 2'-F-5'-methyl;
$n^1$, $n^3$, or $q^1$ is independently 4 to 15 nucleotides in length;
$n^5$, $q^3$ or $q^7$ is independently 1-6 nucleotide(s) in length;
$n^4$, $q^2$ or $q^6$ is independently 1-3 nucleotide(s) in length;
$n^2$ or $q^4$ is independently 0-3 nucleotide(s) in length;
$q^5$ is independently 0-10 nucleotide(s) in length; and
wherein the dsRNA agent has a 3' overhang of 2 nucleotides in length at the 3'-end of the antisense.

In some embodiments, the invention relates to a double-stranded RNA (dsRNA) agent for inhibiting the expression of a target gene. The dsRNA agent comprises a sense strand and an antisense strand, each strand having 15-30 nucleotides:

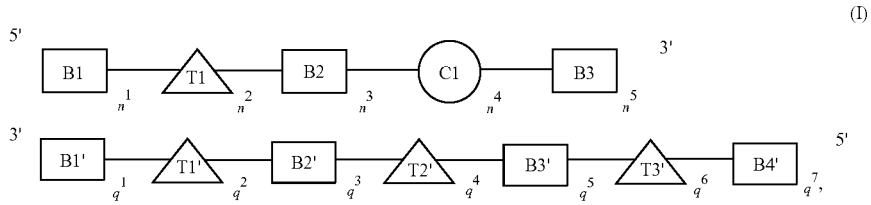

(I)

wherein:
B1, B2, B3, B1', B2', B3', and B4' each independently represent a nucleotide containing a modification 2'-OMe;
C1 is an acyclic nucleotide GNA;
T1, T1', T2', and T3' each are independently DNA or RNA;
$n^1$, $n^3$, or $q^1$ is independently 4 to 15 nucleotides in length;
$n^5$, $q^3$ or $q^7$ is independently 1-6 nucleotide(s) in length;
$n^4$, $q^2$ or $q^6$ is independently 1-3 nucleotide(s) in length;
$n^2$ or $q^4$ is independently 0-3 nucleotide(s) in length;
$q^5$ is independently 0-10 nucleotide(s) in length; and
wherein the dsRNA agent has a 3' overhang of 1-6 nucleotides in length at the 3'-end of the antisense.

In some embodiments, the invention relates to a double-stranded RNA (dsRNA) agent for inhibiting the expression of a target gene. The dsRNA agent comprises a sense strand and an antisense strand, each strand having 19-23 nucleotides:

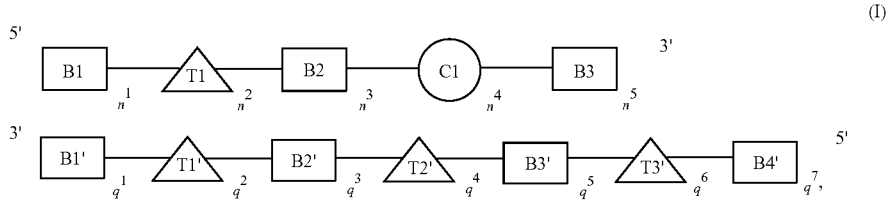

(I)

wherein:
B1, B2, B3, B1', B2', B3', and B4' each independently represent a nucleotide containing a 2'-OMe modification;
C1 is an acyclic nucleotide GNA;
T1, T1', T2', and T3' are independently DNA or RNA;
$n^1$, $n^3$, $q^1$, or $q^3$ is independently 4 to 15 nucleotides in length;
$n^5$, $q^3$ or $q^7$ is independently 1-6 nucleotide(s) in length;
$n^4$, $q^2$ or $q^6$ is independently 1-3 nucleotide(s) in length;
$n^2$, $q^4$ or $q^5$ is independently 0-3 nucleotide(s) in length;
$q^5$ is independently 0-10 nucleotide(s) in length; and
wherein the dsRNA agent has a 3' overhang of 2 nucleotides in length at the 3'-end of the antisense.

In some embodiments, the invention relates to a double-stranded RNA (dsRNA) agent for inhibiting the expression of a target gene. The dsRNA agent comprises a sense strand and an antisense strand, each strand having 14 to 40 nucleotides:

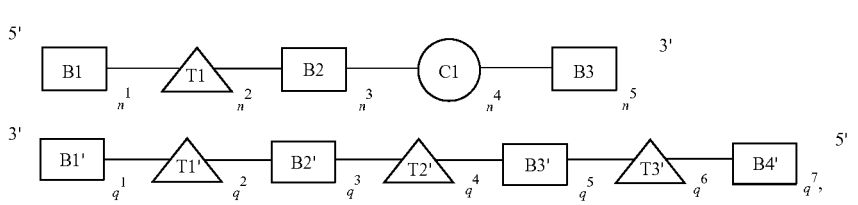

(I)

wherein:
B1, B2, B3, B1', B2', B3', and B4' each independently represent a nucleotide containing a modification selected from the group consisting of 2'-Oalkyl, 2'-substituted alkoxy, 2'-substituted alkyl, 2'-halo, ENA, and BNA/LNA;
C1 is an acyclic nucleotide (e.g., UNA or GNA);
T1, T1', T2', and T3' each independently represent a nucleotide comprising a chemical modification selected from the group consisting of DNA, RNA, LNA, 2'-F, and 2'-F-5'-methyl;
$n^1$, $n^3$, or $q^1$ is independently 4 to 15 nucleotides in length;
$n^5$, $q^3$ or $q^7$ is independently 1-6 nucleotide(s) in length;
$n^4$, $q^2$ or $q^6$ is independently 1-3 nucleotide(s) in length;
$n^2$ or $q^4$ is independently 0-3 nucleotide(s) in length;
$q^5$ is independently 0-10 nucleotide(s) in length; and
wherein the dsRNA agent has a 5' overhang of 1-10 nucleotides in length at the 5'-end of the sense.

In some embodiments, the invention relates to a double-stranded RNA (dsRNA) agent for inhibiting the expression of a target gene. The dsRNA agent comprises a sense strand and an antisense strand, each strand having 14 to 40 nucleotides:

wherein:
B1, B2, B3, B1', B2', B3', and B4' each independently represent a nucleotide containing a modification selected from the group consisting of 2'-Oalkyl, 2'-substituted alkoxy, 2'-substituted alkyl, 2'-halo, ENA, and BNA/LNA;
C1 is an acyclic nucleotide (e.g., UNA or GNA);
T1, T1', T2', and T3' each independently represent a nucleotide comprising a chemical modification selected from the group consisting of DNA, RNA, LNA, 2'-F, and 2'-F-5'-methyl;
$n^1$, $n^3$, or $q^1$ is independently 4 to 15 nucleotides in length;
$n^5$, $q^3$ or $q^7$ is independently 1-6 nucleotide(s) in length;
$n^4$, $q^2$ or $q^6$ is independently 1-3 nucleotide(s) in length;
$n^2$ or $q^4$ is independently 0-3 nucleotide(s) in length;
$q^5$ is independently 0-10 nucleotide(s) in length; and
wherein the dsRNA agent has a 5' overhang of 1-10 nucleotides in length at the 5'-end of the sense and a 3' overhang of 1-10 nucleotides in length at the 5'-end of the antisense strand.

In some embodiments, at least one of the effector molecules in the multi-targeted molecules disclosed herein is a (I)

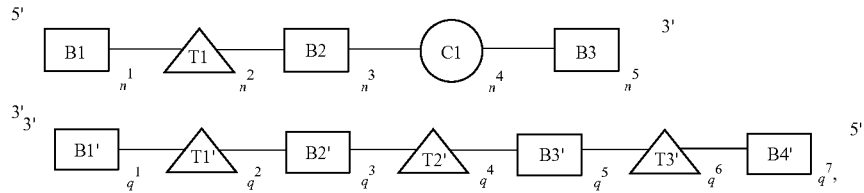

microRNA. In some embodiments, the multi-targeted molecule comprises at least microRNAs covalently linked to each other via a nucleotide-based or non-nucleotide-based linker, e.g., a linker described in the disclosure, or non-covalently linked to each other. MicroRNAs (miRNAs or mirs) are a highly conserved class of small RNA molecules that are transcribed from DNA in the genomes of plants and animals, but are not translated into protein. Pre-microRNAs are processed into miRNAs. Processed microRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

MicroRNAs have also been implicated in modulation of pathogens in hosts. For example, see Jopling, C. L., et al., wherein:
B1, B2, B3, B1', B2', B3', and B4' each independently represent a nucleotide containing a modification selected from the group consisting of 2'-Oalkyl, 2'-substituted alkoxy, 2'-substituted alkyl, 2'-halo, ENA, and BNA/LNA;
C1 is an acyclic nucleotide (e.g., UNA or GNA);
T1, T1', T2', and T3' each independently represent a nucleotide comprising a chemical modification selected from the group consisting of DNA, RNA, LNA, 2'-F, and 2'-F-5'-methyl;
$n^1$, $n^3$, or $q^1$ is independently 4 to 15 nucleotides in length;
$n^5$, $q^3$ or $q^7$ is independently 1-6 nucleotide(s) in length;
$n^4$, $q^2$ or $q^6$ is independently 1-3 nucleotide(s) in length;
$n^2$ or $q^4$ is independently 0-3 nucleotide(s) in length;
$q^5$ is independently 0-10 nucleotide(s) in length; and
wherein the dsRNA agent has a 5' overhang of 1-6 nucleotides in length at the 5'-end of the sense.

In some embodiments, the invention relates to a double-stranded RNA (dsRNA) agent for inhibiting the expression of a target gene. The dsRNA agent comprises a sense strand and an antisense strand, each strand having 14 to 40 nucleotides:

(I)

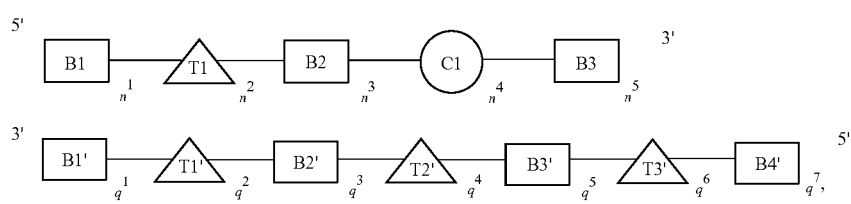

*Science* (2005) vol. 309, pp 1577-1581. Without wishing to be bound by theory, administration of a microRNA, microRNA mimic, and/or anti microRNA oligonucleotide, leads to modulation of pathogen viability, growth, development, and/or replication. In some embodiments, the oligonucleotide is a microRNA, microRNA mimic, and/or anti microRNA, wherein microRNA is a host microRNA.

The number of miRNA sequences identified to date is large and growing, illustrative examples of which can be found, for example, in: "*miRBase: microRNA sequences, targets and gene nomenclature*" Griffiths-Jones S, Grocock R J, van Dongen S, Bateman A, Enright A J. NAR, 2006, 34, Database Issue, D140-D144; "*The microRNA Registry*" Griffiths-Jones S. NAR, 2004, 32, Database Issue, D109-D111; and also on the worldwide web at http://microrna.dot.sanger.dot.ac.dot.uk/sequences/.

The mature miRNA is characterized by a "seed region", generally comprising the bases 2-7 of the 5' end. The seed region is thought to primarily define the specificity of a miRNA towards the 3'UTR of its target mRNAs and has been used for computational target predictions. For each miRNA a few hundred target mRNAs are predicted, whereas relatively few targets have been experimentally validated to date. Recent deep sequencing approaches led to changes in the current miRNA databases and implicate miRNA* as an active miRNA molecule. Furthermore, in some miRNA stemloops, such as mir-302b, both the 5' and the 3' stemloop sequences are annotated as mature miRNAs, suggesting that both miRNA strands can have functional properties.

In some embodiments, at least one of the effector molecules in the multi-targeted molecules disclosed herein is a ribozyme. In some embodiments, the multi-targeted molecule comprises at least two ribozyme covalently linked to each other via a nucleotide-based or non-nucleotide-based linker, for example a linker described in the disclosure, or non-covalently linked to each other.

Ribozymes are oligonucleotides having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). At least six basic varieties of naturally-occurring enzymatic RNAs are known presently. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Methods of producing a ribozyme targeted to any target sequence are known in the art. Ribozymes can be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

In some embodiments, at least one of the effector molecules in the multi-targeted molecules disclosed herein is an aptamer. In some embodiments, the multi-targeted molecule comprises at least two aptamers covalently linked to each other via a nucleotide-based or non-nucleotide-based linker, for example a linker described in the disclosure, or non-covalently linked to each other. Aptamers are nucleic acid or peptide molecules that bind to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9(1999), and Hermann and Patel, Science 287:820-5 (2000). Aptamers can be RNA or DNA based. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer can be prepared by any known method, including synthetic, recombinant, and purification methods, and can be used alone or in combination with other aptamers specific for the same target. Further, as described more fully herein, the term "aptamer" specifically includes "secondary aptamers" containing a consensus sequence derived from comparing two or more known aptamers to a given target.

Because transcription factors recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Accordingly, in some embodiments, at least one of the effector molecules in the multi-targeted molecules disclosed herein is a decoy oligonucleotide. In some embodiments, the multi-targeted molecule comprises at least two decoy oligonucleotides covalently linked to each other via a nucleotide-based or non-nucleotide-based linker, for example a linker described in the disclosure, or non-covalently linked to each other.

Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to up-regulate genes that are suppressed by the binding of a transcription factor. Examples of the utilization of decoy oligonucleotides can be found in Mann et al., J. Clin. Invest., 2000, 106: 1071-1075, which is expressly incorporated by reference herein, in its entirety.

In some embodiments, at least one of the effector molecules in the multi-targeted molecules disclosed herein is a miRNA mimic. In some embodiments, the multi-targeted molecule comprises at least two miRNA mimics covalently linked to each other via a nucleotide-based or non-nucleotide-based linker, for example a linker described in the disclosure, or non-covalently linked to each other. MicroRNA mimics (miRNA mimics) represent a class of molecules that can be used to imitate the gene modulating activity of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression. miRNA mimics can be designed as mature molecules (e.g. single stranded) or mimic precursors (e.g., pri- or pre-miRNAs). In one design, miRNA mimics are double stranded molecules (e.g., with a duplex region of between about 16 and about 31 nucleotides in length) and contain one or more sequences that have identity with the mature strand of a given miRNA.

Double-stranded miRNA mimics have designs similar to as described above for double-stranded oligonucleotides.

In some embodiments, a miRNA mimic comprises a duplex region of between 16 and 31 nucleotides and one or more of the following chemical modification patterns: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3' overhang.

In some embodiments, at least one of the effector molecules in the multi-targeted molecules disclosed herein is a supermir. In some embodiments, the multi-targeted molecule comprises at least two supermirs covalently linked to each other via a nucleotide-based or non-nucleotide-based linker, for example a linker described in the disclosure, or non-covalently linked to each other. A supermir refers to an oligonucleotide, e.g., single stranded, double stranded or partially double stranded, which has a nucleotide sequence that is substantially identical to an miRNA and that is antisense with respect to its target. This term includes oligonucleotides which comprise at least one non-naturally-occurring portion which functions similarly. In a preferred embodiment, the supermir does not include a sense strand, and in another preferred embodiment, the supermir does not self-hybridize to a significant extent. A supermir featured in the invention can have secondary structure, but it is substantially single-stranded under physiological conditions. A supermir that is substantially single-stranded is single-stranded to the extent that less than about 50% (e.g., less than about 40%, 30%, 20%, 10%, or 5%) of the supermir is duplexed with itself. The supermir can include a hairpin segment, e.g., sequence, preferably at the 3' end can self hybridize and form a duplex region, e.g., a duplex region of at least 1, 2, 3, or 4 and preferably less than 8, 7, 6, or 5 nucleotides, e.g., 5 nucleotides. The duplexed region can be connected by a linker, e.g., a nucleotide linker, e.g., 3, 4, 5, or 6 dTs, e.g., modified dTs. In another embodiment the supermir is duplexed with a shorter oligo, e.g., of 5, 6, 7, 8, 9, or 10 nucleotides in length, e.g., at one or both of the 3' and 5' end or at one end and in the non-terminal or middle of the supermir.

In some embodiments, at least one of the effector molecules in the multi-targeted molecules disclosed herein is an antimir. In some embodiments, the multi-targeted molecule comprises at least two antimirs covalently linked to each other via a nucleotide-based or non-nucleotide-based linker, for example a linker described in the disclosure, or non-covalently linked to each other. The terms "antimir" "microRNA inhibitor" or "miR inhibitor" are synonymous and refer to oligonucleotides or modified oligonucleotides that interfere with the activity of specific miRNAs. Inhibitors can adopt a variety of configurations including single stranded, double stranded (RNA/RNA or RNA/DNA duplexes), and hairpin designs, in general, microRNA inhibitors comprise one or more sequences or portions of sequences that are complementary or partially complementary with the mature strand (or strands) of the miRNA to be targeted, in addition, the miRNA inhibitor can also comprise additional sequences located 5' and 3' to the sequence that is the reverse complement of the mature miRNA. The additional sequences can be the reverse complements of the sequences that are adjacent to the mature miRNA in the pri-miRNA from which the mature miRNA is derived, or the additional sequences can be arbitrary sequences (having a mixture of A, G, C, U, or dT). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. MicroRNA inhibitors, when double stranded, can include mismatches between nucleotides on opposite strands. Furthermore, microRNA inhibitors can be linked to conjugate moieties in order to facilitate uptake of the inhibitor into a cell.

MicroRNA inhibitors, including hairpin miRNA inhibitors, are described in detail in Vermeulen et al., "Double-Stranded Regions Are Essential Design Components Of Potent Inhibitors of RISC Function," RNA 13: 723-730 (2007) and in WO2007/095387 and WO 2008/036825 each of which is incorporated herein by reference in its entirety. A person of ordinary skill in the art can select a sequence from the database for a desired miRNA and design an inhibitor useful for the methods disclosed herein.

In some embodiments, at least one of the effector molecules in the multi-targeted molecules disclosed herein is an antagomir. In some embodiments, the multi-targeted molecule comprises at least two antagomirs covalently linked to each other via a nucleotide-based or non-nucleotide-based linker, for example a linker described in the disclosure, or non-covalently linked to each other. Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate intersugar linkage and, for example, a cholesterol-moiety at 3'-end. In a preferred embodiment, antagomir comprises a 2'-O-methyl modification at all nucleotides, a cholesterol moiety at 3'-end, two phsophorothioate intersugar linkages at the first two positions at the 5'-end and four phosphorothioate linkages at the 3'-end of the molecule. Antagomirs can be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein in its entirety.

In some embodiments, at least one of the effector molecules in the multi-targeted molecules disclosed herein is a U1 adaptor. In some embodiments, the multi-targeted molecule comprises at least two U1 adaptors covalently linked to each other via a nucleotide-based or non-nucleotide-based linker, for example a linker described in the disclosure, or non-covalently linked to each other. U1 adaptors inhibit polyA sites and are bifunctional oligonucleotides with a target domain complementary to a site in the target gene's terminal exon and a 'U1 domain' that binds to the U1 smaller nuclear RNA component of the U1 snRNP. See for example, Int. Pat. App. Pub. No. WO2008/121963 and Goraczniak, et al., 2008, Nature Biotechnology, 27(3), 257-263, each of which is expressly incorporated by reference herein, in its entirety. U1 snRNP is a ribonucleoprotein complex that functions primarily to direct early steps in spliceosome formation by binding to the pre-mRNA exon-intron boundary, Brown and Simpson, 1998, Annu Rev Plant Physiol Plant Mol Biol 49:77-95.

In some embodiments, the U1 adaptor comprises at least one annealing domain (targeting domain) linked to at least one effector domain (U1 domain), wherein the annealing domain hybridizes to a target gene sequence and the effector domain hybridizes to the U1 snRNA of U1 snRNP. In some embodiments, the U1 adaptor comprises one annealing domain. In some embodiments, the U1 adaptor comprises one effector domain.

Without wishing to be bound by theory, the annealing domain will typically be from about 10 to about 50 nucleotides in length, more typically from about 10 to about 30 nucleotides or about 10 to about 20 nucleotides. In some preferred embodiments, the annealing domain is 10, 11, 12, 13, 14, 15, 16, 17, 18, 19, 20, or 21 nucleotides in length. The annealing domain may be at least 75%, at least 80%, at least 85%, at least 90%, at least 95%, at least 97%, or, more preferably, 100% complementary to the target gene. In some embodiments, the annealing domain hybridizes with a target site within the 3' terminal exon of a pre-mRNA, which includes the terminal coding region and the 3'UTR and polyadenylation signal sequences (e.g., through the polyadenylation site). In another embodiment, the target sequence is within about 500 basepair, about 250 basepair, about 100 basepair, or about 50 basepair of the poly (A) signal sequence of the pre-mRNA. In some embodiments, the annealing domain comprises 1, 2, 3, or 4, mismatches with the target gene sequence.

The effector domain may be from about 8 nucleotides to about 30 nucleotides, from about 10 nucleotides to about 20 nucleotides, or from about 10 to about 15 nucleotides in length. The U1 domain can hybridize with U1 snRNA, particularly the 5'-end and more specifically nucleotides 2-11. In another embodiment, the U1 domain is perfectly complementary to nucleotides 2-11 of endogenous U1 snRNA. In some embodiments, the U1 domain comprises a nucleotide sequence selected from the group consisting of 5'-GCCAGGUAAGUAU-3', 5'-CCAGGUAAGUAU-3', 5'-CAGGUAAGUAU-3', 5'-CAGGUAAGU-3', 5'-CAGGUAAG-3' and 5'-CAGGUAA-3'. In some embodiments, the U1 domain comprises a nucleotide sequence 5'-CAGGUAAGUA-3'. Without wishing to be bound by theory, increasing the length of the U1 domain to include basepairing into stem 1 and/or basepairing to position 1 of U1 snRNA improves the U1 adaptor's affinity to U1 snRNP.

The annealing and effector domains of the U1 adaptor can be linked such that the effector domain is at the 5' end and/or 3' end of the annealing domain. The two domains can be linked by such that the 3' end of one domain is linked to 5' end of the other domain, or 3' end of one domain is linked to 3' end of the other domain, or 5' end of one domain is linked to 5' end of the other domain. The annealing and effector domains can be linked directly to each other or by a nucleotide based or non-nucleotide based linker. When the linker is nucleotide based, the linker can comprise comprise 1, 2, 3, 4, 5, 6, 7, 8, 9, 10, up to 15, up to 20, or up to 25 nucleotides.

In some embodiments, the linker between the annealing domain and the effector domain is mutlivalent, e.g., trivalent, tetravalent or pentavalent. Without wishing to be bound by theory, a multivalent linker can be used to link together a single annealing domain with a plurality of adaptor domains.

It is to be understood that the U1 adaptor can comprise any oligonucleotide modification described herein. Exemplary modifications for U1 adaptors include those that increase annealing affinity, specificity, bioavailability in the cell and organism, cellular and/or nuclear transport, stability, and/or resistance to degradation.

Recent studies have found that dsRNA can also activate gene expression, a mechanism that has been termed "small RNA-induced gene activation" or RNAa (activating RNA).

See for example Li, L. C. et al. *Proc Natl Acad Sci USA*. (2006), 103(46):17337-42 and Li L. C. (2008). "Small RNA-Mediated Gene Activation". RNA and the Regulation of Gene Expression: A Hidden Layer of Complexity. Caister Academic Press. ISBN 978-1-904455-25-7. It has been shown that dsRNAs targeting gene promoters induce potent transcriptional activation of associated genes. Endogenous miRNA that cause RNAa has also been found in humans. Check E. Nature (2007). 448 (7156): 855-858.

Another surprising observation is that gene activation by RNAa is long-lasting. Induction of gene expression has been seen to last for over ten days. The prolonged effect of RNAa could be attributed to epigenetic changes at dsRNA target sites. In some embodiments, the RNA activator can increase the expression of a gene. In some embodiments, increased gene expression inhibits viability, growth development, and/or reproduction.

Accordingly, in some embodiments, at least one of the effector molecules in the multi-targeted molecules disclosed herein is activating RNA. In some embodiments, the multi-targeted molecule comprises at least two activating RNAs covalently linked to each other via a nucleotide-based or non-nucleotide-based linker, for example a linker described in the disclosure, or non-covalently linked to each other.

Accordingly, in some embodiments, at least one of the effector molecules in the multi-targeted molecules disclosed herein is a triplex forming oligonucleotide (TFO). In some embodiments, the multi-targeted molecule comprises at least two TFOs covalently linked to each other via a nucleotide-based or non-nucleotide-based linker, for example a linker described in the disclosure, or non-covalently linked to each other. Recent studies have shown that triplex forming oligonucleotides can be designed which can recognize and bind to polypurine/polypyrimidine regions in double-stranded helical DNA in a sequence-specific manner. These recognition rules are outline by Maher III, L. J., et al., *Science* (1989) vol. 245, pp 725-730; Moser, H. E., et al., *Science* (1987) vol. 238, pp 645-630; Beal, P. A., et al., *Science* (1992) vol. 251, pp 1360-1363; Conney, M., et al., *Science* (1988) vol. 241, pp 456-459 and Hogan, M. E., et al., EP Publication 375408. Modification of the oligonucleotides, such as the introduction of intercalators and intersugar linkage substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 1 12:487-94). In general, the triplex-forming oligonucleotide has the sequence correspondence:

```
oligo      3'-A G G T
duplex     5'-A G C T
duplex     3'-T C G A
```

However, it has been shown that the A-AT and G-GC triplets have the greatest triple helical stability (Reither and Jeltsch, BMC Biochem, 2002, Sept12, Epub). The same authors have demonstrated that TFOs designed according to the A-AT and G-GC rule do not form non-specific triplexes, indicating that the triplex formation is indeed sequence specific.

Thus for any given sequence a triplex forming sequence can be devised. Triplex-forming oligonucleotides preferably are at least 15, more preferably 25, still more preferably 30 or more nucleotides in length, up to 50 or 100 nucleotides.

Formation of the triple helical structure with the target DNA induces steric and functional changes, blocking transcription initiation and elongation, allowing the introduction of desired sequence changes in the endogenous DNA and resulting in the specific down-regulation of gene expression. Examples of such suppression of gene expression in cells treated with TFOs include knockout of episomal supFG1 and endogenous HPRT genes in mammalian cells (Vasquez et al., Nucl Acids Res. 1999; 27: 1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-I gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both down-regulation and up-regulation of expression of endogenous genes (Seidman and Glazer, J Clin Invest 2003; 112:487-94). Detailed description of the design, synthesis and administration of effective TFOs can be found in U.S. Pat. App. Nos. 2003 017068 and 2003 0096980 to Froehler et al, and 2002 0128218 and 2002 0123476 to Emanuele et al, and U.S. Pat. No. 5,721,138 to Lawn, contents of which are herein incorporated in their entireties.

Nucleic Acid Modifications

In some the multi-targeted molecule comprises at least one nucleic acid modification described herein. For example, at least one modification selected from the group consisting of modified internucleoside linkage, modified nucleobase, modified sugar, and any combinations thereof. Without limitations, such a modification can be present any where in the multi-targeted molecule. For example, the modification can be present in one of the effector molecules or a linker connecting two effector molecules.

Nucleic Acid Modifications (Nucleobases)

The naturally occurring base portion of a nucleoside is typically a heterocyclic base. The two most common classes of such heterocyclic bases are the purines and the pyrimidines. For those nucleosides that include a pentofuranosyl sugar, a phosphate group can be linked to the 2', 3' or 5' hydroxyl moiety of the sugar. In forming oligonucleotides, those phosphate groups covalently link adjacent nucleosides to one another to form a linear polymeric compound. Within oligonucleotides, the phosphate groups are commonly referred to as forming the internucleoside backbone of the oligonucleotide. The naturally occurring linkage or backbone of RNA and of DNA is a 3' to 5' phosphodiester linkage.

In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable with the compounds described herein. The unmodified or natural nucleobases can be modified or replaced to provide oligonucleotides having improved properties. For example, nuclease resistant oligonucleotides can be prepared with these bases or with synthetic and natural nucleobases (e.g., inosine, xanthine, hypoxanthine, nubularine, isoguanisine, or tubercidine) and any one of the oligomer modifications described herein. Alternatively, substituted or modified analogs of any of the above bases and "universal bases" can be employed. When a natural base is replaced by a non-natural and/or universal base, the nucleotide is said to comprise a modified nucleobase and/or a nucleobase modification herein. Modified nucleobase and/or nucleobase modifications also include natural, non-natural and universal bases, which comprise conjugated moieties, e.g. a ligand described herein. Preferred conjugate moieties for conjugation with nucleobases include cationic amino groups which can be conjugated to the nucleobase via an appropriate alkyl, alkenyl or a linker with an amide linkage.

An oligomeric compound described herein can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Exemplary modified nucleobases include, but are not limited to, other synthetic and natural nucleobases such as inosine, xanthine, hypoxanthine, nubularine, isoguanisine, tubercidine, 2-(halo)adenine, 2-(alkyl)adenine, 2-(propyl)adenine, 2-(amino)adenine, 2-(aminoalkyll)adenine, 2-(aminopropyl) adenine, 2-(methylthio)-$N^6$-(isopentenyl)adenine, 6-(alkyl) adenine, 6-(methyl)adenine, 7-(deaza)adenine, 8-(alkenyl) adenine, 8-(alkyl)adenine, 8-(alkynyl)adenine, 8-(amino) adenine, 8-(halo)adenine, 8-(hydroxyl)adenine, 8-(thioalkyl)adenine, 8-(thiol)adenine, $N^6$-(isopentyl)adenine, $N^6$-(methyl)adenine, $N^6$, $N^6$-(dimethyl)adenine, 2-(alkyl)guanine, 2-(propyl)guanine, 6-(alkyl)guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, $N^4$-(acetyl)cytosine, 3-(3-amino-3-carboxypropyl)uracil, 2-(thio)uracil, 5-(methyl)-2-(thio)uracil, 5-(methylaminomethyl)-2-(thio)uracil, 4-(thio)uracil, 5-(methyl)-4-(thio)uracil, 5-(methylaminomethyl)-4-(thio)uracil, 5-(methyl)-2,4-(dithio)uracil, 5-(methylaminomethyl)-2,4-(dithio)uracil, 5-(2-aminopropyl)uracil, 5-(alkyl)uracil, 5-(alkynyl)uracil, 5-(allylamino)uracil, 5-(aminoallyl)uracil, 5-(aminoalkyl) uracil, 5-(guanidiniumalkyl)uracil, 5-(1,3-diazole-1-alkyl) uracil, 5-(cyanoalkyl)uracil, 5-(dialkylaminoalkyl)uracil, 5-(dimethylaminoalkyl)uracil, 5-(halo)uracil, 5-(methoxy) uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl)uracil, 5-(trifluoromethyl)uracil, 6-(azo)uracil, dihydrouracil, $N^3$-(methyl)uracil, 5-uracil (i.e., pseudouracil), 2-(thio)pseudouracil,4-(thio)pseudouracil,2,4-(dithio)psuedouracil,5-(alkyl)pseudouracil, 5-(methyl)pseudouracil, 5-(alkyl)-2-(thio)pseudouracil, 5-(methyl)-2-(thio)pseudouracil, 5-(alkyl)-4-(thio)pseudouracil, 5-(methyl)-4-(thio)pseudouracil, 5-(alkyl)-2,4-(dithio) pseudouracil, 5-(methyl)-2,4-(dithio)pseudouracil, 1-substituted pseudouracil, 1-substituted 2(thio)-pseudouracil, 1-substituted 4-(thio)pseudouracil, 1-substituted 2,4-(dithio) pseudouracil, 1-(aminocarbonylethylenyl)-pseudouracil,1-(aminocarbonylethylenyl)-2(thio)-pseudouracil, 1-(aminocarbonylethylenyl)-4-(thio)pseudouracil, 1-(aminocarbonylethylenyl)-2,4-(dithio)pseudouracil, 1-(aminoalkylaminocarbonylethylenyl)-pseudouracil, 1-(aminoalkylamino-carbonylethylenyl)-2(thio)-pseudouracil, 1-(aminoalkylaminocarbonylethylenyl)-4-(thio)pseudouracil, 1-(aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5-nitroindole, 3-nitropyrrole, 6-(aza) pyrimidine, 2-(amino)purine, 2,6-(diamino)purine, 5-substituted pyrimidines, $N^2$-substituted purines, $N^6$-substituted purines, $O^6$-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ortho-substituted-6-phenyl-pyrrolo-pyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkylhydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof. Alternatively, substituted or modified analogs of any of the above bases and "universal bases" can be employed.

As used herein, a universal nucleobase is any nucleobase that can base pair with all of the four naturally occurring nucleobases without substantially affecting the melting behavior, recognition by intracellular enzymes or activity of the oligonucleotide duplex. Some exemplary universal nucleobases include, but are not limited to, 2,4-difluorotoluene, nitropyrrolyl, nitroindolyl, 8-aza-7-deazaadenine, 4-fluoro-6-methylbenzimidazle, 4-methylbenzimidazle, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylinolyl, 4,6-dimethylindolyl, phenyl, napthalenyl, anthracenyl, phenanthracenyl, pyrenyl, stilbenyl, tet- racenyl, pentacenyl, and structural derivatives thereof (see for example, Loakes, 2001, *Nucleic Acids Research*, 29, 2437-2447).

Further nucleobases include those disclosed in U.S. Pat. No. 3,687,808; those disclosed in International Application No. PCT/US09/038425, filed Mar. 26, 2009; those disclosed in the Concise Encyclopedia Of Polymer Science And Engineering, pages 858-859, Kroschwitz, J. I., ed. John Wiley & Sons, 1990; those disclosed by English et al., Angewandte Chemie, International Edition, 1991, 30, 613; those disclosed in Modified Nucleosides in Biochemistry, Biotechnology and Medicine, Herdewijin, P. Ed. Wiley-VCH, 2008; and those disclosed by Sanghvi, Y. S., Chapter 15, dsRNA Research and Applications, pages 289-302, Crooke, S. T. and Lebleu, B., Eds., CRC Press, 1993. Contents of all of the above are herein incorporated by reference.

In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

Nucleic Acid Modifications (Sugar)

Multi-targeted molecules provided herein can comprise one or more (e.g., 1, 2, 3, 4, 5, 6, 7, 8, 9, 10, 11, 12, 13, 14, 15 or more) monomer, including a nucleoside or nucleotide, having a modified sugar moiety. For example, the furanosyl sugar ring of a nucleoside can be modified in a number of ways including, but not limited to, addition of a substituent group, bridging of two non-geminal ring atoms to form a locked nucleic acid or bicyclic nucleic acid. In certain embodiments, oligomeric compounds comprise one or more (e.g., 1, 2, 3, 4, 5, 6, 7, 8, 9, 10, 11, 12, 13, 14, 15 or more) monomers that are LNA.

In some embodiments of a locked nucleic acid, the 2' position of furnaosyl is connected to the 4' position by a linker selected independently from —[C(R1)(R2)]$_n$—, —[C(R1)(R2)]$_n$—O—, —[C(R1)(R2)]$_n$—N(R1)-, —[C(R1)(R2)]$_n$—N(R1)-O—, —[C(R1R2)]$_n$O—N(R1)—, —C(R1)=C(R2)-O—, —C(R1)=N—, —C(R1)=N—O—, —C(=NR1)-, —C(=NR1)-O—, —C(=O)—, —C(=O)O—, —C(=S)—, —C(=S)O—, —C(=S)S—, —O—, —Si(R1)2-, —S(=O)$_x$— and —N(R1)-;

wherein:

x is 0, 1, or 2;

n is 1, 2, 3, or 4;

each R1 and R2 is, independently, H, a protecting group, hydroxyl, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, heterocycle radical, substituted heterocycle radical, heteroaryl, substituted heteroaryl, C5-C7 alicyclic radical, substituted C5-C7 alicyclic radical, halogen, OJ1, NJ1J2, SJ1, N3, COOJ1, acyl (C(=O)—H), substituted acyl, CN, sulfonyl (S(=O)2-J1), or sulfoxyl (S(=O)-J1); and each J1 and J2 is, independently, H, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, acyl (C(=O)—H), substituted acyl, a heterocycle radical, a substituted heterocycle radical, C1-C12 aminoalkyl, substituted C1-C12 aminoalkyl or a protecting group.

In some embodiments, each of the linkers of the LNA compounds is, independently, —[C(R1)(R2)]n-, —[C(R1)

(R2)]n-O—, —C(R1R2)-N(R1)-O— or —C(R1R2)-O—N(R1)-. In another embodiment, each of said linkers is, independently, 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R1)-2' and 4'-CH$_2$—N(R1)-O-2' wherein each R1 is, independently, H, a protecting group or C1-C12 alkyl.

Certain LNA's have been prepared and disclosed in the patent literature as well as in scientific literature (Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; WO 94/14226; WO 2005/021570; Singh et al., J. Org. Chem., 1998, 63, 10035-10039; Examples of issued US patents and published applications that disclose LNA s include, for example, U.S. Pat. Nos. 7,053,207; 6,268,490; 6,770,748; 6,794,499; 7,034,133; and 6,525,191; and U.S. Pre-Grant Publication Nos. 2004-0171570; 2004-0219565; 2004-0014959; 2003-0207841; 2004-0143114; and 20030082807.

Also provided herein are LNAs in which the 2'-hydroxyl group of the ribosyl sugar ring is linked to the 4' carbon atom of the sugar ring thereby forming a methyleneoxy (4'-CH$_2$—O-2') linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. Nos. 6,268,490 and 6,670,461). The linkage can be a methylene (—CH$_2$—) group bridging the 2' oxygen atom and the 4' carbon atom, for which the term methyleneoxy (4'-CH$_2$—O-2') LNA is used for the bicyclic moiety; in the case of an ethylene group in this position, the term ethyleneoxy (4'-CH$_2$CH$_2$—O-2') LNA is used (Singh et al., Chem. Commun., 1998, 4, 455-456: Morita et al., Bioorganic Medicinal Chemistry, 2003, 11, 2211-2226). Methyleneoxy (4'-CH$_2$—O-2') LNA and other bicyclic sugar analogs display very high duplex thermal stabilities with complementary DNA and RNA (Tm=+3 to +10° C.), stability towards 3'-exonucleolytic degradation and good solubility properties. Potent and nontoxic antisense oligonucleotides comprising BNAs have been described (Wahlestedt et al., Proc. Natl. Acad. Sci. U.S.A., 2000, 97, 5633-5638).

An isomer of methyleneoxy (4'-CH$_2$—O-2') LNA that has also been discussed is alpha-L-methyleneoxy (4'-CH$_2$—O-2') LNA which has been shown to have superior stability against a 3'-exonuclease. The alpha-L-methyleneoxy (4'-CH$_2$—O-2') LNA's were incorporated into antisense gapmers and chimeras that showed potent antisense activity (Frieden et al., Nucleic Acids Research, 2003, 21, 6365-6372).

The synthesis and preparation of the methyleneoxy (4'-CH$_2$—O-2') LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). BNAs and preparation thereof are also described in WO 98/39352 and WO 99/14226.

Analogs of methyleneoxy (4'-CH$_2$—O-2') LNA, phosphorothioate-methyleneoxy (4'-CH$_2$—O-2') LNA and 2'-thio-LNAs, have also been prepared (Kumar et al., Bioorg. Med. Chem. Lett., 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-LNA, a novel comformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Modified sugar moieties are well known and can be used to alter, typically increase, the affinity of the antisense compound for its target and/or increase nuclease resistance. A representative list of preferred modified sugars includes but is not limited to bicyclic modified sugars, including methyleneoxy (4'-CH$_2$—O-2') LNA and ethyleneoxy (4'-(CH$_2$)$_2$—O-2' bridge) ENA; substituted sugars, especially 2'-substituted sugars having a 2'-F, 2'-OCH$_3$ or a 2'-O (CH$_2$)$_2$—OCH$_3$ substituent group; and 4'-thio modified sugars. Sugars can also be replaced with sugar mimetic groups among others. Methods for the preparations of modified sugars are well known to those skilled in the art. Some representative patents and publications that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,531,584; and 6,600,032; and WO 2005/121371.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O(CH$_2$CH$_2$O)$_n$CH$_2$CH$_2$OR, n=1-50; "locked" nucleic acids (LNA) in which the furanose portion of the nucleoside includes a bridge connecting two carbon atoms on the furanose ring, thereby forming a bicyclic ring system; O-AMINE or O—(CH$_2$)$_n$AMINE (n=1-10, AMINE=NH$_2$; alkylamino, dialkylamino, heterocyclyl, arylamino, diaryl amino, heteroaryl amino, diheteroaryl amino, ethylene diamine or polyamino); and O—CH$_2$CH$_2$(NCH$_2$CH$_2$NMe$_2$)$_2$.

"Deoxy" modifications include hydrogen (i.e. deoxyribose sugars, which are of particular relevance to the single-strand overhangs); halo (e.g., fluoro); amino (e.g. NH$_2$; alkylamino, dialkylamino, heterocyclyl, arylamino, diaryl amino, heteroaryl amino, diheteroaryl amino, or amino acid); NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino); —NHC(O)R (R=alkyl, cycloalkyl, aryl, aralkyl, heteroaryl or sugar); cyano; mercapto; alkylthioalkyl; thioalkoxy; thioalkyl; alkyl; cycloalkyl; aryl; alkenyl and alkynyl, which can be optionally substituted with e.g., an amino functionality.

Other suitable 2'-modifications, e.g., modified MOE, are described in U.S. Patent Application Publication No. 20130130378, contents of which are herein incorporated by reference.

A modification at the 2' position can be present in the arabinose configuration The term "arabinose configuration" refers to the placement of a substituent on the C2' of ribose in the same configuration as the 2'-OH is in the arabinose.

The sugar can comprise two different modifications at the same carbon in the sugar, e.g., gem modification. The sugar group can also contain one or more carbons that possess the opposite stereochemical configuration than that of the corresponding carbon in ribose. Thus, an oligomeric compound can include one or more monomers containing e.g., arabinose, as the sugar. The monomer can have an alpha linkage at the 1' position on the sugar, e.g., alpha-nucleosides. The monomer can also have the opposite configuration at the 4'-position, e.g., C5' and H4' or substituents replacing them are interchanged with each other. When the C5' and H4' or substituents replacing them are interchanged with each other, the sugar is said to be modified at the 4' position.

Multi-targeted molecules disclosed herein can also include abasic sugars, i.e., a sugar which lack a nucleobase at C-1' or has other chemical groups in place of a nucleobase at C1'. See for example U.S. Pat. No. 5,998,203, content of which is herein incorporated in its entirety. These abasic sugars can also be further containing modifications at one or more of the constituent sugar atoms. Multi-targeted molecules can also contain one or more sugars that are the L isomer, e.g. L-nucleosides. Modification to the sugar group can also include replacement of the 4'-O with a sulfur, optionally substituted nitrogen or $CH_2$ group. In some embodiments, linkage between C1' and nucleobase is in α configuration.

Sugar modifications can also include acyclic nucleotides, wherein a C—C bonds between ribose carbons (e.g., C1'-C2', C2'-C3', C3'-C4', C4'-O4', C1'-O4') is absent and/or at least one of ribose carbons or oxygen (e.g., C1', C2', C3', C4' or O4') are independently or in combination absent from the nucleotide. In some embodiments, acyclic nucleotide is

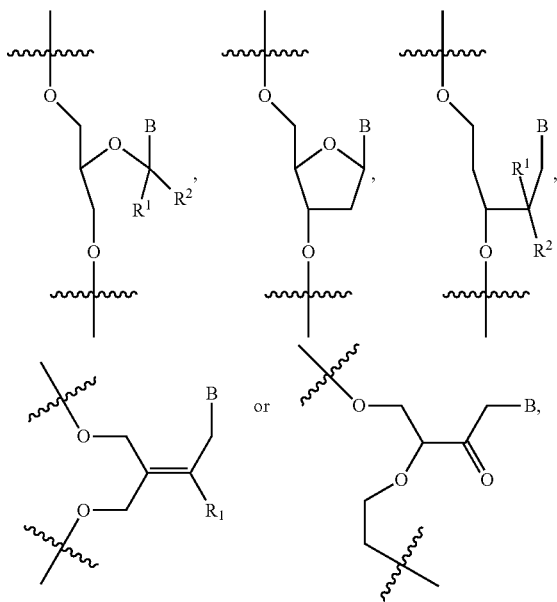

wherein B is a modified or unmodified nucleobase, $R_1$ and $R_2$ independently are H, halogen, $OR_3$, or alkyl; and $R_3$ is H, alkyl, cycloalkyl, aryl, aralkyl, heteroaryl or sugar).

In some embodiments, sugar modifications are selected from the group consisting of 2'-H, 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—$CH_2$-(4'-C) (LNA), 2'-O—$CH_2CH_2$-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE) and gem 2'-OMe/2'F with 2'-O-Me in the arabinose configuration.

It is to be understood that when a particular nucleotide is linked through its 2'-position to the next nucleotide, the sugar modifications described herein can be placed at the 3'-position of the sugar for that particular nucleotide, e.g., the nucleotide that is linked through its 2'-position. A modification at the 3' position can be present in the xylose configuration The term "xylose configuration" refers to the placement of a substituent on the C3' of ribose in the same configuration as the 3'-OH is in the xylose sugar.

The hydrogen attached to C4' and/or C1' can be replaced by a straight- or branched-optionally substituted alkyl, optionally substituted alkenyl, optionally substituted alkynyl, wherein backbone of the alkyl, alkenyl and alkynyl can contain one or more of: O, S, S(O), $SO_2$, N(R'), C(O), N(R')C(O)O, OC(O)N(R'), CH(Z'), phosphorous containing linkage, optionally substituted aryl, optionally substituted heteroaryl, optionally substituted heterocyclic or optionally substituted cycloalkyl, where R' is hydrogen, acyl or optionally substituted aliphatic, Z' is selected from the group consisting of $OR_{11}$, $COR_{11}$, $CO_2R_{11}$,

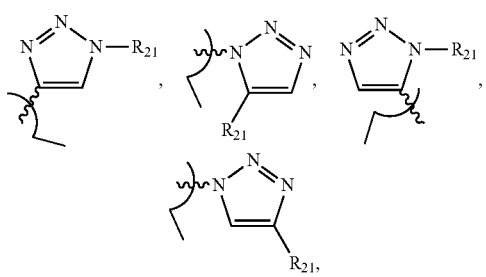

$NR_{21}R_{31}$, $CONR_{21}R_{31}$, $CON(H)NR_{21}R_{31}$, $ONR_{21}R_{31}$, $CON(H)N=CR_{41}R_{51}$, $N(R_{21})C(=NR_{31})NR_{21}R_{31}$, $N(R_{21})C(O)NR_{21}R_{31}$, $N(R_{21})C(S)NR_{21}R_{31}$, $OC(O)NR_{21}R_{31}$, $SC(O)NR_{21}R_{31}$, $N(R_{21})C(S)OR_{11}$, $N(R_{21})C(O)OR_{11}$, $N(R_{21})C(O)SR_{11}$, $N(R_{21})N=CR_{41}R_{51}$, $ON=CR_{41}R_{51}$, $SO_2R_{11}$, $SOR_{11}$, $SR_{11}$, and substituted or unsubstituted heterocyclic; $R_{21}$ and $R_{31}$ for each occurrence are independently hydrogen, acyl, unsubstituted or substituted aliphatic, aryl, heteroaryl, heterocyclic, $OR_{11}$, $COR_{11}$, $CO_2R_{11}$, or $NR_{11}R_{11}'$; or $R_{21}$ and $R_{31}$, taken together with the atoms to which they are attached, form a heterocyclic ring; $R_{41}$ and $R_{51}$ for each occurrence are independently hydrogen, acyl, unsubstituted or substituted aliphatic, aryl, heteroaryl, heterocyclic, $OR_{11}$, $COR_{11}$, or $CO_2R_{11}$, or $NR_{11}R_{11}'$; and $R_{11}$ and $R_{11}'$ are independently hydrogen, aliphatic, substituted aliphatic, aryl, heteroaryl, or heterocyclic. In some embodiments, the hydrogen attached to the C4' of the 5' terminal nucleotide is replaced.

In some embodiments, C4' and C5' together form an optionally substituted heterocyclic, preferably comprising at least one —PX(Y)—, wherein X is H, OH, OM, SH, optionally substituted alkyl, optionally substituted alkoxy, optionally substituted alkylthio, optionally substituted alkylamino or optionally substituted dialkylamino, where M is independently for each occurrence an alki metal or transition metal with an overall charge of +1; and Y is O, S, or NR', where R' is hydrogen, optionally substituted aliphatic. Preferably this modification is at the 5 terminal of the oligonucleotide.

In certain embodiments, LNA's include bicyclic nucleoside having the formula:

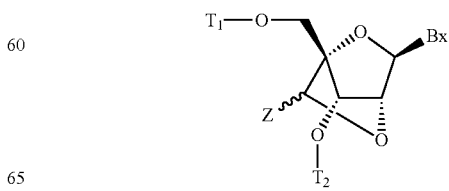

wherein:
Bx is a heterocyclic base moiety;
T1 is H or a hydroxyl protecting group;
T2 is H, a hydroxyl protecting group or a reactive phosphorus group;
Z is C1-C6 alkyl, C2-C6 alkenyl, C2-C6 alkynyl, substituted C1-C6 alkyl, substituted C2-C6 alkenyl, substituted C2-C6 alkynyl, acyl, substituted acyl, or substituted amide.

In some embodiments, each of the substituted groups, is, independently, mono or poly substituted with optionally protected substituent groups independently selected from halogen, oxo, hydroxyl, OJ1, NJ1J2, SJ1, N3, OC(=X)J1, OC(=X)NJ1J2, NJ3C(=X)NJ1J2 and CN, wherein each J1, J2 and J3 is, independently, H or C1-C6 alkyl, and X is O, S or NJ1.

In certain such embodiments, each of the substituted groups, is, independently, mono or poly substituted with substituent groups independently selected from halogen, oxo, hydroxyl, OJ1, NJ1J2, SJ1, N3, OC(=X)J1, and NJ3C(=X)NJ1J2, wherein each J1, J2 and J3 is, independently, H, C1-C6 alkyl, or substituted C1-C6 alkyl and X is O or NJ 1.

In certain embodiments, the Z group is C1-C6 alkyl substituted with one or more Xx, wherein each Xx is independently OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, the Z group is C1-C6 alkyl substituted with one or more Xx, wherein each Xx is independently halo (e.g., fluoro), hydroxyl, alkoxy (e.g., CH3O—), substituted alkoxy or azido.

In certain embodiments, the Z group is —CH2Xx, wherein Xx is OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, the Z group is CH2Xx, wherein Xx is halo (e.g., fluoro), hydroxyl, alkoxy (e.g., CH3O—) or azido.

In certain such embodiments, the Z group is in the (R)-configuration:

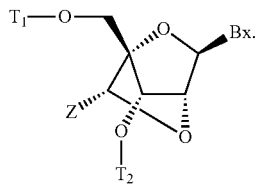

In certain such embodiments, the Z group is in the (S)-configuration:

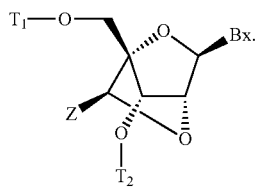

In certain embodiments, each T1 and T2 is a hydroxyl protecting group. A preferred list of hydroxyl protecting groups includes benzyl, benzoyl, 2,6-dichlorobenzyl, t-butyldimethylsilyl, t-butyldiphenylsilyl, mesylate, tosylate, dimethoxytrityl (DMT), 9-phenylxanthine-9-yl (Pixyl) and 9-(p-methoxyphenyl)xanthine-9-yl (MOX). In certain embodiments, T1 is a hydroxyl protecting group selected from acetyl, benzyl, t-butyldimethylsilyl, t-butyldiphenylsilyl and dimethoxytrityl wherein a more preferred hydroxyl protecting group is T1 is 4,4'-dimethoxytrityl.

In certain embodiments, T2 is a reactive phosphorus group wherein preferred reactive phosphorus groups include diisopropylcyanoethoxy phosphoramidite and H-phosphonate. In certain embodiments T1 is 4,4'-dimethoxytrityl and T2 is diisopropylcyanoethoxy phosphoramidite.

In certain embodiments, the multi-targeted molecules comprise at least one monomer of the formula:

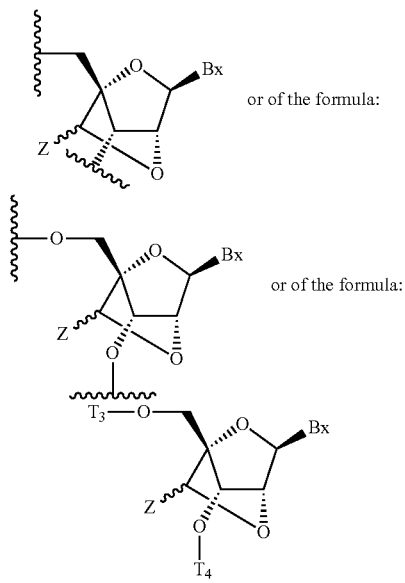

wherein
Bx is a heterocyclic base moiety;
T3 is H, a hydroxyl protecting group, a linked conjugate group or an internucleoside linking group attached to a nucleoside, a nucleotide, an oligonucleoside, an oligonucleotide, a monomeric subunit or an oligomeric compound;
T4 is H, a hydroxyl protecting group, a linked conjugate group or an internucleoside linking group attached to a nucleoside, a nucleotide, an oligonucleoside, an oligonucleotide, a monomeric subunit or an oligomeric compound;
wherein at least one of T3 and T4 is an internucleoside linking group attached to a nucleoside, a nucleotide, an oligonucleoside, an oligonucleotide, a monomeric subunit or an oligomeric compound; and
Z is C1-C6 alkyl, C2-C6 alkenyl, C2-C6 alkynyl, substituted C1-C6 alkyl, substituted C2-C6 alkenyl, substituted C2-C6 alkynyl, acyl, substituted acyl, or substituted amide.

In some embodiments, each of the substituted groups, is, independently, mono or poly substituted with optionally protected substituent groups independently selected from halogen, oxo, hydroxyl, OJ1, NJ1J2, SJ1, N3, OC(=X)J1, OC(=X)NJ1J2, NJ3C(=X)NJ1J2 and CN, wherein each J1, J2 and J3 is, independently, H or C1-C6 alkyl, and X is O, S or NJ1.

In some embodiments, each of the substituted groups, is, independently, mono or poly substituted with substituent groups independently selected from halogen, oxo, hydroxyl, OJ1, NJ1J2, SJ1, N3, OC(=X)J1, and NJ3C(=X)NJ1J2, wherein each J1, J2 and J3 is, independently, H or C1-C6 alkyl, and X is O or NJ1.

In certain such embodiments, at least one Z is C1-C6 alkyl or substituted C1-C6 alkyl. In certain embodiments, each Z is, independently, C1-C6 alkyl or substituted C1-C6 alkyl. In certain embodiments, at least one Z is C1-C6 alkyl. In certain embodiments, each Z is, independently, C1-C6 alkyl. In certain embodiments, at least one Z is methyl. In certain embodiments, each Z is methyl. In certain embodiments, at least one Z is ethyl. In certain embodiments, each Z is ethyl. In certain embodiments, at least one Z is substituted C1-C6 alkyl. In certain embodiments, each Z is, independently, substituted C1-C6 alkyl. In certain embodiments, at least one Z is substituted methyl. In certain embodiments, each Z is substituted methyl. In certain embodiments, at least one Z is substituted ethyl. In certain embodiments, each Z is substituted ethyl.

In certain embodiments, at least one substituent group is C1-C6 alkoxy (e.g., at least one Z is C1-C6 alkyl substituted with one or more C1-C6 alkoxy). In another embodiment, each substituent group is, independently, C1-C6 alkoxy (e.g., each Z is, independently, C1-C6 alkyl substituted with one or more C1-C6 alkoxy).

In certain embodiments, at least one C1-C6 alkoxy substituent group is CH3O— (e.g., at least one Z is CH$_3$OCH$_2$—). In another embodiment, each C1-C6 alkoxy substituent group is CH$_3$O— (e.g., each Z is CH$_3$OCH$_2$—).

In certain embodiments, at least one substituent group is halogen (e.g., at least one Z is C1-C6 alkyl substituted with one or more halogen). In certain embodiments, each substituent group is, independently, halogen (e.g., each Z is, independently, C1-C6 alkyl substituted with one or more halogen). In certain embodiments, at least one halogen substituent group is fluoro (e.g., at least one Z is CH$_2$FCH$_2$—, CHF$_2$CH$_2$— or CF$_3$CH$_2$—). In certain embodiments, each halo substituent group is fluoro (e.g., each Z is, independently, CH$_2$FCH$_2$—, CHF$_2$CH$_2$— or CF$_3$CH$_2$—).

In certain embodiments, at least one substituent group is hydroxyl (e.g., at least one Z is C1-C6 alkyl substituted with one or more hydroxyl). In certain embodiments, each substituent group is, independently, hydroxyl (e.g., each Z is, independently, C1-C6 alkyl substituted with one or more hydroxyl). In certain embodiments, at least one Z is HOCH$_2$—. In another embodiment, each Z is HOCH$_2$—.

In certain embodiments, at least one Z is CH$_3$—, CH$_3$CH$_2$—, CH$_2$OCH$_3$—, CH$_2$F— or HOCH$_2$—. In certain embodiments, each Z is, independently, CH$_3$—, CH$_3$CH$_2$—, CH$_2$OCH$_3$—, CH$_2$F— or HOCH$_2$—.

In certain embodiments, at least one Z group is C1-C6 alkyl substituted with one or more Xx, wherein each Xx is, independently, OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, at least one Z group is C1-C6 alkyl substituted with one or more Xx, wherein each Xx is, independently, halo (e.g., fluoro), hydroxyl, alkoxy (e.g., CH3O—) or azido.

In certain embodiments, each Z group is, independently, C1-C6 alkyl substituted with one or more Xx, wherein each Xx is independently OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, each Z group is, independently, C1-C6 alkyl substituted with one or more Xx, wherein each Xx is independently halo (e.g., fluoro), hydroxyl, alkoxy (e.g., CH3O—) or azido.

In certain embodiments, at least one Z group is —CH$_2$Xx, wherein Xx is OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In certain embodiments, at least one Z group is —CH$_2$Xx, wherein Xx is halo (e.g., fluoro), hydroxyl, alkoxy (e.g., CH3O—) or azido.

In certain embodiments, each Z group is, independently, —CH$_2$Xx, wherein each Xx is, independently, OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, each Z group is, independently, —CH$_2$Xx, wherein each Xx is, independently, halo (e.g., fluoro), hydroxyl, alkoxy (e.g., CH3O—) or azido.

In certain embodiments, at least one Z is CH$_3$—. In another embodiment, each Z is, CH$_3$—.

In certain embodiments, the Z group of at least one monomer is in the (R)-configuration represented by the formula:

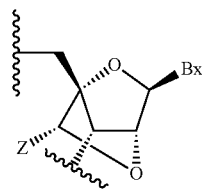

or the formula:

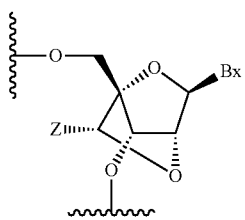

or the formula:

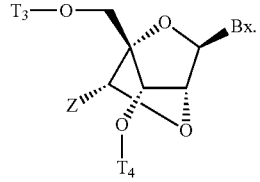

IN certain embodiments, the Z group of each monomer of the formula is in the (R)-configuration.

In certain embodiments, the Z group of at least one monomer is in the (S)-configuration represented by the formula:

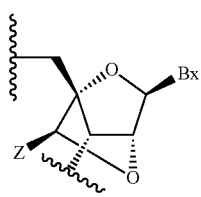

or the formula:

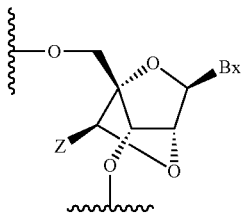

or the formula:

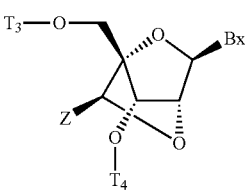

In certain embodiments, the Z group of each monomer of the formula is in the (S)-configuration.

In certain embodiments, T3 is H or a hydroxyl protecting group. In certain embodiments, T4 is H or a hydroxyl protecting group. In a further embodiment T3 is an internucleoside linking group attached to a nucleoside, a nucleotide or a monomeric subunit. In certain embodiments, T4 is an internucleoside linking group attached to a nucleoside, a nucleotide or a monomeric subunit. In certain embodiments, T3 is an internucleoside linking group attached to an oligonucleoside or an oligonucleotide. In certain embodiments, T4 is an internucleoside linking group attached to an oligonucleoside or an oligonucleotide. In certain embodiments, T3 is an internucleoside linking group attached to an oligomeric compound. In certain embodiments, T4 is an internucleoside linking group attached to an oligomeric compound. In certain embodiments, at least one of T3 and T4 comprises an internucleoside linking group selected from phosphodiester or phosphorothioate.

In certain embodiments, multi-targeted molecules comprise at least one region of at least two contiguous monomers of the formula:

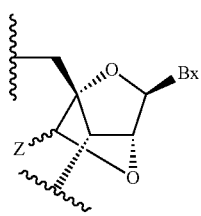

or of the formula:

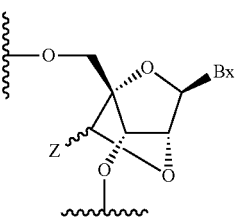

or of the formula:

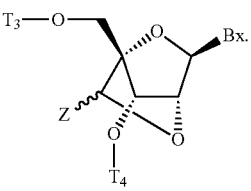

In certain such embodiments, LNAs include, but are not limited to, (A) α-L-Methyleneoxy (4'-CH2-O-2') LNA, (B) β-D-Methyleneoxy (4'-CH2-O-2') LNA, (C) Ethyleneoxy (4'-(CH2)2-O-2') LNA, (D) Aminooxy (4'-CH2-O—N(R)-2') LNA and (E) Oxyamino (4'-CH2-N(R)—O-2') LNA, as depicted below:

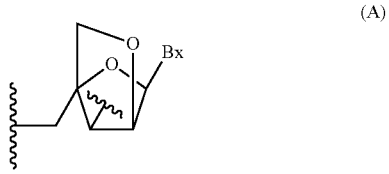

(A)

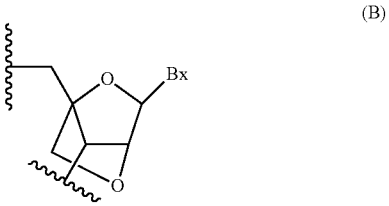

(B)

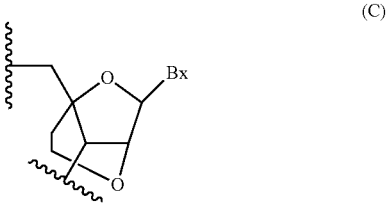

(C)

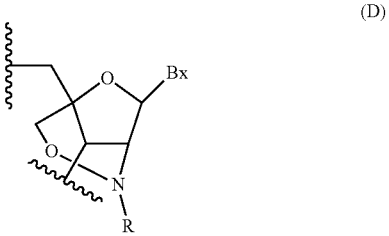

(D)

-continued

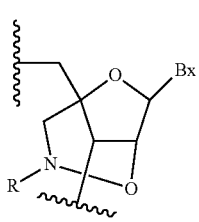

(E)

In certain embodiments, the multi-targeted molecule comprises at least two regions of at least two contiguous monomers of the above formula. In certain embodiments, the multi-targeted molecule comprises a gapped motif. In certain embodiments, the multi-targeted molecule comprises at least one region of from about 8 to about 14 contiguous β-D-2'-deoxyribofuranosyl nucleosides. In certain embodiments, the Multi-targeted molecule comprises at least one region of from about 9 to about 12 contiguous β-D-2'-deoxyribofuranosyl nucleosides.

In certain embodiments, the multi-targeted molecule comprises at least one (e.g., 1, 2, 3, 4, 5, 6, 7, 8, 9, 10, 11, 12, 13, 14, 15 or more) comprises at least one (S)-cEt monomer of the formula:

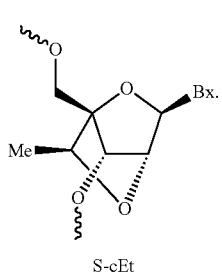

S-cEt (C)

wherein Bx IS heterocyclic base moiety.

In certain embodiments, monomers include sugar mimetics. In certain such embodiments, a mimetic is used in place of the sugar or sugar-internucleoside linkage combination, and the nucleobase is maintained for hybridization to a selected target. Representative examples of a sugar mimetics include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

Nucleic Acid Modifications (Intersugar Linkage)

Described herein are linking groups that link monomers (including, but not limited to, modified and unmodified nucleosides and nucleotides) together, thereby forming an oligomeric compound, e.g., an oligonucleotide. Such linking groups are also referred to as intersugar linkage. The two main classes of linking groups are defined by the presence or absence of a phosphorus atom. Representative phosphorus containing linkages include, but are not limited to, phosphodiesters (P=O), phosphotriesters, methylphosphonates, phosphoramidate, and phosphorothioates (P=S). Representative non-phosphorus containing linking groups include, but are not limited to, methylenemethylimino (—CH2-N(CH3)-O—CH2-), thiodiester (—O—C(O)—S—), thionocarbamate (—O—C(O)(NH)—S—); siloxane (—O—Si(H)2-O—); and N,N'-dimethylhydrazine (—CH2-N(CH3)-N(CH3)-). Modified linkages, compared to natural phosphodiester linkages, can be used to alter, typically increase, nuclease resistance of the oligonucleotides. In certain embodiments, linkages having a chiral atom can be prepared as racemic mixtures, as separate enantiomers. Representative chiral linkages include, but are not limited to, alkylphosphonates and phosphorothioates. Methods of preparation of phosphorous-containing and non-phosphorous-containing linkages are well known to those skilled in the art.

The phosphate group in the linking group can be modified by replacing one of the oxygens with a different substituent. One result of this modification can be increased resistance of the oligonucleotide to nucleolytic breakdown. Examples of modified phosphate groups include phosphorothioate, phosphoroselenates, borano phosphates, borano phosphate esters, hydrogen phosphonates, phosphoroamidates, alkyl or aryl phosphonates and phosphotriesters. In some embodiments, one of the non-bridging phosphate oxygen atoms in the linkage can be replaced by any of the following: S, Se, $BR_3$ (R is hydrogen, alkyl, aryl), C (i.e. an alkyl group, an aryl group, etc. . . . ), H, $NR_2$ (R is hydrogen, optionally substituted alkyl, aryl), or OR (R is optionally substituted alkyl or aryl). The phosphorous atom in an unmodified phosphate group is achiral. However, replacement of one of the non-bridging oxygens with one of the above atoms or groups of atoms renders the phosphorous atom chiral; in other words a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligonucleotides diastereomers. Thus, while not wishing to be bound by theory, modifications to both non-bridging oxygens, which eliminate the chiral center, e.g. phosphorodithioate formation, can be desirable in that they cannot produce diastereomer mixtures. Thus, the non-bridging oxygens can be independently any one of O, S, Se, B, C, H, N, or OR (R is alkyl or aryl).

The phosphate linker can also be modified by replacement of bridging oxygen, (i.e. oxygen that links the phosphate to the sugar of the monomer), with nitrogen (bridged phosphoroamidates), sulfur (bridged phosphorothioates) and carbon (bridged methylenephosphonates). The replacement can occur at the either one of the linking oxygens or at both linking oxygens. When the bridging oxygen is the 3'-oxygen of a nucleoside, replacement with carbon is preferred. When the bridging oxygen is the 5'-oxygen of a nucleoside, replacement with nitrogen is preferred.

Modified phosphate linkages where at least one of the oxygen linked to the phosphate has been replaced or the phosphate group has been replaced by a non-phosphorous group, are also referred to as "non-phosphodiester intersugar linkage" or "non-phosphodiester linker."

In certain embodiments, the phosphate group can be replaced by non-phosphorus containing connectors, e.g. dephospho linkers. Dephospho linkers are also referred to as non-phosphodiester linkers herein. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include, but are not limited to, amides (for example amide-3 (3'-$CH_2$—C(=O)—N(H)-5') and amide-4 (3'-$CH_2$—N(H)—C(=O)-5')), hydroxylamino, siloxane (dialkylsiloxxane), carboxamide, carbonate, carboxymethyl, carbamate, carboxylate ester, thioether, ethylene oxide linker, sulfide,sulfonate, sulfonamide, sulfonate ester, thioformacetal (3'-S—$CH_2$—O-5'), formacetal (3'-O—$CH_2$—O-5), oxime, methyleneimino, methykenecarbonylamino, methylenemethylimino 3'-$CH_2$—N($CH_3$)—O-5'), methylenehydrazo, methylenedimethylhydrazo, methyleneoxymethylimino, ethers (C3'—O—C5'), thioethers (C3'—S—C5'), thioacetamido (C3'—N(H)—C(=O)—$CH_2$—S—C5', C3'—O—P(O)—O—SS—C5', C3'—$CH_2$—NH—NH—C5', 3'—NHP(O)($OCH_3$)—O-5' and 3'-NHP(O)($OCH_3$)—O-5' and nonionic linkages containing mixed N, O, S and $CH_2$ component parts. See for example, Carbohydrate Modifications in Antisense Research; Y. S. Sanghvi and P. D. Cook Eds. ACS Symposium Series 580; Chapters 3 and 4, (pp. 40-65). Preferred embodiments include methylenemethylimino (MMI), methylenecarbonylamino, amides, carbamate and ethylene oxide linker.

One skilled in the art is well aware that in certain instances replacement of a non-bridging oxygen can lead to enhanced cleavage of the intersugar linkage by the neighboring 2'-OH, thus in many instances, a modification of a non-bridging oxygen can necessitate modification of 2'-OH, e.g., a modification that does not participate in cleavage of the neighboring intersugar linkage, e.g., arabinose sugar, 2'-O-alkyl, 2'-F, LNA and ENA.

Preferred non-phosphodiester intersugar linkages include phosphorothioates, phosphorothioates with an at least 1%, 5%, 10%, 20%, 30%, 40%, 50%, 60%, 70%, 80%, 90% 95% or more enantiomeric excess of Sp isomer, phosphorothioates with an at least 1%, 5%, 10%, 20%, 30%, 40%, 50%, 60%, 70%, 80%, 90% 95% or more enantiomeric excess of Rp isomer, phosphorodithioates, phosphotriesters, aminoalkylphosphotriesters, alkyl-phosphonaters (e.g., methylphosphonate), selenophosphates, phosphoramidates (e.g., N-alkylphosphoramidate), and boranophosphonates.

In some embodiments, the multi-targeted molecule comprises at least one (e.g., 1, 2, 3, 4, 5, 6, 7, 8, 9, 10, 11, 12, 13, 14, 15 or more and upto including all) modified or nonphosphodiester linkages. In some embodiments, the multi-targeted molecule comprises at least one (e.g., 1, 2, 3, 4, 5, 6, 7, 8, 9, 10, 11, 12, 13, 14, 15 or more and upto including all) phosphorothioate linkages.

The multi-targeted molecules can also be constructed wherein the phosphate linker and the sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the morpholino, cyclobutyl, pyrrolidine, peptide nucleic acid (PNA), aminoethylglycyl PNA (aegPNA) and backnone-extended pyrrolidine PNA (bepPNA) nucleoside surrogates. A preferred surrogate is a PNA surrogate.

The multi-targeted molecules described herein can contain one or more asymmetric centers and thus give rise to enantiomers, diastereomers, and other stereoisomeric configurations that may be defined, in terms of absolute stereochemistry, as (R) or (S), such as for sugar anomers, or as (D) or (L) such as for amino acids et al. Included in the multi-targeted molecules provided herein are all such possible isomers, as well as their racemic and optically pure forms.

Nucleic Acid Modifications (Terminal Modifications)

Ends of the multi-targeted molecules or the effector molecules included in the multi-targeted molecule can be modified. Such modifications can be at one end or both ends. For example, the 3' and/or 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

When a linker/phosphate-functional molecular entity-linker/phosphate array is interposed between two strands of a double stranded oligomeric compound, this array can substitute for a hairpin loop in a hairpin-type oligomeric compound.

Terminal modifications useful for modulating activity include modification of the 5' end of oligonucleotides with phosphate or phosphate analogs. In certain embodiments, the 5' end of an oligonucleotide is phosphorylated or includes a phosphoryl analog. Exemplary 5'-phosphate modifications include those which are compatible with RISC mediated gene silencing. Modifications at the 5'-terminal end can also be useful in stimulating or inhibiting the immune system of a subject. In some embodiments, the 5'-end of the oligomeric compound comprises the modification

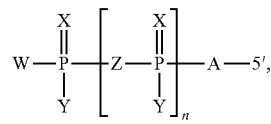

wherein W, X and Y are each independently selected from the group consisting of O, OR (R is hydrogen, alkyl, aryl), S, Se, $BR_3$ (R is hydrogen, alkyl, aryl), $BH_3^-$, C (i.e. an alkyl group, an aryl group, etc. . . . ), H, $NR_2$ (R is hydrogen, alkyl, aryl), or OR (R is hydrogen, alkyl or aryl); A and Z are each independently for each occurrence absent, O, S, $CH_2$, NR (R is hydrogen, alkyl, aryl), or optionally substituted alkylene, wherein backbone of the alkylene can comprise one or more of O, S, SS and NR (R is hydrogen, alkyl, aryl) internally and/or at the end; and n is 0-2. In some embodiments, n is 1 or 2. It is understood that A is replacing the oxygen linked to 5' carbon of sugar. When n is 0, W and Y together with the P to which they are attached can form an optionally substituted 5-8 membered heterocyclic, wherein W an Y are each independently O, S, NR' or alkylene. Preferably the heterocyclic is substituted with an aryl or heteroaryl. In some embodiments, one or both hydrogen on C5' of the 5'-terminal nucleotides are replaced with a halogen, e.g., F.

Exemplary 5'-modifications include, but are not limited to, 5'-monophosphate ((HO)₂(O)P—O-5'); 5'-diphosphate ((HO)₂(O)P—O—P(HO)(O)—O-5'); 5'-triphosphate ((HO)₂(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); 5'-alpha-thiotriphosphate; 5'-beta-thiotriphosphate; 5'-gamma-thiotriphosphate; 5'-phosphoramidates ((HO)₂(O)P—NH-5', (HO)(NH₂)(O)P—O-5'). Other 5'-modification include 5'-alkylphosphonates (R(OH)(O)P—O-5', R=alkyl, e.g., methyl, ethyl, isopropyl, propyl, etc. . . . ), 5'-alkyletherphosphonates (R(OH)(O)P—O-5', R=alkylether, e.g., methoxymethyl (CH₂OMe), ethoxymethyl, etc. . . . ). Other exemplary 5'-modifications include where Z is optionally substituted alkyl at least once, e.g., ((HO)₂(X)P—ORCH₂)$_a$—O—P(X)(OH)—O]$_b$-5', ((HO)2(X)P—O[CH₂]$_a$—P(X)(OH)—O]$_b$-5', ((HO)²(X)P—[—(CH₂)$_a$—O—P(X)(OH)—O]$_b$-5'; dialkyl terminal phosphates and phosphate mimics: HO[—(CH₂)$_a$—O—P(X)(OH)—O]$_b$-5', H₂N[—(CH₂)$_a$—O—P(X)(OH)—O]$_b$-5', H[—(CH₂)$_a$—O—P(X)(OH)—O]$_b$-5', Me₂N[—(CH₂)$_a$—O—P(X)(OH)—O]$_b$-5', HO[—(CH₂)$_a$—P(X)(OH)—O]$_b$-5', H₂N[—(CH₂)$_a$—P(X)(OH)—O]$_b$-5', H[—(CH₂)$_a$—P(X)(OH)—O]$_b$-5', Me₂N[—(CH₂)$_a$—P(X)(OH)—O]$_b$-5', wherein a and b are each independently 1-10. Other embodiments, include replacement of oxygen and/or sulfur with BH₃, BH₃⁻ and/or Se.

Terminal modifications can also be useful for monitoring distribution, and in such cases the preferred groups to be added include fluorophores, e.g., fluorescein or an Alexa dye, e.g., Alexa 488. Terminal modifications can also be useful for enhancing uptake, useful modifications for this include targeting ligands. Terminal modifications can also be useful for cross-linking an oligonucleotide to another moiety; modifications useful for this include mitomycin C, psoralen, and derivatives thereof.

Thermally Destabilizing Modifications

The effector molecules, such as siRNAs or dsRNA agents, can be optimized for RNA interference by increasing the propensity of the dsRNA duplex to disassociate or melt (decreasing the free energy of duplex association) by introducing a thermally destabilizing modification in the sense strand at a site opposite to the seed region of the antisense strand (i.e., at positions 2-8 of the 5'-end of the antisense strand). This modification can increase the propensity of the duplex to disassociate or melt in the seed region of the antisense strand.

The thermally destabilizing modifications can include abasic modification; mismatch with the opposing nucleotide in the opposing strand; and sugar modification such as 2'-deoxy modification or acyclic nucleotide, e.g., unlocked nucleic acids (UNA) or glycerol nuceltic acid (GNA).

Exemplified abasic modifications are:

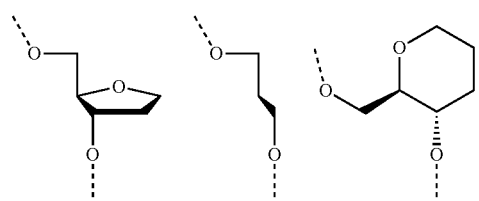

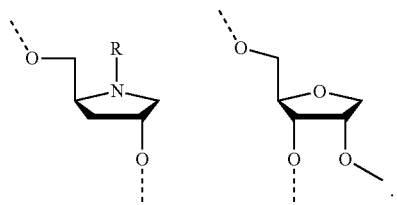

Exemplified sugar modifications are:

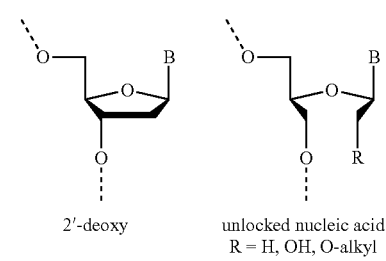

2'-deoxy    unlocked nucleic acid
            R = H, OH, O-alkyl

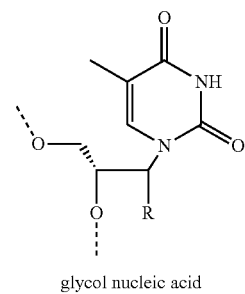

glycol nucleic acid
R = H, OH, O-alkyl

The term "acyclic nucleotide" refers to any nucleotide having an acyclic ribose sugar, for example, where any of bonds between the ribose carbons (e.g., C1'-C2', C2'-C3', C3'-C4', C4'-C4', or C1'-C4') is absent and/or at least one of ribose carbons or oxygen (e.g., C1', C2', C3', C4' or C4') are independently or in combination absent from the nucleotide. In some embodiments, acyclic nucleotide is

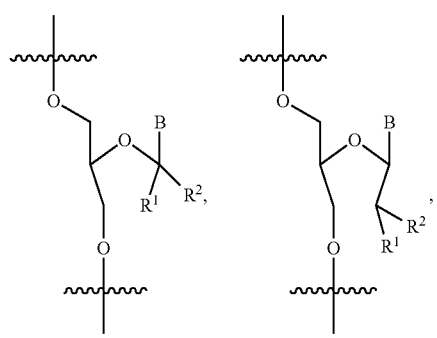

-continued

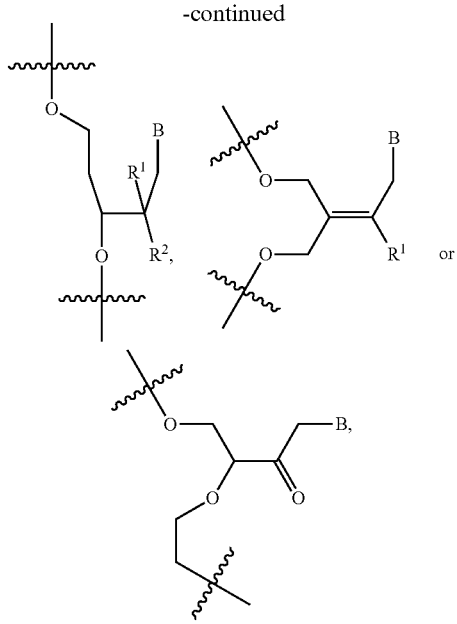

wherein B is a modified or unmodified nucleobase, $R^1$ and $R^2$ independently are H, halogen, $OR_3$, or alkyl; and $R_3$ is H, alkyl, cycloalkyl, aryl, aralkyl, heteroaryl or sugar). The term "UNA" refers to unlocked acyclic nucleic acid, wherein any of the bonds of the sugar has been removed, forming an unlocked "sugar" residue. In one example, UNA also encompasses monomers with bonds between C1'—C4' being removed (i.e. the covalent carbon-oxygen-carbon bond between the C1' and C4' carbons). In another example, the C2'—C3' bond (i.e. the covalent carbon-carbon bond between the C2' and C3' carbons) of the sugar is removed (see Mikhailov et. al., Tetrahedron Letters, 26 (17): 2059 (1985); and Fluiter et al., Mol. Biosyst., 10: 1039 (2009), which are hereby incorporated by reference in their entirety). The acyclic derivative provides greater backbone flexibility without affecting the Watson-Crick pairings. The acyclic nucleotide can be linked via 2'-5' or 3'-5' linkage.

The term 'GNA' refers to glycol nucleic acid which is a polymer similar to DNA or RNA but differing in the composition of its "backbone" in that is composed of repeating glycerol units linked by phosphodiester bonds:

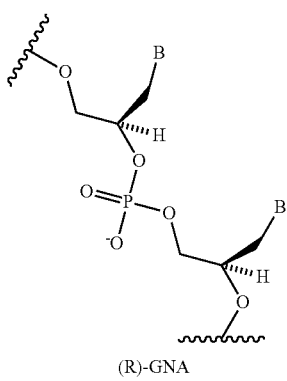

(R)-GNA

The thermally destabilizing modification can be mismatches (i.e., noncomplementary base pairs) between the thermally destabilizing nucleotide and the opposing nucleotide in the opposite strand within the dsRNA duplex. Exemplary mismatch basepairs include G:G, G:A, G:U, G:T, A:A, A:C, C:C, C:U, C:T, U:U, T:T, U:T, or a combination thereof. Other mismatch base pairings known in the art are also amenable to the present invention. A mismatch can occur between nucleotides that are either naturally occurring nucleotides or modified nucleotides, i.e., the mismatch base pairing can occur between the nucleobases from respective nucleotides independent of the modifications on the ribose sugars of the nucleotides. In certain embodiments, the effector molecule, such as siRNA or dsRNA agent, contains at least one nucleobase in the mismatch pairing that is a 2'-deoxy nucleobase; e.g., the 2'-deoxy nucleobase is in the sense strand.

More examples of abasic nucleotide, acyclic nucleotide modifications (including UNA and GNA), and mismatch modifications have been described in detail in WO 2011/133876, which is herein incorporated by reference in its entirety.

The thermally destabilizing modifications may also include universal base with reduced or abolished capability to form hydrogen bonds with the opposing bases, and phosphate modifications.

Nucleobase modifications with impaired or completely abolished capability to form hydrogen bonds with bases in the opposite strand have been evaluated for destabilization of the central region of the dsRNA duplex as described in WO 2010/0011895, which is herein incorporated by reference in its entirety. Exemplary nucleobase modifications are:

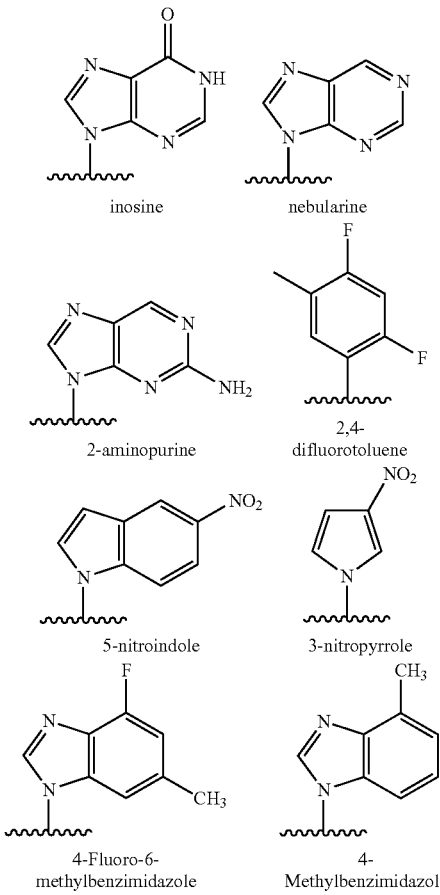

Exemplary phosphate modifications known to decrease the thermal stability of dsRNA duplexes compared to natural phosphodiester linkages are:

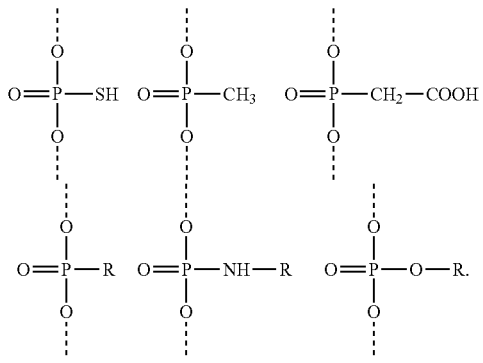

R = alkyl

In some embodiments, an effector molecule in the multi-targeted molecule can comprise 2'-5' linkages (with 2'-H, 2'-OH and 2'-OMe and with P=O or P=S). For example, the 2'-5' linkages modifications can be used to promote nuclease resistance or to inhibit binding of the sense to the antisense strand, or can be used at the 5' end of the sense strand to avoid sense strand activation by RISC.

In another embodiment, an effector molecule in the multi-targeted molecule can comprise L sugars (e.g., L ribose, L-arabinose with 2'-H, 2'-OH and 2'-OMe). For example, these L sugar modifications can be used to promote nuclease resistance or to inhibit binding of the sense to the antisense strand, or can be used at the 5' end of the sense strand to avoid sense strand activation by RISC.

In one embodiment the dsRNA agent of the invention is conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3] dioxolane, oxazolidinyl, isoxazolidinyl, morpholinyl, thiazolidinyl, isothiazolidinyl, quinoxalinyl, pyridazinonyl, tetrahydrofuryl and and decalin; preferably, the acyclic group is selected from serinol backbone or diethanolamine backbone.

In some embodiments, at least one strand of at least one effector molecule in the multi-targeted molecules disclosed herein is 5' phosphorylated or includes a phosphoryl analog at the 5' prime terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7 m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, 5'-alkenylphosphonates (i.e. vinyl, substituted vinyl), (OH)2(O)P-5'-CH2-), 5'-alkyletherphosphonates (R=alkylether=methoxymethyl (MeOCH2-), ethoxymethyl, etc., e.g. RP(OH)(O)—O-5'-).

Target Genes

Without limitations, target genes for siRNAs include, but are not limited to genes promoting unwanted cell proliferation, growth factor gene, growth factor receptor gene, genes expressing kinases, an adaptor protein gene, a gene encoding a G protein super family molecule, a gene encoding a transcription factor, a gene which mediates angiogenesis, a viral gene, a gene required for viral replication, a cellular gene which mediates viral function, a gene of a bacterial pathogen, a gene of an amoebic pathogen, a gene of a parasitic pathogen, a gene of a fungal pathogen, a gene which mediates an unwanted immune response, a gene which mediates the processing of pain, a gene which mediates a neurological disease, an allene gene found in cells characterized by loss of heterozygosity, or one allege gene of a polymorphic gene.

Specific exemplary target genes for the siRNAs include, but are not limited to, PCSK-9, ApoC3, AT3, AGT, ALAS1, TMPR, HAO1, AGT, C5, CCR-5, PDGF beta gene; Erb-B gene, Src gene; CRK gene; GRB2 gene; RAS gene; MEKK gene; JNK gene; RAF gene; Erk1/2 gene; PCNA(p21) gene; MYB gene; c-MYC gene; JUN gene; FOS gene; BCL-2 gene; Cyclin D gene; VEGF gene; EGFR gene; Cyclin A gene; Cyclin E gene; WNT-1 gene; beta-catenin gene; c-MET gene; PKC gene; NFKB gene; STAT3 gene; survivin gene; Her2/Neu gene; topoisomerase I gene; topoisomerase II alpha gene; p73 gene; p21(WAF1/CIP1) gene, p27(KIP1) gene; PPM1D gene; caveolin I gene; MIB I gene; MTAI gene; M68 gene; tumor suppressor genes; p53 gene; DN-p63 gene; pRb tumor suppressor gene; APC1 tumor suppressor gene; BRCA1 tumor suppressor gene; PTEN tumor suppressor gene; MEL fusion genes, e.g., MLL-AF9, BCR/ABL fusion gene; TEL/AML1 fusion gene; EWS/FLI1 fusion gene; TLS/FUS1 fusion gene; PAX3/FKHR fusion gene; AML1/ETO fusion gene; alpha v-integrin gene; Flt-1 receptor gene; tubulin gene; Human Papilloma Virus gene, a gene required for Human Papilloma Virus replication, Human Immunodeficiency Virus gene, a gene required for Human Immunodeficiency Virus replication, Hepatitis A Virus gene, a gene required for Hepatitis A Virus replication, Hepatitis B Virus gene, a gene required for Hepatitis B Virus replication, Hepatitis C Virus gene, a gene required for Hepatitis C Virus replication, Hepatitis D Virus gene, a gene required for Hepatitis D Virus replication, Hepatitis E Virus gene, a gene required for Hepatitis E Virus replication, Hepatitis F Virus gene, a gene required for Hepatitis F Virus replication, Hepatitis G Virus gene, a gene required for Hepatitis G Virus replication, Hepatitis H Virus gene, a gene required for Hepatitis H Virus replication, Respiratory Syncytial Virus gene, a gene that is required for Respiratory Syncytial Virus replication, Herpes Simplex Virus gene, a gene that is required for Herpes Simplex Virus replication, herpes Cytomegalovirus gene, a gene that is required for herpes Cytomegalovirus replication, herpes Epstein Barr Virus gene, a gene that is required for herpes Epstein Barr Virus replication, Kaposi's Sarcoma-associated Herpes Virus gene, a gene that is required for Kaposi's Sarcoma-associated Herpes Virus replication, JC Virus gene, human gene that is required for JC Virus replication, myxovirus gene, a gene that is required for myxovirus gene replication, rhinovirus gene, a gene that is required for rhinovirus replication, coronavirus gene, a gene that is required for coronavirus replication, West Nile Virus gene, a gene that is required for West Nile Virus replication, St. Louis Encephalitis gene, a gene that is required for St. Louis Encephalitis replication, Tick-borne encephalitis virus gene, a gene that is required for Tick-borne encephalitis virus replication, Murray Valley encephalitis virus gene, a gene that is required for Murray Valley encephalitis virus replication, dengue virus gene, a gene that is required for dengue virus gene replication, Simian Virus 40 gene, a gene that is required for Simian Virus 40 replication, Human T Cell Lymphotropic Virus gene, a gene that is required for Human T Cell Lymphotropic Virus replication, Moloney-Murine Leukemia Virus gene, a gene that is required for Moloney-Murine Leukemia Virus replication, encephalomyocarditis virus gene, a gene that is required for encephalomyocarditis virus replication, measles virus gene, a gene that is required for measles virus replication, Vericella zoster virus gene, a gene that is required for Vericella zoster virus replication, adenovirus gene, a gene that is required for adenovirus replication, yellow fever virus gene, a gene that is required for yellow fever virus replication, poliovirus gene, a gene that is required for poliovirus replication, poxvirus gene, a gene that is required for poxvirus replication, plasmodium gene, a gene that is required for plasmodium gene replication, *Mycobacterium ulcerans* gene, a gene that is required for *Mycobacterium ulcerans* replication, *Mycobacterium tuberculosis* gene, a gene that is required for *Mycobacterium tuberculosis* replication, *Mycobacterium leprae* gene, a gene that is required for *Mycobacterium leprae* replication, *Staphylococcus aureus* gene, a gene that is required for *Staphylococcus aureus* replication, *Streptococcus pneumoniae* gene, a gene that is required for *Streptococcus pneumoniae* replication, *Streptococcus pyogenes* gene, a gene that is required for *Streptococcus pyogenes* replication, *Chlamydia pneumoniae* gene, a gene that is required for *Chlamydia pneumoniae* replication, *Mycoplasma pneumoniae* gene, a gene that is required for *Mycoplasma pneumoniae* replication, an integrin gene, a selectin gene, complement system gene, chemokine gene, chemokine receptor gene, GCSF gene, Gro1 gene, Gro2 gene, Gro3 gene, PF4 gene, MIG gene, Pro-Platelet Basic Protein gene, MIP-1I gene, MIP-1J gene, RANTES gene, MCP-1 gene, MCP-2 gene, MCP-3 gene, CMBKR1 gene, CMBKR2 gene, CMBKR3 gene, CMBKR5v, AIF-1 gene, 1-309 gene, a gene to a component of an ion channel, a gene to a neurotransmitter receptor, a gene to a neurotransmitter ligand, amyloid-family gene, presenilin gene, HD gene, DRPLA gene, SCA1 gene, SCA2 gene, MJD1 gene, CACNL1A4 gene, SCAT gene, SCA8 gene, allele gene found in loss of heterozygosity (LOH) cells, one allele gene of a polymorphic gene and combinations thereof.

The loss of heterozygosity (LOH) can result in hemizygosity for sequence, e.g., genes, in the area of LOH. This can result in a significant genetic difference between normal and disease-state cells, e.g., cancer cells, and provides a useful difference between normal and disease-state cells, e.g., cancer cells. This difference can arise because a gene or other sequence is heterozygous in duploid cells but is hemizygous in cells having LOH. The regions of LOH will often include a gene, the loss of which promotes unwanted proliferation, e.g., a tumor suppressor gene, and other sequences including, e.g., other genes, in some cases a gene which is essential for normal function, e.g., growth. Methods of the invention rely, in part, on the specific modulation of one allele of an essential gene with a composition of the invention.

In certain embodiments, the invention provides a multi-targeted molecule that modulates a micro-RNA.

Ligands

In certain embodiments, the multi-targeted molecules are modified by covalent attachment of one or more conjugate groups. In general, conjugate groups modify one or more properties of the attached multi-targeted molecule including but not limited to pharmacodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

Preferred conjugate groups amenable to the present invention include lipid moieties such as a cholesterol moiety (Letsinger et al., Proc. Natl. Acad. Sci. USA, 1989, 86, 6553); cholic acid (Manoharan et al., Bioorg. Med. Chem. Lett., 1994, 4, 1053); a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765); a thiocholesterol (Oberhauser et al., Nucl. Acids Res., 1992, 20, 533); an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49); a phospholipid, e.g., di-hexadecyl-rac-glycerol or triethylammonium-1,2-di-O-hexadecyl-rac-glycero-3-H-phosphonate (Manoharan et al., Tetrahedron Lett., 1995, 36, 3651; Shea et al., Nucl. Acids Res., 1990, 18, 3777); a polyamine or a polyethylene glycol chain (Manoharan et al., Nucleosides & Nucleotides, 1995, 14, 969); adamantane acetic acid (Manoharan et al., Tetrahedron Lett., 1995, 36, 3651); a palmityl moiety (Mishra et al., Biochim. Biophys. Acta, 1995, 1264, 229); or an octadecylamine or hexylamino-carbonyl-oxycholesterol moiety (Crooke et al., J. Pharmacol. Exp. Ther., 1996, 277, 923).

Generally, a wide variety of entities, e.g., ligands, can be coupled to the oligomeric compounds described herein. Ligands can include naturally occurring molecules, or recombinant or synthetic molecules. Exemplary ligands include, but are not limited to, polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG, e.g., PEG-2K, PEG-5K, PEG-10K, PEG-12K, PEG-15K, PEG-20K, PEG-40K), MPEG, $[MPEG]_2$, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g, steroids, bile acids, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), and a cell-permeation agent (e.g., a.helical cell-permeation agent).

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides. A peptidomimetic (also referred to herein as an oligopeptidomimetic) is a molecule capable of folding into a defined three-dimensional structure similar to a natural peptide. The peptide or peptidomimetic ligand can be about 5-50 amino acids long, e.g., about 5, 10, 15, 20, 25, 30, 35, 40, 45, or 50 amino acids long.

Exemplary amphipathic peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, H$_2$A peptides, Xenopus peptides, esculentinis-1, and caerins.

As used herein, the term "endosomolytic ligand" refers to molecules having endosomolytic properties. Endosomolytic ligands promote the lysis of and/or transport of the composition of the invention, or its components, from the cellular compartments such as the endosome, lysosome, endoplasmic reticulum (ER), Golgi apparatus, microtubule, peroxisome, or other vesicular bodies within the cell, to the cytoplasm of the cell. Some exemplary endosomolytic ligands include, but are not limited to, imidazoles, poly or oligoimidazoles, linear or branched polyethyleneimines (PEIs), linear and brached polyamines, e.g. spermine, cationic linear and branched polyamines, polycarboxylates, polycations, masked oligo or poly cations or anions, acetals, polyacetals, ketals/polyketals, orthoesters, linear or branched polymers with masked or unmasked cationic or anionic charges, dendrimers with masked or unmasked cationic or anionic charges, polyanionic peptides, polyanionic peptidomimetics, pH-sensitive peptides, natural and synthetic fusogenic lipids, natural and synthetic cationic lipids.

Exemplary endosomolytic/fusogenic peptides include, but are not limited to, AALEALAEALEALAEALA- LAEAAAAGGC (GALA) (SEQ ID NO:1); AALAEA- LAEALAEALAEALAEALAAAAGGC (EALA) (SEQ ID NO: 2); ALEALAEALEALAEA (SEQ ID NO: 3); GLFEAIEGFIENGWEGMIWDYG (INF-7) (SEQ ID NO: 4); GLFGAIAGFIENGWEGMIDGWYG (Inf HA-2) (SEQ ID NO: 5); GLFEAIEGFIENGWEG- MIDGWYGCGLFEAIEGFIENGWEGMID GWYGC (di-INF-7) (SEQ ID NO: 6); GLFEAIEGFIENGWEG- MIDGGCGLFEAIEGFIENGWEGMIDGGC (diINF-3) (SEQ ID NO: 7); GLFGALAEALAEALAEHLAEA- LAEALEALAAGGSC (GLF) (SEQ ID NO: 8); GLFEAIEGFIENGWEGLAEALAEALEALAAGGSC (GALA-INF3) (SEQ ID NO: 9); GLF EAI EGFI ENGW EGnI DG K GLF EAI EGFI ENGW EGnI DG (INF-5, n is norleucine) (SEQ ID NO: 10); LFEALLELLESLWELL- LEA (JTS-1) (SEQ ID NO: 11); GLFKALLKLLKSLWKLLLKA (ppTG1) (SEQ ID NO: 12); GLFRALLRLLRSLWRLLLRA (ppTG20) (SEQ ID NO: 13); WEAKLAKALAKALAKHLAKALAKALKA- CEA (KALA) (SEQ ID NO: 14); GLFFEAI- AEFIEGGWEGLIEGC (HA) (SEQ ID NO: 15); GIGAVLKVLTTGLPALISWIKRKRQQ (Melittin) (SEQ ID NO: 16); H$_5$WYG (SEQ ID NO: 17); and CHK$_6$HC (SEQ ID NO: 18).

Without wishing to be bound by theory, fusogenic lipids fuse with and consequently destabilize a membrane. Fusogenic lipids usually have small head groups and unsaturated acyl chains. Exemplary fusogenic lipids include, but are not limited to, 1,2-dileoyl-sn-3-phosphoethanolamine (DOPE), phosphatidylethanolamine (POPE), palmitoyloleoylphosphatidylcholine (POPC), (6Z,9Z,28Z,31Z)-heptatriaconta-6,9,28,31-tetraen-19-ol (Di-Lin), N-methyl(2,2-di((9Z,12Z)-octadeca-9,12-dienyl)-1,3-dioxolan-4-yl)methanamine (DLin-k-DMA) and N-methyl-2-(2,2-di((9Z,12Z)-octadeca-9,12-dienyl)-1,3-dioxolan-4-yl)ethanamine (also referred to as XTC herein).

Synthetic polymers with endosomolytic activity amenable to the present invention are described in U.S. Pat. App. Pub. Nos. 2009/0048410; 2009/0023890; 2008/0287630; 2008/0287628; 2008/0281044; 2008/0281041; 2008/0269450; 2007/0105804; 20070036865; and 2004/0198687, contents of which are hereby incorporated by reference in their entirety.

Exemplary cell permeation peptides include, but are not limited to, RQIKIWFQNRRMKWKK (penetratin) (SEQ ID NO: 19); GRKKRRQRRRPPQC (Tat fragment 48-60) (SEQ ID NO: 20); GALFLGWL- GAAGSTMGAWSQPKKKRKV (signal sequence based peptide) (SEQ ID NO: 21); LLIILRRRIRKQAHAHSK (PVEC) (SEQ ID NO: 22); GWTLNSAGYLLKINLKA- LAALAKKIL (transportan) (SEQ ID NO: 23); KLALKLA- LKALKAALKLA (amphiphilic model peptide) (SEQ ID NO: 24); RRRRRRRRR (Arg9) (SEQ ID NO: 25); KFFKFFKFFK (Bacterial cell wall permeating peptide) (SEQ ID NO: 26); LLGDFFRK- SKEKIGKEFKRIVQRIKDFLRNLVPRTES (LL-37) (SEQ ID NO: 27); SWLSKTAKKLENSAKKRISEGIAIAI- QGGPR (cecropin P1) (SEQ ID NO: 28); ACYCRIPA- CIAGERRYGTCIYQGRLWAFCC (α-defensin) (SEQ ID NO: 29); DHYNCVSSGGQCLYSACPIFTKIQGT- CYRGKAKCCK (β-defensin) (SEQ ID NO: 30); RRRPRP- PYLPRPRPPPFFPPRLPPRIPPGFPPRFPPRFPGKR-NH2 (PR-39) (SEQ ID NO: 31); ILPWKWPWWPWRR-NH2 (indolicidin) (SEQ ID NO: 32); AAVALLPAVLLALLAP (RFGF) (SEQ ID NO: 33); AALLPVLLAAP (RFGF analogue) (SEQ ID NO: 34); and RKCRIVVIRVCR (bactenecin) (SEQ ID NO: 35).

Exemplary cationic groups include, but are not limited to, protonated amino groups, derived from e.g., O-AMINE (AMINE=NH$_2$; alkylamino, dialkylamino, heterocyclyl, arylamino, diaryl amino, heteroaryl amino, or diheteroaryl amino, ethylene diamine, polyamino); aminoalkoxy, e.g., O(CH$_2$)$_n$AMINE, (e.g., AMINE=NH$_2$; alkylamino, dialkylamino, heterocyclyl, arylamino, diaryl amino, heteroaryl amino, or diheteroaryl amino, ethylene diamine, polyamino); amino (e.g. NH$_2$; alkylamino, dialkylamino, heterocyclyl, arylamino, diaryl amino, heteroaryl amino, diheteroaryl amino, or amino acid); and NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino).

As used herein the term "targeting ligand" refers to any molecule that provides an enhanced affinity for a selected target, e.g., a cell, cell type, tissue, organ, region of the body, or a compartment, e.g., a cellular, tissue or organ compartment. Some exemplary targeting ligands include, but are not limited to, antibodies, antigens, folates, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands.

Carbohydrate based targeting ligands include, but are not limited to, D-galactose, multivalent galactose, N-acetyl-D-galactose (GalNAc), multivalent GalNAc, e.g. GalNAc2 and GalNAc3; D-mannose, multivalent mannose, multivalent lactose, N-acetyl-galactosamine, N-acetyl-gulucosamine, multivalent fucose, glycosylated polyaminoacids and lectins. The term multivalent indicates that more than one monosaccharide unit is present. Such monosaccharide subunits can be linked to each other through glycosidic linkages or linked to a scaffold molecule.

A number of folate and folate analogs amenable to the present invention as ligands are described in U.S. Pat. Nos. 2,816,110; 5,552,545; 6,335,434 and 7,128,893, contents of which are herein incorporated in their entireties by reference.

As used herein, the terms "PK modulating ligand" and "PK modulator" refers to molecules which can modulate the pharmacokinetics of the composition of the invention. Some exemplary PK modulator include, but are not limited to, lipophilic molecules, bile acids, sterols, phospholipid analogues, peptides, protein binding agents, vitamins, fatty acids, phenoxazine, aspirin, naproxen, ibuprofen, suprofen, ketoprofen, (S)-(+)-pranoprofen, carprofen, PEGS, biotin, and transthyretia-binding ligands (e.g., tetraiidothyroacetic acid, 2, 4, 6-triiodophenol and flufenamic acid). Oligomeric compounds that comprise a number of phosphorothioate intersugar linkages are also known to bind to serum protein, thus short oligomeric compounds, e.g. oligonucleotides of comprising from about 5 to 30 nucleotides (e.g., 5 to 25 nucleotides, preferably 5 to 20 nucleotides, e.g., 5, 6, 7, 8, 9, 10, 11, 12, 13, 14, 15, 16, 17, 18, 19, or 20 nucleotides), and that comprise a plurality of phosphorothioate linkages in the backbone are also amenable to the present invention as ligands (e.g. as PK modulating ligands). The PK modulating oligonucleotide can comprise at least 3, 4, 5, 6, 7, 8, 9, 10, 11, 12, 13, 14, 15 or more phosphorothioate and/or phosphorodithioate linkages. In some embodiments, all internucleotide linkages in PK modulating oligonucleotide are phosphorothioate and/or phosphorodithioates linkages. In addition, aptamers that bind serum components (e.g. serum proteins) are also amenable to the present invention as PK modulating ligands. Binding to serum components (e.g. serum proteins) can be predicted from albumin binding assays, such as those described in Oravcova, et al., Journal of Chromatography B (1996), 677: 1-27.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

The ligand or tethered ligand can be present on a monomer when said monomer is incorporated into a component of the multi-targeted molecule (e.g., an effector molecule or linker). In some embodiments, the ligand can be incorporated via coupling to a "precursor" monomer after said "precursor" monomer has been incorporated into a component of the multi-targeted molecule (e.g., an effector molecule or linker). For example, a monomer having, e.g., an amino-terminated tether (i.e., having no associated ligand), e.g., monomer-linker-NH$_2$ can be incorporated into into a component of the multi-targeted molecule (e.g., an effector molecule or linker). In a subsequent operation, i.e., after incorporation of the precursor monomer into a component of the multi-targeted molecule (e.g., an effector molecule or linker), a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction can be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

In some embodiments, ligand can be conjugated to nucleobases, sugar moieties, or internucleosidic linkages of the multi-targeted molecule. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. When a ligand is conjugated to a nucleobase, the preferred position is one that does not interfere with hybridization, i.e., does not interfere with the hydrogen bonding interactions needed for base pairing.

Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithioate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligonuclotides. Generally, an oligonucleotide is attached to a conjugate moiety by contacting a reactive group (e.g., OH, SH, amine, carboxyl, aldehyde, and the like) on the oligonucleotide with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

The ligand can be attached to the multi-targeted molecules via a carrier monomer, e.g., a ligand carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier monomer into the backbone, e.g., the phosphate, or modified phosphate, e.g., sulfur containing, backbone, of an oligonucleotide. A "tethering attachment point" (TAP) in refers to an atom of the carrier monomer, e.g., a carbon atom or a heteroatom (distinct from an atom which provides a backbone attachment point), that connects a selected moiety. The selected moiety can be, e.g., a carbohydrate, e.g. monosaccharide, disaccharide, trisaccharide, tetrasaccharide, oligosaccharide and polysaccharide. Optionally, the selected moiety is connected by an intervening tether to the carrier monomer. Thus, the carrier will often include a functional group, e.g., an amino group, or generally, provide a bond, that is suitable for incorporation or tethering of another chemical entity, e.g., a ligand to the constituent atom.

Representative U.S. patents that teach the preparation of conjugates of nucleic acids include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,149,782; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,672,662; 5,688,941; 5,714,166; 6,153,737; 6,172,208; 6,300,319; 6,335,434; 6,335,437; 6,395,437; 6,444,806; 6,486,308; 6,525,031; 6,528,631; 6,559, 279; contents of which are herein incorporated in their entireties by reference.

In certain embodiments, the multi-targeted molecule comprises a ligand having a structure shown below:

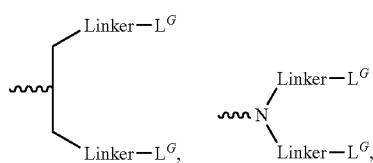

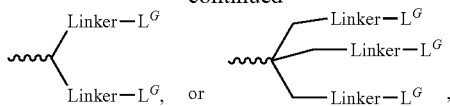

wherein:
$L^G$ is independently for each occurrence a ligand, e.g., carbohydrate, e.g. monosaccharide, disaccharide, trisaccharide, tetrasaccharide, polysaccharide; and
Z', Z", Z''' and Z'''' are each independently for each occurrence O or S.

In certain embodiments, the multi-targeted molecule comprises a ligand of Formula (II), (III), (IV) or (V):

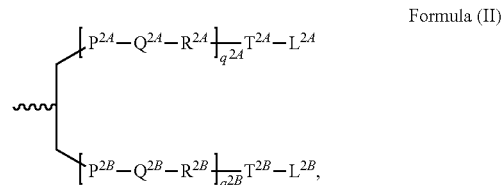
Formula (II)

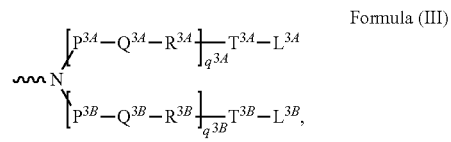
Formula (III)

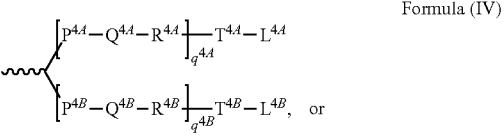
Formula (IV)

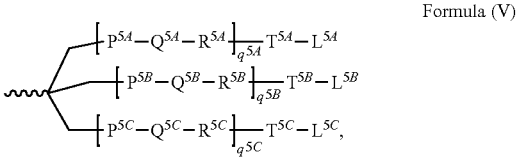
Formula (V)

wherein:
$q^{2A}$, $q^{2B}$, $q^{3A}$, $q^{3B}$, $q^{4A}$, $q^{4B}$, $q^{5A}$, $q^{5B}$ and $q^{5C}$ represent independently for each occurrence 0-20 and wherein the repeating unit can be the same or different;

Q and Q' are independently for each occurrence is absent, —($P^7$-$Q^7$-$R^7$)$_p$-$T^7$- or -$T^7$-$Q^7$-$T^{7'}$-B-$T^8$-$Q^8$-$T^{8'}$;
$P^{2A}$, $P^{2B}$, $P^{3A}$, $P^{3B}$, $P^{4A}$, $P^{4B}$, $P^{5A}$, $P^{5B}$, $P^{5C}$, $P^7$, $T^{2A}$, $T^{2B}$, $T^{3A}$, $T^{3B}$, $T^{4A}$, $T^{4B}$, $T^{4A}$, $T^{5B}$, $T^{5C}$, $T^7$, $T^{7'}$, $T^8$ and $T^{8'}$ are each independently for each occurrence absent, CO, NH, O, S, OC(O), NHC(O), $CH_2$, $CH_2NH$ or $CH_2O$;
B is —$CH_2$—N($B^L$)—$CH_2$—;
$B^L$ is -$T^B$-$Q^B$-$T^{B'}$-$R^x$;
$Q^{2A}$, $Q^{2B}$, $Q^{3A}$, $Q^{3B}$, $Q^{4A}$, $Q^{4B}$, $Q^{5A}$, $Q^{5B}$, $Q^{5C}$, $Q^7$, $Q^8$ and $Q^B$ are independently for each occurrence absent, alkylene, substituted alkylene and wherein one or more methylenes can be interrupted or terminated by one or more of O, S, S(O), $SO_2$, N($R^N$), C(R')=C(R'), C≡C or C(O);
$T^B$ and $T^{B'}$ are each independently for each occurrence absent, CO, NH, O, S, OC(O), OC(O)O, NHC(O), NHC(O) NH, NHC(O)O, $CH_2$, $CH_2NH$ or $CH_2O$;
$R^x$ is a lipophile (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid,O3-(oleoyl)litho-cholic acid, O3-(oleoyl)cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, Friedelin, epifriedelanol derivatized lithocholic acid), or a cationic lipid;

$R^1, R^2, R^{2A}, R^{2B}, R^{3A}, R^{3B}, R^{4A}, R^{4B}, R^{5A}, R^{5B}, R^{5C}, R^7$ are each independently for each occurrence absent, NH, O, S, CH$_2$, C(O)O, C(O)NH, NHCH(R$^a$)C(O), —C(O)—CH(R$^a$)—NH—, CO, CH=N—O,

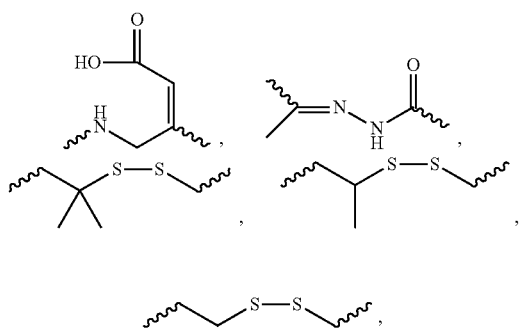

or heterocyclyl;

$L^1, L^{2A}, L^{2B}, L^{3A}, L^{3B}, L^{4A}, L^{4B}, L^{5A}, L^{5B}$ and $L^{5C}$ are each independently for each occurrence a carbohydrate, e.g., monosaccharide, disaccharide, trisaccharide, tetrasaccharide, oligosaccharide and polysaccharide;

R' and R'' are each independently H, $C^1$-$C_6$ alkyl, OH, SH, or N(R$^N$)$_2$, $R^N$ is independently for each occurrence H, methyl, ethyl, propyl, isopropyl, butyl or benzyl;

$R^a$ is H or amino acid side chain;

Z', Z'', Z''' and Z'''' are each independently for each occurrence O or S;

p represent independently for each occurrence 0-20.

In certain embodiments, the multi-targeted molecule comprises a ligand of structure:

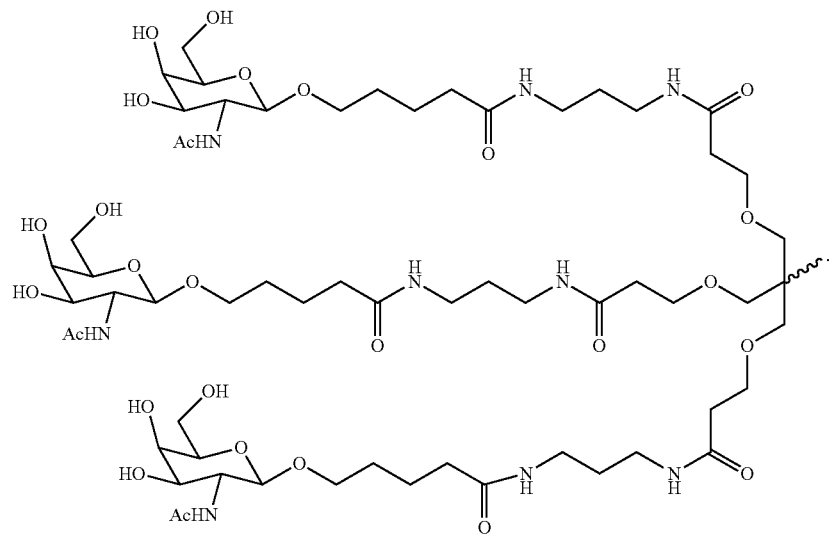 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In certain embodiments, the multi-targeted molecule comprises a ligand of structure:

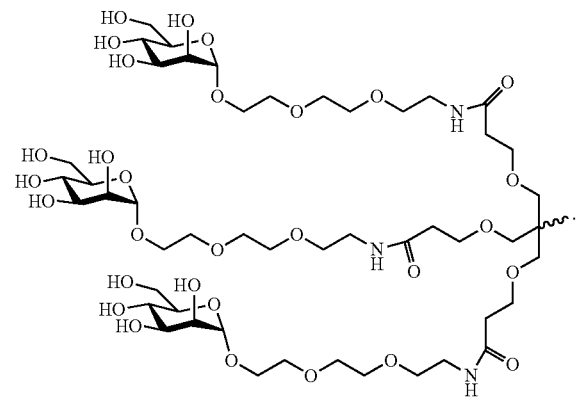

In certain embodiments, the multi-targeted molecule comprises a ligand of structure:

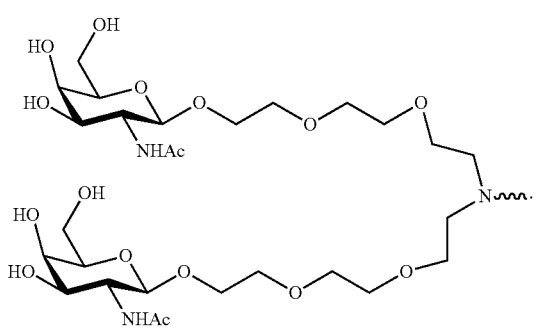

In certain embodiments, the multi-targeted molecule comprises a ligand of structure:

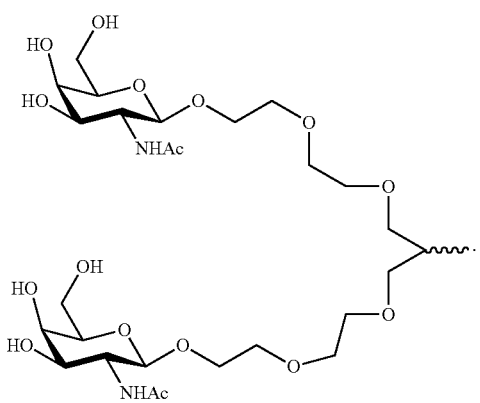
In certain embodiments, the multi-targeted molecule comprises a ligand of structure:
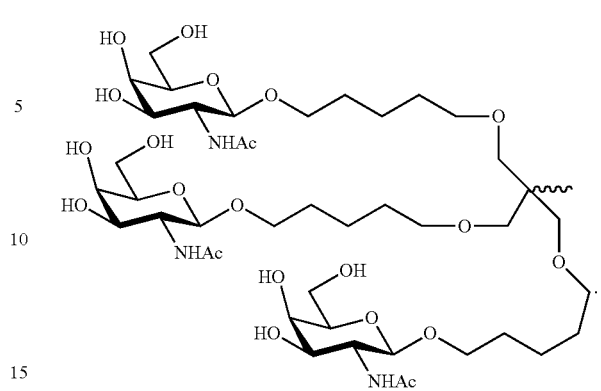
In certain embodiments, the multi-targeted molecule comprises a ligand of structure:
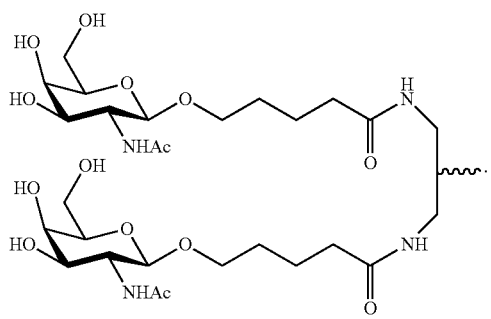
In certain embodiments, the multi-targeted molecule comprises a ligand of structure:
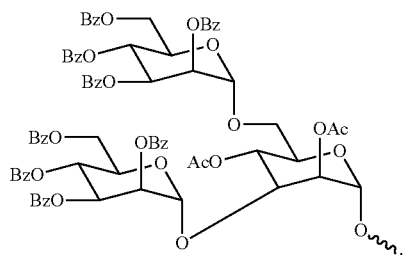
In certain embodiments, the multi-targeted molecule comprises a ligand of structure:
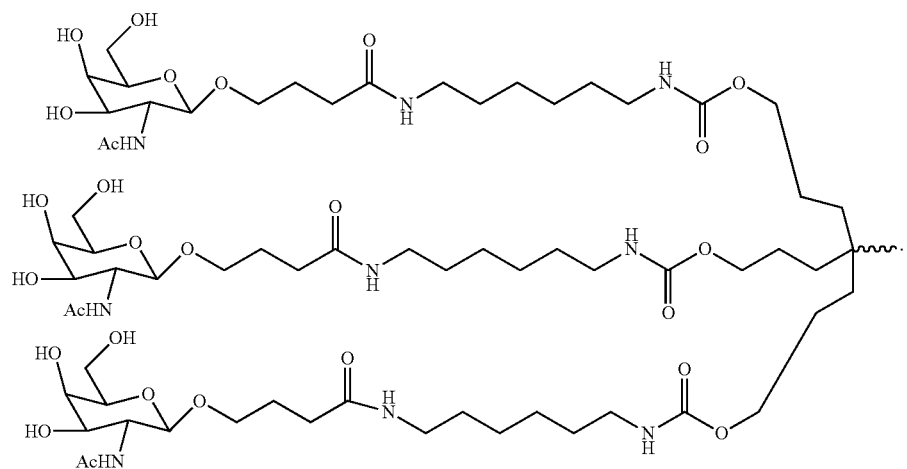 [SMILES: CC(=O)NC1C(OCCCC(=O)NCCCCCCNC(=O)OCCCC(C)(CCCOC(=O)NCCCCCCNC(=O)CCCOC2OC(CO)C(O)C(O)C2NC(C)=O)CCCOC(=O)NCCCCCCNC(=O)CCCOC2OC(CO)C(O)C(O)C2NC(C)=O)OC(CO)C(O)C1O]

In certain embodiments, the multi-targeted molecule comprises a ligand of structure:
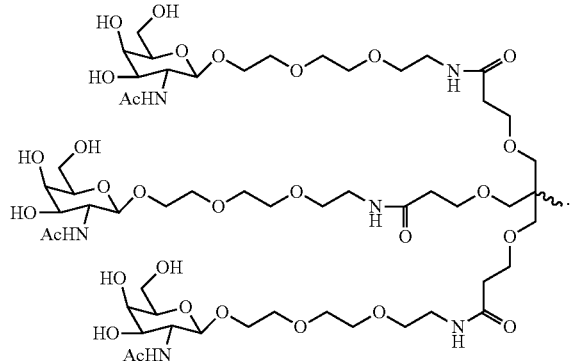 [SMILES: CC(=O)NC1C(OCCOCCOCCNC(=O)CCOCC(C)(COCCC(=O)NCCOCCOCCOC2OC(CO)C(O)C(O)C2NC(C)=O)COCCC(=O)NCCOCCOCCOC2OC(CO)C(O)C(O)C2NC(C)=O)OC(CO)C(O)C1O]
In certain embodiments, the multi-targeted molecule comprises a ligand of structure:
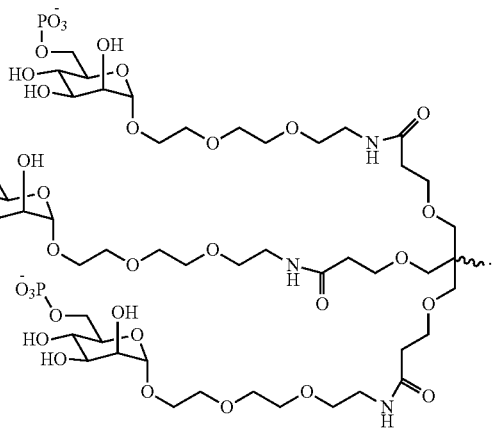
In certain embodiments, the multi-targeted molecule comprises a ligand of structure:
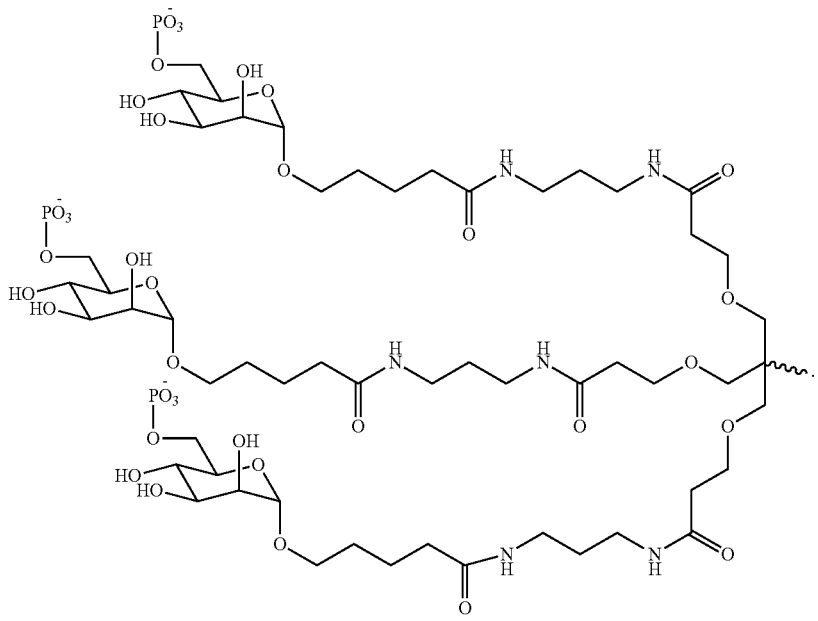
In certain embodiments, the multi-targeted molecule comprises a monomer of structure:
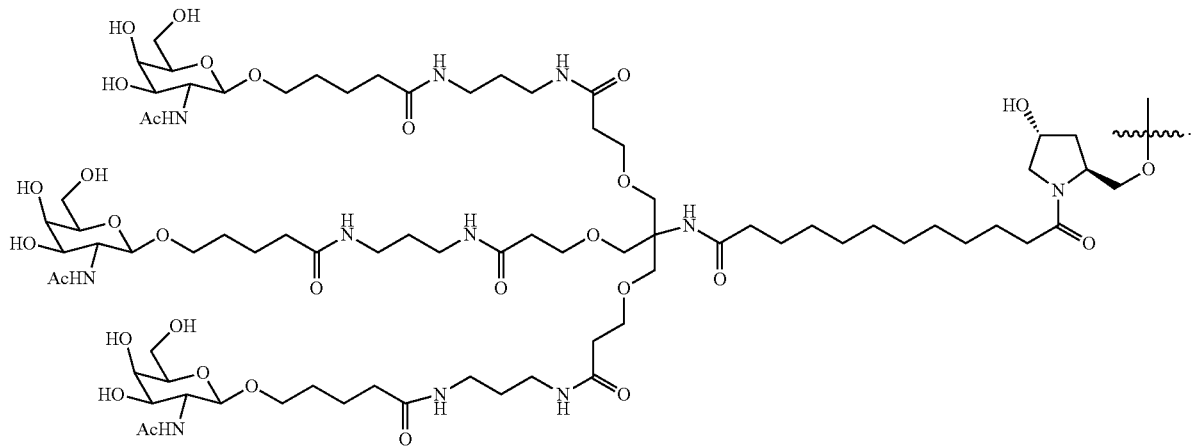 [SMILES: *OC[C@@H]1C[C@@H](O)CN1C(=O)CCCCCCCCCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]

In certain embodiments, the multi-targeted molecule comprises a ligand of structure:
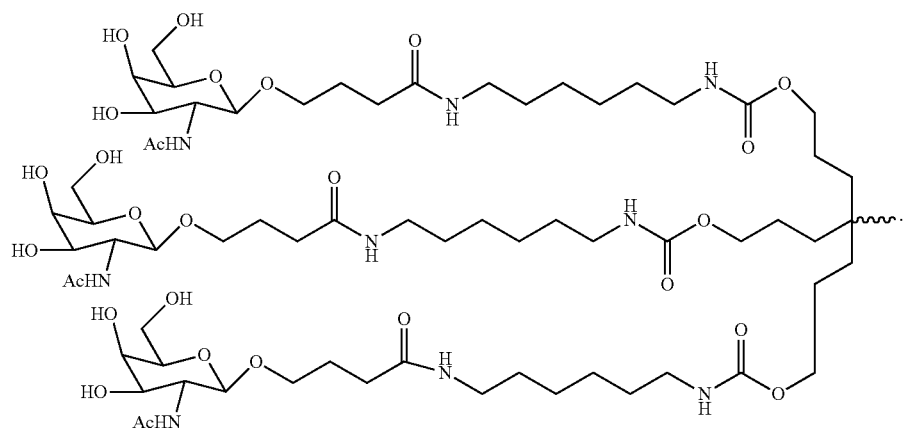 [SMILES: CC(=O)NC1C(OCCCC(=O)NCCCCCCNC(=O)OCCCC(C)(CCCOC(=O)NCCCCCCNC(=O)CCCOC2OC(CO)C(O)C(O)C2NC(C)=O)CCCOC(=O)NCCCCCCNC(=O)CCCOC2OC(CO)C(O)C(O)C2NC(C)=O)OC(CO)C(O)C1O]
Exemplary Ligand Monomers
In certain embodiments, the multi-targeted molecule comprises a monomer of structure:
MONOMER 1
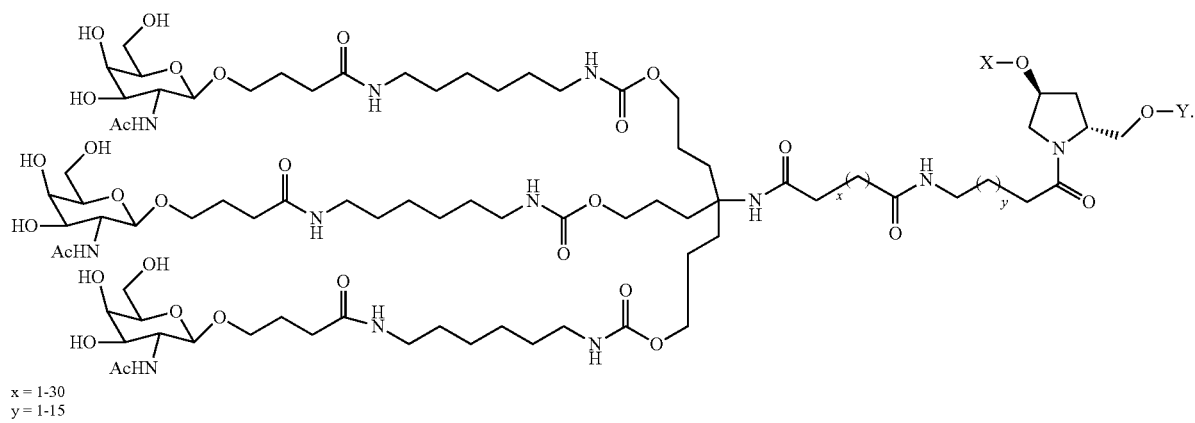
x = 1-30
y = 1-15
In certain embodiments, the multi-targeted molecule comprises a monomer of structure:
MONOMER 2
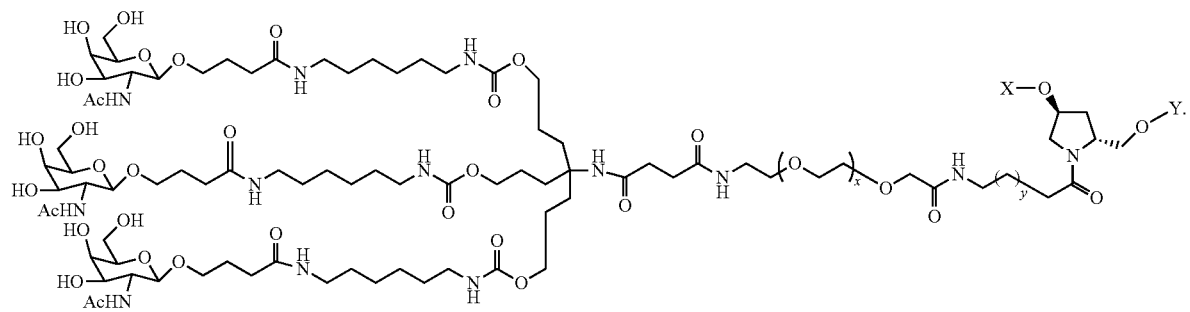
x = 1-30
y = 1-15

In certain embodiments, the multi-targeted molecule comprises a monomer of structure:
MONOMER 3
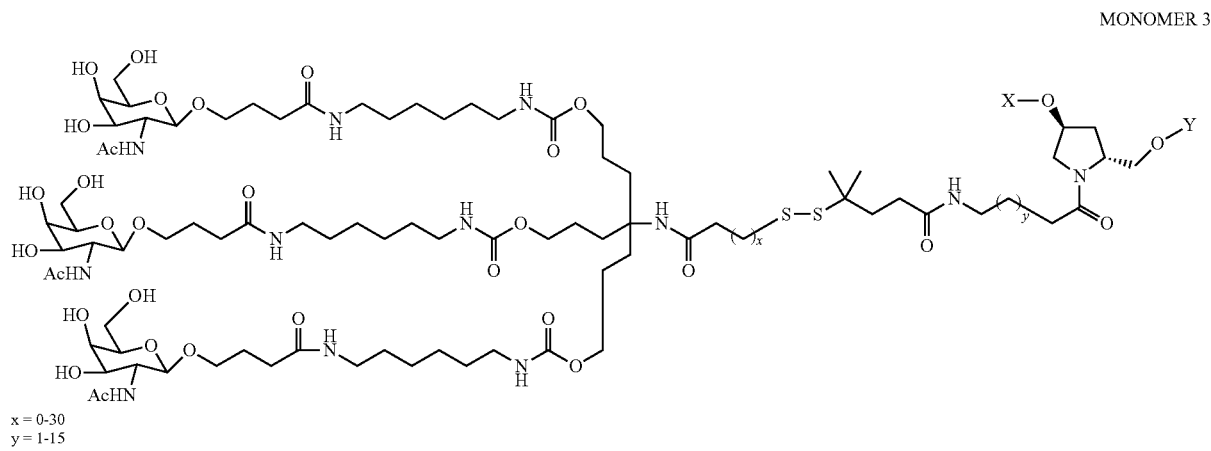
x = 0-30
y = 1-15
In certain embodiments, the multi-targeted molecule comprises a monomer of structure:
MONOMER 4
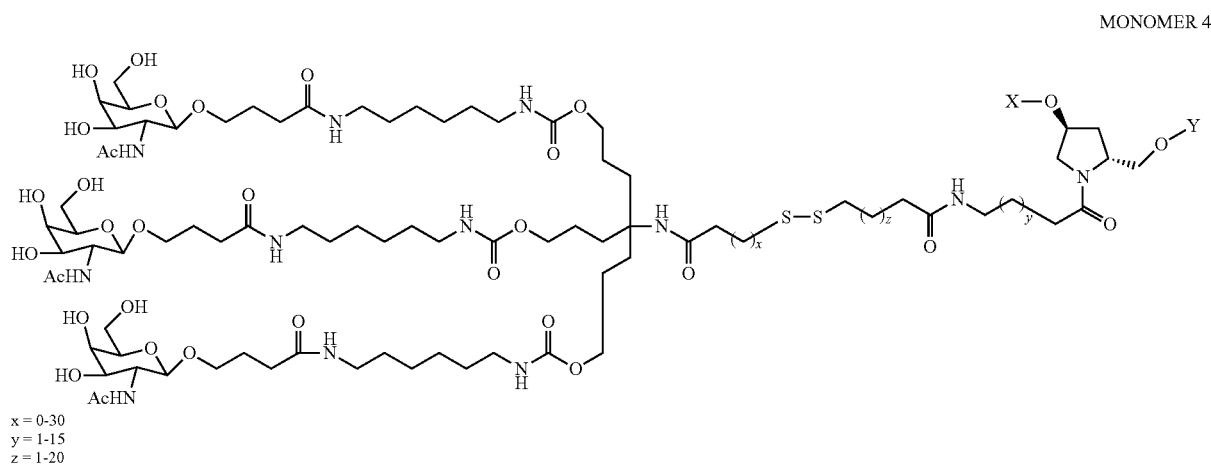
x = 0-30
y = 1-15
z = 1-20
In certain embodiments, the multi-targeted molecule comprises a monomer of structure:
MONOMER 5
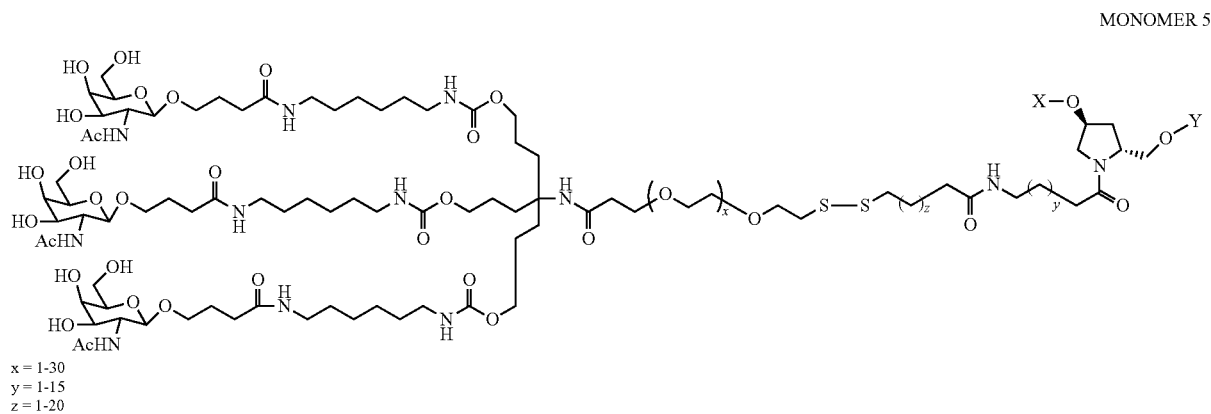
x = 1-30
y = 1-15
z = 1-20

In certain embodiments, the multi-targeted molecule comprises a monomer of structure:

MONOMER 6

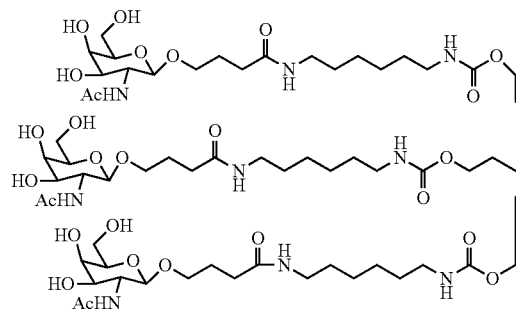
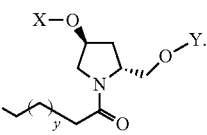

x = 1-30
y = 1-15
z = 1-20

In certain embodiments, the multi-targeted molecule comprises a ligand of structure:

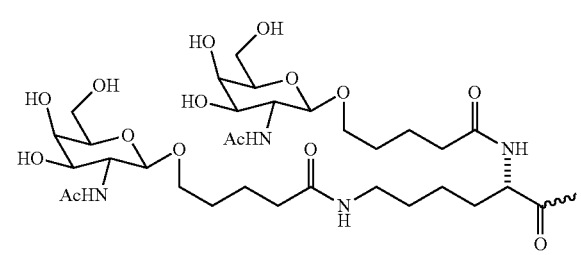

In certain embodiments, the multi-targeted molecule comprises a ligand of structure:

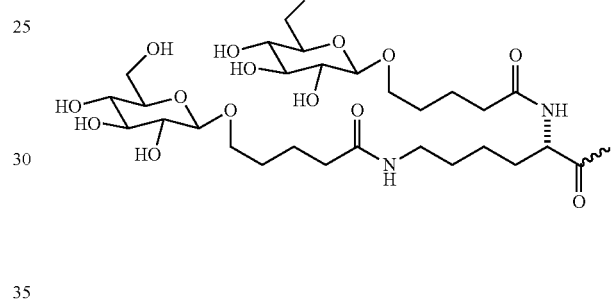

In certain embodiments, the multi-targeted molecule comprises a ligand of structure:

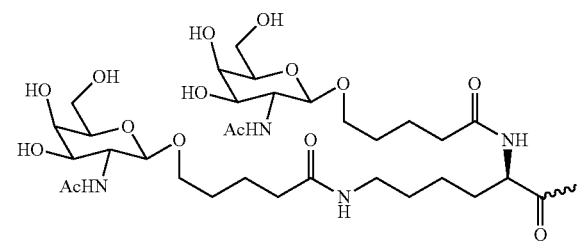

In certain embodiments, the multi-targeted molecule comprises a ligand of structure:

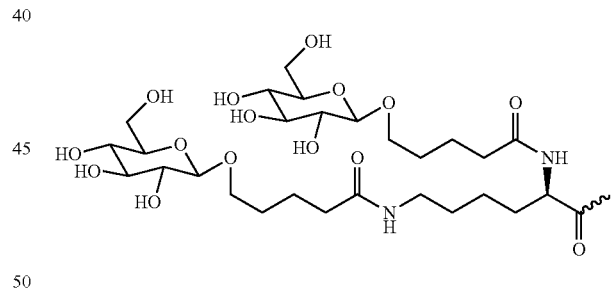

In certain embodiments, the multi-targeted molecule comprises a ligand of structure:

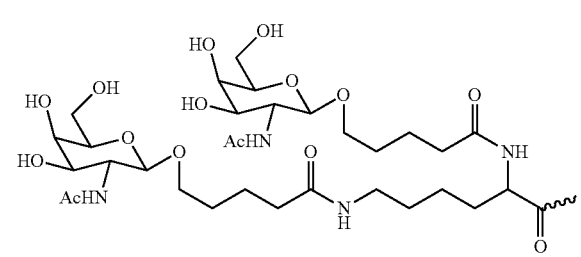

In certain embodiments, the multi-targeted molecule comprises a ligand of structure:

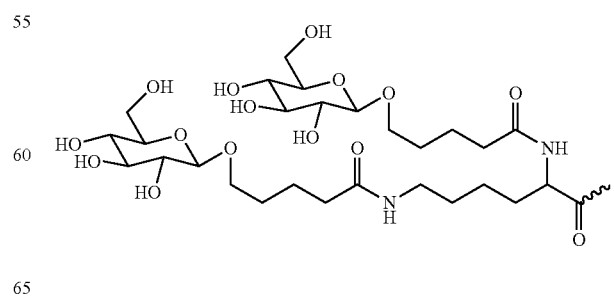

In certain embodiments, the multi-targeted molecule comprises a ligand of structure:

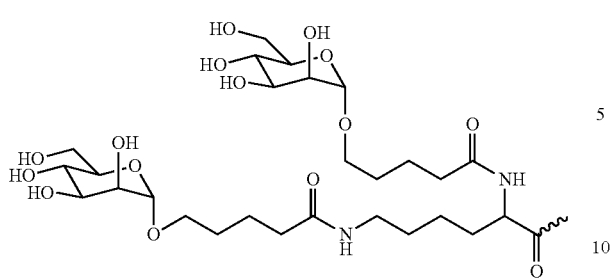

In certain embodiments, the multi-targeted molecule comprises a ligand of structure:

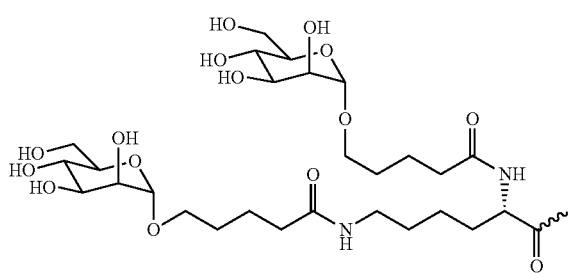

In certain embodiments, the multi-targeted molecule comprises a ligand of structure:

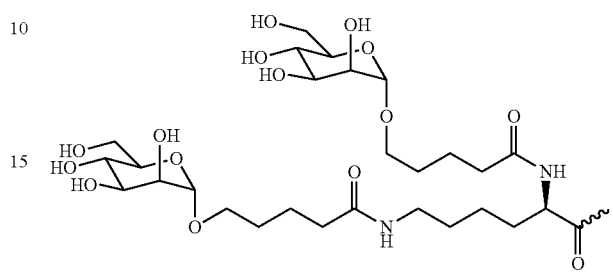

In certain embodiments, the multi-targeted molecule comprises a monomer of structure:

MONOMER 7

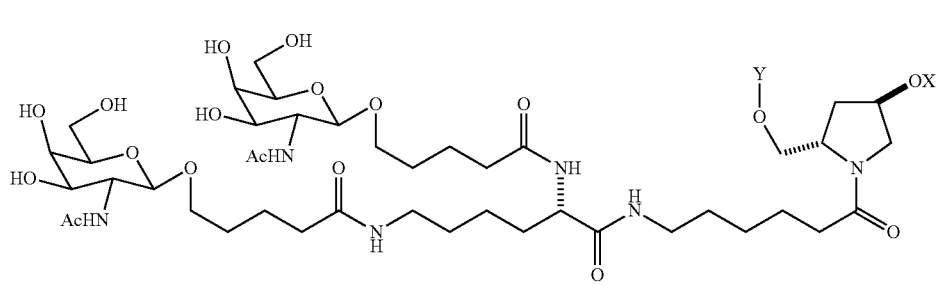

In certain embodiments, the multi-targeted molecule comprises a monomer of structure:

MONOMER 8

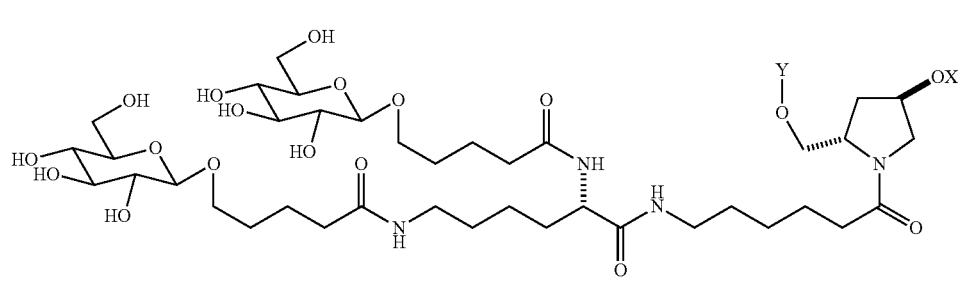

In certain embodiments, the multi-targeted molecule comprises a monomer of structure:

MONOMER 9

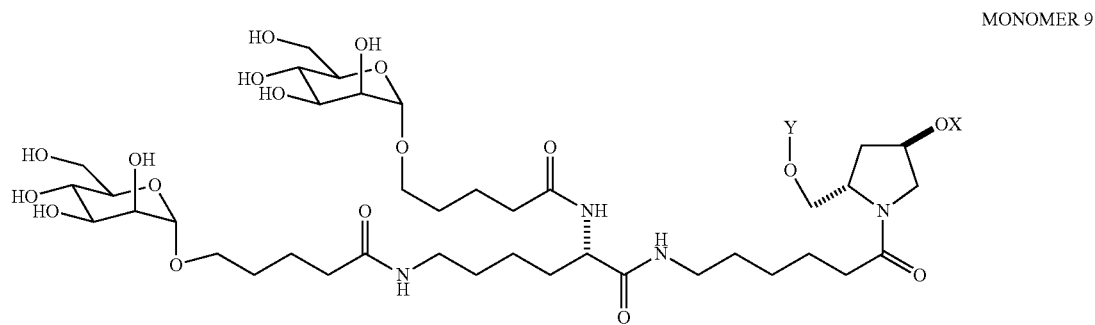

In certain embodiments, the multi-targeted molecule comprises a monomer of structure:

MONOMER 10

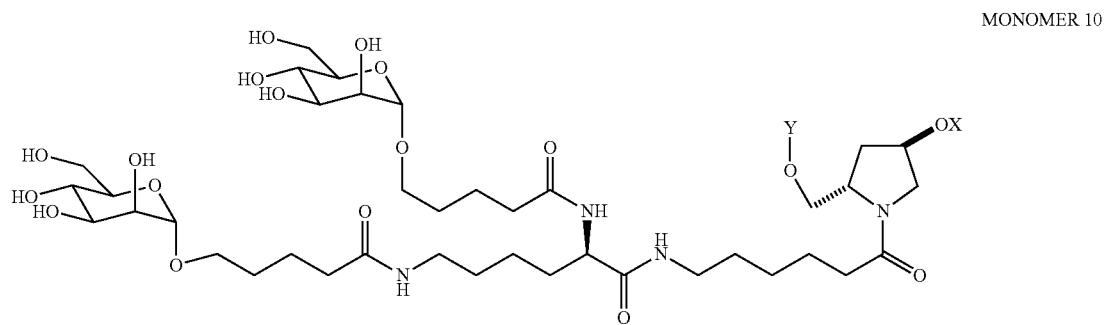

In certain embodiments, the multi-targeted molecule comprises a monomer of structure:

MONOMER 11

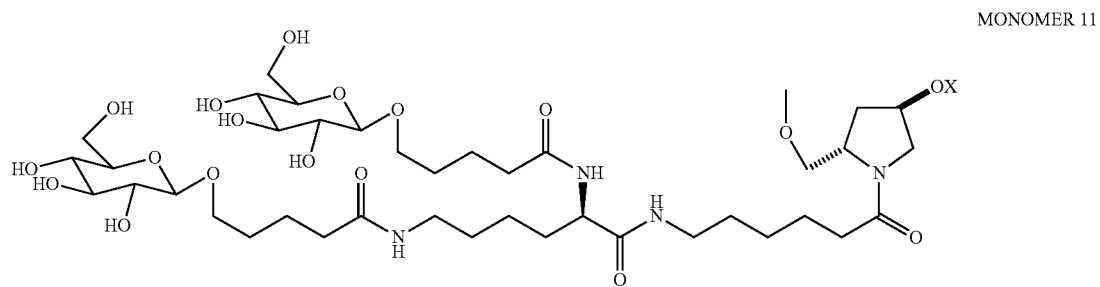

In certain embodiments, the multi-targeted molecule comprises a monomer of structure:

MONOMER 12

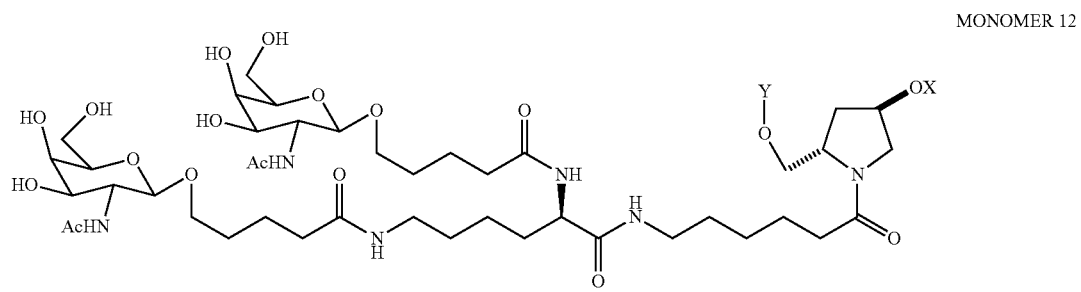

In some embodiments both $L^{2A}$ and $L^{2B}$ are different.

In some preferred embodiments both $L^{3A}$ and $L^{3B}$ are the same.

In some embodiments both $L^{3A}$ and $L^{3B}$ are different.

In some preferred embodiments both $L^{4A}$ and $L^{4B}$ are the same.

In some embodiments both $L^{4A}$ and $L^{4B}$ are different.

In some preferred embodiments all of $L^{5A}$, $L^{5B}$ and $L^{5C}$ are the same.

In some embodiments two of $L^{5A}$, $L^{5B}$ and $L^{5C}$ are the same

In some embodiments $L^{5A}$ and $L^{5B}$ are the same.

In some embodiments $L^{5A}$ and $L^{5C}$ are the same.

In some embodiments $L^{5B}$ and $L^{5C}$ are the same.

In certain embodiments, the multi-targeted molecule comprises a monomer of structure:

In certain embodiments, the multi-targeted molecule comprises a monomer of structure:

MONOMER 15

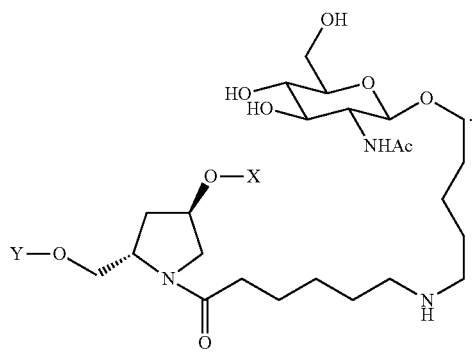

In certain embodiments, the multi-targeted molecule comprises a monomer of structure:

MONOMER 13

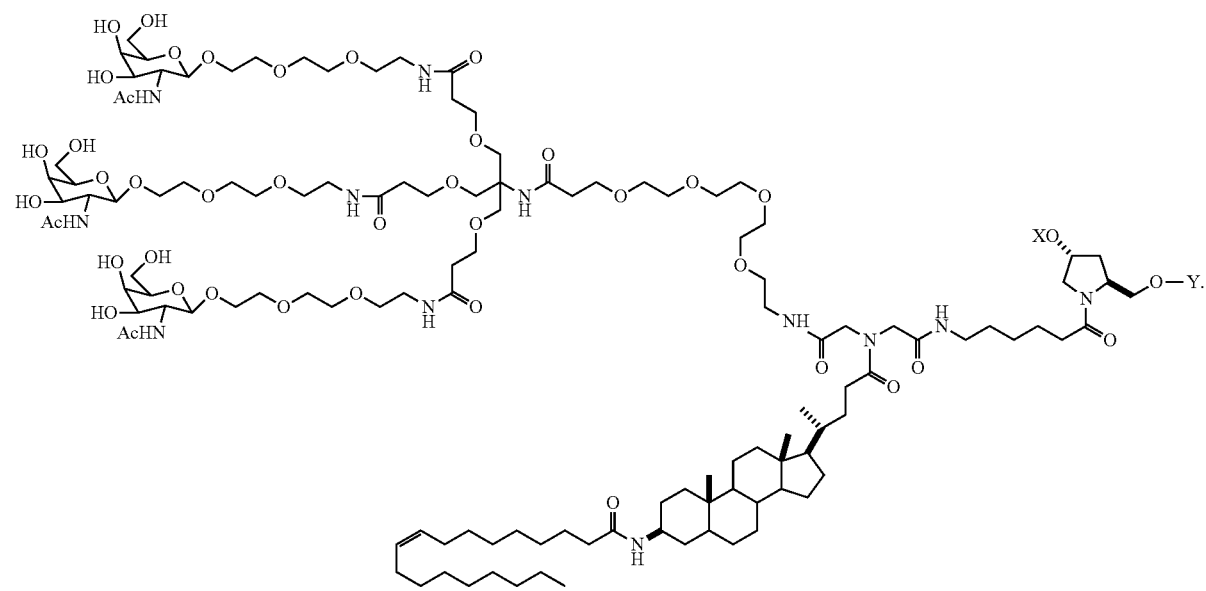

In certain embodiments, the multi-targeted molecule comprises a monomer of structure:

MONOMER 14

MONOMER 16

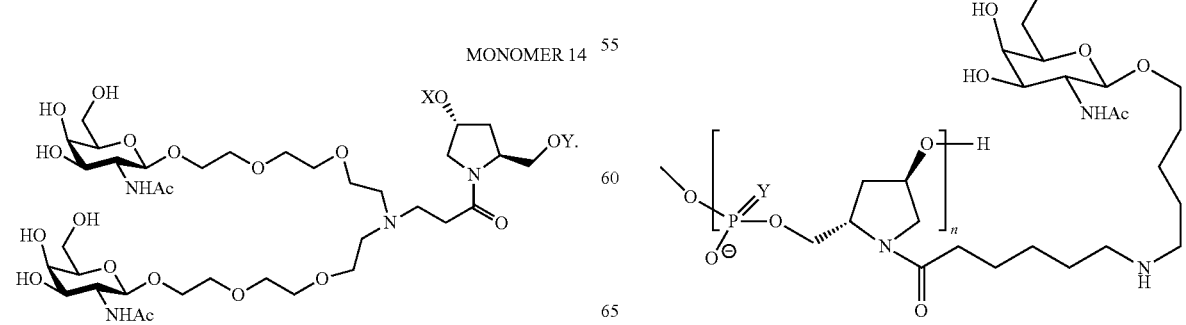

wherein Y is O or S and n is 1-6.

In certain embodiments, the multi-targeted molecule comprises a monomer of structure:

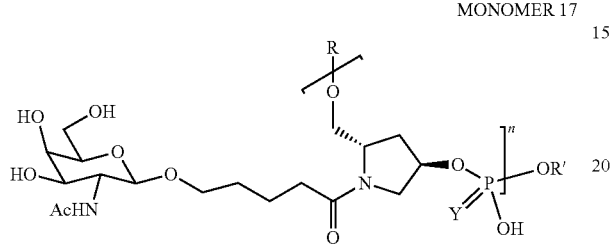

MONOMER 17

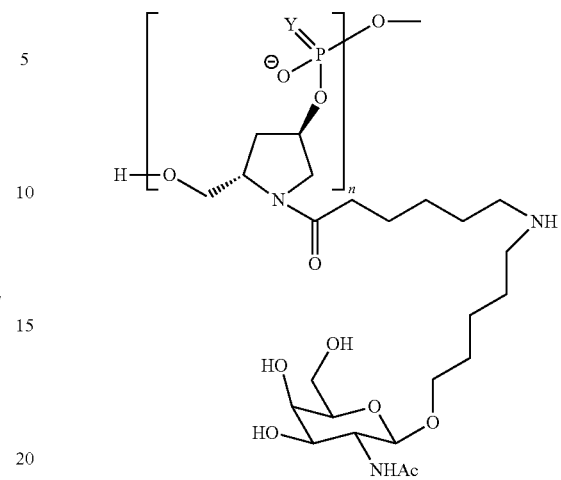

MONOMER 18 wherein Y is O or S and n is 1-6.

In certain embodiments, the multi-targeted molecule comprises at least 1, 2, 3 or 4 monomer of structure:

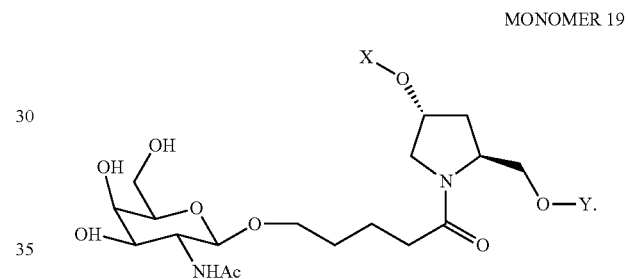

MONOMER 19 wherein Y=O or S. n is 1-6, R is hydrogen or nucleic acid, R' is nucleic acid.

In certain embodiments, the multi-targeted molecule comprises a monomer of structure:

In certain embodiments, the multi-targeted molecule comprises a monomer of structure:

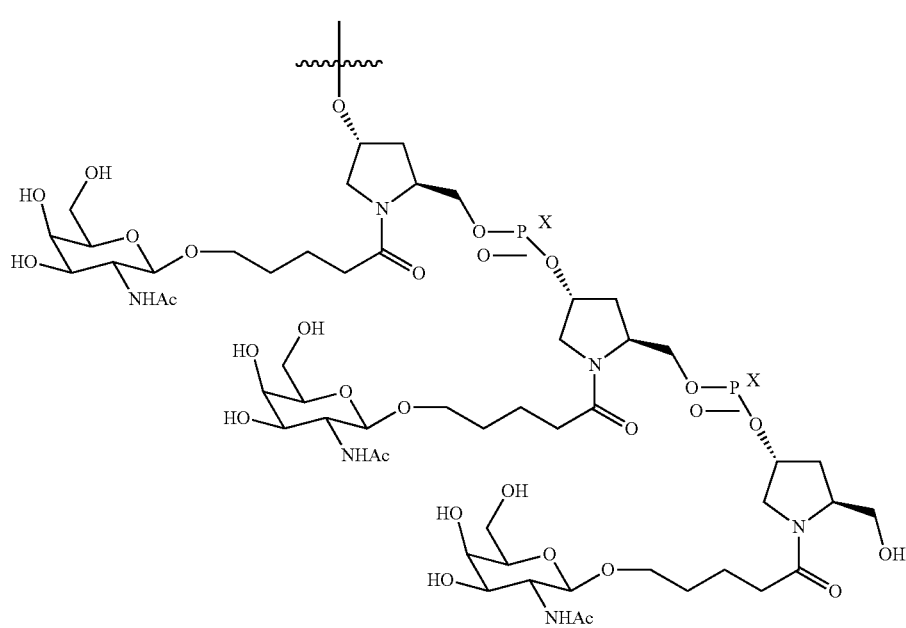

MONOMER 20 wherein X is O or S.

In certain embodiments, the multi-targeted molecule comprises a monomer of structure:

MONOMER 21

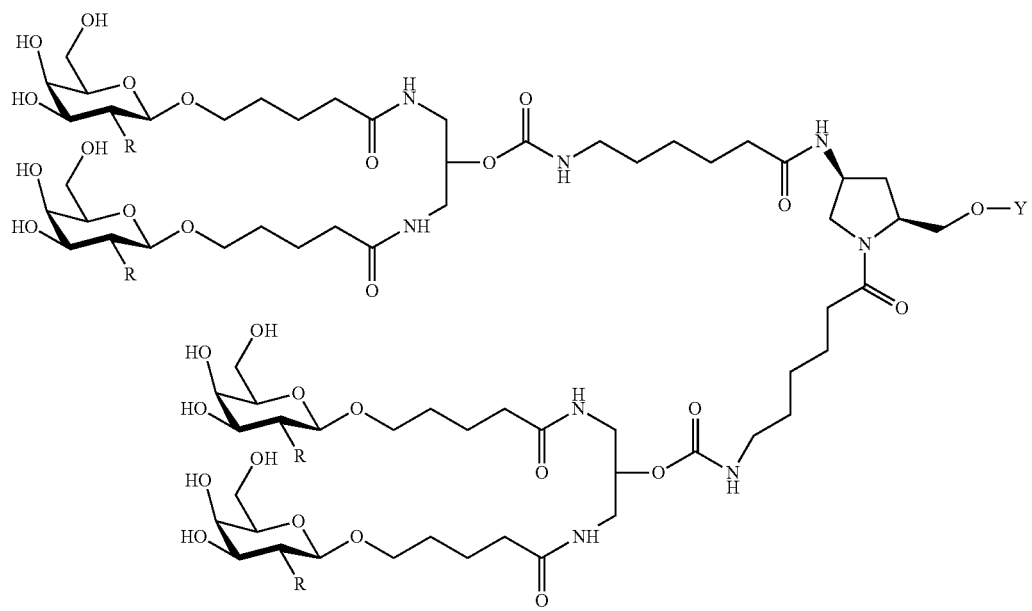

wherein R is OH or NHCOOH.

In certain embodiments, the multi-targeted molecule comprises a monomer of structure:

MONOMER 22

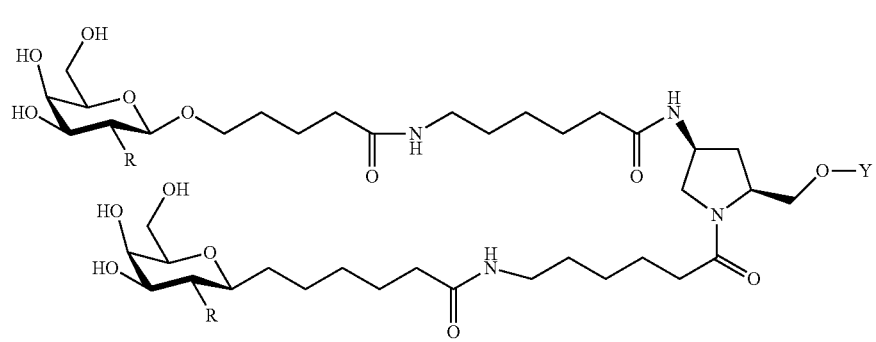

wherein R is OH or NHCOOH.

In certain embodiments, the multi-targeted molecule comprises a monomer of structure:

Formula (VII)

MONOMER 23

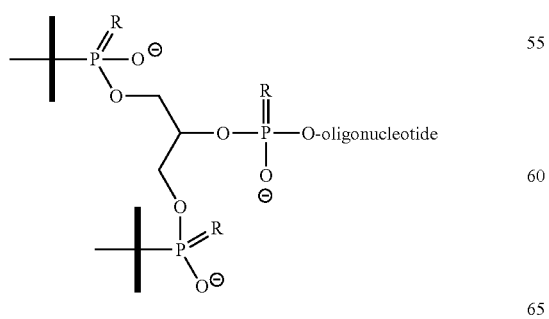

wherein R is O or S.

In certain embodiments, the multi-targeted molecule comprises a monomer of structure:
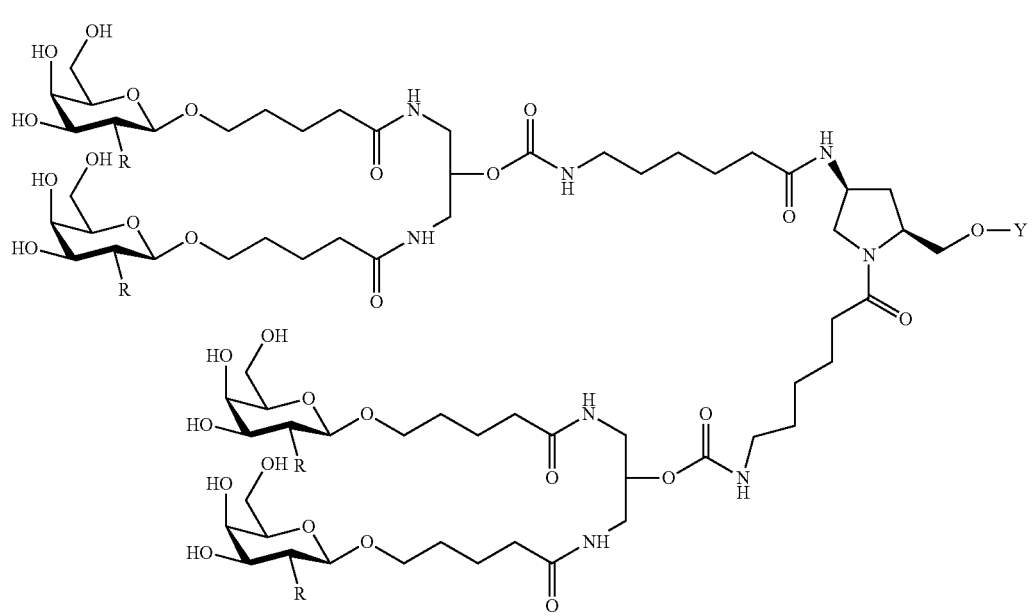
MONOMER 24
wherein R is OH or NHCOOH.
In certain embodiments, the multi-targeted molecule comprises a monomer of structure:
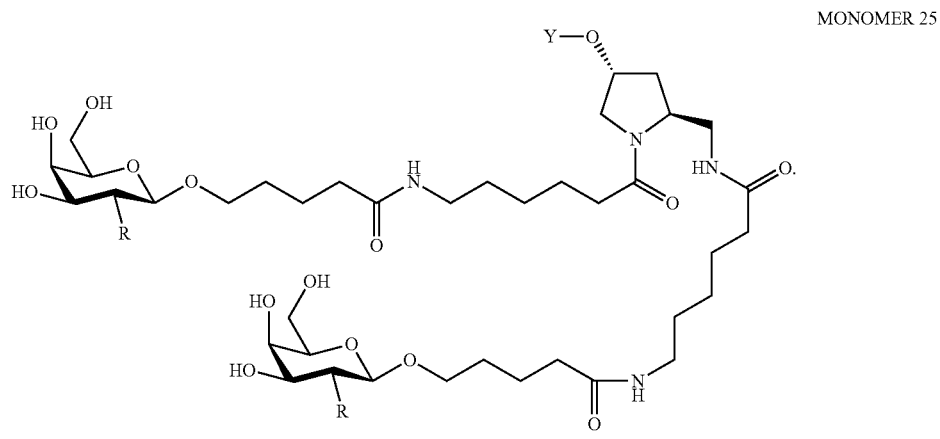
MONOMER 25
In certain embodiments, the multi-targeted molecule comprises a monomer of structure:
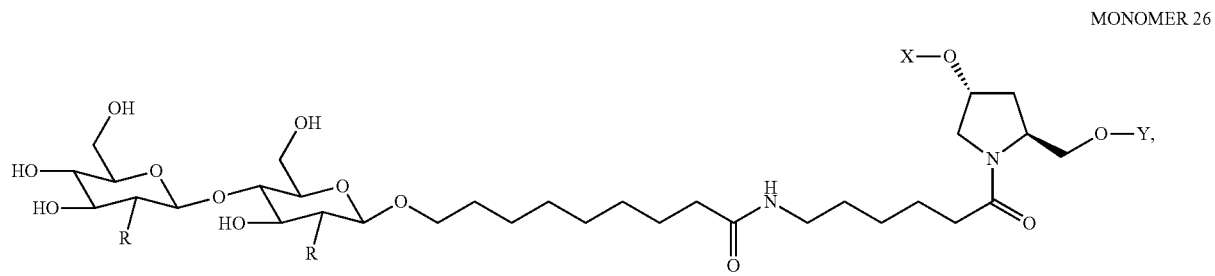
MONOMER 26
wherein R is OH or NHCOOH.

In certain embodiments, the multi-targeted molecule comprises a monomer of structure:
MONOMER 27
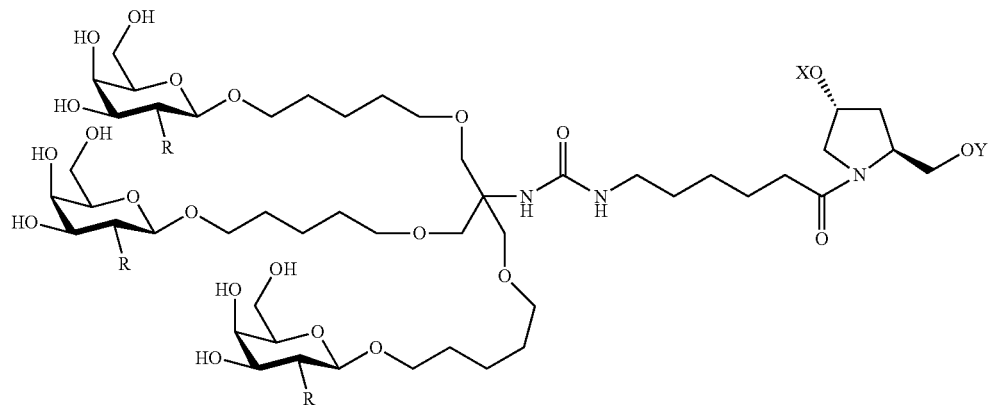
wherein R is OH or NHCOOH.
In certain embodiments, the multi-targeted molecule comprises a monomer of structure:
MONOMER 28
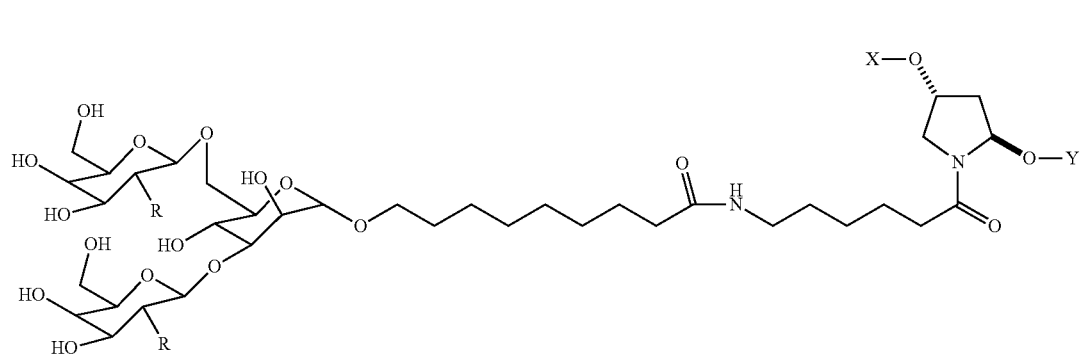
wherein R is OH or NHCOOH.
In certain embodiments, the multi-targeted molecule comprises a monomer of structure:
MONOMER 29
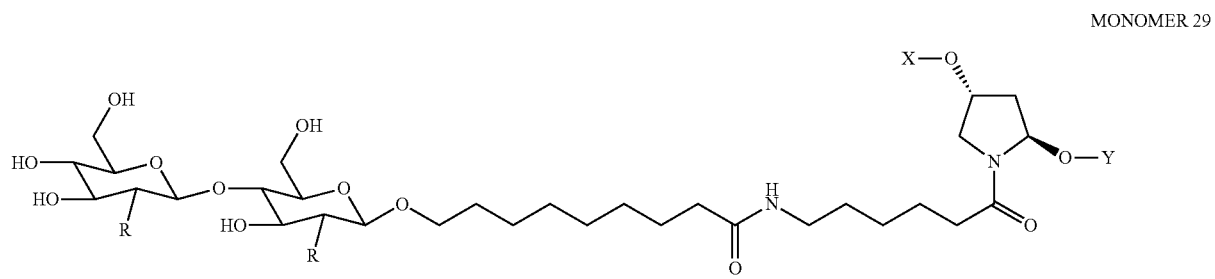
wherein R is OH or NHCOOH.

In certain embodiments, the multi-targeted molecule comprises a monomer of structure:

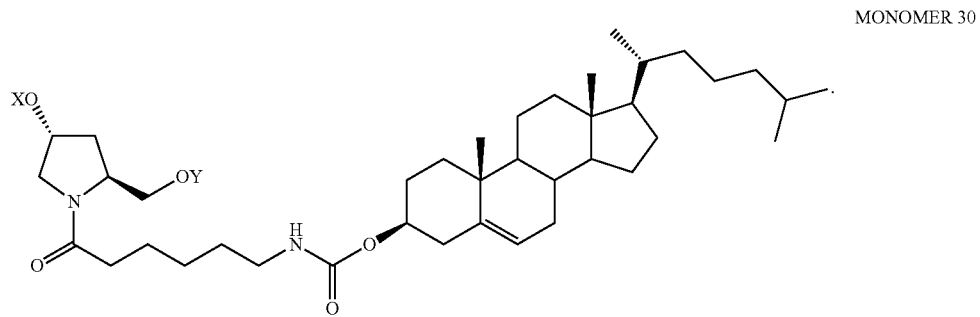

MONOMER 30

In the above described monomers, X and Y are each independently for each occurrence H, a protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a polymer, a nucleotide, a nucleoside, or an oligonucleotide; and Z' and Z" are each independently for each occurrence O or S.

In certain embodiments, the multi-targeted molecule is conjugated with a ligand of structure:

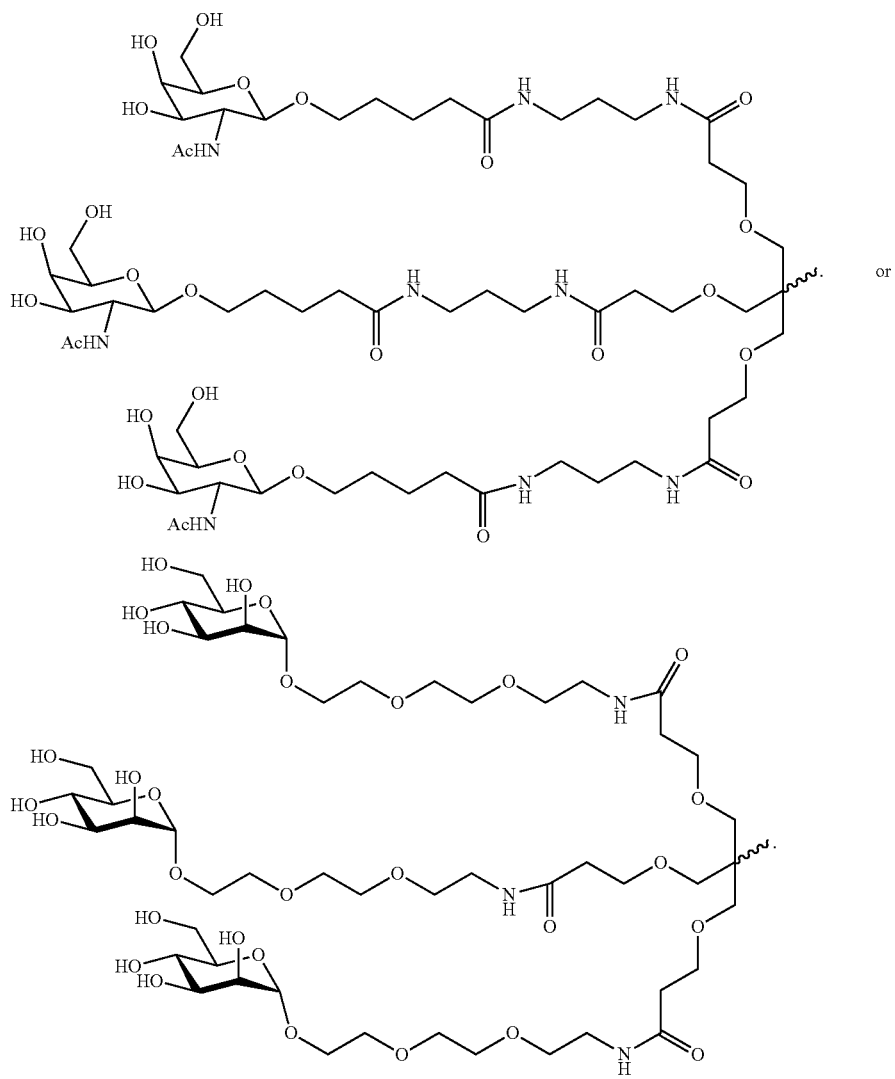

In certain embodiments, the multi-targeted molecule comprises a ligand of structure:
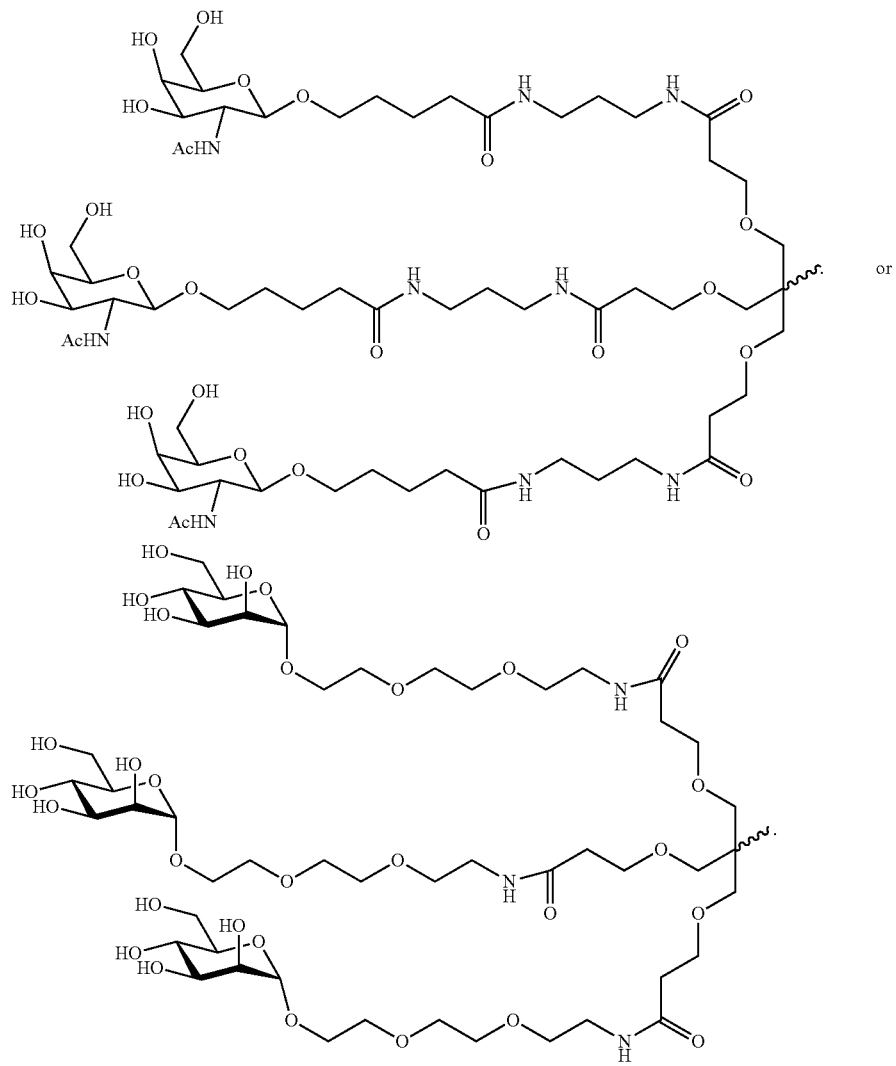
In certain embodiments, the multi-targeted molecule comprises a monomer of structure:
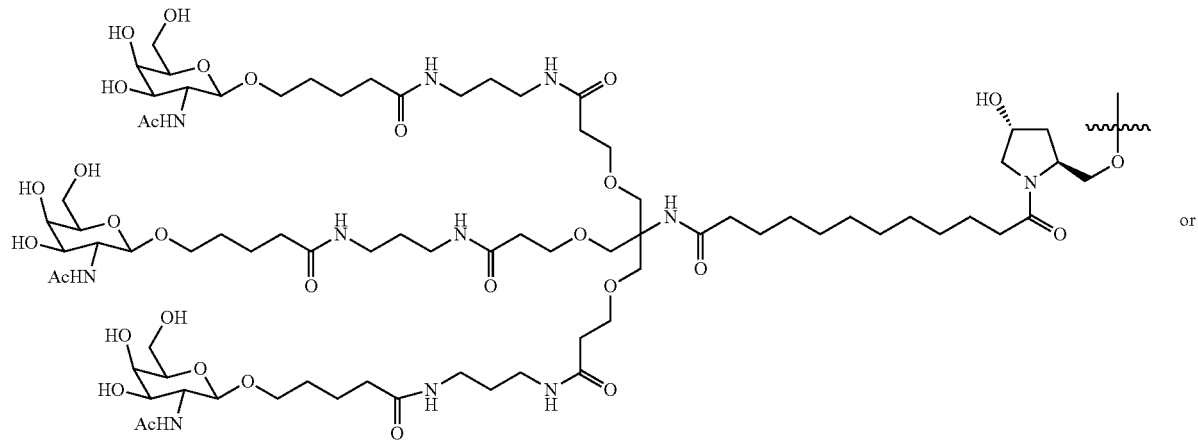

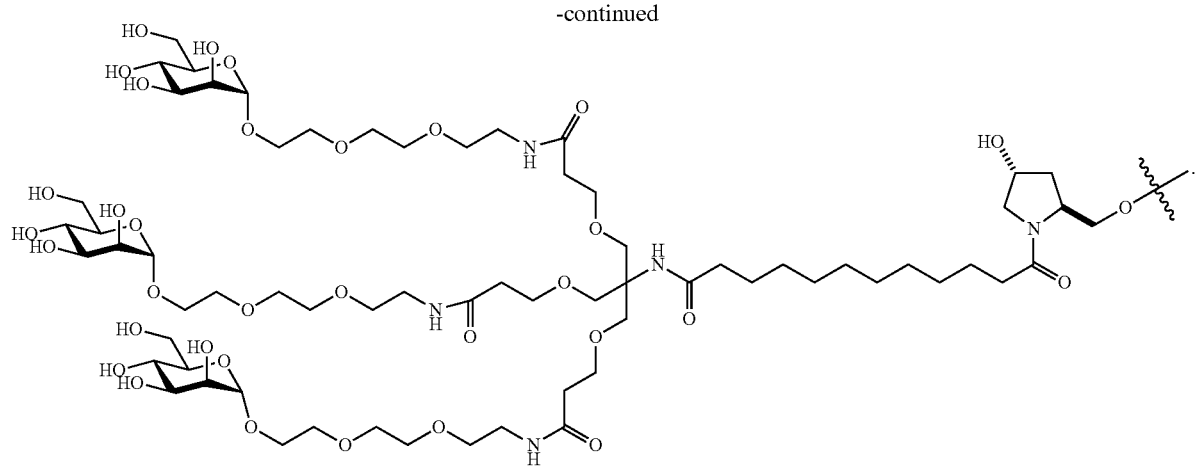

Synthesis of above described ligands and monomers is described, for example, in U.S. Pat. No. 8,106,022, content of which is incorporated herein by reference in its entirety.

Linking groups or bifunctional linking moieties such as those known in the art are amenable to the compounds provided herein. Linking groups are useful for attachment of chemical functional groups, conjugate groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted C1-C10 alkyl, substituted or unsubstituted C2-C10 alkenyl or substituted or unsubstituted C2-C10 alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, the ligand is conjugated with the multi-targeted molecule via a linker.

As used herein, the term "linker" means an organic moiety that connects two parts of a compound. Linkers typically comprise a direct bond or an atom such as oxygen or sulfur, a unit such as $NR^1$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In some embodiments, the linker is $—[(P-Q''-R)_q—X—(P'-Q'''-R')_{q'}]_q-T-$, wherein: P, R, T, P', R' and T are each independently for each occurrence absent, CO, NH, O, S, OC(O), NHC(O), $CH_2$, $CH_2NH$, $CH_2O$; $NHCH(R^a)C(O)$, $—C(O)—CH(R^a)—NH—$, $CH=N—O$,

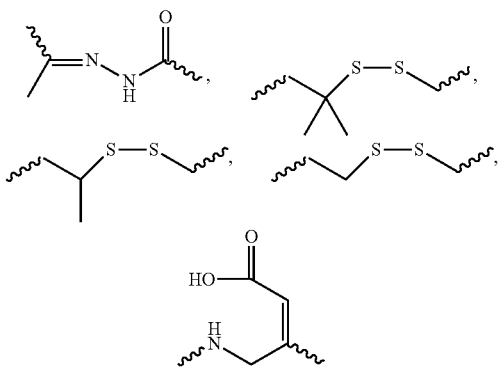

or heterocyclyl; Q" and Q''' are each independently for each occurrence absent, $—(CH_2)_n—$, $—C(R^1)(R^2)(CH_2)_n—$, $—(CH_2)_nC(R^1)(R^2)—$, $—(CH_2CH_2O)_mCH_2CH_2—$, or $—(CH_2CH_2O)_mCH_2CH_2NH—$;

X is absent or a cleavable linking group;

$R^a$ is H or an amino acid side chain;

$R^1$ and $R^2$ are each independently for each occurrence H, $CH_3$, OH, SH or $N(R^N)_2$;

$R^N$ is independently for each occurrence H, methyl, ethyl, propyl, isopropyl, butyl or benzyl;

q, q' and q" are each independently for each occurrence 0-20 and wherein the repeating unit can be the same or different;

n is independently for each occurrence 1-20; and m is independently for each occurrence 0-50.

In some embodiments, the linker comprises at least one cleavable linking group.

In some embodiments, the linker is a branched linker. The branchpoint of the branched linker may be at least trivalent, but can be a tetravalent, pentavalent or hexavalent atom, or a group presenting such multiple valencies. In some embodiments, the branchpoint is, —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branchpoint is glycerol or derivative thereof.

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid celavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where $R^A$ and $R^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleavable in an acidic environment with a pH od about 6.5 or lower (e.g., about 6., 5.5, 5.0, or lower), or by agents such as enzymes that can act as a general acid.

Linker that are not oligonucleotides or do not comprise a nucleotide or nucleoside are also referred to as non-nucleotide based linkers.

Motifs

The present invention also includes multi-targeted molecules which are chimeric compounds. "Chimeric" compounds or "chimeras," in the context of this invention, are compounds which contain two or more chemically distinct regions, each made up of at least one monomer unit, e.g., a modified or unmodified nucleotide in the case of an oligonucleotide. Chimeric compounds can be described as having a particular motif. In some embodiments, the motifs include, but are not limited to, an alternating motif, a gapped motif, a hemimer motif, a uniformly fully modified motif and a positionally modified motif. As used herein, the phrase "chemically distinct region" refers to a region in the multi-targeted molecule which is different from other regions by having a modification that is not present elsewhere in the compound or by not having a modification that is present elsewhere in the compound. A multi-targeted molecule can comprise two or more chemically distinct regions. As used herein, a region that comprises no modifications is also considered chemically distinct.

A chemically distinct region can be repeated within a multi-targeted molecule compound. Thus, a pattern of chemically distinct regions in multi-targeted molecule can be realized such that a first chemically distinct region is followed by one or more second chemically distinct regions. This sequence of chemically distinct regions can be repeated one or more times. Preferably, the sequence is repeated more than one time. For example, both strands of a double-stranded effector molecule can comprise these sequences. Each chemically distinct region can actually comprise as little as single monomers, e.g., nucleotides. In some embodiments, each chemically distinct region comprises 1, 2, 3, 4, 5, 6, 7, 8, 9, 10, 11, 12, 13, 14, 15, 16, 17 or 18 monomers, e.g., nucleotides.

In some embodiments, alternating nucleotides comprise the same modification, e.g. all the odd number nucleotides in a strand have the same modification and/or all the even number nucleotides in a strand have the similar modification to the first strand. In some embodiments, all the odd number nucleotides in double-stranded effector molecule or the multi-targeted molecule have the same modification and all the even numbered nucleotides have a modification that is not present in the odd number nucleotides and vice versa.

When both strands of a double-stranded molecule comprise the alternating modification patterns, nucleotides of one strand can be complementary in position to nucleotides of the second strand which are similarly modified. In an alternative embodiment, there is a phase shift between the patterns of modifications of the first strand, respectively, relative to the pattern of similar modifications of the second strand. Preferably, the shift is such that the similarly modified nucleotides of the first strand and second strand are not in complementary position to each other.

In some embodiments, the first strand has an alternating modification pattern wherein alternating nucleotides comprise a 2'-modification, e.g., 2'-O-Methyl modification. In some embodiments, the first strand comprises an alternating 2'-O-Methyl modification and the second strand comprises an alternating 2'-fluoro modification. In other embodiments, both strands of a double-stranded oligonucleotide comprise alternating 2'-0-methyl modifications.

When both strands of a double-stranded oligonucleotide comprise alternating 2'-O-methyl modifications, such 2'-modified nucleotides can be in complementary position in the duplex region. Alternatively, such 2'-modified nucleotides may not be in complementary positions in the duplex region.

In some embodiments, the an oligonucleotide present in the multi-targeted molecule comprises two chemically distinct regions, wherein each region is 1, 2, 3, 4, 5, 6, 7, 8, 9 or 10 nucleotides in length.

In other embodiments, an oligonucleotide present in the multi-targeted molecule comprises three chemically distinct region. The middle region is about 5-15, (e.g., 5, 6, 7, 8, 9, 10, 11, 12, 13, 14 or 15) nucleotide in length and each flanking or wing region is independently 1-10 (e.g., 1, 2, 3, 4, 5, 6, 7, 8, 9 or 10) nucleotides in length. All three regions can have different modifications or the wing regions can be similarly modified to each other. In some embodiments, the wing regions are of equal length, e.g. 1, 2, 3, 4, 5, 6, 7, 8, 9 or 10 nucleotides long.

As used herein the term "alternating motif" refers to compound comprising a contiguous sequence of linked monomer subunits wherein the monomer subunits have two different types of sugar groups that alternate for essentially the entire sequence of the compound. Oligonucleotides having an alternating motif can be described by the formula: 5'-A(-L-B-L-A)n(-L-B)m-3' where A and B are monomelic subunits that have different sugar groups, each L is an internucleoside linking group, n is from about 4 to about 12 and m is 0 or 1. This permits a compound with an alternating motif from about 9 to about 26 monomer subunits in length. This length range is not meant to be limiting as longer and shorter compounds are also amenable to the present invention. In some embodiments, one of A and B is a 2'-modified nucleoside as provided herein.

As used herein, "type of modification" in reference to a nucleoside or a nucleoside of a "type" refers to the modification of a nucleoside and includes modified and unmodified nucleosides. Accordingly, unless otherwise indicated, a "nucleoside having a modification of a first type" may be an unmodified nucleoside.

As used herein, "type region" refers to a portion of a compound wherein the nucleosides and internucleoside linkages within the region all comprise the same type of modifications; and the nucleosides and/or the internucleoside linkages of any neighboring portions include at least one different type of modification. As used herein the term "uniformly fully modified motif" refers to an oligonucleotide comprising a contiguous sequence of linked monomer subunits that each have the same type of sugar group. In some embodiments, the uniformly fully modified motif includes a contiguous sequence of nucleosides of the invention. In some embodiments, one or both of the 3' and 5'-ends of the contiguous sequence of the nucleosides provided herein, comprise terminal groups such as one or more unmodified nucleosides.

In certain embodiments, the 5'-terminal monomer of a compound, e.g., multi-targeted molecule or an effector molecule, comprises a phosphorous moiety at the 5'-end. In certain embodiments the 5'-terminal monomer comprises a 2'-modification. In certain such embodiments, the 2'-modification of the 5'-terminal monomer is a cationic modification. In certain embodiments, the 5'-terminal monomer comprises a 5'-modification. In certain embodiments, the 5'-terminal monomer comprises a 2'-modification and a 5'-modification. In certain embodiments, the 5'-terminal monomer is a 5'-stabilizing nucleoside. In certain embodiments, the modifications of the 5'-terminal monomer stabilize the 5'-phosphate. In certain embodiments, compounds comprising modifications of the 5'-terminal monomer are resistant to exonucleases. In certain embodiments, compounds comprising modifications of the 5'-terminal monomer have improved gene expression modulating properties.

In certain embodiments, the 5'terminal monomer is attached to the rest of the compound via a modified linkage. In certain such embodiments, the 5'-terminal monomer is attached to the rest of the compound by a phosphorothioate linkage.

In certain embodiments, oligomeric compounds of the present invention comprise one or more regions of alternating modifications. In certain embodiments, oligomeric compounds comprise one or more regions of alternating nucleoside modifications. In certain embodiments, oligomeric compounds comprise one or more regions of alternating linkage modifications. In certain embodiments, oligomeric compounds comprise one or more regions of alternating nucleoside and linkage modifications.

In certain embodiments, oligomeric compounds of the present invention comprise one or more regions of alternating 2'-F modified nucleosides and 2'-OMe modified nucleosides. In certain such embodiments, such regions of alternating 2'F modified and 2'OMe modified nucleosides also comprise alternating linkages. In certain such embodiments, the linkages at the 3' end of the 2'-F modified nucleosides are phosphorothioate linkages. In certain such embodiments, the linkages at the 3' end of the 2'OMe nucleosides are phosphodiester linkages. In certain such embodiments, such alternating regions are:

(2'-F)—(PS)-(2'-OMe)-(PO)

In certain embodiments, oligomeric compounds comprise 2, 3, 4, 5, 6, 7, 8, 9, 10, or 11 such alternating regions. Such regions may be contiguous or may be interrupted by differently modified nucleosides or linkages.

In certain embodiments, one or more alternating regions in an alternating motif include more than a single nucleoside of a type. For example, oligomeric compounds of the present invention may include one or more regions of any of the following nucleoside motifs:

ABA;
ABBA;
AABA;
AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and B is a nucleoside of a second type. In certain embodiments, A and B are each selected from 2'-F, 2'-OMe, LNA, DNA and MOE.

In certain embodiments, A is DNA. In certain embodiments B is DNA. In some embodiments, A is 4'-CH$_2$O-2'-LNA. In certain embodiments, B is 4'-CH$_2$O-2'-LNA. In certain embodiments, A is DNA and B is 4'-CH$_2$O-2'-LNA. In certain embodiments A is 4'-CH$_2$O-2'-LNA and B is DNA.

In certain embodiments, A is 2'-OMe. In certain embodiments B is 2'-OMe. In certain embodiments, A is 2'-OMe and B is 4'-CH$_2$O-2'-LNA. In certain embodiments A is 4'-CH$_2$O-2'-LNA and B is 2'-OMe. In certain embodiments, A is 2'-OMe and B is DNA. In certain embodiments A is DNA and B is 2'-OMe.

In certain embodiments, A is (S)-cEt. In some embodiments, B is (S)-cEt. In certain embodiments, A is 2'-OMe and B is (S)-cEt. In certain embodiments A is (S)-cEt and B is 2'-OMe. In certain embodiments, A is DNA and B is (S)-cEt. In certain embodiments A is (S)-cEt and B is DNA.

In certain embodiments, A is 2'-F. In certain embodiments B is 2'-F. In certain embodiments, A is 2'-F and B is 4'-CH$_2$O-2'-LNA. In certain embodiments A is 4'-CH$_2$O-2'-LNA and B is 2'-F. In certain embodiments, A is 2'-F and B is (S)-cEt. In certain embodiments A is (S)-cEt and B is 2'-F. In certain embodiments, A is 2'-F and B is DNA. In certain embodiments A is DNA and B is 2'-F. In certain embodiments, A is 2'-OMe and B is 2'-F. In certain embodiments, A is DNA and B is 2'-OMe. In certain embodiments, A is 2'-OMe and B is DNA.

In certain embodiments, oligomeric compounds having such an alternating motif also comprise a 5' terminal nucleoside comprising a phosphate stabilizing modification. In certain embodiments, oligomeric compounds having such an alternating motif also comprise a 5' terminal nucleoside comprising a 2'-cationic modification. In certain embodiments, oligomeric compounds having such an alternating motif also comprise a 5' terminal modification.

Two-Two-Three motifs

In certain embodiments, an oligonucleotide in the multi-targeted molecule comprises a region having a 2-2-3 motif. Such regions comprises the following motif:

5'-(E)$_w$-(A)$_2$-(B)$_x$-(A)$_2$-(C)$_y$-(A)$_3$-(D)$_z$ wherein: A is a first type of modified nucleoside;
B, C, D, and E are nucleosides that are differently modified than A, however, B, C, D, and E may have the same or different modifications as one another;

w and z are from 0 to 15;
x and y are from 1 to 15.

In certain embodiments, A is a 2'-OMe modified nucleoside. In certain embodiments, B, C, D, and E are all 2'-F modified nucleosides. In certain embodiments, A is a 2'-OMe modified nucleoside and B, C, D, and E are all 2'-F modified nucleosides.

In certain embodiments, the linkages of a 2-2-3 motif are all modified linkages. In certain embodiments, the linkages are all phosphorothioate linkages. In certain embodiments, the linkages at the 3'-end of each modification of the first type are phosphodiester.

In certain embodiments, Z is 0. In such embodiments, the region of three nucleosides of the first type are at the 3'-end of the oligonucleotide. In certain embodiments, such region is at the 3'-end of the oligomeric compound, with no additional groups attached to the 3' end of the region of three nucleosides of the first type. In certain embodiments, an oligomeric compound comprising an oligonucleotide where Z is 0, may comprise a terminal group attached to the 3'-terminal nucleoside. Such terminal groups may include additional nucleosides. Such additional nucleosides are typically non-hybridizing nucleosides.

In certain embodiments, Z is 1-3. In certain embodiments, Z is 2. In certain embodiments, the nucleosides of Z are 2'-MOE nucleosides. In certain embodiments, Z represents non-hybridizing nucleosides. To avoid confusion, it is noted that such non-hybridizing nucleosides might also be described as a 3'-terminal group with Z=0.

Combination Motifs

It is to be understood, that certain of the above described motifs and modifications can be combined. Since a motif may comprise only a few nucleotides, a particular oligonucleotide can comprise two or more motifs. By way of non-limiting example, in certain embodiments, an oligonucleotide in the multi-targeted molecule can have two or more nucleotide motifs selected from LNAs, phosphorthioate linkages, 2'-OMe, conjugated ligand(s).

Without limitations, the multi-targeted molecules of the invention having any of the various nucleotide motifs described herein, can have also have any linkage motif. For example, in an oligonucleotide of present in the multi-targeted molecule, the first 1, 2, 3, 4 or 5 intersugar linkages at the 5'-end can be modified intersugar linkages and the first 4, 5, 6, 7 or 8 intersugar linkages at the 3'-end can be modified intersugar linkages. The central region of such modified oligonucleotides can have intersugar linkages based on any of the other motifs described herein, for example, uniform, alternating, hemimer, gapmer, and the like. In some embodiments, an oligonucleotide of present in the multi-targeted molecule comprises a phosphorothioate linkage between the first and second monomer at the 5'-terminus, alternating phosphorothioate/phosphodiester linkages in the central region and 6, 7, or 8 phosphorothioate linkages at the 3'-terminus.

It is to be noted that the lengths of the regions defined by a nucleotide motif and that of a linkage motif need not be the same.

In some embodiments, single-stranded oligonucleotides or at least one strand of a double-stranded oligonucleotide, includes at least one of the following motifs:

(a) 5'-phosphorothioate or 5'-phosphorodithioate;
(b) a cationic modification of nucleotides 1 and 2 on the 5' terminal, wherein the cationic modification is at C5 position of pyrimidines and C2, C6, C8, exocyclic N2 or exocyclic N6 of purines;
(c) at least one G-clamp nucleotide in the first two terminal nucleotides at the 5' end and the other nucleotide having a cationic modification, wherein the cationic modification is at C5 position of pyrimidines or C2, C6, C8, exocyclic N2 or exocyclic N6 position of purines;
(d) at least one 2'-F modified nucleotide comprising a nucleobase base modification;
(e) at least one gem-2'-O-methyl/2'-F modified nucleotide comprising a nucleobase modification, preferably the methyl substituent is in the up configuration, e.g. in the arabinose configuration;
(f) a 5'-PuPu-3' dinucleotide at the 3' terminal wherein both nucleotides comprise a modified MOE at 2'-position as described in U.S. Patent Application Publication No. 20130130378, content of which is incorporated herein by reference in its entirety,
(g) a 5'-PuPu-3' dinucleotide at the 5' terminal wherein both nucleotides comprise a modified MOE at 2'-position as described in U.S. Patent Application Publication No. 20130130378;
(h) nucleotide at the 5' terminal having a modified MOE at 2'-position as described in U.S. Patent Application Publication No. 20130130378;
(i) nucleotide at the 5' terminal having a 3'-F modification;
(j) 5' terminal nucleotide comprising a 4'-substituent;
(k) 5' terminal nucleotide comprising a O4' modification;
(l) 3' terminal nucleotide comprising a 4'-substituent; and
(m) combinations thereof.

In some embodiments, both strands of a double-stranded oligonucleotide independently comprise at least one of the above described motifs. In some other embodiments, both strands of a double-stranded oligonucleotide comprise at least one at least one of the above described motifs, which motifs can be same or different or some combination of same and different.

The above examples are provided solely to illustrate how the described motifs may be used in combination and are not intended to limit the invention to the particular combinations or the particular modifications used in illustrating the combinations. Further, specific examples herein, including, but not limited to those in the above table are known to encompass more generic embodiments. For example, column A in the above table exemplifies a region of alternating 2'-OMe and 2'-F nucleosides. Thus, that same disclosure also exemplifies a region of alternating different 2'-modifications. It also exemplifies a region of alternating 2'-O-alkyl and 2'-halogen nucleosides. It also exemplifies a region of alternating differently modified nucleosides. All of the examples throughout this specification contemplate such generic interpretation.

It is also noted that the lengths of compounds, e.g., an oligonucleotide present in the multi-targeted molecule can be easily manipulated by lengthening or shortening one or more of the described regions, without disrupting the motif.

In some embodiments, an oligonucleotide in the multi-targeted molecule comprises two or more chemically distinct regions and has a structure as described in International Application No. PCT/US09/038433, filed Mar. 26, 2009, contents of which are herein incorporated in their entirety.

Synthesis, Purification and Analysis

Oligomerization of modified and unmodified nucleosides and nucleotides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Nucleic acids, such as oligonucleotides, can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The invention is not limited by the method of synthesis.

Methods of purification and analysis of nucleic acids are known to those skilled in the art. Analysis methods include capillary electrophoresis (CE) and electrospray-mass spectroscopy. Such synthesis and analysis methods can be performed in multi-well plates. The method of the invention is not limited by the method of oligomer purification.

Nucleic acids, such as oligonucleotides, can also be prepared using solution-phase or solid-phase organic synthesis, or enzymatically by methods known in the art. Organic synthesis offers the advantage that the oligonucleotide strands comprising non-natural or modified nucleotides can be easily prepared. Any other means for such synthesis known in the art can additionally or alternatively be employed. It is also known to use similar techniques to prepare other nucleic acids, such as those comprising phosphorothioates, phosphorodithioates and alkylated derivatives of intersugar linkages. The double-stranded nucleic acids can be prepared using a two-step procedure. First, the individual strands of the double-stranded molecule are prepared separately. Then, the component strands are annealed.

Regardless of the method of synthesis, nucleic acids can be prepared in a solution (e.g., an aqueous and/or organic solution) that is appropriate for formulation. For example, the nucleic acid preparation can be precipitated and redissolved in pure double-distilled water, and lyophilized. The dried nucleic acid can then be resuspended in a solution appropriate for the intended formulation process.

Teachings regarding the synthesis of particular modified nucleic acids can be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having beta-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups can be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, and 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-fluoro-oligonucleotides.

Compositions and Methods for Formulating Pharmaceutical Compositions

Multi-targeted molecules can be admixed with pharmaceutically acceptable active and/or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Multi-targeted molecules can be utilized in pharmaceutical compositions by combining such oligomeric compounds with a suitable pharmaceutically acceptable diluent or carrier. A pharmaceutically acceptable diluent includes phosphate-buffered saline (PBS). PBS is a diluent suitable for use in compositions to be delivered parenterally. Accordingly, In some embodiments, employed in the methods described herein is a pharmaceutical composition comprising an antisense compound and/or antidote compound and a pharmaceutically acceptable diluent. In certain embodiments, the pharmaceutically acceptable diluent is PBS.

Pharmaceutical compositions comprising Multi-targeted molecules encompass any pharmaceutically acceptable salts, esters, or salts of such esters. In certain embodiments, pharmaceutical compositions comprising Multi-targeted molecules comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a multi-targeted molecule which are cleaved by endogenous nucleases within the body, to form the active molecule.

The pharmaceutical compositions of the present invention may be administered in a number of ways depending upon whether local or systemic treatment is desired and upon the area to be treated. Administration may be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration. The multi-targeted molecules can be delivered in a manner to target a particular tissue, such as the liver (e.g., the hepatocytes of the liver).

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which the multi-targeted molecules featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). Multi-targeted molecules featured in the invention may be encapsulated within liposomes or may form complexes thereto, in particular to cationic liposomes. Alternatively, the multi-targeted molecules may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{1215G}$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) described PEG-containing liposomes that can be further derivatized with functional moieties on their surfaces.

A number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include a dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Research Tools

In certain instances, oligonucleotides capable of modulating gene expression have been used as research tools. For example, researchers investigating the function of a particular gene product can design oligonucleotides to reduce the amount of that gene product present in a cell or an animal and observe phenotypic changes in the cell or animal. In certain embodiments, the present invention provides methods for reducing the amount of two different targets in a cell or animal. In some embodiments, the two different targets can be two different genes or gene products. In some embodiments, the two different targets can be the same gene or gene product. In certain embodiments, investigators can use such techniques to characterize proteins or untranslated nucleic acids. In certain embodiments, such experiments are used to investigate kinetics and/or turnover of gene products and/or certain cellular functions. In some embodiments, such experiments are used to investigate relationship or correlation between different genes or gene products.

Kits

In certain embodiments, the present invention provides kits comprising one or more multi-targeted molecules. In certain embodiments, such kits are intended for therapeutic application. In certain embodiments, such kits are intended for research use.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Definitions

Unless specific definitions are provided, the nomenclature utilized in connection with, and the procedures and techniques of, analytical chemistry, synthetic organic chemistry, and medicinal and pharmaceutical chemistry described herein are those well-known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

As used herein, the term "target nucleic acid" refers to any nucleic acid molecule the expression or activity of which is capable of being modulated by an siRNA compound. Target nucleic acids include, but are not limited to, RNA (including, but not limited to pre-mRNA and mRNA or portions thereof) transcribed from DNA encoding a target protein, and also cDNA derived from such RNA, and miRNA. For example, the target nucleic acid can be a cellular gene (or mRNA transcribed from the gene) whose expression is associated with a particular disorder or disease state. In some embodiments, a target nucleic acid can be a nucleic acid molecule from an infectious agent.

As used herein, "gene silencing" by a RNA interference molecule refers to a decrease in the mRNA level in a cell for a target gene by at least about 5%, at least about 10%, at least about 20%, at least about 30%, at least about 40%, at least about 50%, at least about 60%, at least about 70%, at least about 80%, at least about 90%, at least about 95%, at least about 99% up to and including 100%, and any integer in between of the mRNA level found in the cell without the presence of the miRNA or RNA interference molecule. In one preferred embodiment, the mRNA levels are decreased by at least about 70%, at least about 80%, at least about 90%, at least about 95%, at least about 99%, up to and including 100% and any integer in between 5% and 100%."

As used herein the term "modulate gene expression" means that expression of the gene, or level of RNA molecule or equivalent RNA molecules encoding one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

As used herein, gene expression modulation happens when the expression of the gene, or level of RNA molecule or equivalent RNA molecules encoding one or more proteins or protein subunits is at least 5%, 10%, 20%, 30%, 40%, 50%, 60%, 70%, 80%, 90%, 100%, 2-fold, 3-fold, 4-fold, 5-fold or more different from that observed in the absence of the siRNA, e.g., RNAi agent. The % and/or fold difference can be calculated relative to the control or the non-control, for example, $$\% \text{ difference} = \frac{[\text{expression with } siRNA - \text{expression without } siRNA]}{\text{expression without } siRNA}$$

or $$\% \text{ difference} = \frac{[\text{expression with } siRNA - \text{expression without } siRNA]}{\text{expression without } siRNA}$$

As used herein, the term "inhibit", "down-regulate", or "reduce" in relation to gene expression, means that the expression of the gene, or level of RNA molecules or equivalent RNA molecules encoding one or more proteins or protein subunits, or activity of one or more proteins or protein subunits, is reduced below that observed in the absence of modulator. The gene expression is down-regulated when expression of the gene, or level of RNA molecules or equivalent RNA molecules encoding one or more proteins or protein subunits, or activity of one or more proteins or protein subunits, is reduced at least 10% lower relative to a corresponding non-modulated control, and preferably at least 10%, 20%, 30%, 40%, 50%, 60%, 70%, 80%, 90%, 95%, 98%, 99% or most preferably, 100% (i.e., no gene expression).

As used herein, the term "increase" or "up-regulate" in relation to gene expression means that the expression of the gene, or level of RNA molecules or equivalent RNA molecules encoding one or more proteins or protein subunits, or activity of one or more proteins or protein subunits, is increased above that observed in the absence of modulator. The gene expression is up-regulated when expression of the gene, or level of RNA molecules or equivalent RNA molecules encoding one or more proteins or protein subunits, or activity of one or more proteins or protein subunits, is increased at least 10% relative to a corresponding non-modulated control, and preferably at least 10%, 20%, 30%, 40%, 50%, 60%, 70%, 80%, 90%, 95%, 98%, 100%, 1.1-fold, 1.25-fold, 1.5-fold, 1.75-fold, 2-fold, 3-fold, 4-fold, 5-fold, 10-fold, 50-fold, 100-fold or more.

The term "increased" or "increase" as used herein generally means an increase by a statically significant amount; for the avoidance of any doubt, "increased" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "reduced" or "reduce" as used herein generally means a decrease by a statistically significant amount. However, for avoidance of doubt, "reduced" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

By "specifically hybridizable" and "complementary" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al, 1987, *CSH Symp. Quant. Biol.* LII pp. 123-133; Frier et al., 1986, *Proc. Nat. Acad. Sci.* USA 83:9373-9377; Turner et al., 1987, */. Am. Chem. Soc.* 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9,10 out of 10 being 50%, 60%, 70%, 80%, 90%, and 100% complementary). "Perfectly complementary" or 100% complementarity means that all the contiguous residues of a nucleic acid sequence will hydrogen bond with the same number of contiguous residues in a second nucleic acid sequence. Less than perfect complementarity refers to the situation in which some, but not all, nucleoside units of two strands can hydrogen bond with each other. "Substantial complementarity" refers to polynucleotide strands exhibiting 90% or greater complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

The term "off-target" and the phrase "off-target effects" refer to any instance in which an effector molecule against a given target causes an unintended affect by interacting either directly or indirectly with another target sequence, a DNA sequence or a cellular protein or other moiety. For example, an "off-target effect" may occur when there is a simultaneous degradation of other transcripts due to partial homology or complementarity between that other transcript and the sense and/or antisense strand of an siRNA.

As used herein, the term "nucleoside" means a glycosylamine comprising a nucleobase and a sugar. Nucleosides includes, but are not limited to, naturally occurring nucleosides, abasic nucleosides, modified nucleosides, and nucleosides having mimetic bases and/or sugar groups.

As used herein, the term "nucleotide" refers to a glycosamine comprising a nucleobase and a sugar having a phosphate group covalently linked to the sugar. Nucleotides may be modified with any of a variety of substituents.

As used herein, the term "nucleobase" refers to the base portion of a nucleoside or nucleotide. A nucleobase may comprise any atom or group of atoms capable of hydrogen bonding to a base of another nucleic acid.

As used herein, the term "heterocyclic base moiety" refers to a nucleobase comprising a heterocycle.

As used herein, the term "oligomeric compound" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antidote compounds. In certain embodiments, oligomeric compounds comprise conjugate groups.

As used herein "oligonucleoside" refers to an oligonucleotide in which the internucleoside linkages do not contain a phosphorus atom.

As used herein, the term "oligonucleotide" refers to an oligomeric compound comprising a plurality of linked nucleosides. In certain embodiment, one or more nucleotides of an oligonucleotide is modified. In certain embodiments, an oligonucleotide comprises ribonucleic acid (RNA) or deoxyribonucleic acid (DNA). In certain embodiments, oligonucleotides are composed of naturally- and/or non-naturally-occurring nucleobases, sugars and covalent internucleoside linkages, and can further include non-nucleic acid conjugates.

As used herein "internucleoside linkage" refers to a covalent linkage between adjacent nucleosides.

As used herein "naturally occurring internucleoside linkage" refers to a 3' to 5' phosphodiester linkage.

As used herein the term "detecting siRNA activity" or "measuring siRNA activity" means that a test for detecting or measuring siRNA activity is performed on a particular sample and compared to that of a control sample. Such detection and/or measuring can include values of zero. Thus, if a test for detection of siRNA activity results in a finding of no siRNA activity (siRNA activity of zero), the step of "detecting siRNA activity" has nevertheless been performed.

As used herein the term "control sample" refers to a sample that has not been contacted with a reporter oligomer compound.

As used herein, the term "motif" refers to the pattern of unmodified and modified nucleotides in an oligomeric compound.

As used herein, the term "chimeric oligomer" refers to an oligomeric compound, having at least one sugar, nucleobase or internucleoside linkage that is differentially modified as compared to at least on other sugar, nucleobase or internucleoside linkage within the same oligomeric compound. The remainder of the sugars, nucleobases and internucleoside linkages can be independently modified or unmodified, the same or different.

As used herein, the term "chimeric oligonucleotide" refers to an oligonucleotide, having at least one sugar, nucleobase or internucleoside linkage that is differentially modified as compared to at least on other sugar, nucleobase or internucleoside linkage within the same oligonucleotide. The remainder of the sugars, nucleobases and internucleoside linkages can be independently modified or unmodified, the same or different.

As used herein, the term "mixed-backbone oligomeric compound" refers to an oligomeric compound wherein at least one internucleoside linkage of the oligomeric compound is different from at least one other internucleoside linkage of the oligomeric compound.

As used herein, the term "target protein" refers to a protein, the modulation of which is desired.

As used herein, the term "target gene" refers to a gene encoding a target protein.

As used herein, the term "targeting" or "targeted to" refers to the association of antisense strand of an siRNA to a particular target nucleic acid molecule or a particular region of nucleotides within a target nucleic acid molecule.

As used herein, the term "nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

As used herein, the term "non-complementary nucleobase" refers to a pair of nucleobases that do not form hydrogen bonds with one another or otherwise support hybridization.

As used herein, the term "complementary" refers to the capacity of an oligomeric compound to hybridize to another oligomeric compound or nucleic acid through nucleobase complementarity. In certain embodiments, an oligomeric compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are oligomeric compounds (e.g., siRNas, multi-targeted molecules and the like) that may comprise up to about 20% nucleotides that are mismatched (i.e., are not nucleobase complementary to the corresponding nucleotides of the target). Preferably the oligomeric compounds, such as siRNAs and multi-targeted molecules, contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid.

As used herein, "hybridization" means the pairing of complementary oligomeric compounds (e.g., an antisense strand of an siRNA and its target nucleic acid or an antisense strand and sense strand of an siRNA). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, the term "specifically hybridizes" refers to the ability of an oligomeric compound to hybridize to one nucleic acid site with greater affinity than it hybridizes to another nucleic acid site. In certain embodiments, the antisense strand of an siRNA specifically hybridizes to more than one target site.

As used herein, "designing" or "designed to" refer to the process of designing an oligomeric compound that specifically hybridizes with a selected nucleic acid molecule.

As used herein, the term "modulation" refers to a perturbation of function or activity when compared to the level of the function or activity prior to modulation. For example, modulation includes the change, either an increase (stimulation or induction) or a decrease (inhibition or reduction) in gene expression. As further example, modulation of expression can include perturbing splice site selection of pre-mRNA processing.

As used herein, the term "expression" refers to all the functions and steps by which a gene's coded information is converted into structures present and operating in a cell. Such structures include, but are not limited to the products of transcription and translation.

As used herein, "variant" refers to an alternative RNA transcript that can be produced from the same genomic region of DNA. Variants include, but are not limited to "pre-mRNA variants" which are transcripts produced from the same genomic DNA that differ from other transcripts produced from the same genomic DNA in either their start or stop position and contain both intronic and exonic sequence. Variants also include, but are not limited to, those with alternate splice junctions, or alternate initiation and termination codons.

As used herein, "high-affinity modified monomer" refers to a monomer having at least one modified nucleobase, internucleoside linkage or sugar moiety, when compared to naturally occurring monomers, such that the modification increases the affinity of an antisense compound comprising the high-affinity modified monomer to its target nucleic acid. High-affinity modifications include, but are not limited to, monomers (e.g., nucleosides and nucleotides) comprising 2'-modified sugars.

As used herein, the term "2'-modified" or "2'-substituted" means a sugar comprising substituent at the 2' position other than H or OH. 2'-modified monomers, include, but are not limited to, BNA's and monomers (e.g., nucleosides and nucleotides) with 2'-substituents, such as allyl, amino, azido, thio, O-allyl, O—$C_1$-$C_{10}$ alkyl, —OCF3, O—$(CH_2)_2$—O—$CH_3$, 2'—O$(CH_2)_2$S$CH_3$, O—$(CH_2)_2$—O—N(Rm)(Rn), or O—$CH_2$—C(=O)—N(Rm)(Rn), where each Rm and Rn is, independently, H or substituted or unsubstituted $C_1$-$C_{10}$ alkyl. In certain embodiments, oligomeric compounds comprise a 2' modified monomer that does not have the formula 2'-O$(CH_2)_n$H, wherein n is one to six. In certain embodiments, oligomeric compounds comprise a 2' modified monomer that does not have the formula 2'-O$CH_3$. In certain embodiments, oligomeric compounds comprise a 2' modified monomer that does not have the formula or, in the alternative, 2'-O$(CH_2)_2$O$CH_3$.

As used herein, the term "locked nucleic acid" or "LNA" or "locked nucleoside" or "locked nucleotide" refers to a nucleoside or nucleotide wherein the furanose portion of the nucleoside includes a bridge connecting two carbon atoms on the furanose ring, thereby forming a bicyclic ring system. Locked nucleic acids are also referred to as bicyclic nucleic acids (BNA).

As used herein, unless otherwise indicated, the term "methyleneoxy LNA" alone refers to β-D-methyleneoxy LNA.

As used herein, the term "MOE" refers to a 2'-O-methoxyethyl substituent.

As used herein, the term "gapmer" refers to a chimeric oligomeric compound comprising a central region (a "gap") and a region on either side of the central region (the "wings"), wherein the gap comprises at least one modification that is different from that of each wing. Such modifications include nucleobase, monomeric linkage, and sugar modifications as well as the absence of modification (unmodified). Thus, in certain embodiments, the nucleotide linkages in each of the wings are different than the nucleotide linkages in the gap. In certain embodiments, each wing comprises nucleotides with high affinity modifications and the gap comprises nucleotides that do not comprise that modification. In certain embodiments the nucleotides in the gap and the nucleotides in the wings all comprise high affinity modifications, but the high affinity modifications in the gap are different than the high affinity modifications in the wings. In certain embodiments, the modifications in the wings are the same as one another. In certain embodiments, the modifications in the wings are different from each other. In certain embodiments, nucleotides in the gap are unmodified and nucleotides in the wings are modified. In certain embodiments, the modification(s) in each wing are the same. In certain embodiments, the modification(s) in one wing are different from the modification(s) in the other wing. In certain embodiments, oligomeric compounds are gapmers having 2'-deoxynucleotides in the gap and nucleotides with high-affinity modifications in the wing.

As used herein, the term "prodrug" refers to a therapeutic agent that is prepared in an inactive form that is converted to an active form (i.e., drug) within the body or cells thereof by the action of endogenous enzymes or other chemicals and/or conditions.

As used herein, the term "pharmaceutically acceptable salts" refers to salts of active compounds that retain the desired biological activity of the active compound and do not impart undesired toxicological effects thereto.

As used herein, the term "cap structure" or "terminal cap moiety" refers to chemical modifications, which have been incorporated at either terminus of an antisense compound.

As used herein, the term "prevention" refers to delaying or forestalling the onset or development of a condition or disease for a period of time from hours to days, preferably weeks to months.

As used herein, the term "amelioration" refers to a lessening of at least one activity or one indicator of the severity of a condition or disease. The severity of indicators may be determined by subjective or objective measures which are known to those skilled in the art.

As used herein, the term "treatment" refers to administering a composition of the invention to effect an alteration or improvement of the disease or condition. Prevention, amelioration, and/or treatment may require administration of multiple doses at regular intervals, or prior to onset of the disease or condition to alter the course of the disease or condition. Moreover, a single agent may be used in a single individual for each prevention, amelioration, and treatment of a condition or disease sequentially, or concurrently.

As used herein, the term "pharmaceutical agent" refers to a substance that provides a therapeutic benefit when administered to a subject. In certain embodiments, a pharmaceutical agent is an active pharmaceutical agent. In certain embodiments, a pharmaceutical agent is a prodrug.

As used herein, the term "therapeutically effective amount" refers to an amount of a pharmaceutical agent that provides a therapeutic benefit to an animal.

As used herein, "administering" means providing a pharmaceutical agent to an animal, and includes, but is not limited to administering by a medical professional and self-administering.

As used herein, the term "co-administering" means providing more than one pharmaceutical agent to an animal. In certain embodiments, such more than one pharmaceutical agents are administered together. In certain embodiments, such more than one pharmaceutical agents are administered separately. In certain embodiments, such more than one pharmaceutical agents are administered at the same time. In certain embodiments, such more than one pharmaceutical agents are administered at different times. In certain embodiments, such more than one pharmaceutical agents are administered through the same route of administration. In certain embodiments, such more than one pharmaceutical agents are administered through different routes of administration. In certain embodiments, such more than one pharmaceutical agents are contained in the same pharmaceutical formulation. In certain embodiments, such more than one pharmaceutical agents are in separate formulations.

As used herein, the term "pharmaceutical composition" refers to a mixture of substances suitable for administering to an individual. For example, a pharmaceutical composition may comprise an antisense oligonucleotide and a sterile aqueous solution. In certain embodiments, a pharmaceutical composition includes a pharmaceutical agent and a diluent and/or carrier.

As used herein, the term "in vitro" refers to events that occur in an artificial environment, e.g., in a test tube or reaction vessel, in cell culture, etc., rather than within an organism (e.g. animal or a plant). As used herein, the term "ex vivo" refers to cells which are removed from a living organism and cultured outside the organism (e.g., in a test tube). As used herein, the term "in vivo" refers to events that occur within an organism (e.g. animal, plant, and/or microbe).

As used herein, the term "subject" or "patient" refers to any organism to which a composition disclosed herein can be administered, e.g., for experimental, diagnostic, and/or therapeutic purposes. Typical subjects include animals (e.g., mammals such as mice, rats, rabbits, non-human primates, and humans) and/or plants. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of human diseases and disorders. In addition, compounds, compositions and methods described herein can be used to with domesticated animals and/or pets.

In some embodiments, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species. In some embodiments, the subject can be of European ancestry. In some embodiments, the subject can be of African American ancestry. In some embodiments, the subject can be of Asian ancestry.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "parenteral administration," refers to administration through injection or infusion. Parenteral administration includes, but is not limited to, subcutaneous administration, intravenous administration, or intramuscular administration.

As used herein, the term "subcutaneous administration" refers to administration just below the skin. "Intravenous administration" means administration into a vein.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

As used herein, the term "dosage unit" refers to a form in which a pharmaceutical agent is provided. In certain embodiments, a dosage unit is a vial comprising lyophilized antisense oligonucleotide. In certain embodiments, a dosage unit is a vial comprising reconstituted antisense oligonucleotide.

As used herein, the term "active pharmaceutical ingredient" refers to the substance in a pharmaceutical composition that provides a desired effect.

As used herein, the term "side effects" refers to physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

As used herein, the term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms (C1-C12 alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein, the term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, the term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, the term "aminoalkyl" as used herein, refers to an amino substituted alkyl radical. This term is meant to include C1-C12 alkyl groups having an amino substituent at any position and wherein the alkyl group attaches the aminoalkyl group to the parent molecule. The alkyl and/or amino portions of the aminoalkyl group can be further substituted with substituent groups.

As used herein, the term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substituent groups.

As used herein, the term "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups. As used herein, the term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substitutent groups. As used herein, the terms "halo" and "halogen," as used herein, refer to an atom selected from fluorine, chlorine, bromine and iodine.

As used herein, the terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, the terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substitutent groups attached to the alkyl, the aryl or both groups that form the radical group.

As used herein, the term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms.

A heterocyclic group typically includes at least one atom selected from sulfur, nitrogen or oxygen. Examples of heterocyclic groups include, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substitutent groups. As used herein, the terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substituent groups.

As used herein, the term "heteroarylalkyl," as used herein, refers to a heteroaryl group as previously defined having an alky radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substituent groups on one or both of the heteroaryl or alkyl portions.

As used herein, the term "mono or poly cyclic structure" as used in the present invention includes all ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom, through a substituent group or a bifunctional linking moiety.

As used herein, the term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, the term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

As used herein, the terms "substituent" and "substituent group," as used herein, include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)Raa), carboxyl (—C(O)O—Raa), aliphatic groups, alicyclic groups, alkoxy, substituted oxo (—O—Raa), aryl, aralkyl, heterocyclic, heteroaryl, heteroarylalkyl, amino (—NRbbRcc), imino (=NRbb), amido (—C(O)N—RbbRcc or —N(Rbb)C(O)Raa), azido (—N3), nitro (—NO2), cyano (—CN), carbamido (—OC(O)NRbbRcc or —N(Rbb)C(O)ORaa), ureido (—N(Rbb)C(O)NRbbRcc), thioureido (—N(Rbb)C(S)NRbbRcc), guanidinyl (—N(Rbb)C(=NRbb)NRbbRcc), amidinyl (—C(=NRbb)-NRbbRcc or —N(Rbb)C(NRbb)Raa), thiol (—SRbb), sulfinyl (—S(O)Rbb), sulfonyl (—S(O)2Rbb), sulfonamidyl (—S(O)2NRbbRcc or —N(Rbb)S(O)2Rbb) and conjugate groups. Wherein each Raa, Rbb and Rcc is, independently, H, an optionally linked chemical functional group or a further substituent group with a preferred list including without limitation H, alkyl, alkenyl, alkynyl, aliphatic, alkoxy, acyl, aryl, aralkyl, heteroaryl, alicyclic, heterocyclic and heteroarylalkyl.

EXAMPLES

Example 1

Synthesis of bis(siRNA) with Parallel and Antiparallel Strand Orientations

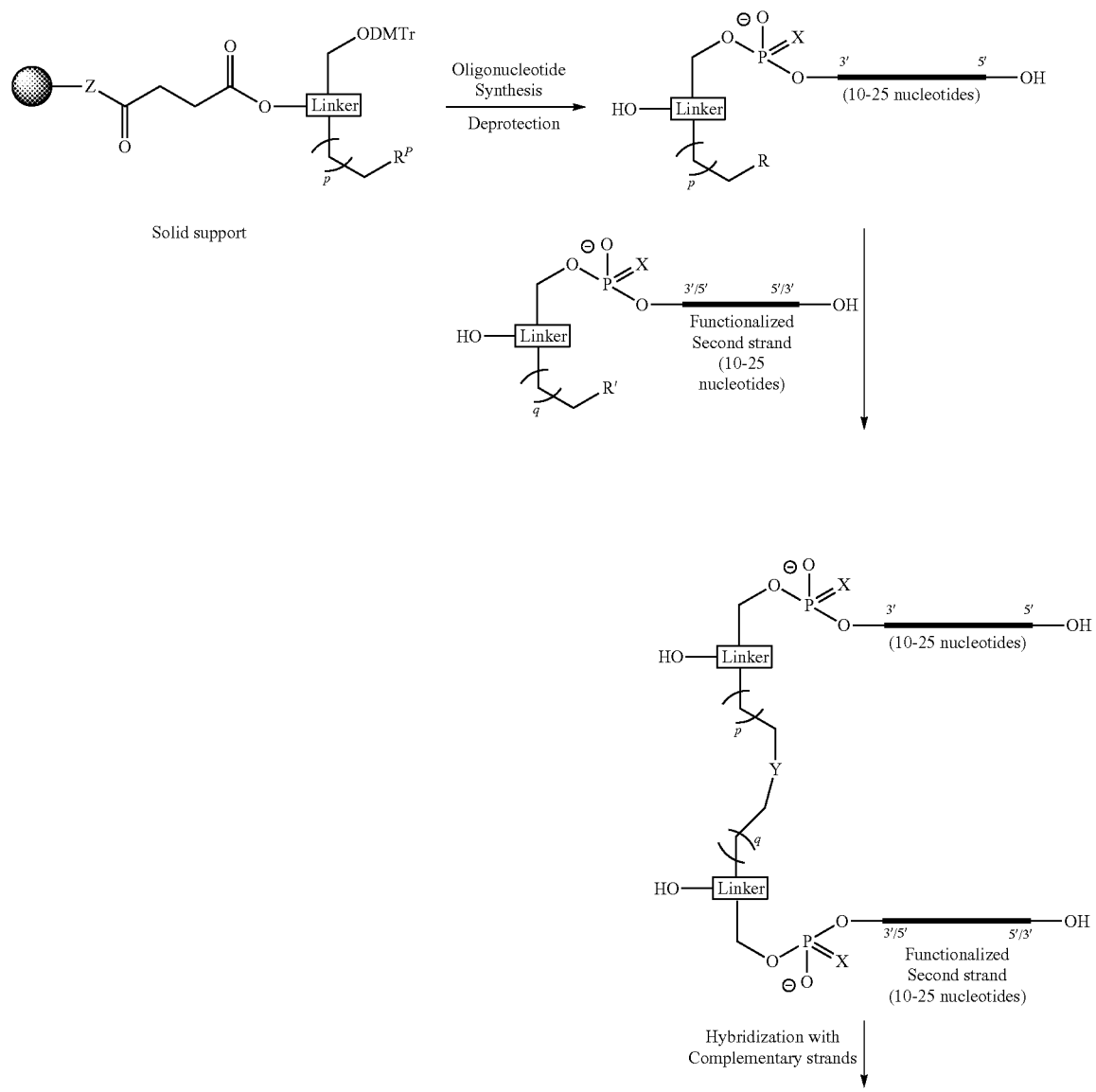

Scheme 1.

-continued

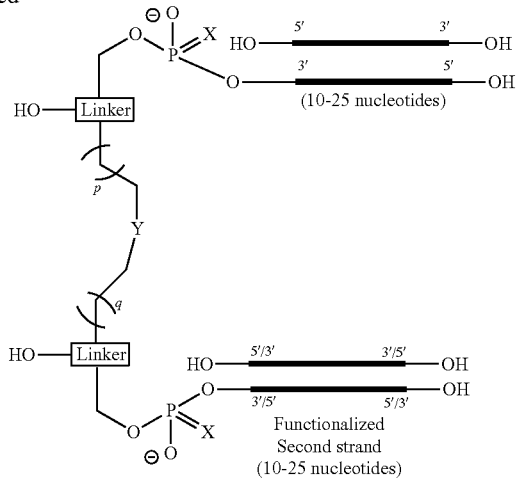

$R^P$ = protected amine, protected disulfide, protected SH, maleimide moiety, protected carboxyl, alkyne moeity; R = $NH_2$, SH, maleimide moiety, COOH, activated carboxyl or activated disulfide, alkyne moiety, azide; R' = $NH_2$, SH, malemide moiety, COOH, activated disulfide, alkyne moeity, azide; X = O or S; Y = —C(O)NH—, —NHC(O)—, —S—S—, thioether, triazolide (click adduct); Z = O or NH; p, q, = 0-10

The bis(siRNA) is synthesized from the solid support and the functionalized second strand followed by hybridization to complementary strands as shown in the Scheme 1.

Example 2

Synthesis of bis(siRNA) with Parallel and Antiparallel Strand Orientations containing a Targeting Ligand Scheme 2.

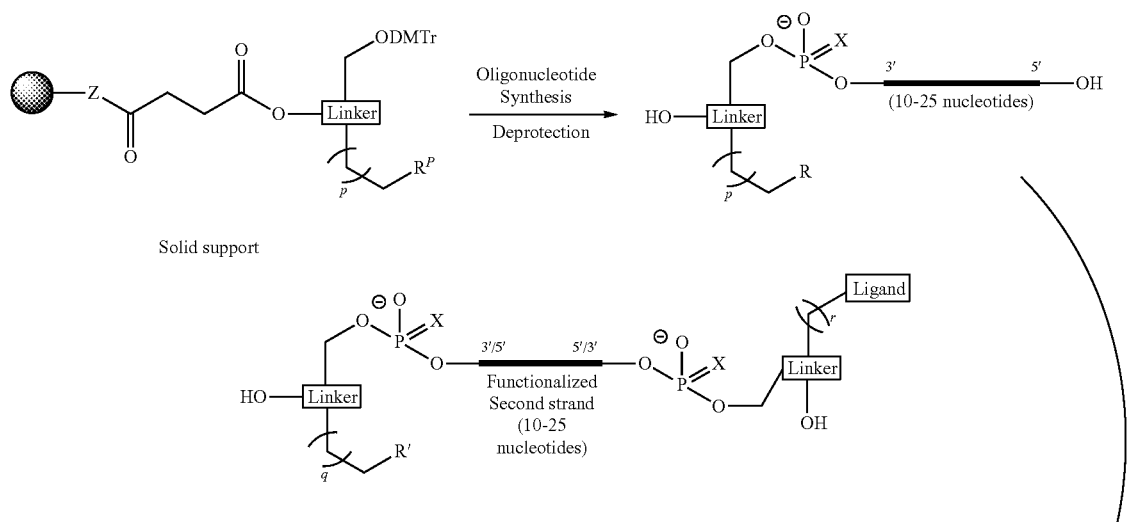

-continued

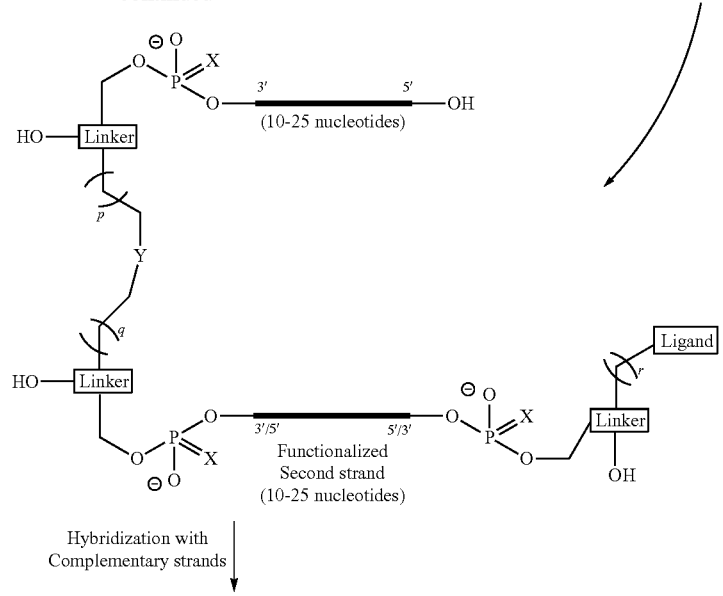

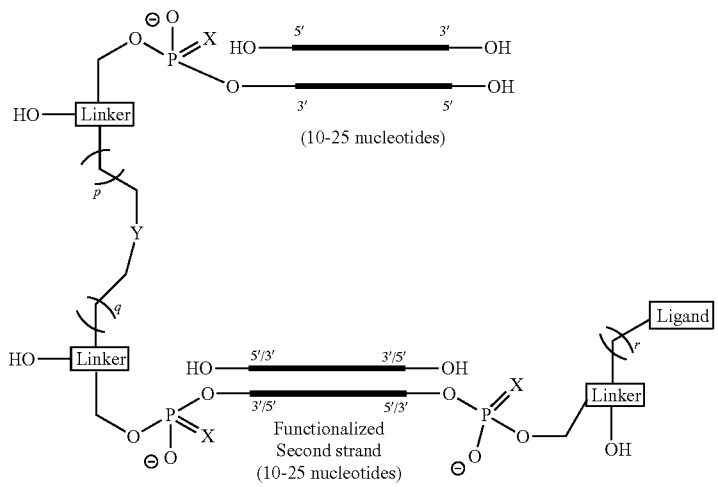

$R^P$ = protected amine, protected disulfide, protected SH, maleimide moiety, protected carboxyl, alkyne moeity; R = $NH_2$, SH, maleimide moiety, COOH, activated carboxyl or activated disulfide, alkyne moiety, azide; R' = $NH_2$, SH, malemide moiety, COOH, activated disulfide, alkyne moeity, azide; X = O or S; Y = —C(O)NH—, —NHC(O)—, —S—S—, thioether, triazolide (click adduct); Z = O or NH; p, q, = 0-10.

The bis(siRNA) is synthesized from the solid support and the functionalized second strand containing a ligand followed by hybridization to complementary strands as shown in the Scheme 2.

Example 3
Synthesis of bis(siRNA) with Parallel and Antiparallel Strand Orientations containing a Targeting Ligand on Different Location
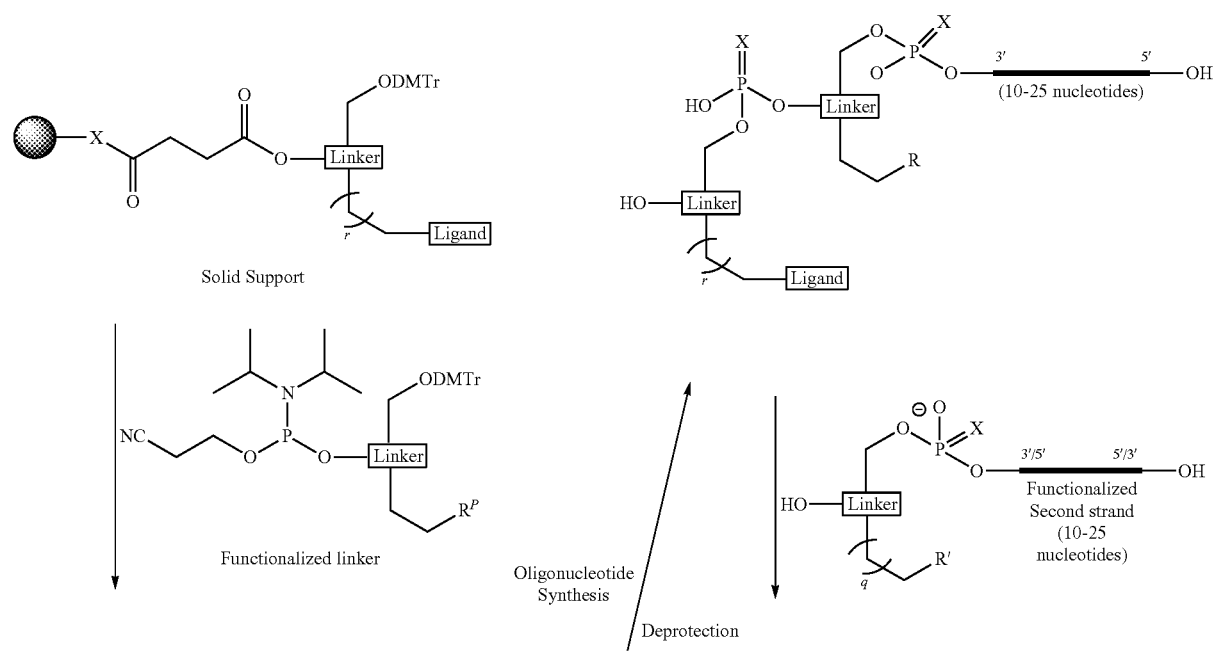
Scheme 3.
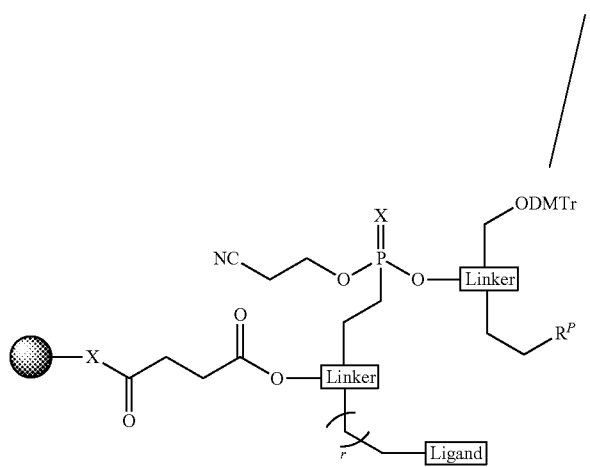

-continued

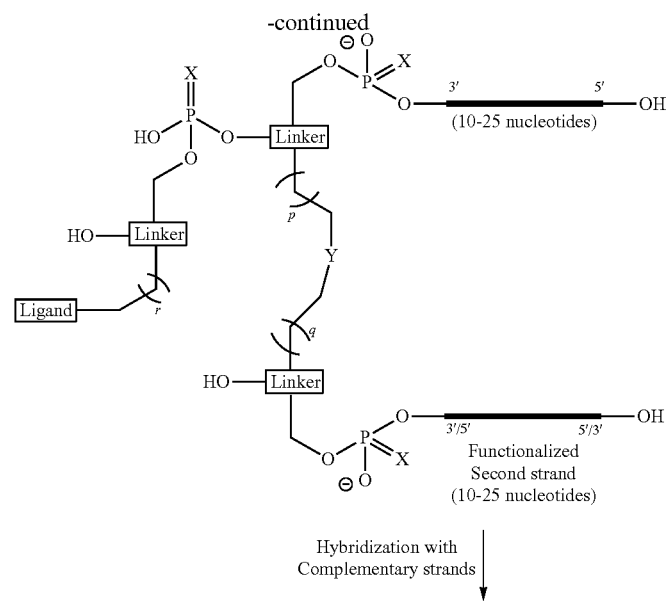

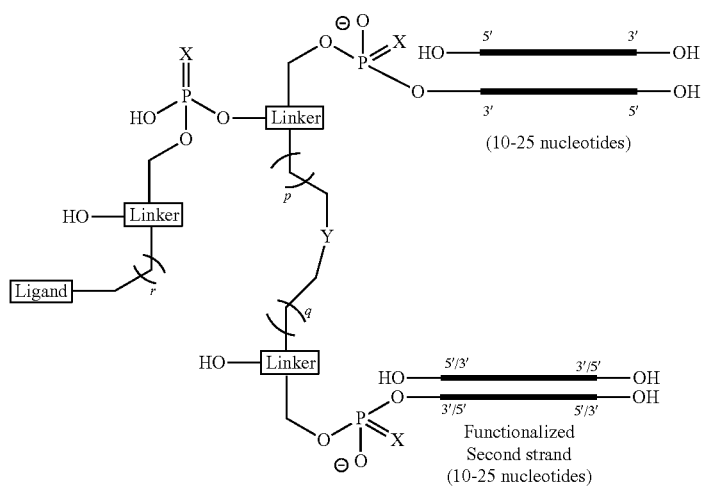

$R^P$ = protected amine, protected disulfide, protected SH, maleimide moiety, protected carboxyl, alkyne moeity; R = NH$_2$, SH, maleimide moiety, COOH, activated carboxyl or activated disulfide, alkyne moiety, azide; R' = NH$_2$, SH, malemide moiety, COOH, activated disulfide, alkyne moeity, azide; X = O or S; Y = —C(O)NH—, —NHC(O)—, —S—S—, thioether, triazolide (click adduct); Z = O or NH; p, q, = 0-10.

The bis(siRNA) is synthesized from the solid support and the functionalized second strand followed by hybridization to complementary strands as shown in the Scheme 3

Example 4
Synthesis of bis(siRNA) with Parallel and Antiparallel Strand Orientations containing Two or more Ligand on Different Locations
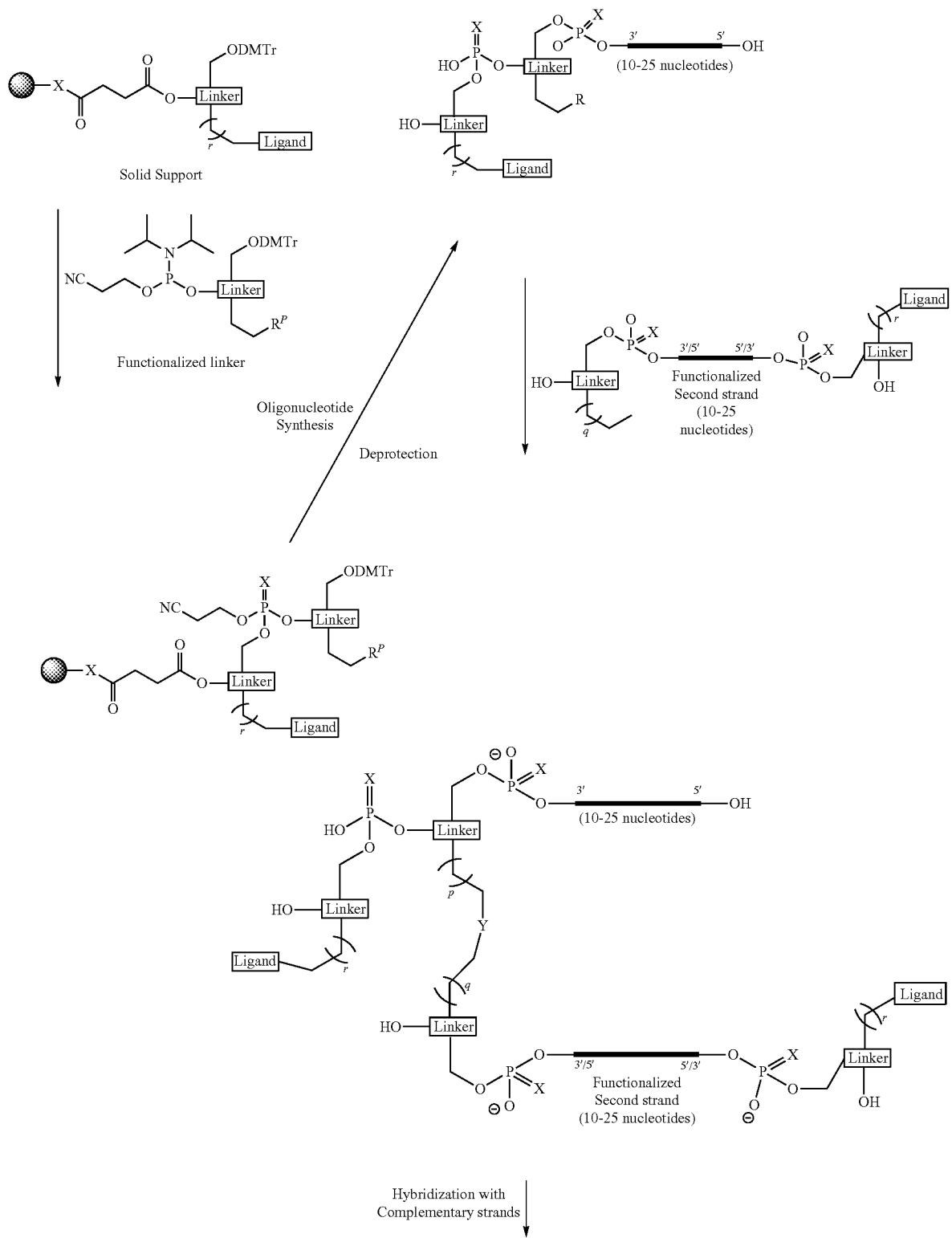
Scheme 4.

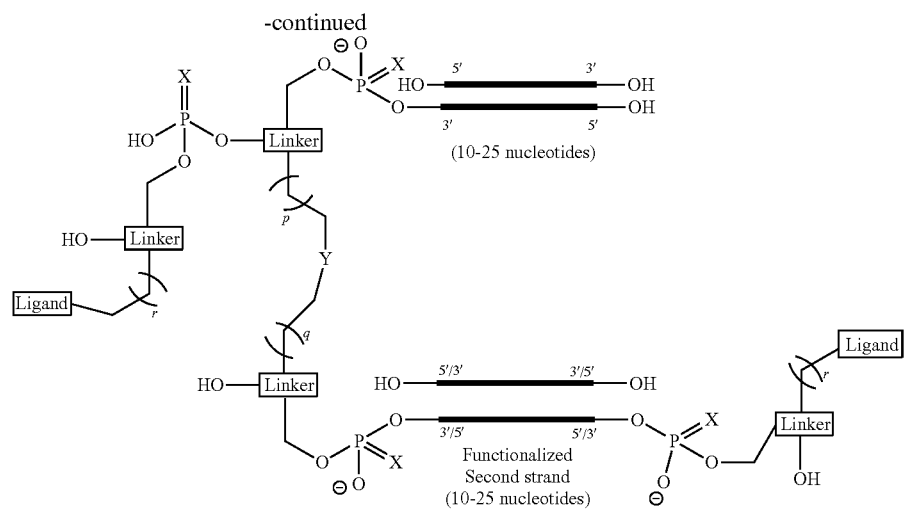

-continued (10-25 nucleotides)

Functionalized Second strand (10-25 nucleotides)

$R^P$ = protected amine, protected disulfide, protected SH, maleimide moiety, protected carboxyl, alkyne moeity; R = $NH_2$, SH, maleimide moiety, COOH, activated carboxyl or activated disulfide, alkyne moiety, azide; R' = $NH_2$, SH, malemide moiety, COOH, activated disulfide, alkyne moeity, azide; X = O or S; Y = —C(O)NH—, —NHC(O)—, —S—S—, thioether, triazolide (click adduct); Z = O or NH; p, q, = 0-10.

The bis(siRNA) is synthesized from the solid support, functionalized monomer and the functionalized second strand containing a ligand, followed by hybridization with complementary strands as shown in the Scheme 4.

Example 5

Synthesis of bis(siRNA) with Parallel and Antiparallel Strand Orientations containing where the Ligand is Conjugated to One of the Short-Mer Complementary Oligonucleotides Scheme 5.

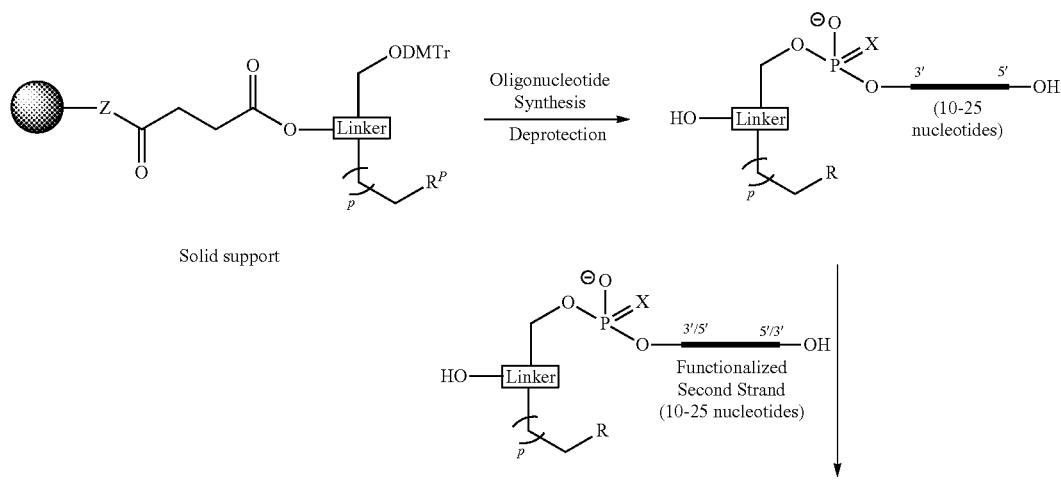

-continued

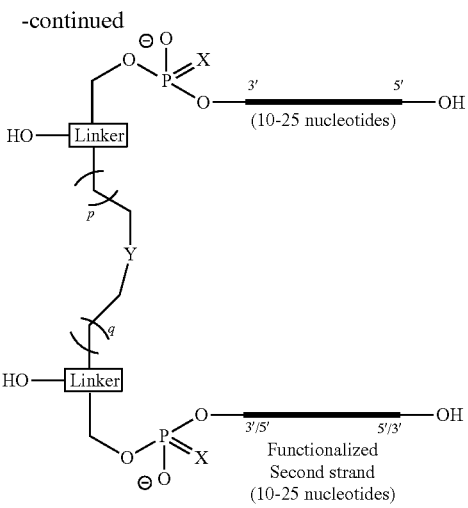

Hybridization with
Complementary strands
(one containing a ligand)

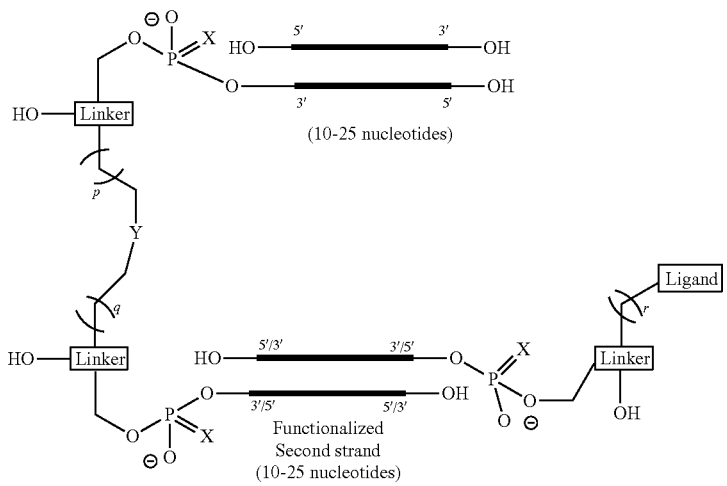

$R^P$ = protected amine, protected disulfide, protected SH, maleimide moiety, protected carboxyl, alkyne moeity; R = $NH_2$, SH, maleimide moiety, COOH, activated carboxyl or activated disulfide, alkyne moiety, azide; R' = $NH_2$, SH, maleimide moiety, COOH, activated disulfide, alkyne moeity, azide; X = O or S; Y = —C(O)NH—, —NHC(O)—, —S—S—, thioether, triazolide (click adduct); Z = O or NH; p, q, = 0-10.

The bis(siRNA) is synthesized from the solid support and the functionalized second strand followed by hybridization with complementary strands of which one contains a ligand as shown in the Scheme 5.

Example 6
Synthesis of bis(siRNA) from Monomers containing both Ligand and Functional Tether for Conjugation to Second siRNA
Scheme 6.
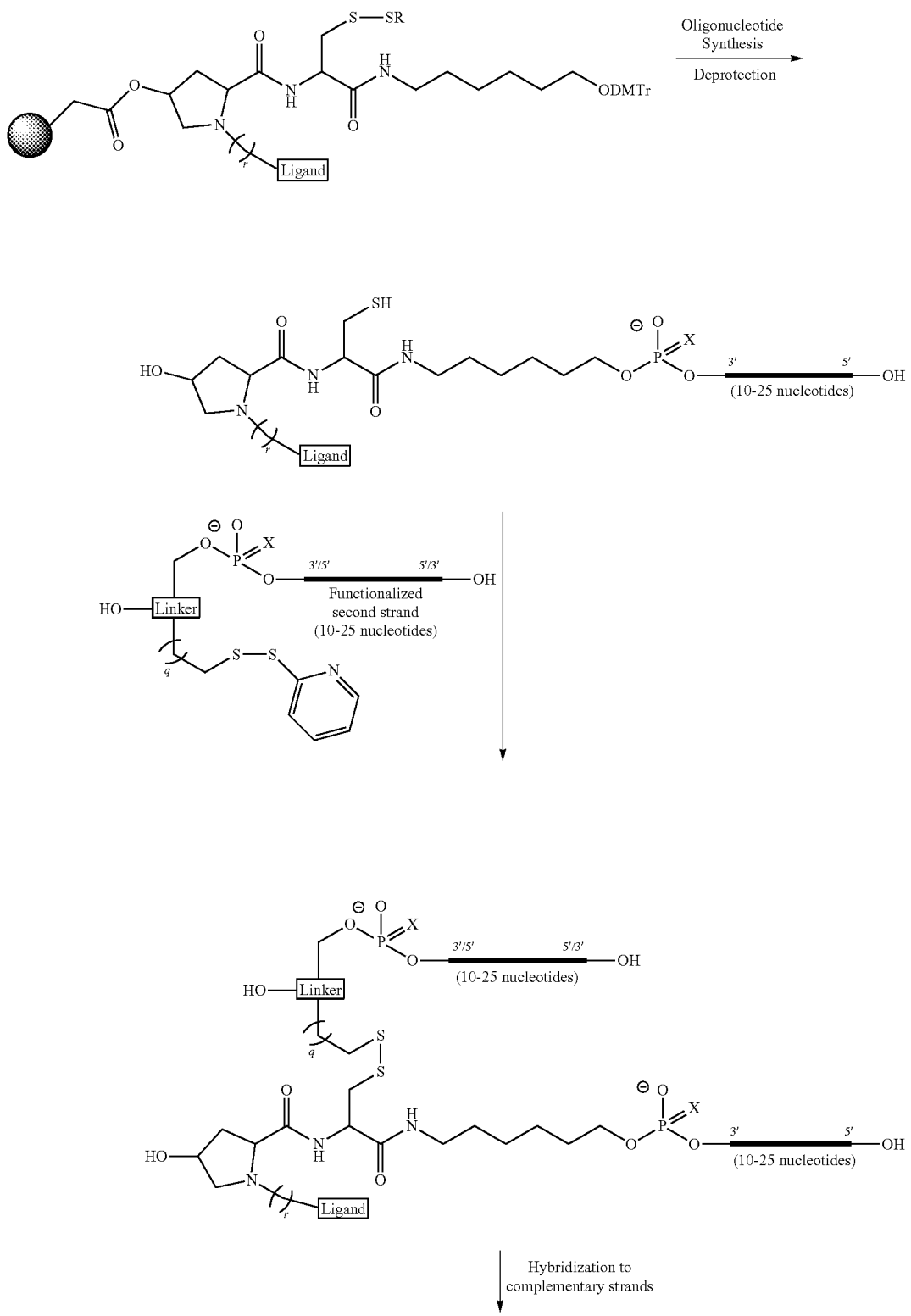

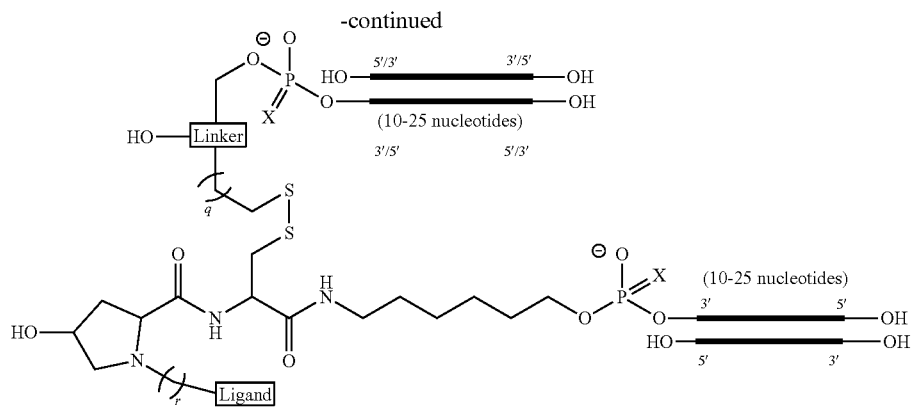
The bis(siRNA) is synthesized from the solid support and the functionalized second strand containing activated disulfide followed by hybridization with complementary strands as shown in the Scheme 6.
Example 7
Synthesis of bis(siRNA) from Monomers containing both Ligand and Functional Tether for Conjugation to Second siRNA
Scheme 7.
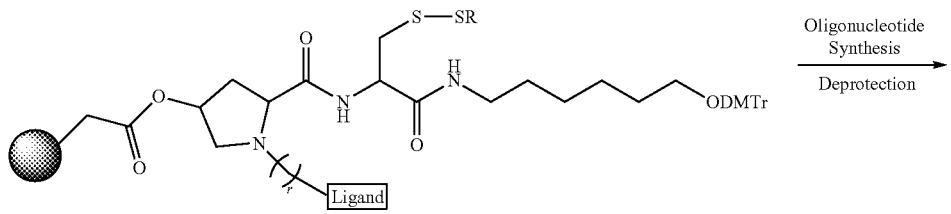
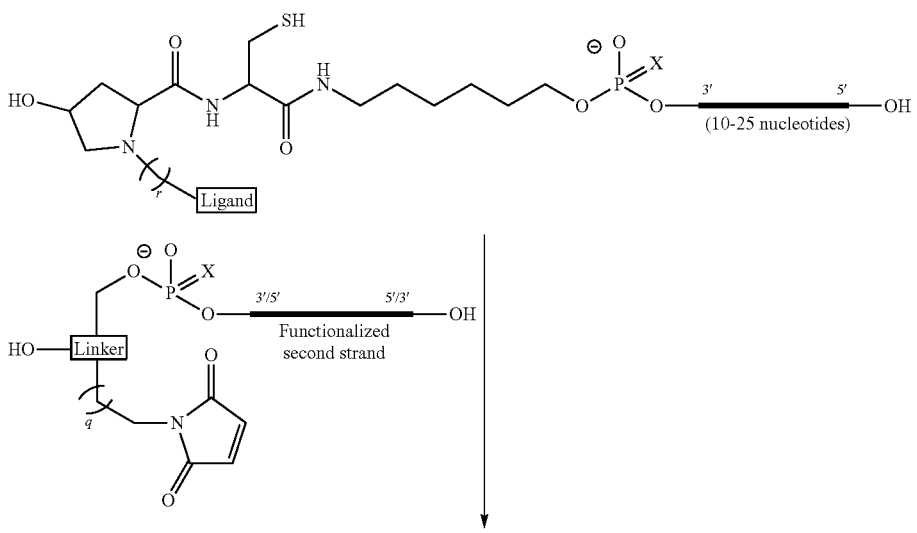

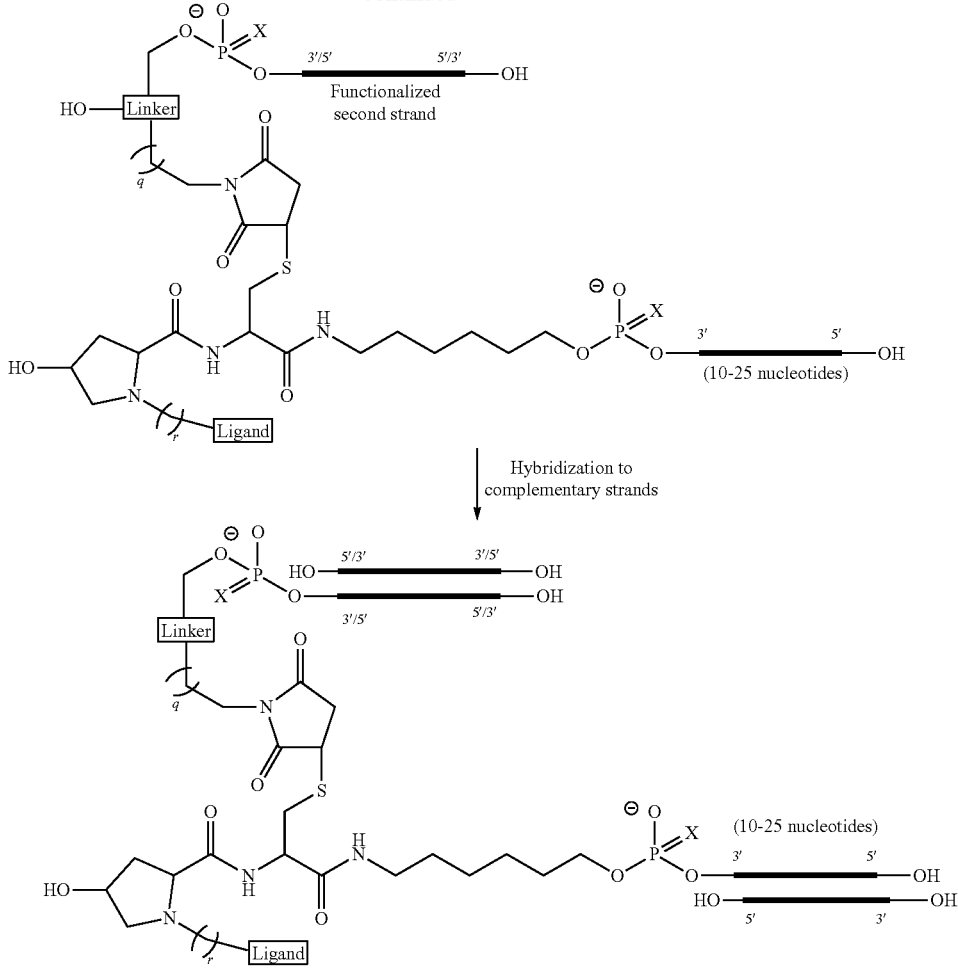
The bis(siRNA) is synthesized from the solid support and the functionalized second strand containing a maleimide moiety followed by hybridization with complementary strands as shown in the Scheme 7.
Example 8
Functionalized Linkers, Solid Supports and Phosphoramidites
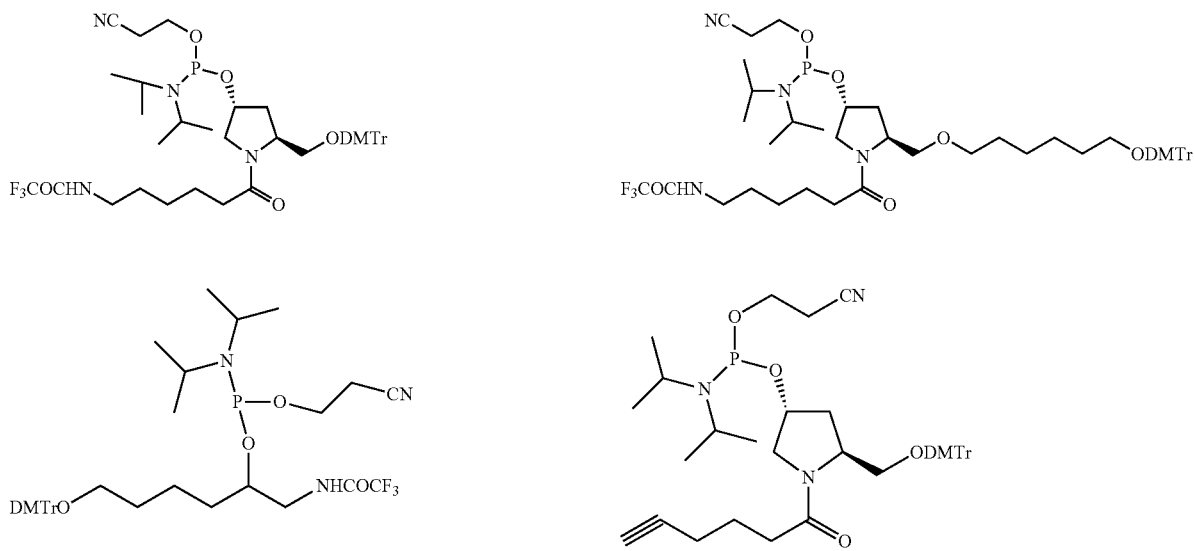

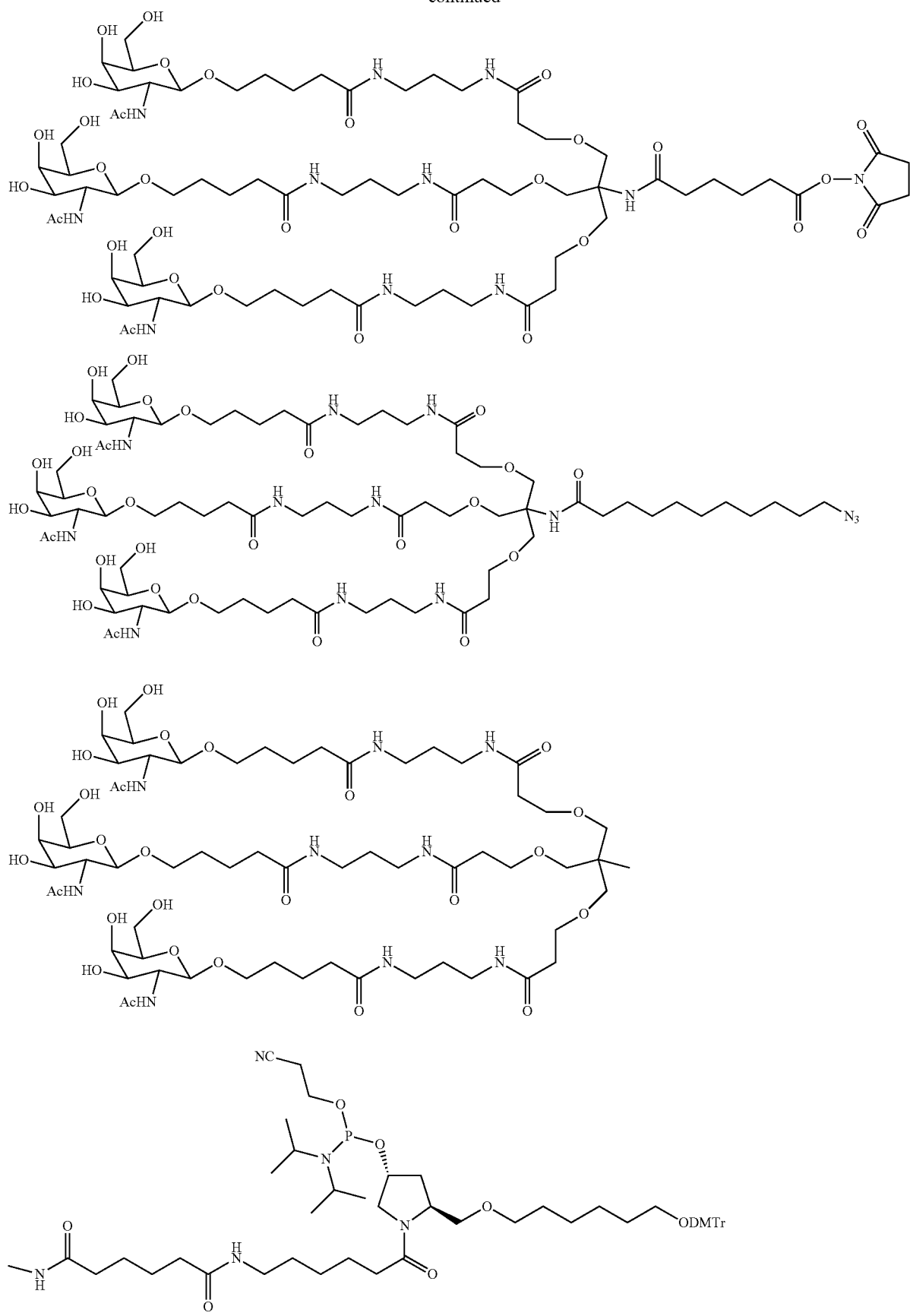

-continued
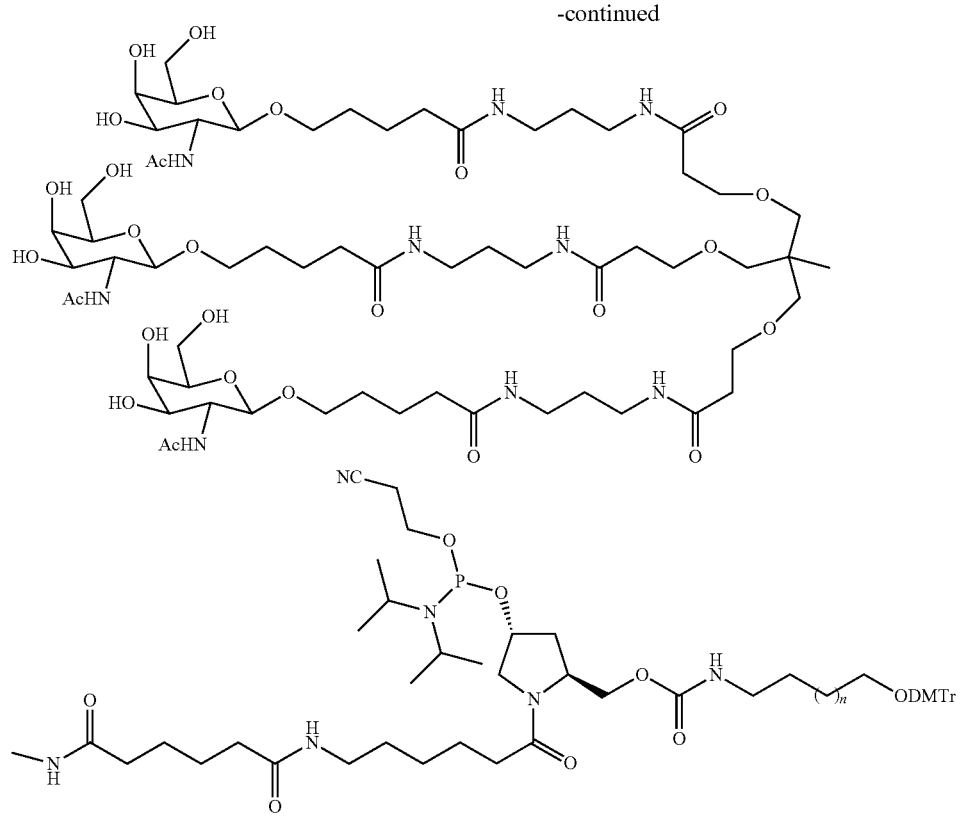
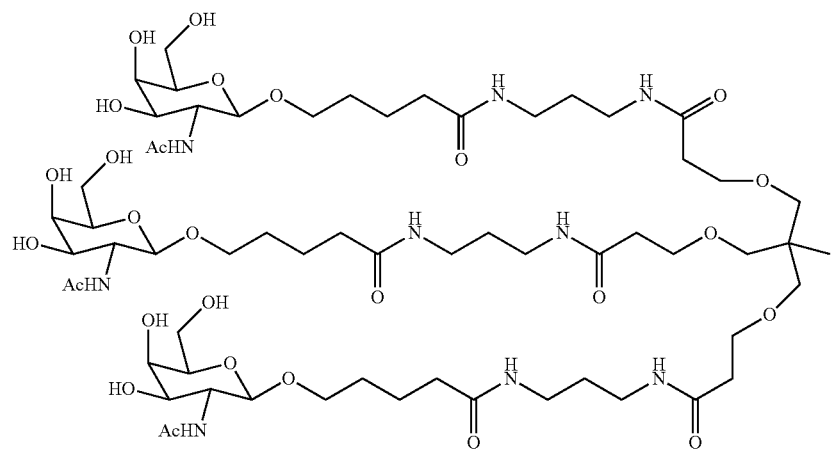
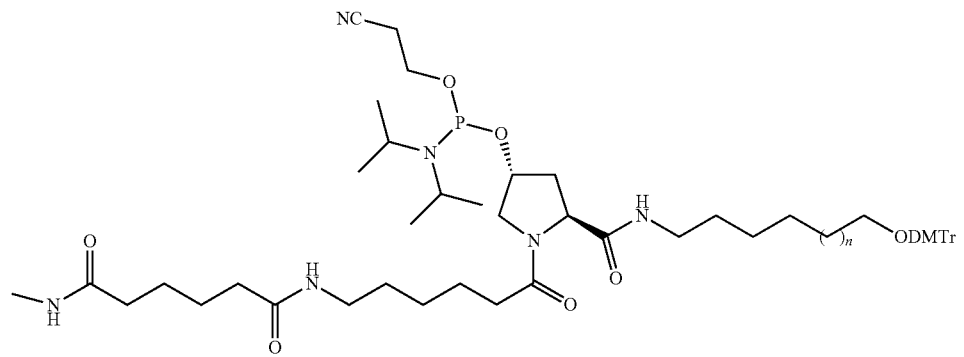

149 150
-continued
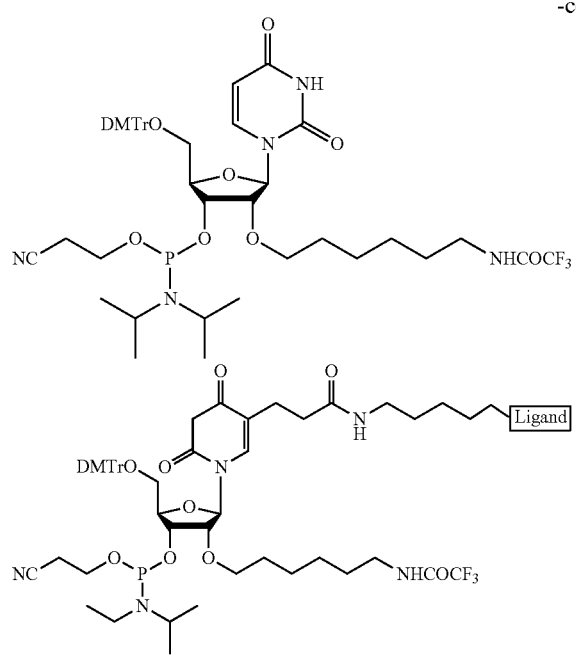 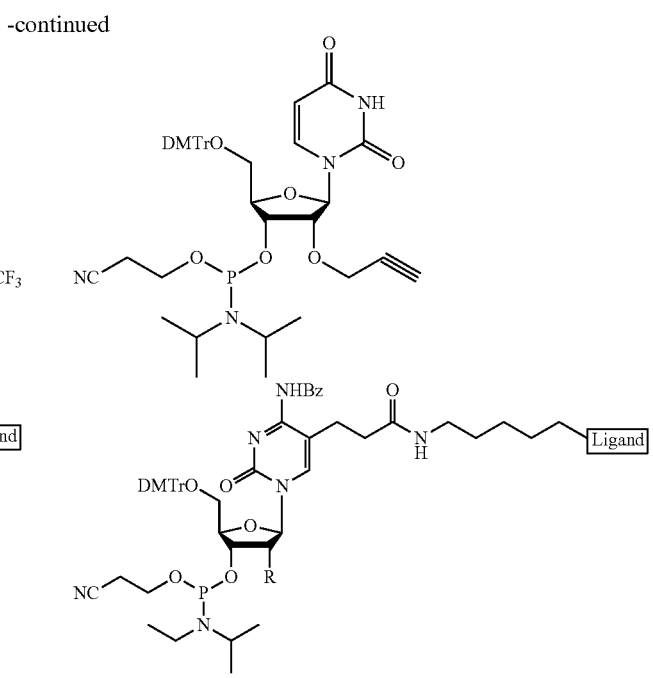
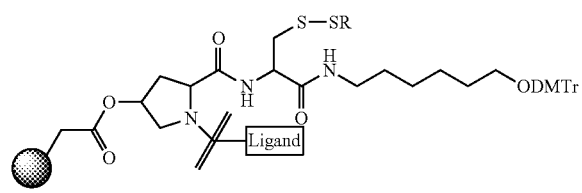 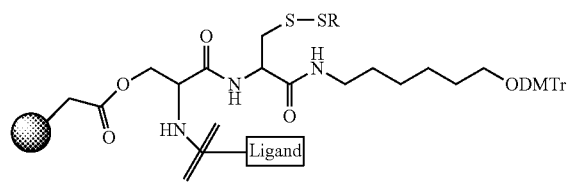
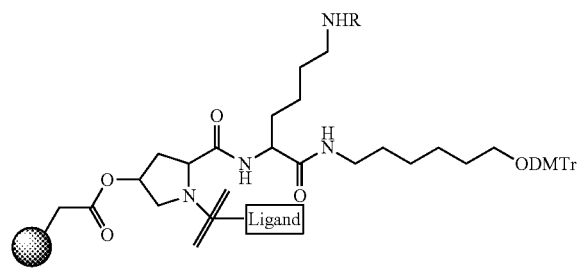 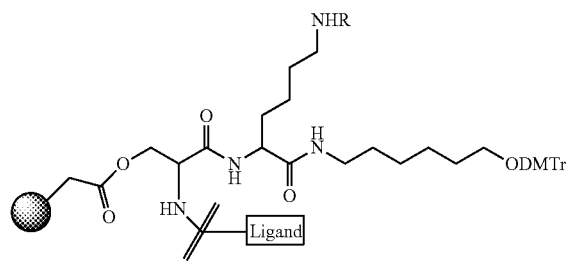
Example 9
Peptidase Cleavable Linkers for Multi-Mer siRNA Solid Phase and Post-Synthesis
5001 5002
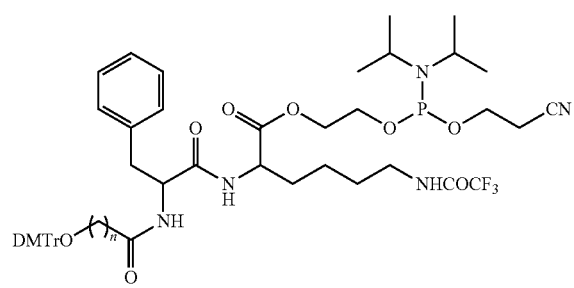 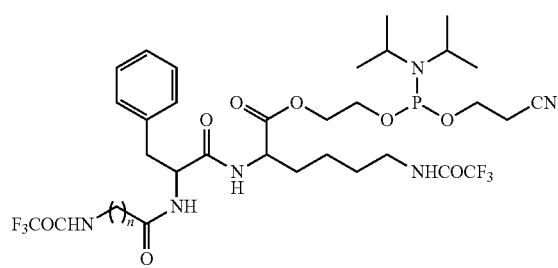

151 152
-continued
5003
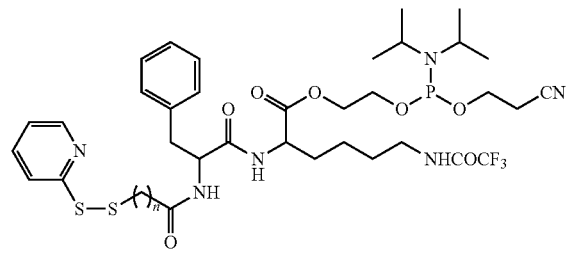
5004
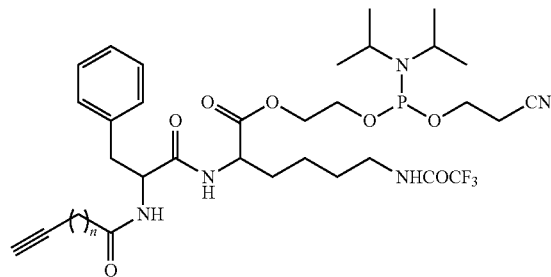
5005
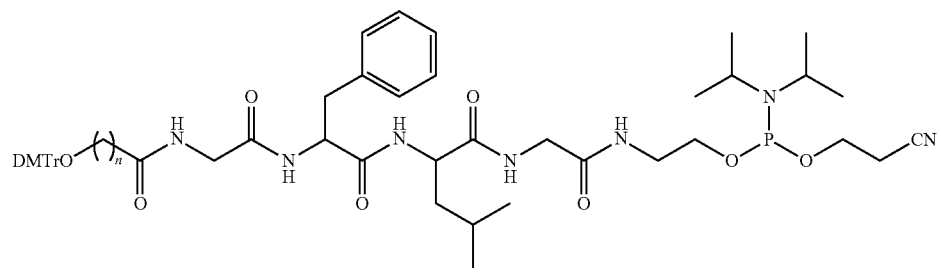
5006
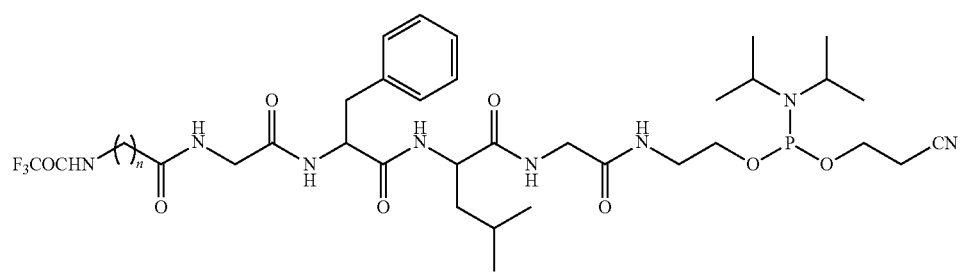
5007
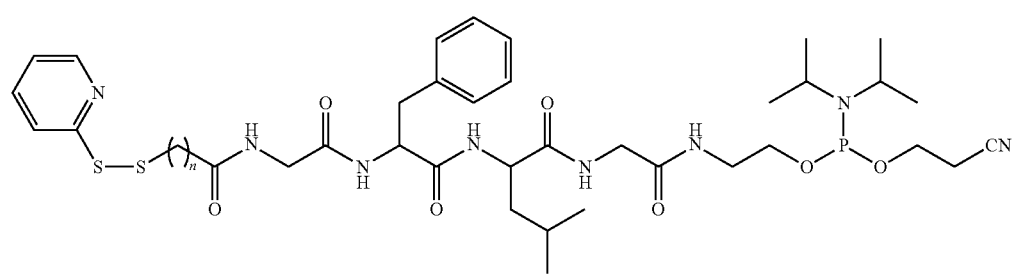
5008
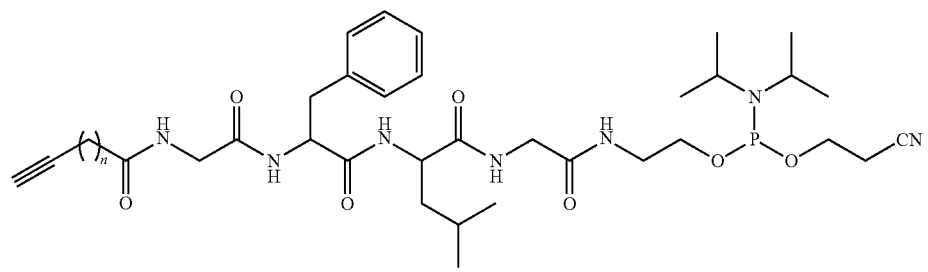
5009
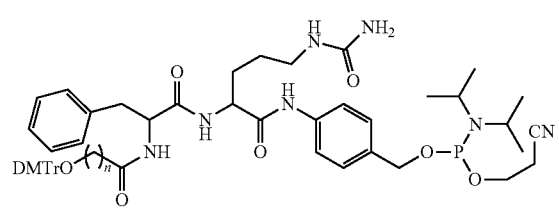
5010
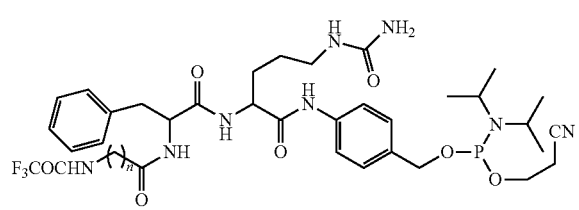

-continued

5011

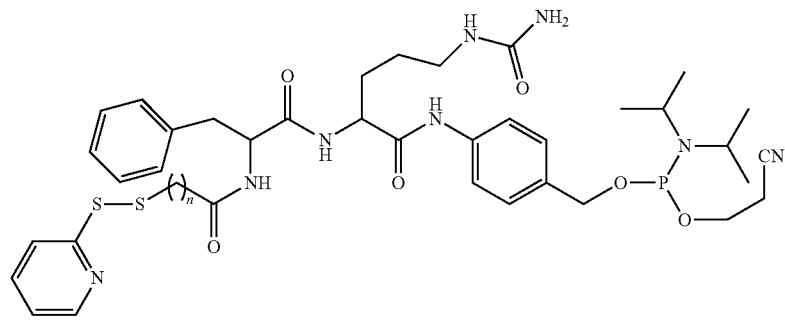

5012

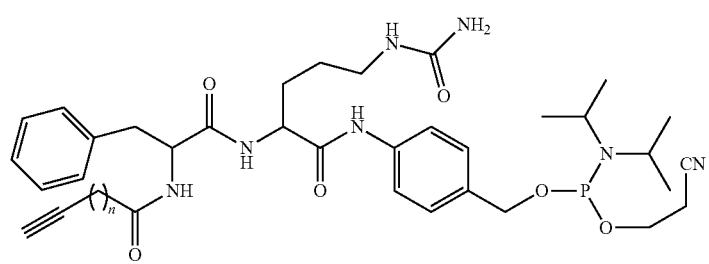

n = 1-12

Each asymmetric center is racemic, or chirally pure R or S and combinations such as (R,R), (R,S), (S,R) and (S,S). Monomers with ODMTr protection is used for solid phase covalent attachment of 2 or more single stranded oligonucleotides. Monomers containing NHC(O)CF₃, acetylene or disulfide moiety are used for on column and/or solution phase post-synthetic covalent attachment of 2 or more single stranded oligonucleotides with complementary reactive group on incoming single strand.

Example 10

Glycosylate and/or Acid Cleavable Likers for Multi-Mer siRNA Solid Phase and Post-Synthesis

6001

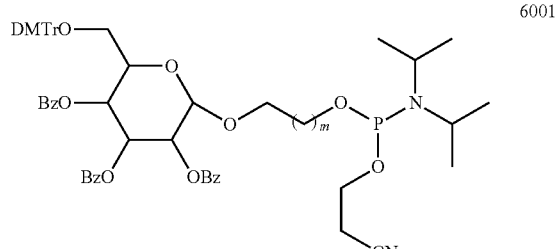

6002

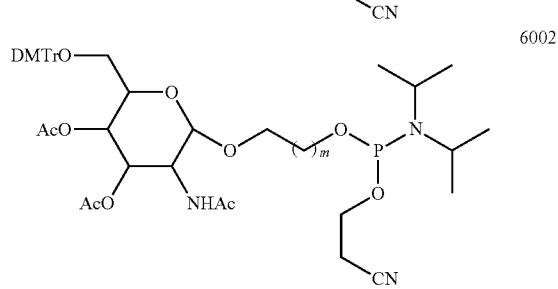

-continued

6003

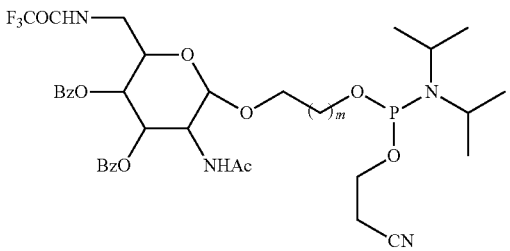

6004

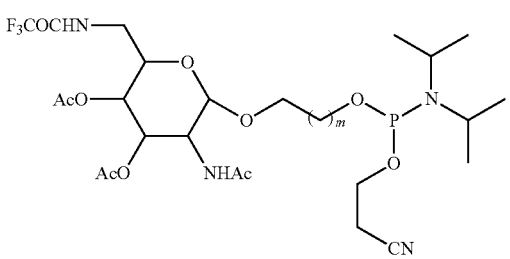

6005

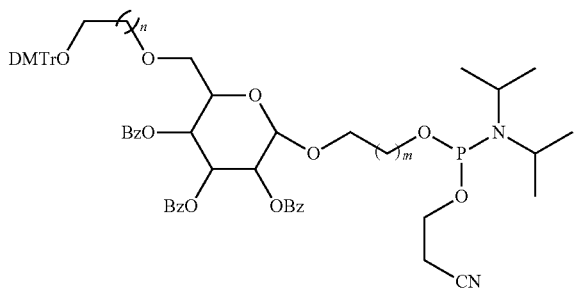

-continued
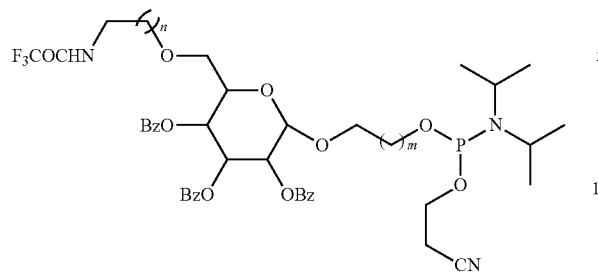
6006
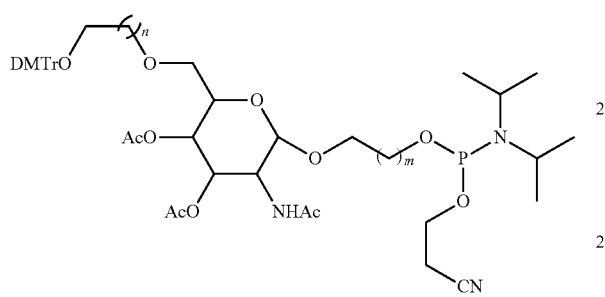
6007
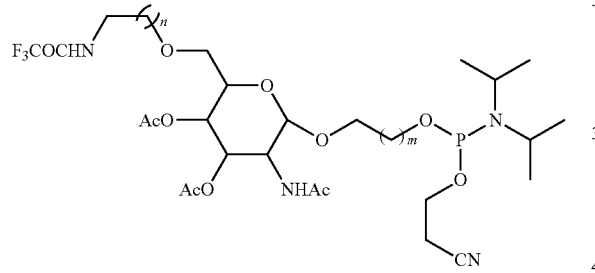
6008
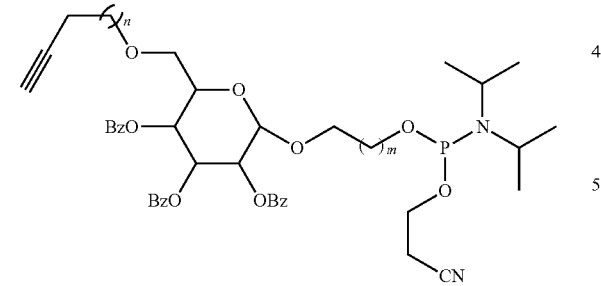
6009
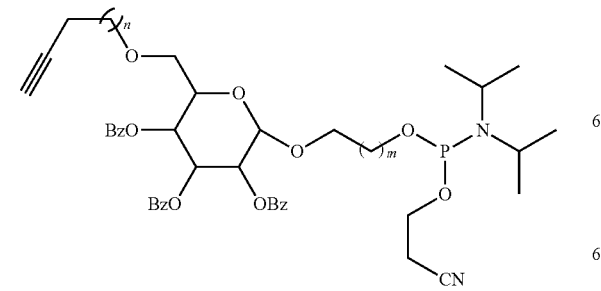
6010
-continued
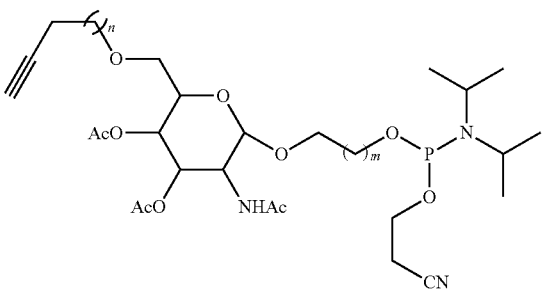
6011
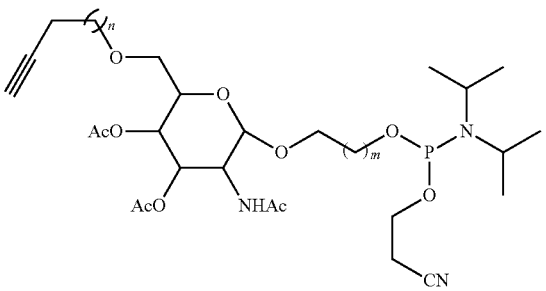
6012
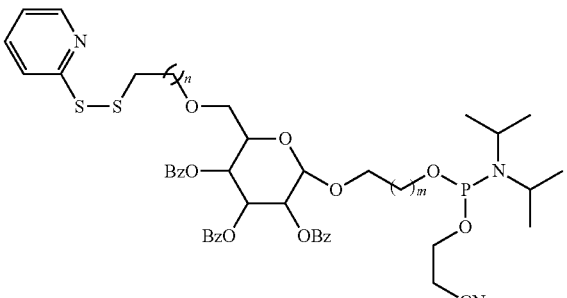
6013
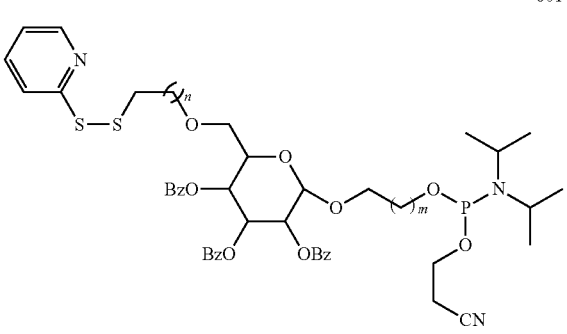
6014
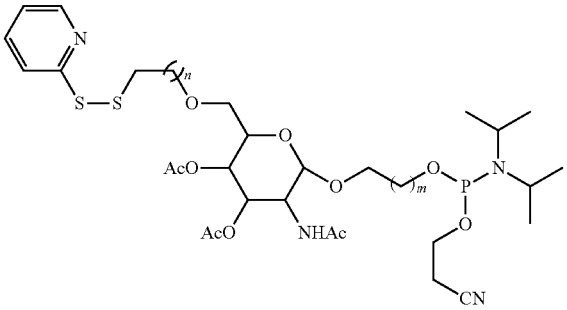
6015

-continued
6016
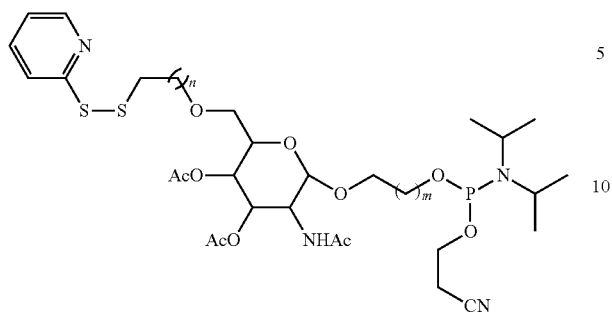
6017
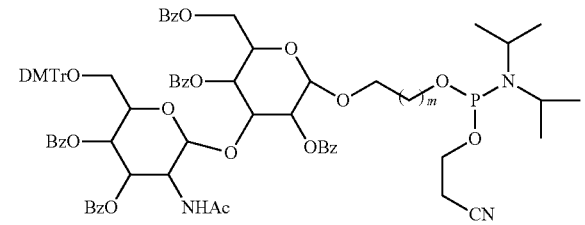
6018
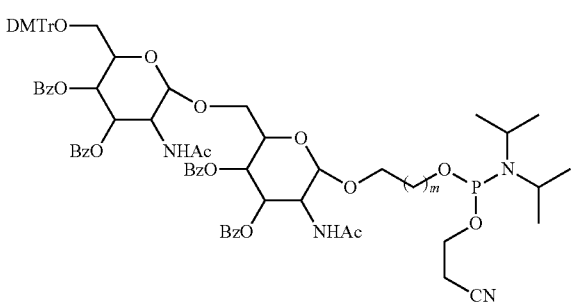
6019
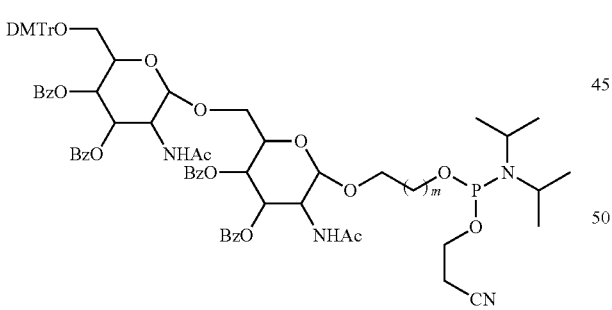
6020
-continued
6021
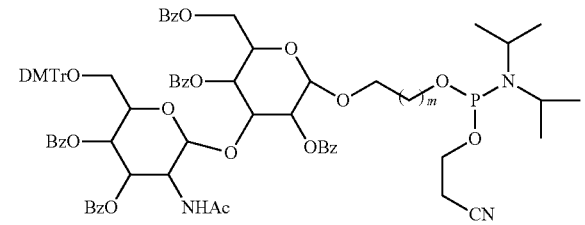
6022
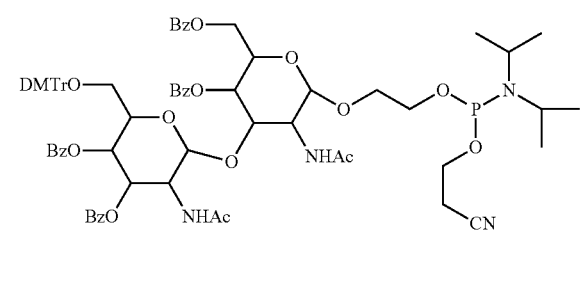
6023
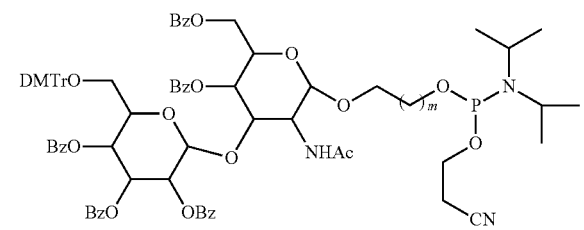
6024
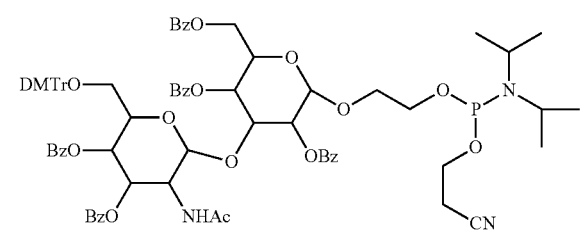
6025
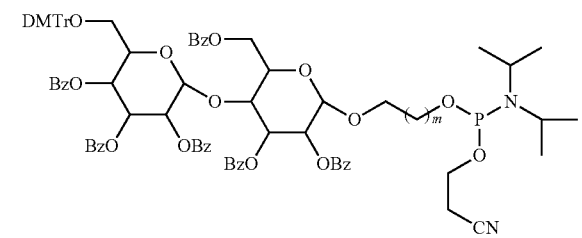

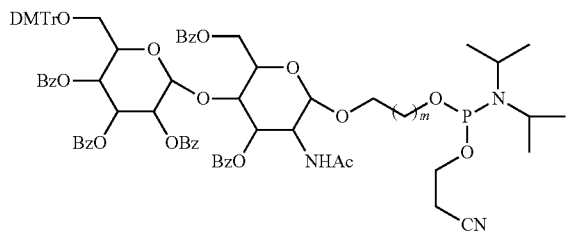

6026

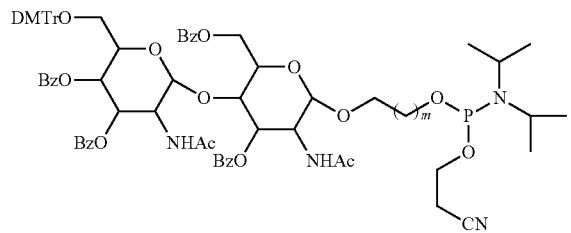

6028 n = 1-12; n = 1-12

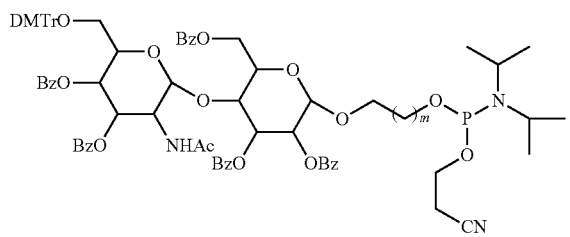

6027

Each asymmetric center is racemic or chirally pure R or S and combinations thereof Monomers with ODMTr protection is used for solid phase covalent attachment of 2 or more single stranded oligonucleotides. Monomers containing NHC(O)CF$_3$, acetylene or disulfide moiety are used for on column and/or solution phase post-synthetic covalent attachment of 2 or more single stranded oligonucleotides with complementary reactive group on incoming single strand.

Example 11

Prolinol N-carbamate Linker: Post-Synthesis

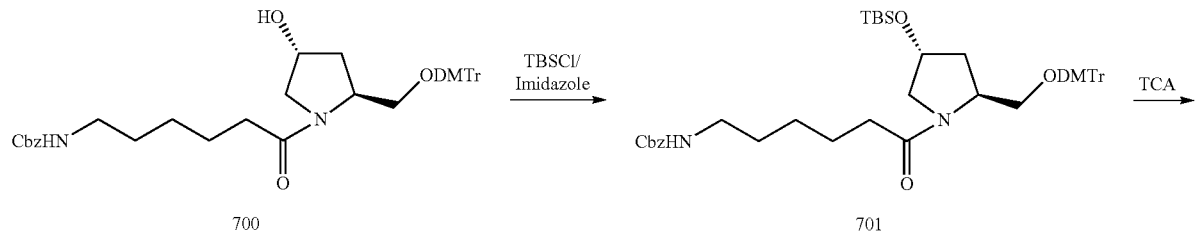

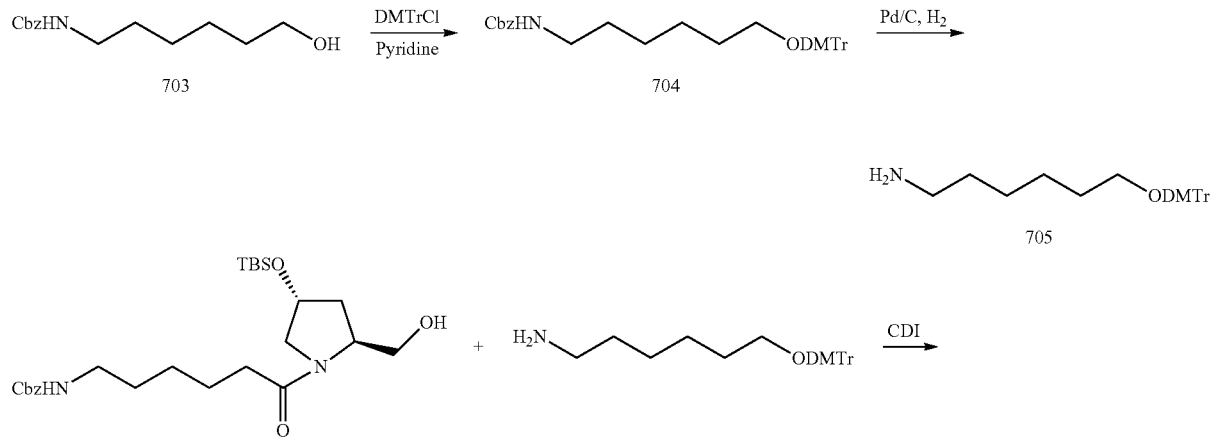

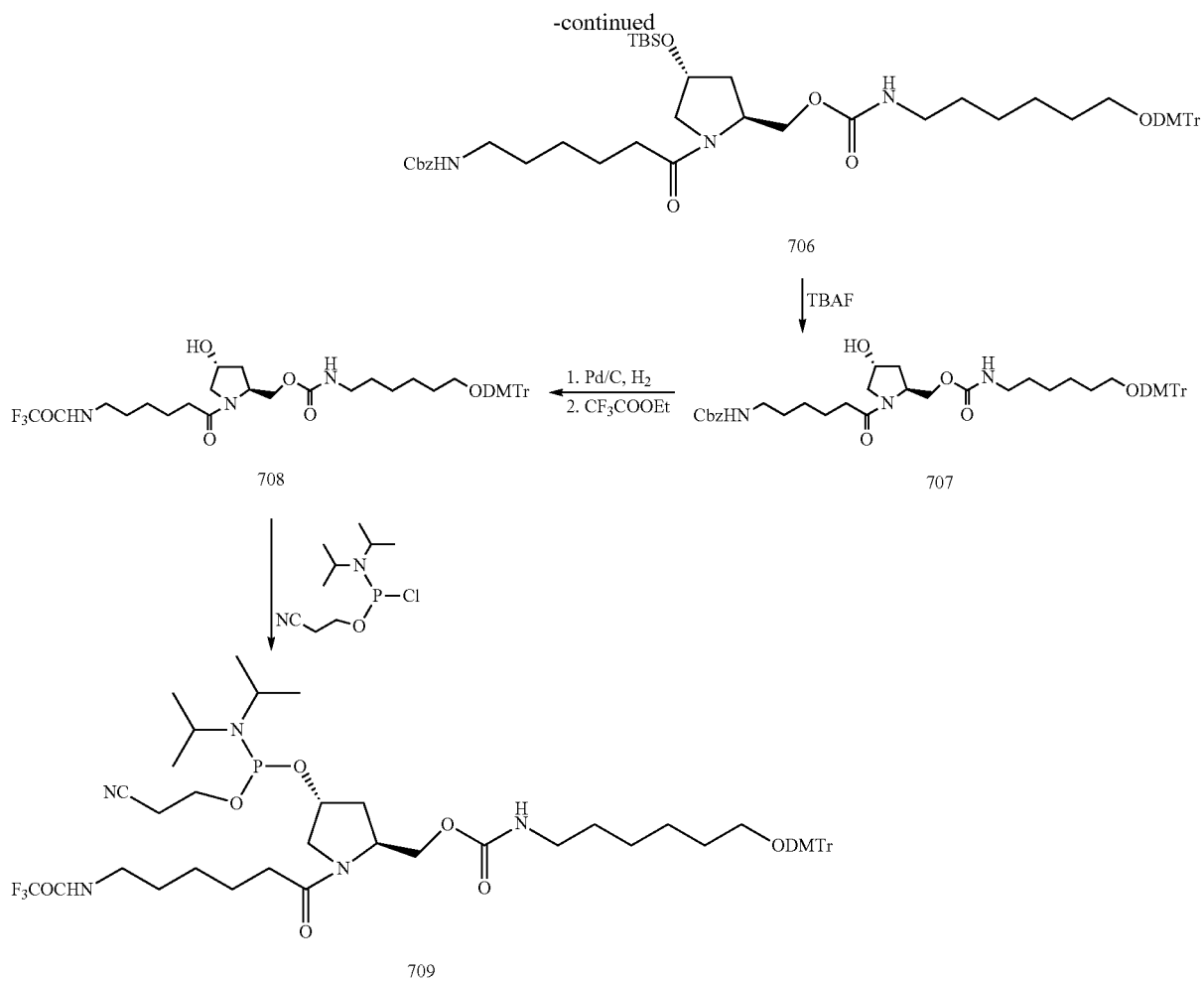

Synthesis of Compound 702:

To a stirred solution of alcohol 700 (50 g, 75 mmol) in DCM (250 mL) were added TBSCl (13.6 g, 90 mmol) and imidazole (12.75 g, 187.5 mmol) and stirred at room temperature for 14 h. 50 ml of water was added followed by extraction with DCM (250 mL), washed with saturated NaHCO$_3$ (50 mL), brine (50 mL) and the organic layer was dried over anhydrous Na$_2$SO$_4$. Concentration of the solvent gave the crude material. This material was dissolved in DCM (150 mL) and trichloroacetic acid (150 mL) and stirred at room temperature for 3 h. Concentration of the solvent followed by purification by column chromatography gave the product 702 (30 g, 85%). LCMS for compound 702: Calculated for C$_{25}$H$_{42}$N$_2$O$_5$Si: 478.70 (M$^+$).

Found: XXX.

Synthesis of Compound 704:

To a stirred solution of alcohol 703 (21.4 g, 85.3 mmol) in Pyridine (100 mL) was added DMTrCl (31.7 g, 93.5 mmol) and stirred at room temperature for 14 h. 50 ml of water was added followed by extraction with DCM (250 mL), washed with saturated NaHCO$_3$ (100 mL), brine (100 mL) and the organic layer was dried over anhydrous Na$_2$SO$_4$. Concentration of the solvent gave the crude material which was purified by column chromatography to get pure product 704 (40 g, 85%).

Synthesis of Compound 705:

To a stirred solution of 704 (4.28 g, 35.5 mmol) in MeOH (100 mL) was added 10% Pd/C (1 g) and the reaction mixture was stirred under hydrogen atmosphere at room temperature for 14 h. Filtered off the catalyst followed by concentration of the solvent gave the corresponding product 705 (3.2 g, 98%).

Synthesis of Compound 706:

To a stirred solution of alcohol 702 (5.9 g, 12.53 mmol) in DMF (100 mL) was added CDI (2.03 g, 12.53 mmol) and stirred at room temperature for 1 h. To the above solution was added amine 705 (5.3 g, 12.6 mmol) and stirred at room temperature overnight. 50 mL of water was added followed by extraction with ethyl acetate (250 mL), washed with saturated NaHCO$_3$ (50 mL), brine (50 mL) and the organic layer was dried over anhydrous Na$_2$SO$_4$. Concentration of the solvent gave the crude material which was purified by column chromatography to get the pure product 706 (6.18 g, 55%).

C$_{53}$H$_{73}$N$_3$O$_8$S: 908.26

Synthesis of Compound 708:

To a stirred solution of alcohol 706 (6.0 g, 6.5 mmol) in THF (100 mL) was added 1M TBAF in THF (8.1 mL, 8.1 mmol) and stirred at room temperature overnight. 50 mL of water was added followed by extraction with DCM (50 mL), washed with water (50 mL), brine (50 mL) and the organic layer was dried over anhydrous Na$_2$SO$_4$. Concentration of the solvent gave the crude material 707 (6.0 g) which was dissolved in MeOH (40 mL) and 10% Pd/C (1.0 g) was added and stirred under hydrogen atmosphere at room temperature for 14 h. Filtered off the catalyst followed by concentration of the solvent gave the corresponding amine (5.5 g). This amine was dissolved in $CH_3CN$ (50 mL) followed by ethyltrifluoro acetate (2 mL) and triethyl amine (2 mL) were added and stirred at room temperature overnight. Concentration of the reaction mixture followed by column chromatography gave pure product 708 (4.0 g, 80%).

Synthesis of Compound 709:

To a stirred solution of alcohol 708 (4.0 g, 5.18 mmol) in DCM (80 mL) were added DIEA (1.34 g, 10.34 mmol) and 2-Cyanoethyl N,N-diisopropylchlorophosphoramidite (1.53 g, 6.47 mmol) and the reaction mixture was stirred at room temperature overnight. 10 mL of saturated $NaHCO_3$ solution was added followed by extraction with DCM (50 mL×2), washed with water (50 mL), brine (50 mL) and the organic layer was dried over anhydrous $Na_2SO_4$. Concentration of the solvent gave the crude material which was purified by column chromatography to get the pure product 709 (3.5 g, 69%).

Example 12

Prolinol Amide Linker

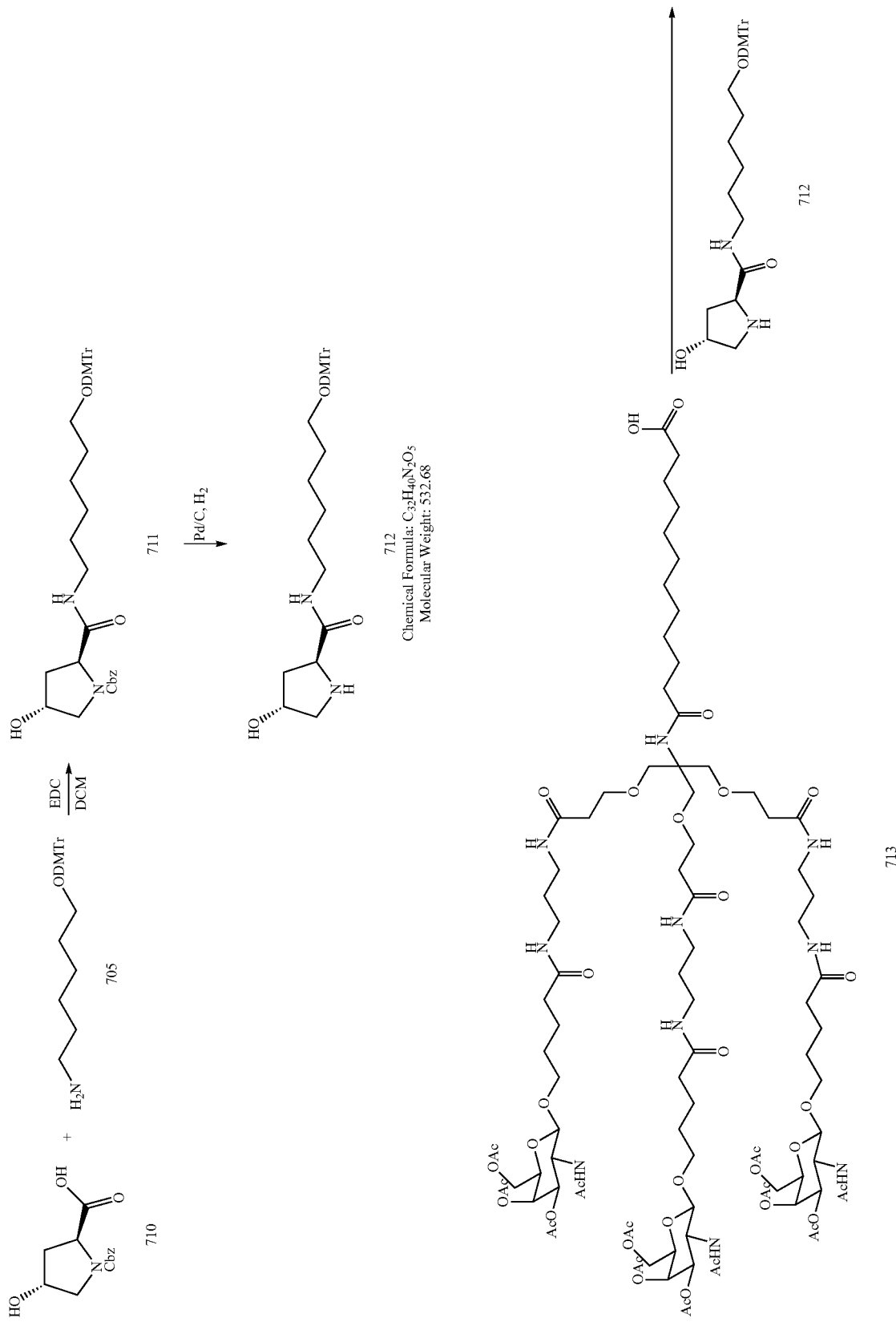

-continued
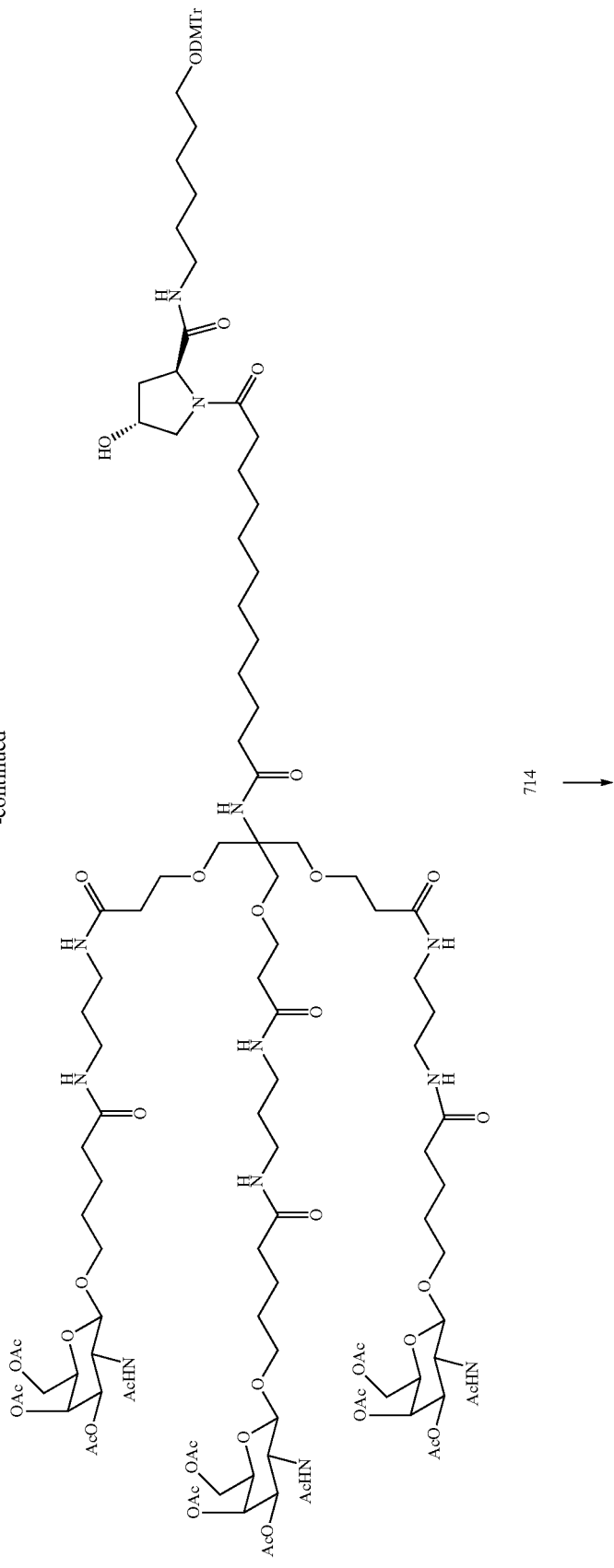

-continued
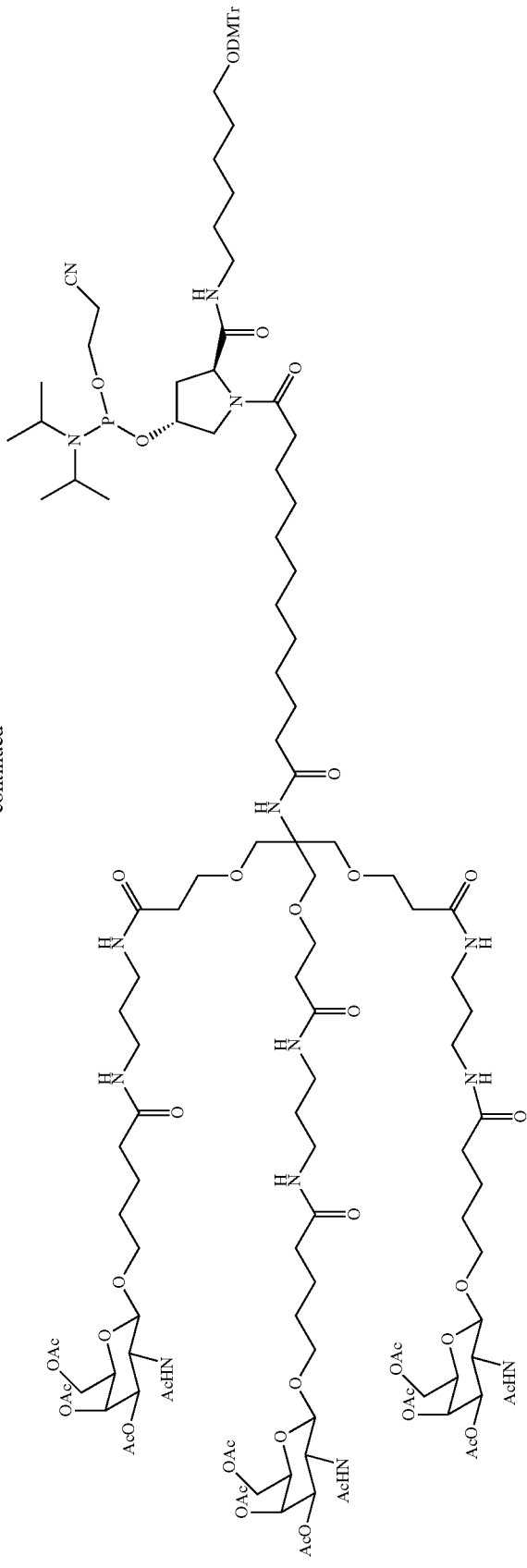
715

Synthesis of Compound 711:

To a stirred solution of acid 710 (2.9 g, 10.9 mmol) in DCM (50 mL) were added EDC (2.1 g, 10.9 mmol), HOBt (1.5 g, 9.6 mmol), amine 705 (3.7 g, 8.8 mmol) and DIEA (1.34 g, 10.34 mmol) and the reaction mixture was stirred at room temperature overnight. 50 mL of water was added followed by extraction with DCM (50 mL×2), washed with water (50 mL), brine (50 mL) and the organic layer was dried over anhydrous $Na_2SO_4$. Concentration of the solvent gave the crude material which was purified by column chromatography to get the pure product 711 (5.79 g, 80%).

Synthesis of Compound 712:

To a stirred solution of 711 (5.79 g, 8.7 mmol) in MeOH (50 mL) and 10% Pd/C (1.0 g) was added and the reaction mixture was stirred under hydrogen atmosphere at room temperature for 14 h. Filtered off the catalyst followed by concentration of the solvent gave the corresponding amine (5.0 g). LCMS for calculated for $C_{32}H_{40}N_2O_5$: 532.68 (M); found: 555.20 ($M^+$+$Na^+$).

Synthesis of Compound 714:

To a stirred solution of acid 713 (9.2 g, 4.6 mmol) in DMF (150 mL) were added HBTU (2.1 g, 5.54 mmol), HOBt (1.0 g, 6.4 mmol), amine 712 (2.4 g, 4.6 mmol) and DIEA (1.5 g, 11.62 mmol) and the reaction mixture was stirred at room temperature overnight. 50 mL of water was added followed by extraction with DCM (50 mL×2), washed with water (50 mL), brine (50 mL) and the organic layer was dried over anhydrous $Na_2SO_4$. Concentration of the solvent gave the crude material which was purified by column chromatography to get the pure product 714 (5.0 g, 43%).

MALDI for compound 714: Calculated for $C_{123}H_{186}N_{12}O_{43}$: 2519.27 ($M^+$), Found: 2542.43.

Synthesis of Compound 715:

To a stirred solution of alcohol 714 (3.2 g, 1.27 mmol) in DCM (60 mL) were added DIEA (0.8 g, 6.34 mmol) and 2-Cyanoethyl N,N-diisopropylchlorophosphoramidite (301 mg, 1.27 mmol) and the reaction mixture was stirred at room temperature overnight. 10 mL of saturated $NaHCO_3$ solution was added followed by extraction with DCM (50 mL×2), washed with water (50 mL), brine (50 mL) and the organic layer was dried over anhydrous $Na_2SO_4$. Concentration of the solvent gave the crude product 715 (3.0 g).

Example 13

Prolinol N-carbamate Linker

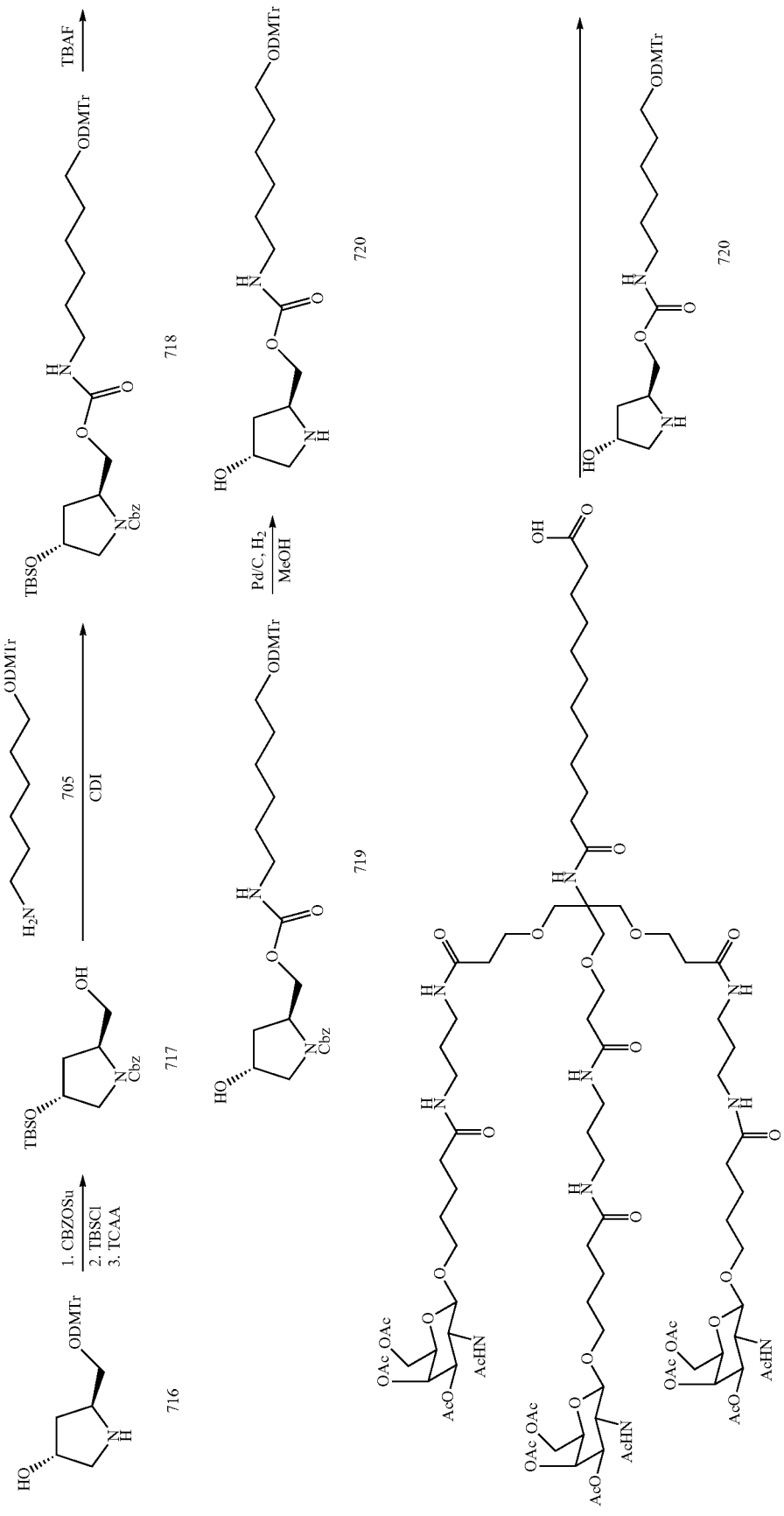

-continued
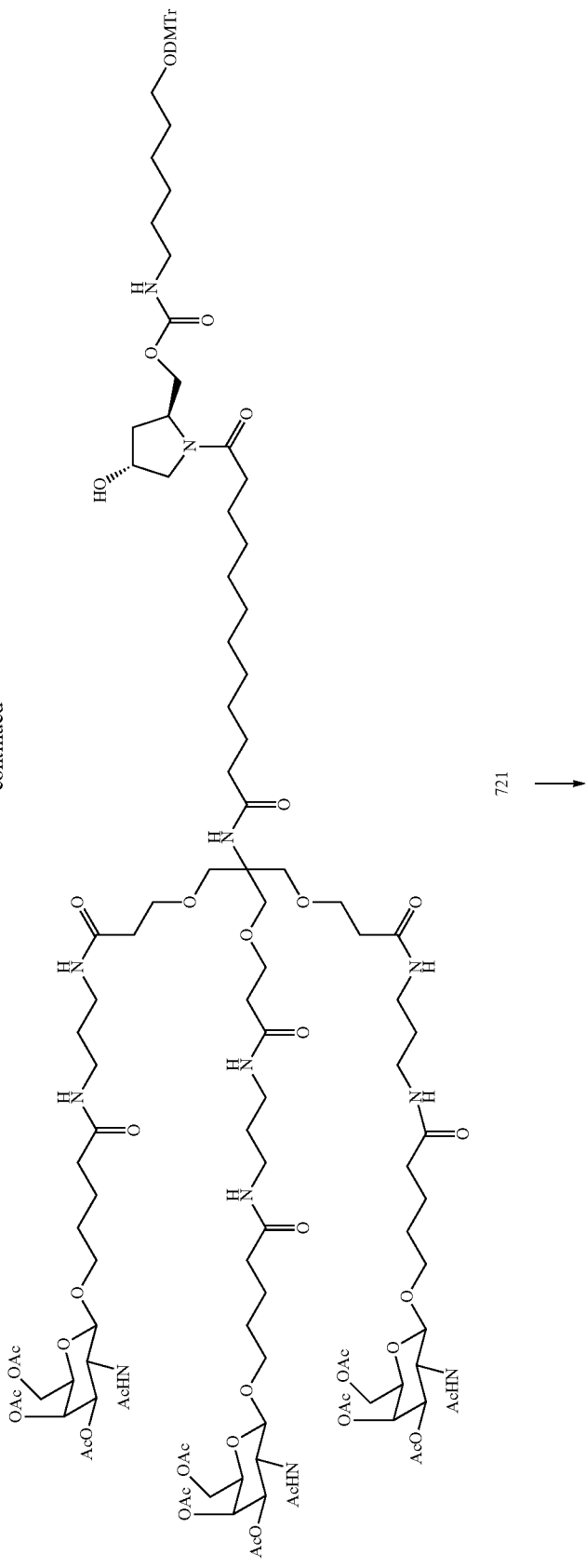

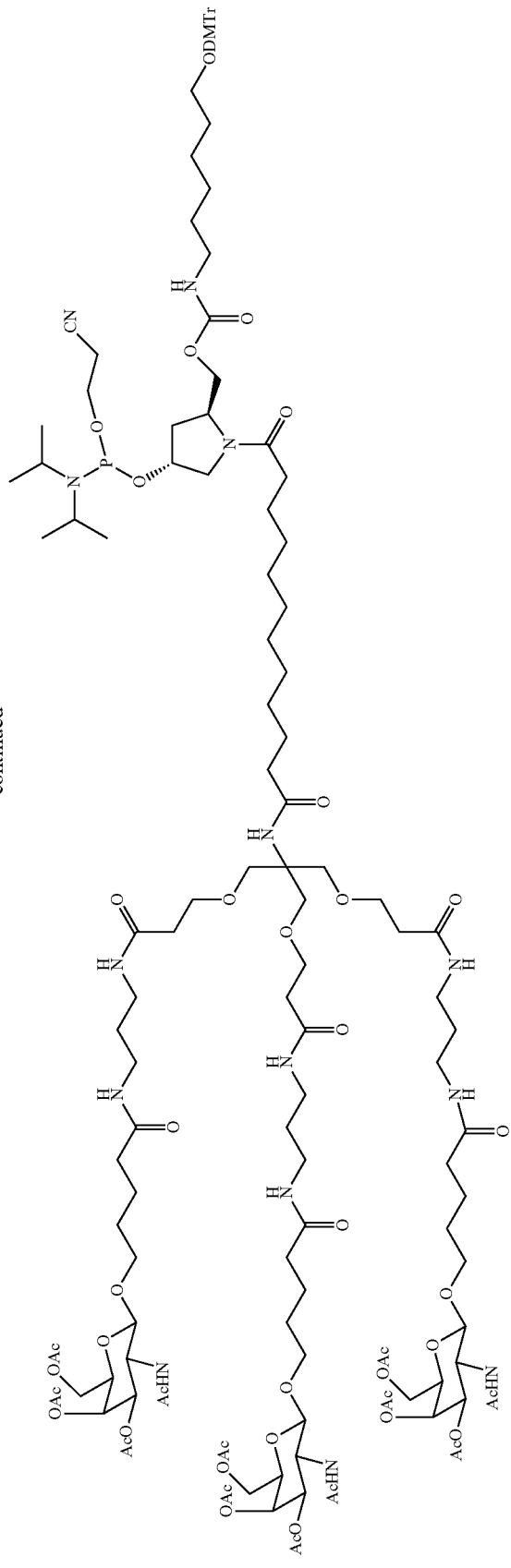

Synthesis of Compound 717:

To a stirred solution of alcohol 716 (20 g, 48 mmol) in THF (250 mL) were added Cbz-OSu (12 g, 48 mmol) and aqueous $NaHCO_3$ (50 mL) and the reaction mixture was stirred at room temperature overnight. 10 mL of saturated $NaHCO_3$ solution was added followed by extraction with ethyl acetate (250 mL×2), washed with water (50 mL), brine (50 mL) and the organic layer was dried over anhydrous $Na_2SO_4$. Concentration of the solvent gave the crude product which was dissolved in DCM 9250 mL). To the above solution were added TBSCl (8.6 g) and imidazole (8.2 g) and the reaction mixture was stirred at room temperature overnight. 50 mL of saturated $NaHCO_3$ solution was added followed by extraction with DCM (250 mL×2), washed with water (100 mL), brine (100 mL) and the organic layer was dried over anhydrous $Na_2SO_4$. Concentration of the solvent gave the crude product which was dissolved in trichloroacetic acid (100 mL) and DCM (250 mL) and stirred at room temperature for 2 h. Concentration followed by column chromatography gave the product 717 (13 g, 74%). LCMS for calculated for $C_{19}H_{31}NO_4Si$: 365.20 ($M^+$); found: 366.1 $M^+$+1).

Synthesis of Compound 718:

To a stirred solution of alcohol 717 (1.65 g, 4.5 mmol) in DCM (20 mL) was added CDI (730 mg, 4.5 mmol) and stirred at room temperature for 1 h. To the above solution was added amine 705 (1.89 g, 4.5 mmol) and stirred at room temperature overnight. 5 mL of water was added followed by extraction with DCM (50 mL), washed with saturated $NaHCO_3$ (50 mL), brine (50 mL) and the organic layer was dried over anhydrous $Na_2SO_4$. Concentration of the solvent gave the crude material which was purified by column chromatography to get the pure product 717 (2.32 g, 64%).

Synthesis of Compound 719:

To a stirred solution of alcohol 718 (2.32 g, 2.86 mmol) in THF (30 mL) was added 1M TBAF in THF (5.2 mL) and stirred at room temperature overnight. 10 mL of water was added followed by extraction with DCM (50 mL), washed with water (50 mL), brine (50 mL) and the organic layer was dried over anhydrous $Na_2SO_4$. Concentration of the solvent gave the crude material which was purified by column chromatography to get the product 719 (1.67 g, 84%). LCMS for calculated for $C_{41}H_{48}N_2O_8$: 696.34 ($M^+$); found: 731.2 ($M^+$+$Cl^-$).

Synthesis of Compound 721:

To a stirred solution of 719 (1.65 g, 2.37 mmol) dissolved in MeOH (20 mL) and 10% Pd/C (250 mg) was added and stirred under hydrogen atmosphere at room temperature for 14 h. Filtered off the catalyst followed by concentration of the solvent gave the corresponding amine 720 (1.29 g, 97%). This amine was dissolved in DCM (80 mL) followed by HBTU (1.06 g), HOBt (428 mg), and DIEA (0.78 mL) were added and stirred at room temperature overnight. 50 mL of water was added followed by extraction with DCM (250 mL), washed with saturated $NaHCO_3$ (50 mL), brine (50 mL) and the organic layer was dried over anhydrous $Na_2SO_4$. Concentration of the solvent gave the crude material which was purified by column chromatography to get the pure product 721 (3.97 g, 66%). MALDI calculated for $C_{124}H_{188}N_{12}O_{44}$: 2549.28 ($M^+$), Found: 2569.53 ($M^+$+$Na^+$).

Example 14

Prolinol Ether Linker

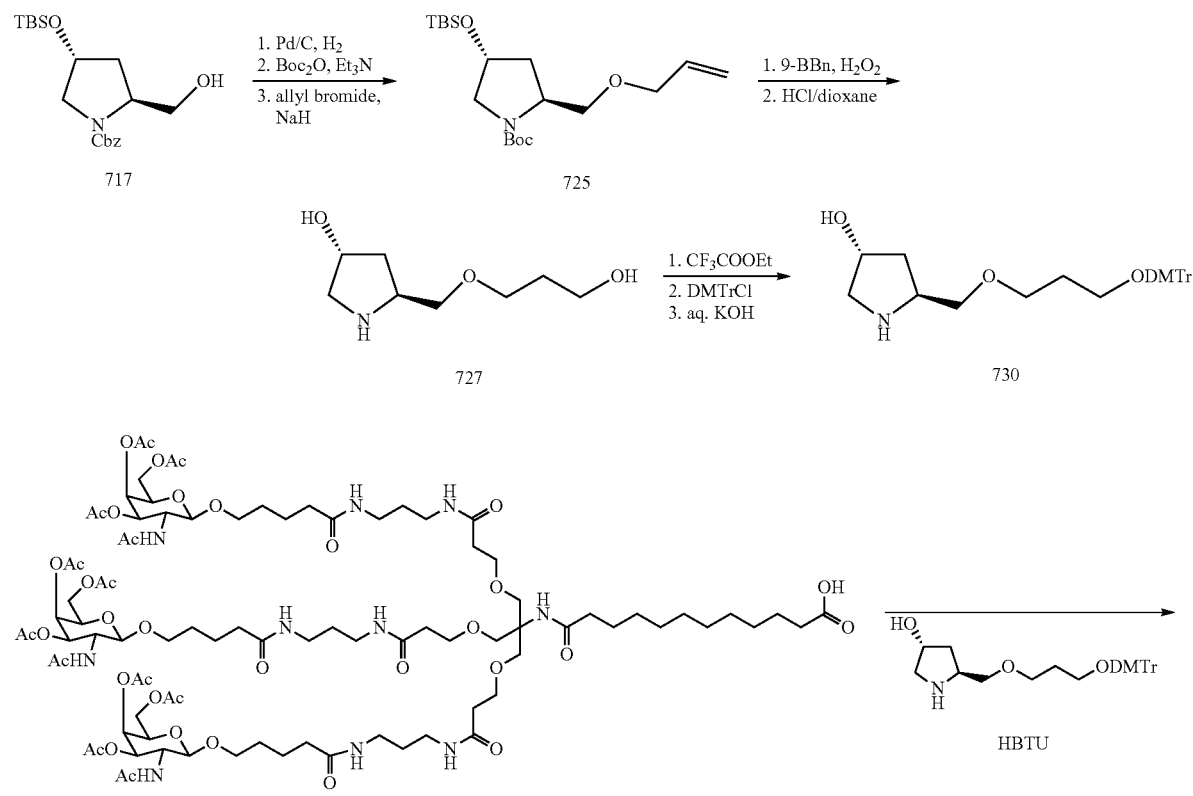

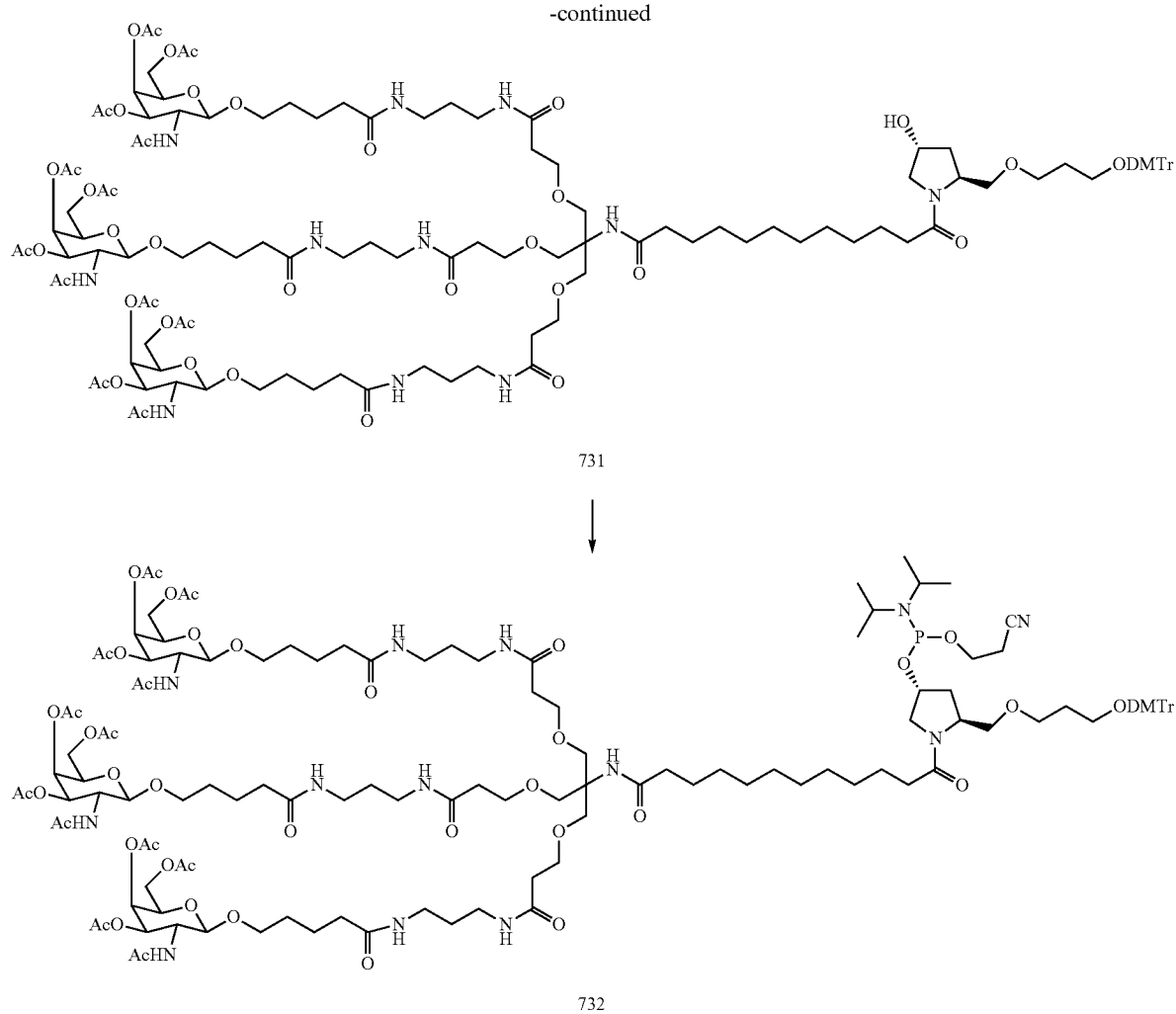

Synthesis of Compound 724:

To a stirred solution of 717 (9 g, 24.65 mmol) dissolved in MeOH (250 mL) and 10% Pd/C (2.0 g) was added and stirred under hydrogen atmosphere at room temperature for 14 h. Filtered off the catalyst followed by concentration of the solvent gave the corresponding amine 723 (6.2 g) which was re-dissolved in DCM (100 mL). To the above solution were added Boc$_2$O (6.4 g) and triethyl amine (7.6 mL) and the reaction mixture was stirred at room temperature overnight. 50 mL of water was added followed by extraction with DCM (250 mL), washed with saturated NaHCO$_3$ (50 mL), brine (50 mL) and the organic layer was dried over anhydrous Na$_2$SO$_4$. Concentration of the solvent gave the crude material which was purified by column chromatography to get the pure product 724 (8.0 g, 98%).

Synthesis of Compound 725:

To a stirred solution of alcohol 724 (8.0 g, 24.13 mmol) in THF (100 mL) was added NaH (1.2 g, 60% in mineral oil) and stirred at room temperature 30 min. To the above solution was added allyl bromide (5.8 g) at 0° C. and the reaction mixture was stirred at room temperature overnight. 5 mL of water was added followed by extraction with ethyl acetate (250 mL), washed with water (50 mL), brine (50 mL) and the organic layer was dried over anhydrous Na$_2$SO$_4$. Concentration of the solvent gave the crude material which was purified by column chromatography to get the product 725 (6.44 g, 71%).

Synthesis of Compound 726:

To a stirred solution of alcohol 725 (6.4 g, 24.9 mmol) in THF (30 mL) was added 60 mL of 1M 9-BBN and the reaction mixture was stirred at room temperature overnight. To the above solution was added 20 mL of 3M NaOAc and 20 mL of H$_2$O$_2$ and the reaction mixture was stirred at room temperature overnight. 50 mL of water was added followed by extraction with ethyl acetate (250 mL×2), washed with water (50 mL), brine (50 mL) and the organic layer was dried over anhydrous Na$_2$SO$_4$. Concentration of the solvent gave the crude material which was purified by column chromatography to get the product 726 (6.6 g, 62%). LCMS for calculated for C$_{19}$H$_{39}$NO$_5$Si: 389.26 (M$^+$); found: 390.1 (M$^+$+1).

Synthesis of Compound 729:

To a stirred solution of alcohol 726 (6.0 g) in dioxane (50 mL) was added 4M HCl in dioxane and stirred at room temperature 3 h. decanted the solvent, ringed with 50 mL of dioxane and the obtained viscous material was dried under reduced pressure. This material was suspended in DCM followed by ethyl trifluoracetate (5 mL) and triethyl amine (5 mL) were added and stirred at room temperature 24 h.

Concentration followed by purification by column chromatography gave the product 728 (1.9 g). To the above material 728 (1.9 g, 7.01 mmol) in pyridine (30 mL) was added DMTrCl (2.6 g) and stirred at room temperature overnight. 20 mL of water was added followed by extraction with ethyl acetate (50 mL), washed with water (50 mL), brine (50 mL) and the organic layer was dried over anhydrous Na$_2$SO$_4$. Concentration of the solvent gave the crude material which was purified by column chromatography to get the product 729 (3.36 g, 84%).

Synthesis of Compound 730:

To a stirred solution of 729 (3.36 g, 5.86 mmol) in acetonitrile (50 mL) was added aqueous KOH (20 mL) and stirred at room temperature overnight. 20 mL of water was added followed by extraction with ethyl acetate (100 mL), washed with water (50 mL), brine (50 mL) and the organic layer was dried over anhydrous Na$_2$SO$_4$. Concentration of the solvent gave the crude material which was purified by column chromatography to get the product 730 (2.65 g, 95%).

Synthesis of Compound 731:

To a stirred solution of acid 730 (1.55 g, 3.25 mmol) in DCM (60 mL) were added 713 (6.5 g, 3.25 mmol), HBTU (2.5 g), HOBt (1.0 g) and DIEA (1.6 g) and the reaction mixture was stirred at room temperature overnight. 50 mL of water was added followed by extraction with DCM (100 mL×2), washed with water (50 mL), brine (50 mL) and the organic layer was dried over anhydrous Na$_2$SO$_4$. Concentration of the solvent gave the crude material which was purified by column chromatography to get the pure product 731 (3.7 g, 46%). MALDI calculated for C$_{120}$H$_{181}$N$_{11}$O$_{43}$: 2464.23 (M$^+$), Found: 2484.61 (M$^+$+Na$^+$).

Example 15

Prolinol Ether Linker: Post-Synthesis Amidite

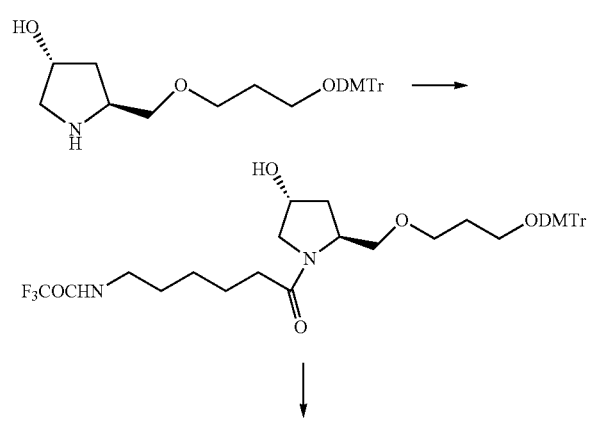

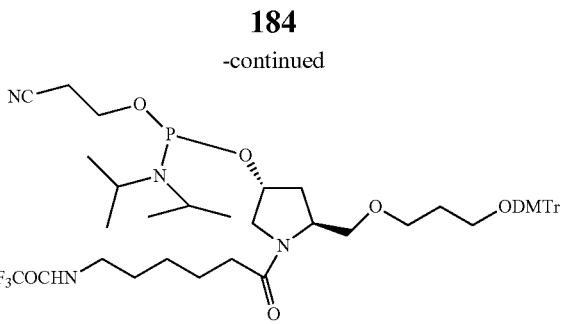

Example 16

Biodegradable Linkages

1. Enzymatic Degradation a) Esters (Cleavable by Esterases)

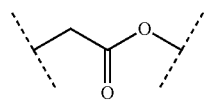

b) Acetals: Sugar Based Acetals

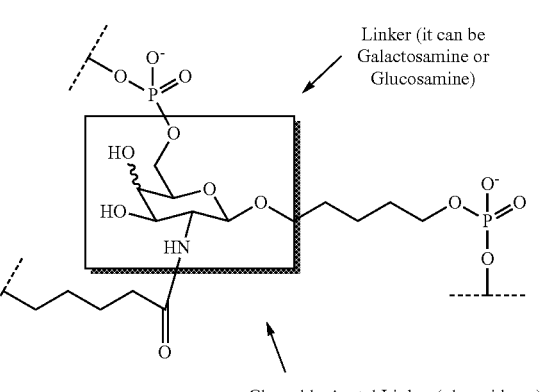

Cleavable Acetal Linker (glycosidases)

2. Acyclic Acetals/Ketals (Acidic pH Degradation)

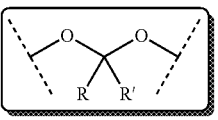

3. Redox Reaction

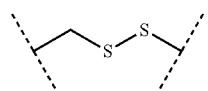

1. a) Synthesis of Esters:
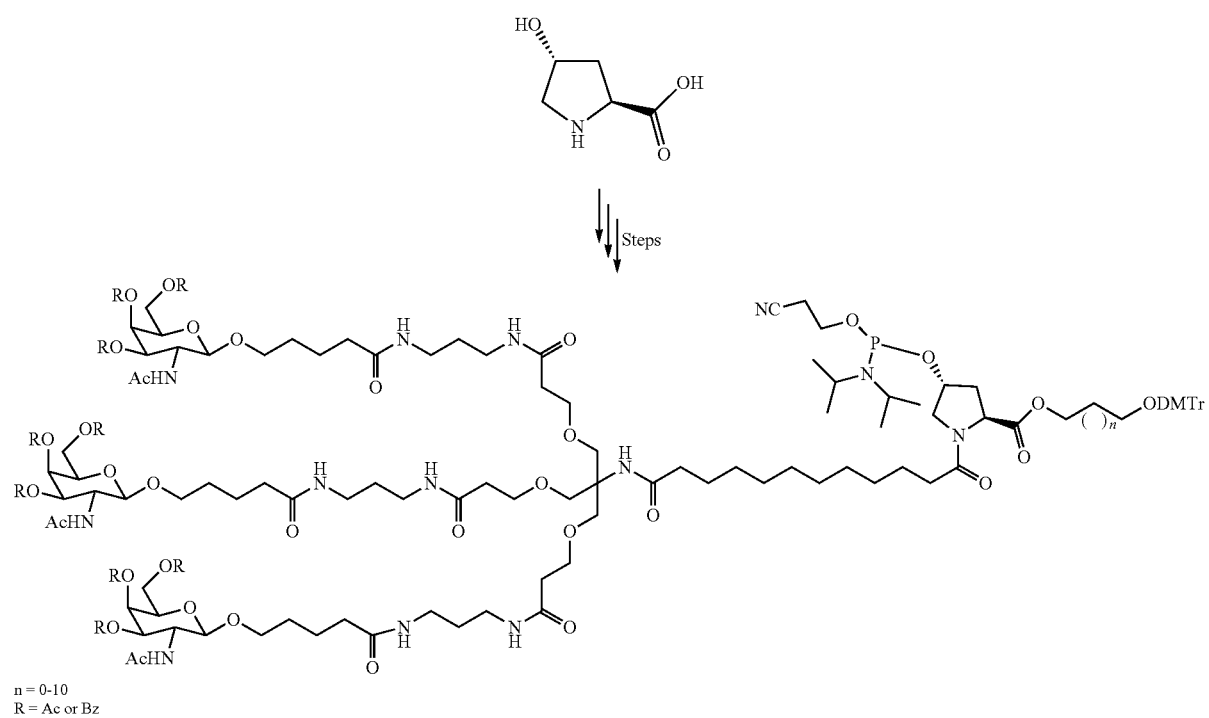
n = 0-10
R = Ac or Bz
b) Synthesis of Sugar Based Acetals:

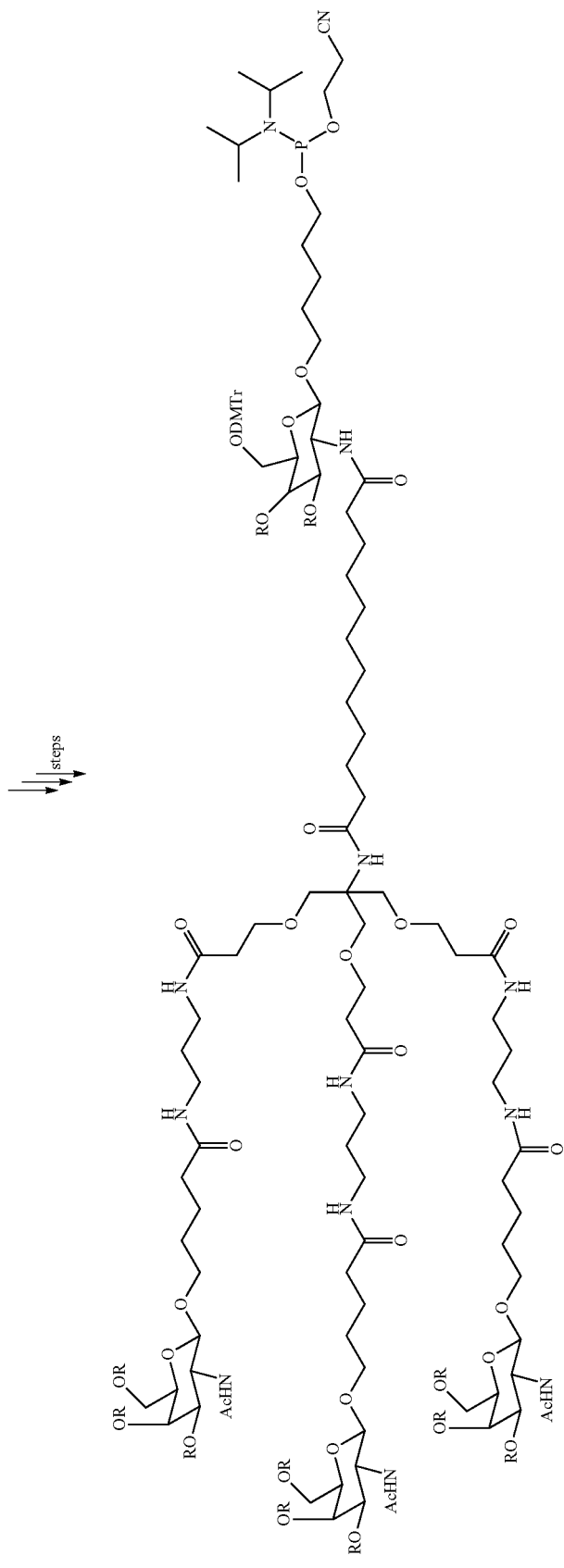

Example 17

Synthesis of Precursors for Post Synthesis Triantennary GalNAc Ligand 191 192
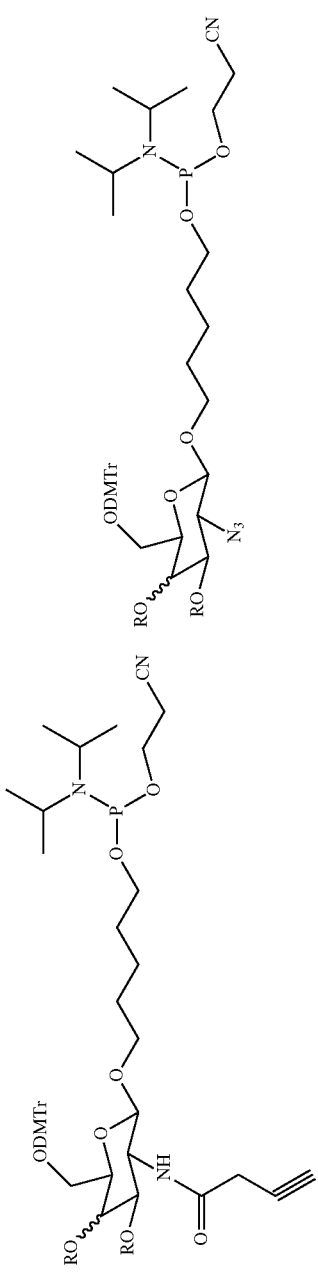
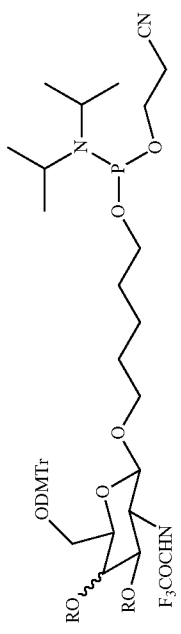
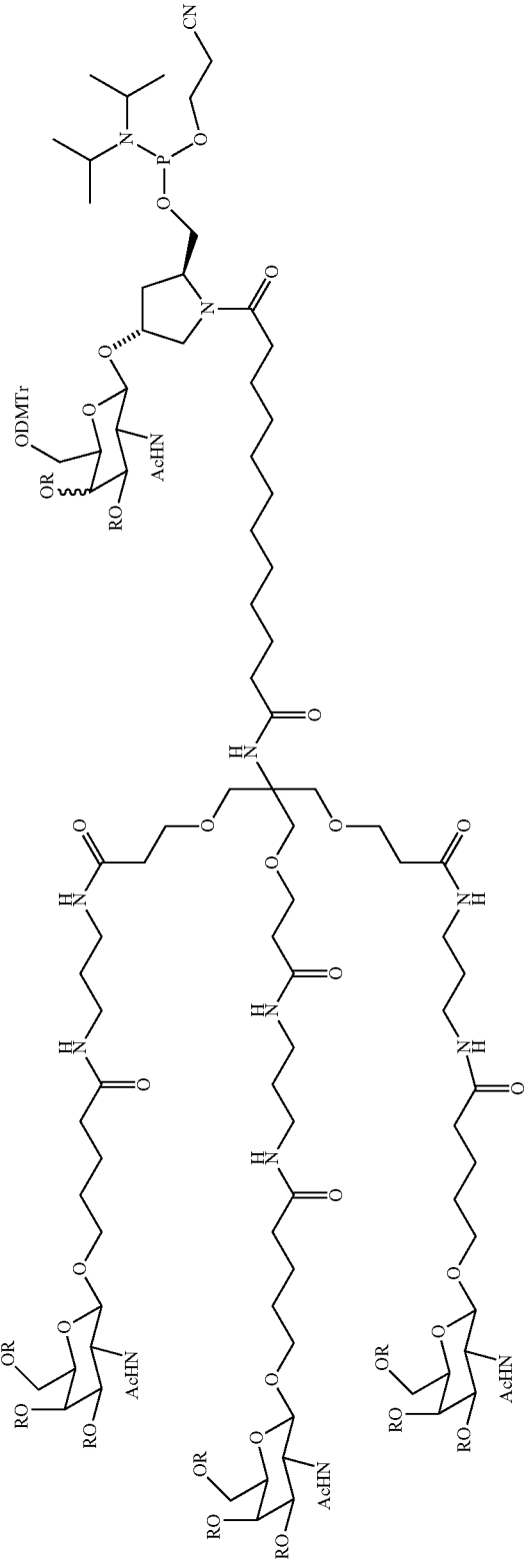

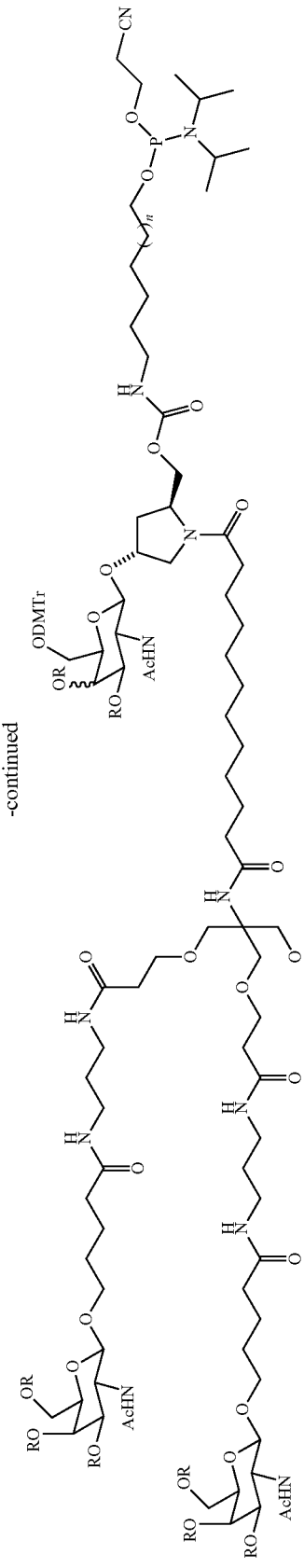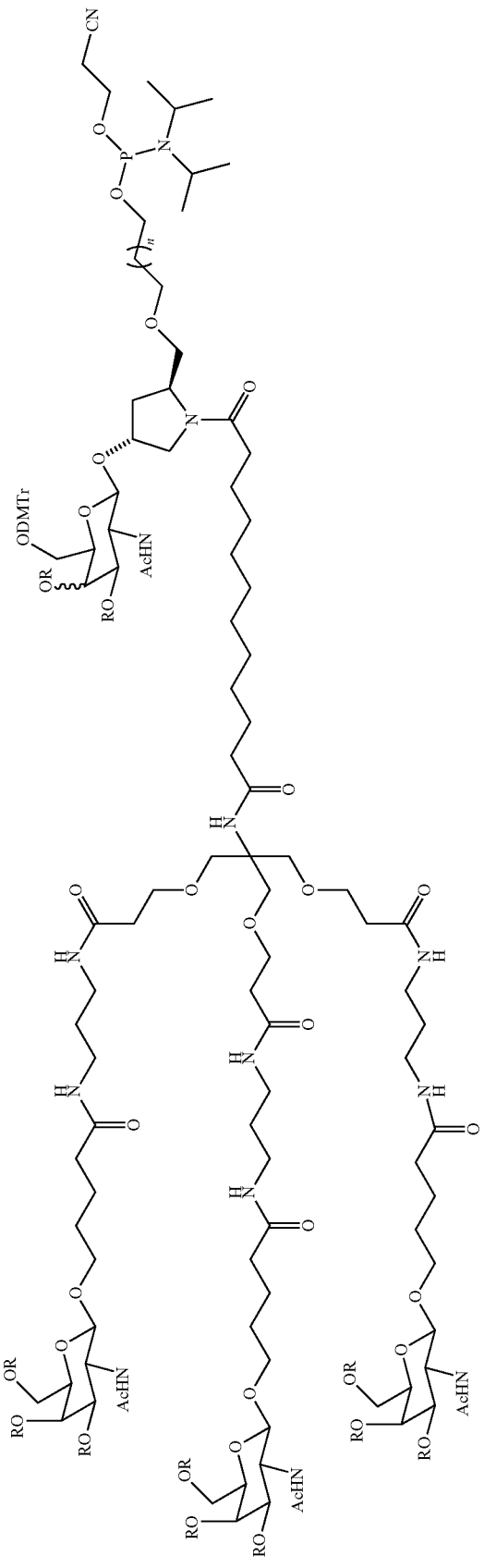
R = Ac or Bz
n = 0-10

Example 18
Linear Multi-GalNAc Ligands
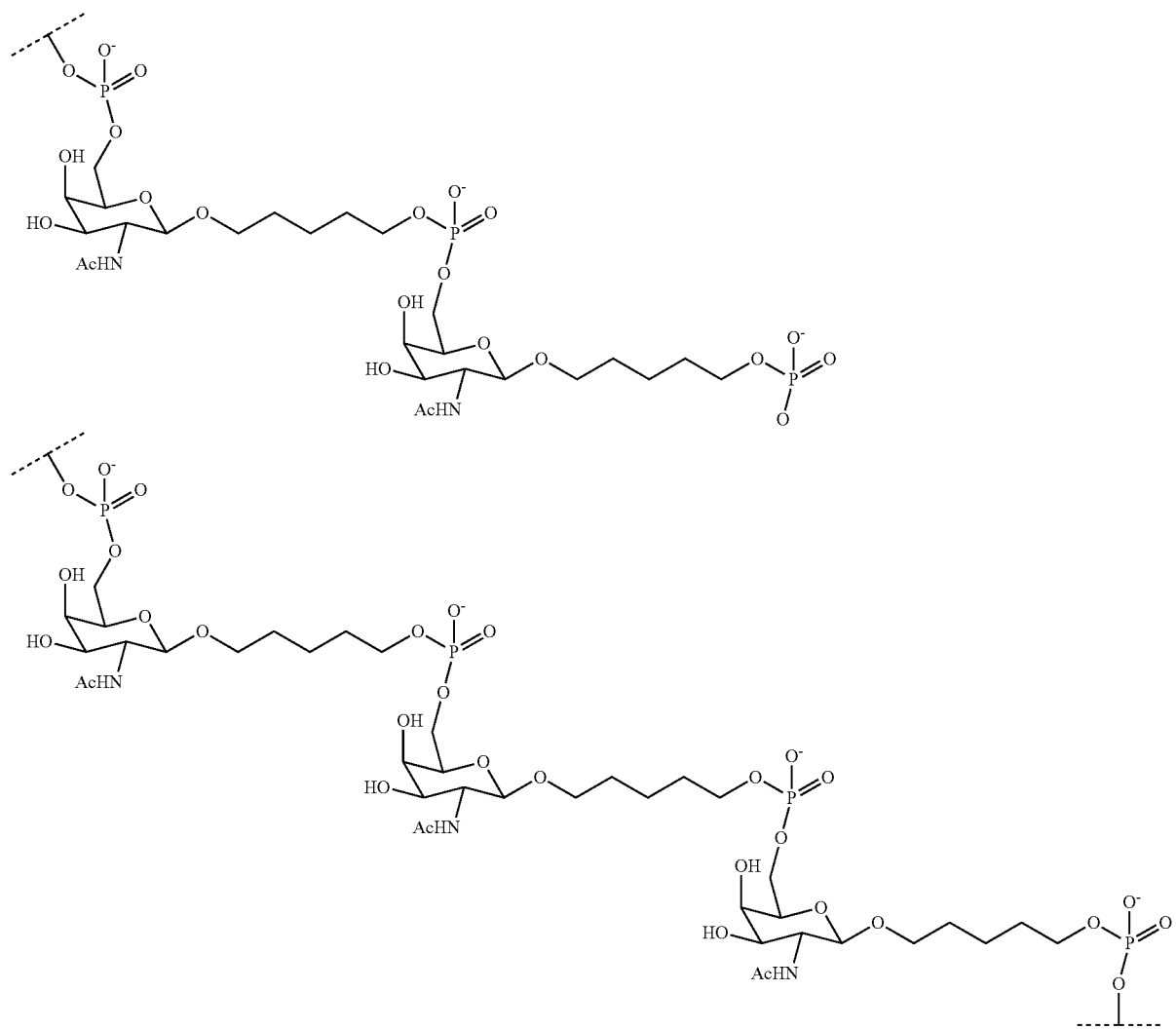
Synthesis of Precursors:
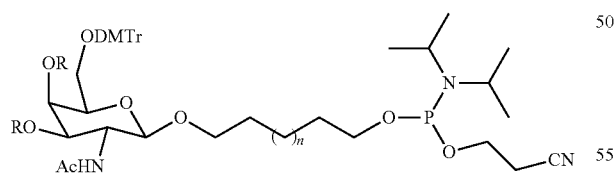
R = Ac or Bz
n = 0-10
Example 19
Synthesis of Acyclic Acetals
i) Synthesis of Linear Multi-GalNAc Ligand Precursors

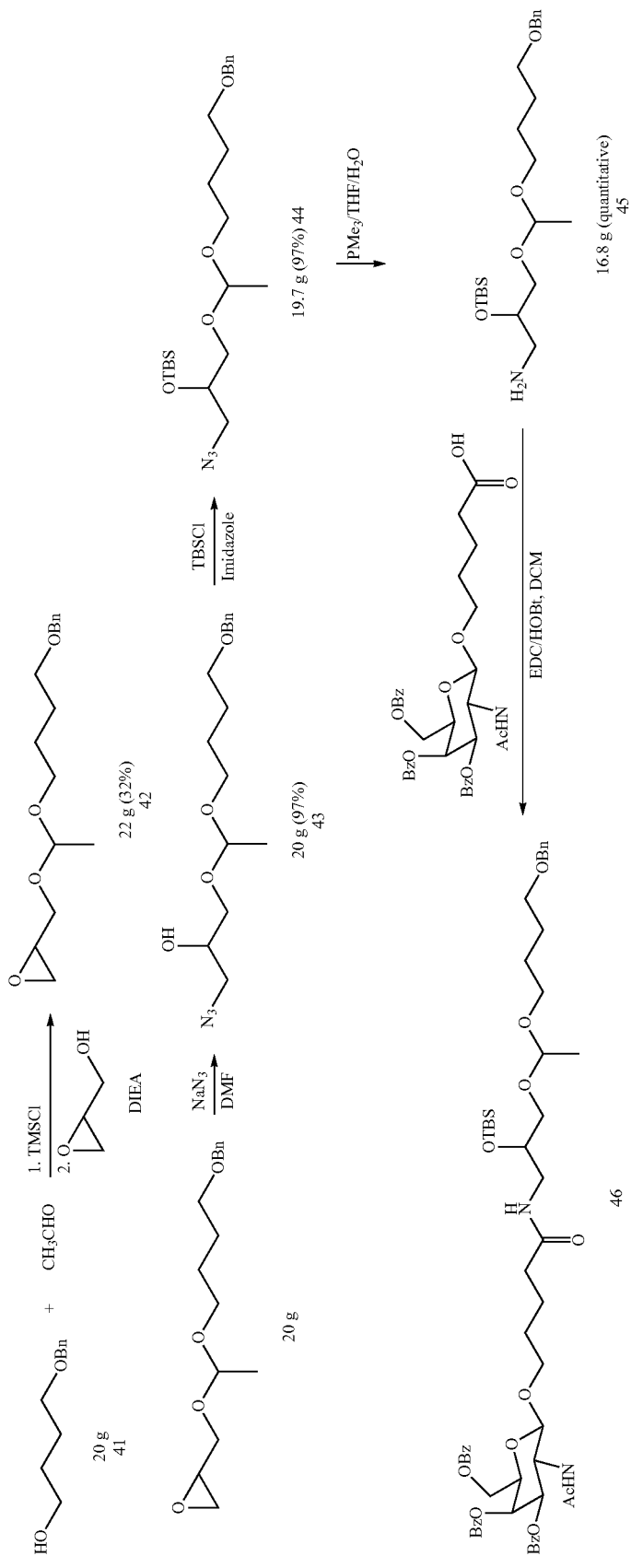

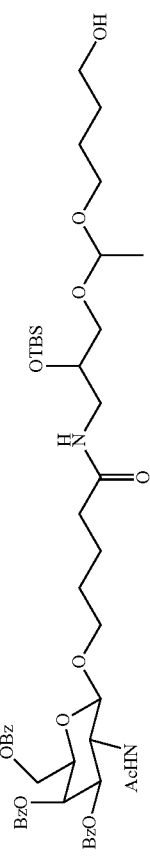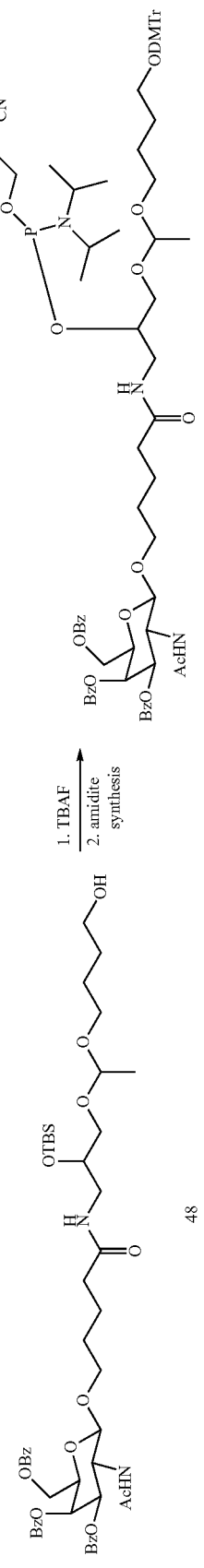

ii) Synthesis of Linear Triantennary GalNAc Ligand Precursors
Synthesis of Biodegradable Acetal Mono-GalNAc Ligand Precursors:

(i) trimethylsilyl chloride, acetaldehyde rt; (ii) glycidol, DIEA/DCM, rt 77%; (iii) sodium azide, ammonium chloride, H₂O/MeOH, 80° C. reflux, 97%; (iv) tert-butyldimethylsilyl chloride, imidazole, DCM, rt, 97%; (v) trimethylphosphine, H₂O/THF, rt, 99%; (vi) Mono-GalNAc acid, EDAC hydrochloride, HOBt, DIEA/DCM, rt, 82%; (vii) H₂/Pd—C, EtOAc/MeOH, rt, 99%; (viii) DMTr-Cl, DMAP, pyridine, rt, 96% (ix) tetrabutylammonium fluoride, THF, 0° C., 99%;

Synthesis of Compound 42:

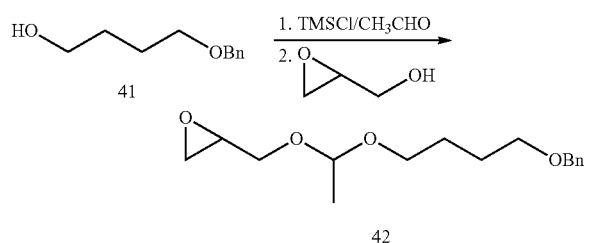

4-Benzyloxy-1-butanol, 41 (19.5 mL, 110 mmol) and trimethylsilyl chloride (70 mL) were added to a 200 mL round bottom flask and stirred at room temperature. To the mixture, acetaldehyde (6.24 mL, 110 mmol) was added and the reaction stirred at ambient temperature for 1 hour. The reaction mixture was then evaporated to dryness and placed under high vacuum for 2 hours. The resulting crude was then dissolved in anhydrous dichloromethane (80 mL). N,N-diisopropylethylamine (40 mL, 220 mmol) was added to the mixture as it stirred at ambient temperature under argon. To the mixture, glycidol (7.36 mL, 110 mmol) was added and the reaction stirred at ambient temperature under argon overnight. The reaction mixture was diluted in dichloromethane (100 mL) washed with saturated bicarbonate solution (150 mL). The organic layer was collected dried over sodium sulfate, filtered, and evaporated to dryness. The resulting crude was purified by ISCO column chromatography, yielding pure 22 g (77%) of Compound 42 (Rf=0.24, 20% EtOAc/hexanes) as a clear liquid. Mass calculated for [M+1] $C_{16}H_{24}O_4$, 281.2. Found 281.3.

Synthesis of Compound 43:

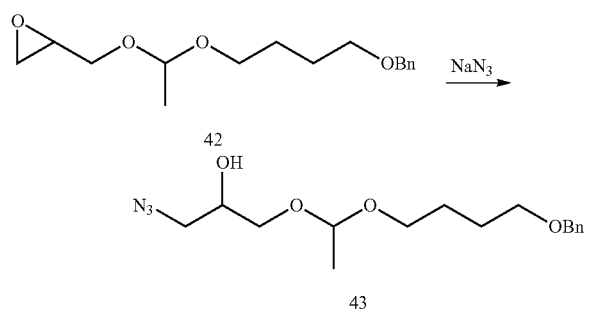

Anhydrous sodium azide (18.8 g, 315 mmol) and ammonium chloride (9.6 g, 175 mmol) were added to a methanol:H₂O (8:2) solution (400 mL). Compound 42 (20 g, 70 mmol) was added drop wise to the mixture, which refluxed at 80° C. under argon overnight. The reaction was monitored by TLC and upon completion, the reaction mixture was washed with dichloromethane (200 mL). The aqueous layer was washed with another portion of dichloromethane (200 mL). The organic layers were then combined and washed with brine (200 mL), dried over sodium sulfate, filtered, and evaporated to dryness affording 20 g (97%) of Compound 43 as a clear liquid, which was used without further purification. Mass calculated for [M+1] $C_{16}H_{25}N_3O_4$, 323.1 Found 323.1.

Synthesis of Compound 44:

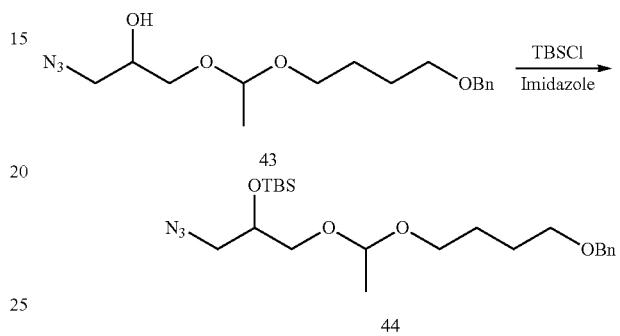

Compound 43 (19 g, 62 mmol) and imidazole (10.53 g, 155 mmol) were dissolved in dichloromethane (300 mL) and it was stirred under nitrogen at 0° C. tert-Butyldimethylsilyl chloride (11.62 g, 78 mmol) was slowly added to the reaction mixture, which stirred under argon at ambient temperature. After 18 hours, the reaction mixture was washed with water (250 mL) followed by saturated brine (200 mL). The organic layer was then dried over sodium sulfate, filtered, and evaporated to dryness. The resulting crude was purified by ISCO column chromatography, affording 19.7 g (97%) of Compound 44 (Rf=0.33, 20% EtOAc/hexanes) as a clear syrup. Mass calculated for [M-N₂] $C_{22}H_{39}N_3O_4Si$, 409.2 Found 409.2.

Synthesis of Compound 45:

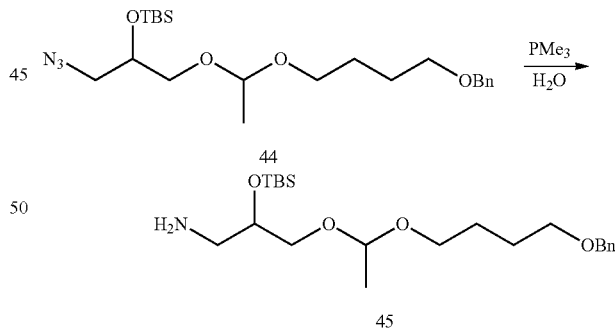

Compound 44 (13.68 g, 31.26 mmol) was added to a tetrahydrofuran:H₂O (300:2) solution (302 mL). Trimethylphosphine (40 mL) was added to the solution drop wise as the reaction mixture stirred at ambient temperature overnight. The reaction mixture was evaporated to dryness, and then diluted in ethyl acetate (300 mL). The organic layer was washed with water (200 mL) and brine (200 mL), dried over sodium sulfate, filtered, and evaporated to dryness. The resulting crude was purified by ISCO column chromatography, affording 16.8 g (99%) of Compound 45 (Rf=0.30, 10% MeOH/DCM) as a clear syrup. Mass calculated for [M+1] $C_{22}H_{41}NO_4Si$, 412.3 Found 412.3.

Synthesis of Compound 46:

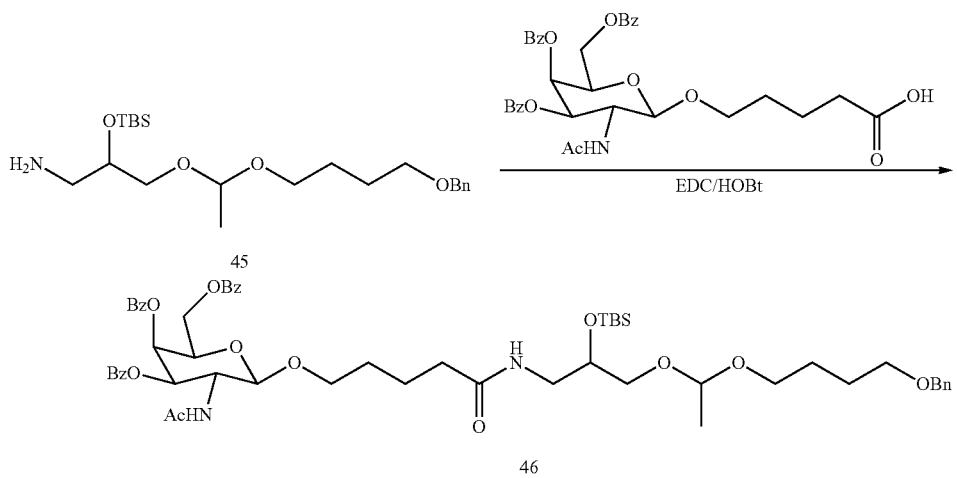

Mono GalNAc acid (7.7 g, 12 mmol), EDAC hydrochloride (4.7 g, 30 mmol), and hydroxybenzotriazole (3.3 g, 25 mmol) were dissolved in anhydrous dichloromethane (80 mL). N,N-diisopropylethylamine (8.5 mL, 45 mmol) was added drop wise to the reaction mixture as it stirred at ambient temperature under argon. A solution of Compound 45 (5.0 g, 12 mmol) in anhydrous dichloromethane (20 mL) was added drop wise to the reaction mixture, which stirred at ambient temperature under argon overnight. Upon completion, the reaction mixture was washed with water (100 mL), saturated bicarbonate solution (100 mL), another portion of water, followed by brine (100 mL). The organic layer was dried over sodium sulfate, filtered, and evaporated to dryness. The resulting crude was purified by ISCO column chromatography, yielding 8.4 g (82%) of Compound 46 (Rf=0.53 10% MeOH/DCM) as a white foam. Mass calculated for [M+1] $C_{56}H_{74}N_2O_{14}Si$, 1027.5 Found 1027.5.

Synthesis of Compound 47:

Compound 46 (8.3 g, 8.0 mmol) was dissolved in 10% methanol/ethyl acetate (300 mL). To the reaction mixture was added 10% palladium by wt. on active carbon wet Degussa type (100 mg). The flask was purged with argon. The flask was purged with hydrogen twice, then hydrogen was bubbled through the reaction mixture for 10 seconds. The reaction mixture continued to stir under hydrogen atmosphere at room temperature overnight. The reaction mixture was decanted onto a sintered funnel packed with celite and washed twice with methanol. The organic layer was evaporated to dryness affording 7.50 g (99%) Compound 47 (Rf=0.32 10% methanol/dichloromethane) as a white solid, which required no further purification. Mass calculated for [M+Na] $C_{49}H_{68}N_2O_{14}SiNa$, 959.3 Found 959.3.

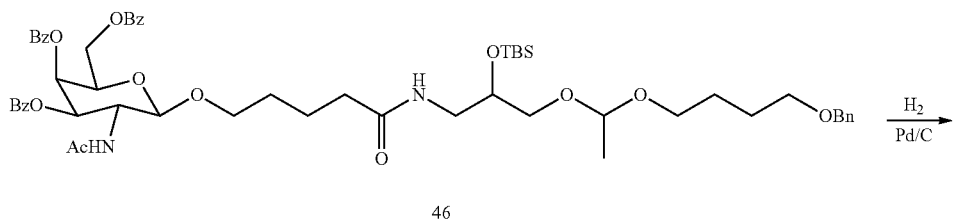

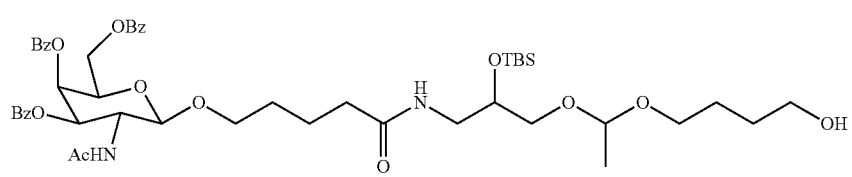

Synthesis of Compound 48:

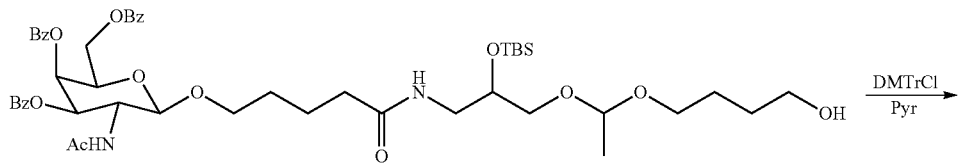

47

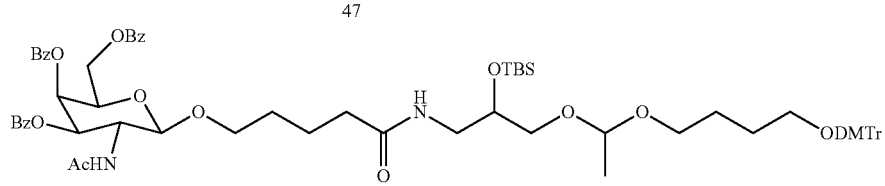

48

Compound 47 (5.0 g, 5.3 mmol) was co-evaporated with anhydrous pyridine (75 mL) twice. Then the compound was placed under high vacuum for 2 hours. Compound 47 was taken from vacuum and dissolved in anhydrous pyridine (75 mL). The reaction mixture stirred under argon at 0° C. Then DMTr-Cl (2.3 g, 6.8 mmol) was added to the solution at 0° C. To this solution a catalytic amount of dimehtylaminopyridine (0.2 g, 1.44 mmol) was added. The mixture stirred under vacuum followed by argon, and stirring was continued under argon at room temperature overnight. The reaction mixture was evaporated to dryness, and diluted in dichloromethane (80 mL). The organic layer was washed with water (80 mL), saturated sodium bicarbonate (80 mL), another portion of water, and brine (80 mL). The organic layer was dried over sodium sulfate, filtered and evaporated to dryness. The resulting crude was purified by ISCO column chromatography, affording 5.04 g (96%) of Compound 48 (Rf=0.6 10% MeOH/DCM) as a yellow foam. Mass calculated for [M+1] $C_{70}H_{86}N_2O_{16}Si$, 1238.6 Found 1238.6.

Synthesis of Compound 49:

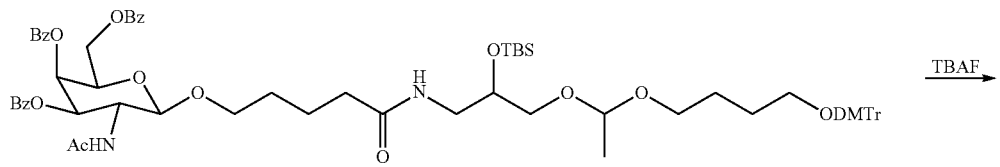

48

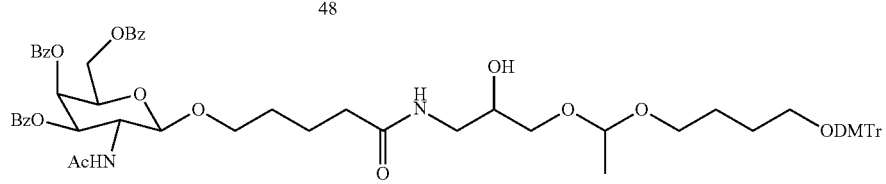

49

Compound 48 (4.8 g, 3.9 mmol) was dissolved in THF (100 mL). The reaction mixture stirred at 0° C. 1M solution of tetrabutylammonium fluoride in THF (4.30 mL) was added drop wise to the mixture, which continued to stir a 0° C. overnight. Upon completion, the reaction was evaporated to dryness. The resulting crude was purified by ISCO column chromatography, yielding 3.60 g (99%) of Compound 49 (Rf=0.3 10% MeOH/DCM) as a clear syrup. Mass calculated for [M+1] $C_{64}H_{72}N_2O_{16}$, 1124.5 Found 1124.5.

Synthesis of Biodegradable Acetal Triantinary-GalNAc Ligand:

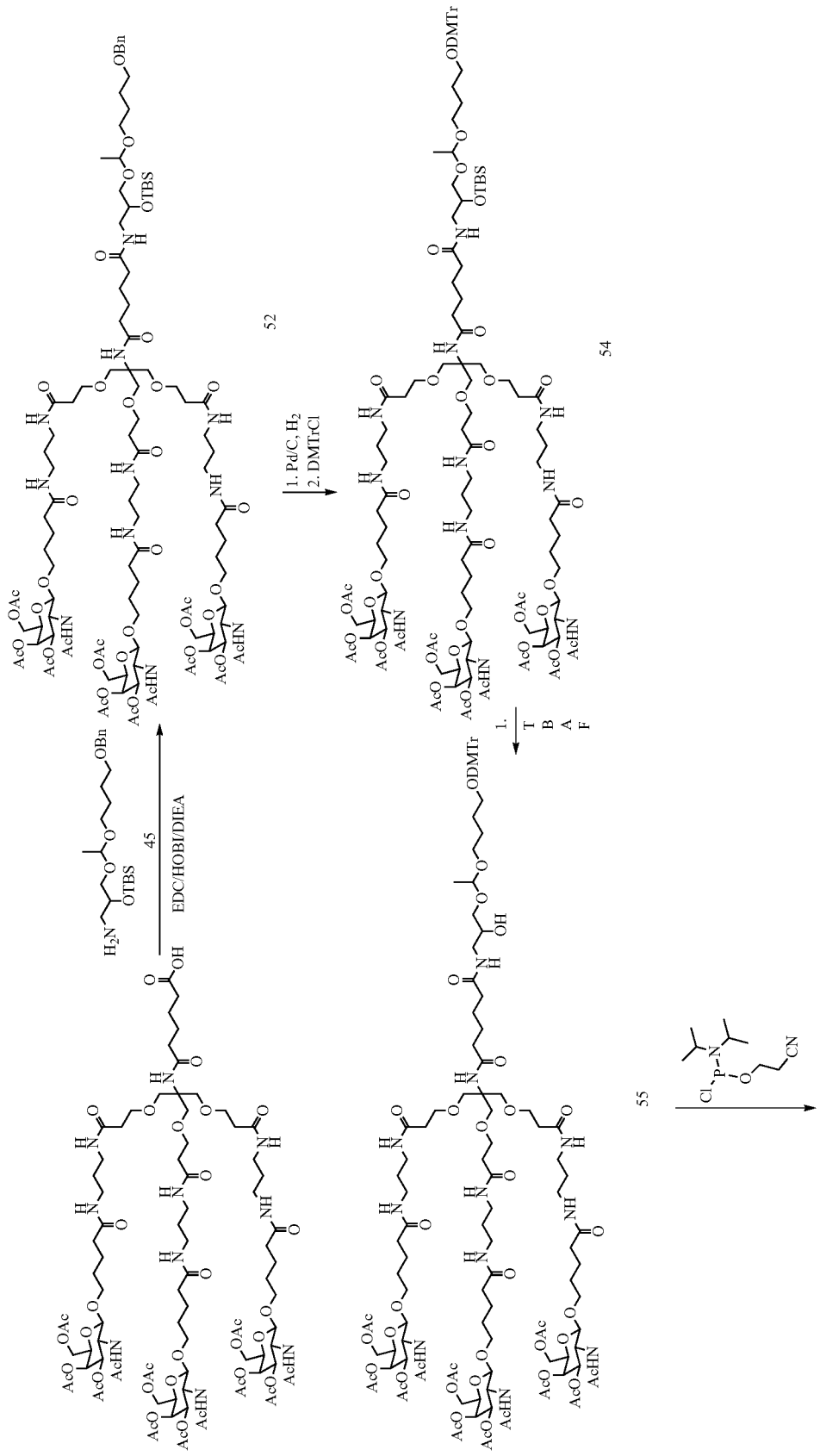

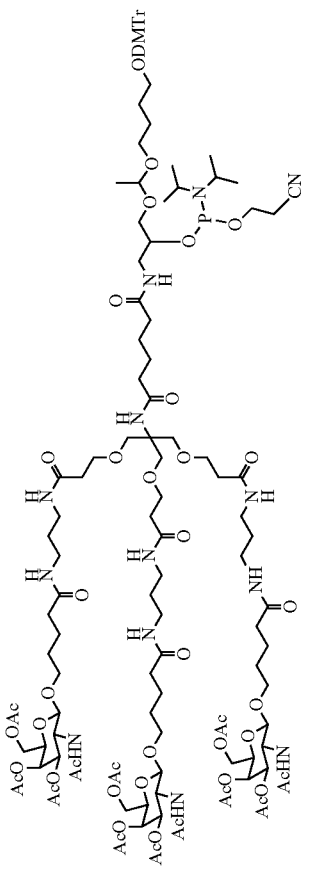
56

(i) Triantennary-GalNAc acid, EDAC hydrochloride, HOBt, DIEA/DCM, rt, (74%); (vii) H₂/Pd—C, EtOAc/MeOH, rt, 99%; (viii) DMTr-Cl, DMAP, pyridine, rt, 94% (ix) tetrabutylammonium fluoride, THF, 0° C., 93%; (x) succinic anhydride, DMAP, TEA/DCM, rt, 60%; (xi) HBTU, DIEA/DMF, CPG support, loading 57 50 μmol/g Synthesis of Compound 52:

stirred at ambient temperature under argon. A solution of Compound 45 (5.0 g, 12 mmol) in anhydrous dichloromethane (20 mL) was then added drop wise to the reaction mixture, which stirred at ambient temperature under argon overnight. Upon completion, the reaction mixture was washed with water (200 mL), saturated bicarbonate solution (200 mL), another portion of water, followed by brine (200

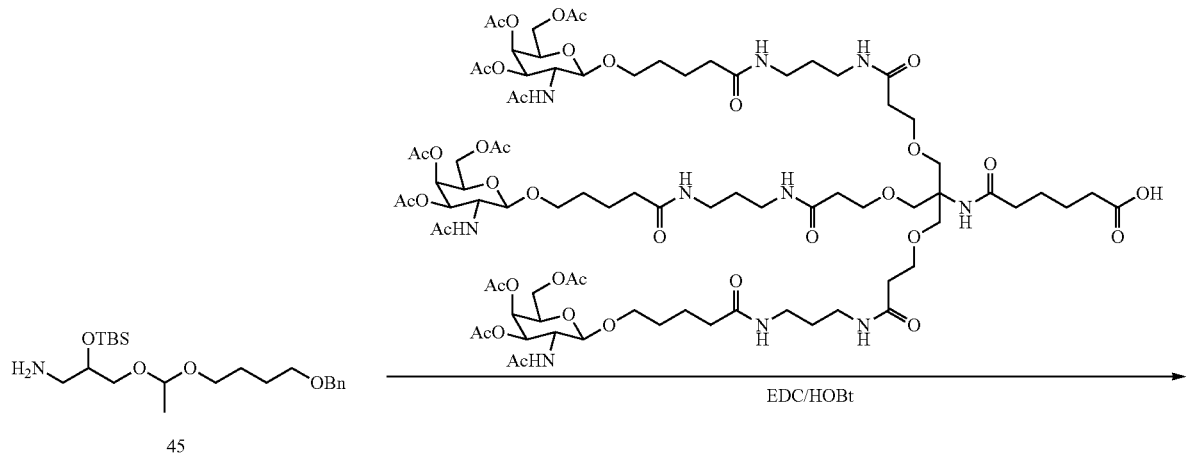

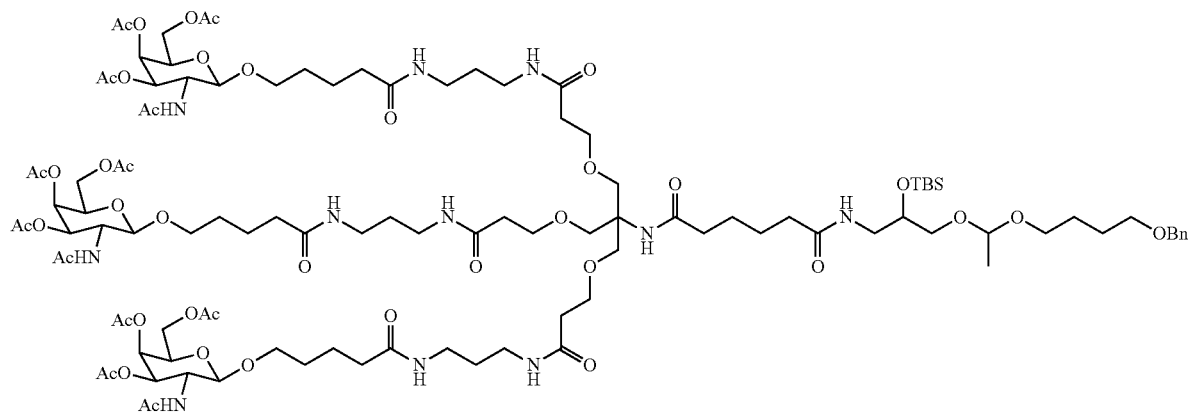

Triantennary GalNAc acid (24.3 g, 12.2 mmol), EDAC hydrochloride (4.7 g, 30 mmol), and hydroxybenzotriazole (3.3 g, 25 mmol) were dissolved in anhydrous dichloromethane (180 mL). N,N-diisopropylethylamine (8.5 mL, 45 mmol) was added drop wise to the reaction mixture as it mL). The organic layer was dried over sodium sulfate, filtered, and evaporated to dryness. The resulting crude was purified by ISCO column chromatography, yielding 20.3 g (74%) of Compound 52 (Rf=0.33 10% MeOH/DCM) as a white foam.

Synthesis of Compound 53:

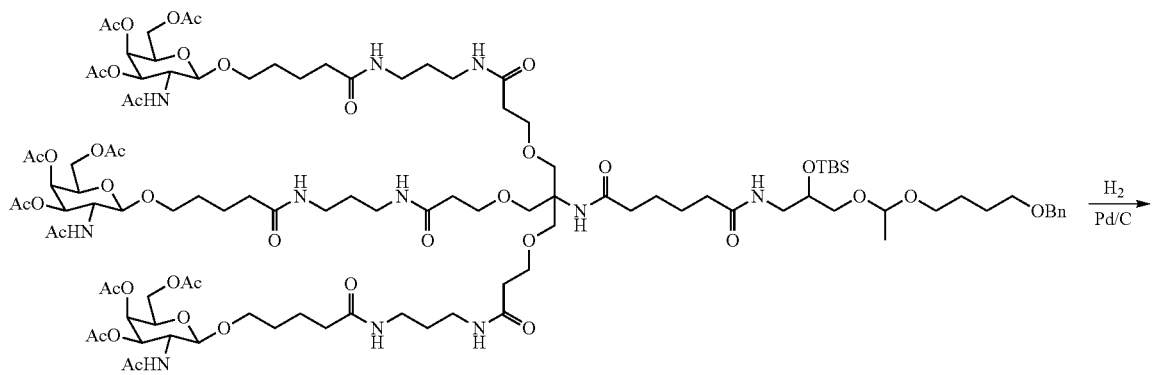

52

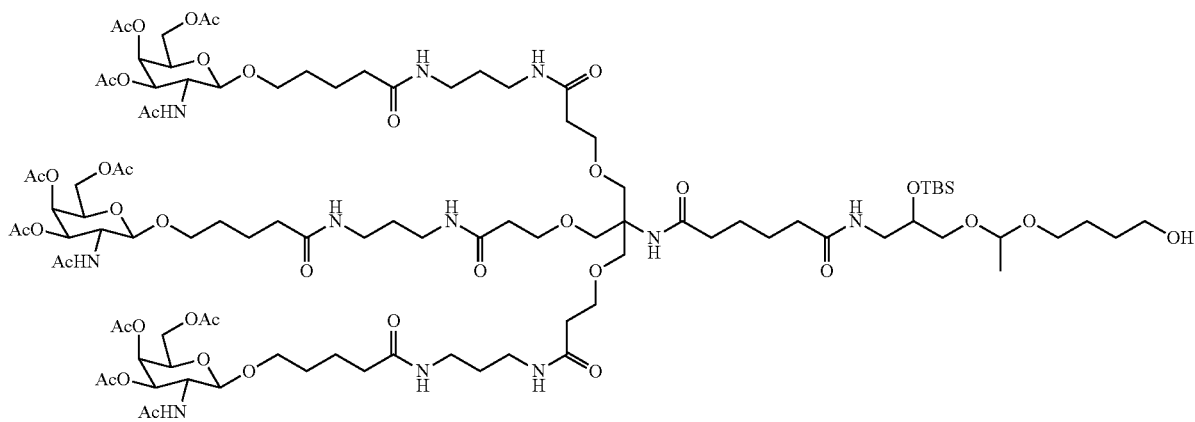

53

Compound 52 (20.0 g, 8.75 mmol) was dissolved in 10% methanol/ethyl acetate (600 mL). To the reaction mixture was added 10% palladium by wt. on active carbon wet Degussa type (100 mg). The flask was purged with argon. The flask was purged with hydrogen twice, then hydrogen was bubbled through the reaction mixture for 10 seconds. The reaction mixture continued to stir under hydrogen atmosphere at room temperature overnight. The reaction mixture was decanted onto a sintered funnel packed with celite and washed twice with methanol. The organic layer was evaporated to dryness affording 19.5 g (99%) Compound 53 (Rf=0.30 20% MeOH/DCM) as a white solid, which required no further purification.

Synthesis of Compound 54:

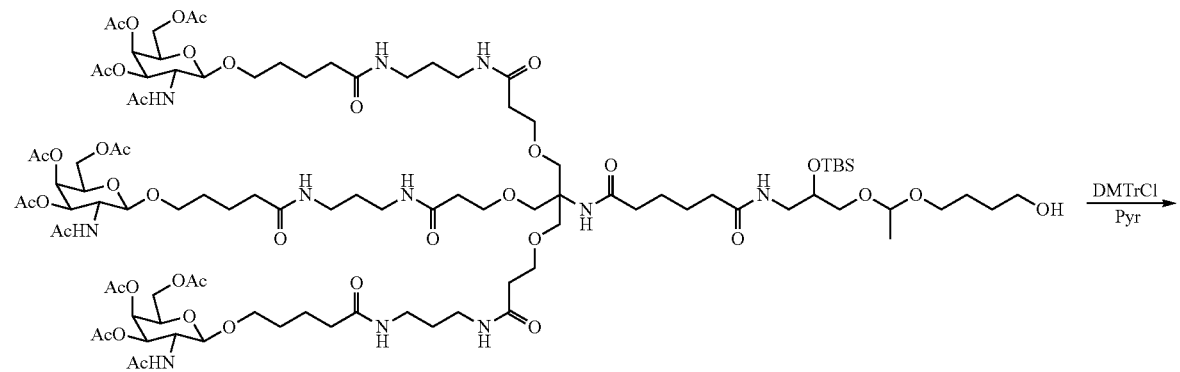

53

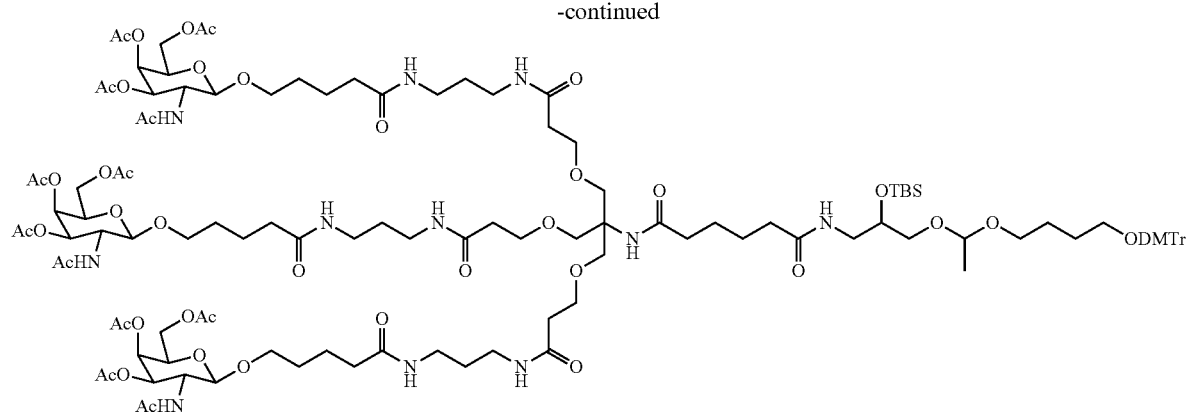

54

Compound 53 (5.0 g, 2.2 mmol) was co-evaporated with anhydrous pyridine (75 mL) twice. Then the compound was placed under high vacuum for 2 hours. Compound 53 was taken from high vacuum and dissolved in anhydrous pyridine (75 mL). The reaction mixture stirred under argon at 0° C. Then DMT-Cl (950 mg, 2.8 mmol) was added to the solution at 0° C. To this solution, a catalytic amount of dimehtylaminopyridine (30 mg, 0.22 mmol) was added. The mixture stirred under vacuum followed by argon, and stirring was continued under argon at room temperature overnight. The reaction mixture was evaporated to dryness, and diluted in dichloromethane (80 mL). The organic layer was washed with water (80 mL), saturated sodium bicarbonate (80 mL), another portion of water, and brine (80 mL). The organic layer was dried over sodium sulfate, filtered and evaporated to dryness. The resulting crude was purified by ISCO column chromatography, affording 5.4 g (94%) of compound 13 (Rf=0.34 10% MeOH/DCM) as an orange foam.

Synthesis of Compound 55:

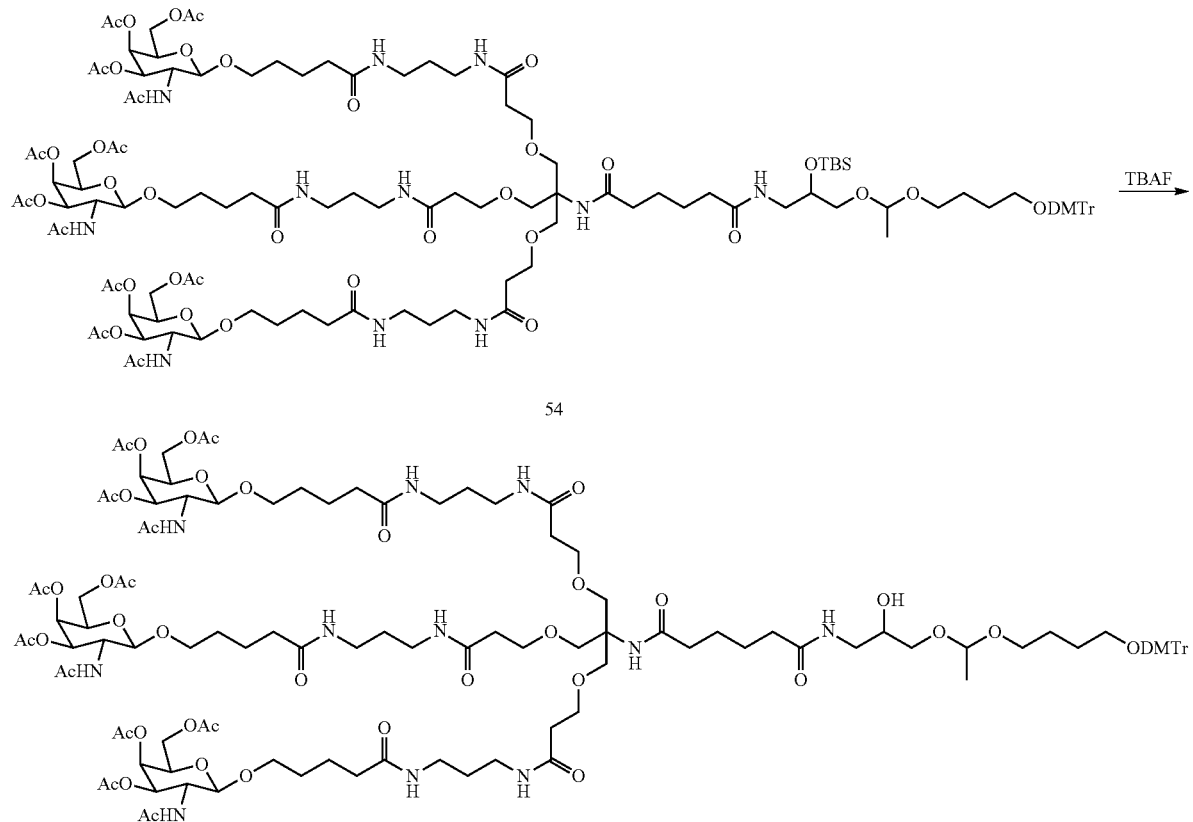

55

Compound 54 (5.0 g, 2.0 mmol) was dissolved in THF (100 mL). The reaction mixture stirred at 0° C. 1M solution of tetrabutylamonium fluoride in THF (2.40 mL) was added drop wise to the mixture, which continued to stir a 0° C. overnight. Upon completion, the reaction was evaporated to dryness. The resulting crude was purified by ISCO column chromatography, yielding 4.5 g (93%) of Compound 55 (Rf=0.33 20% MeOH/DCM) as a clear syrup.

Example 20

Synthesis of TriGalNAc Amidite

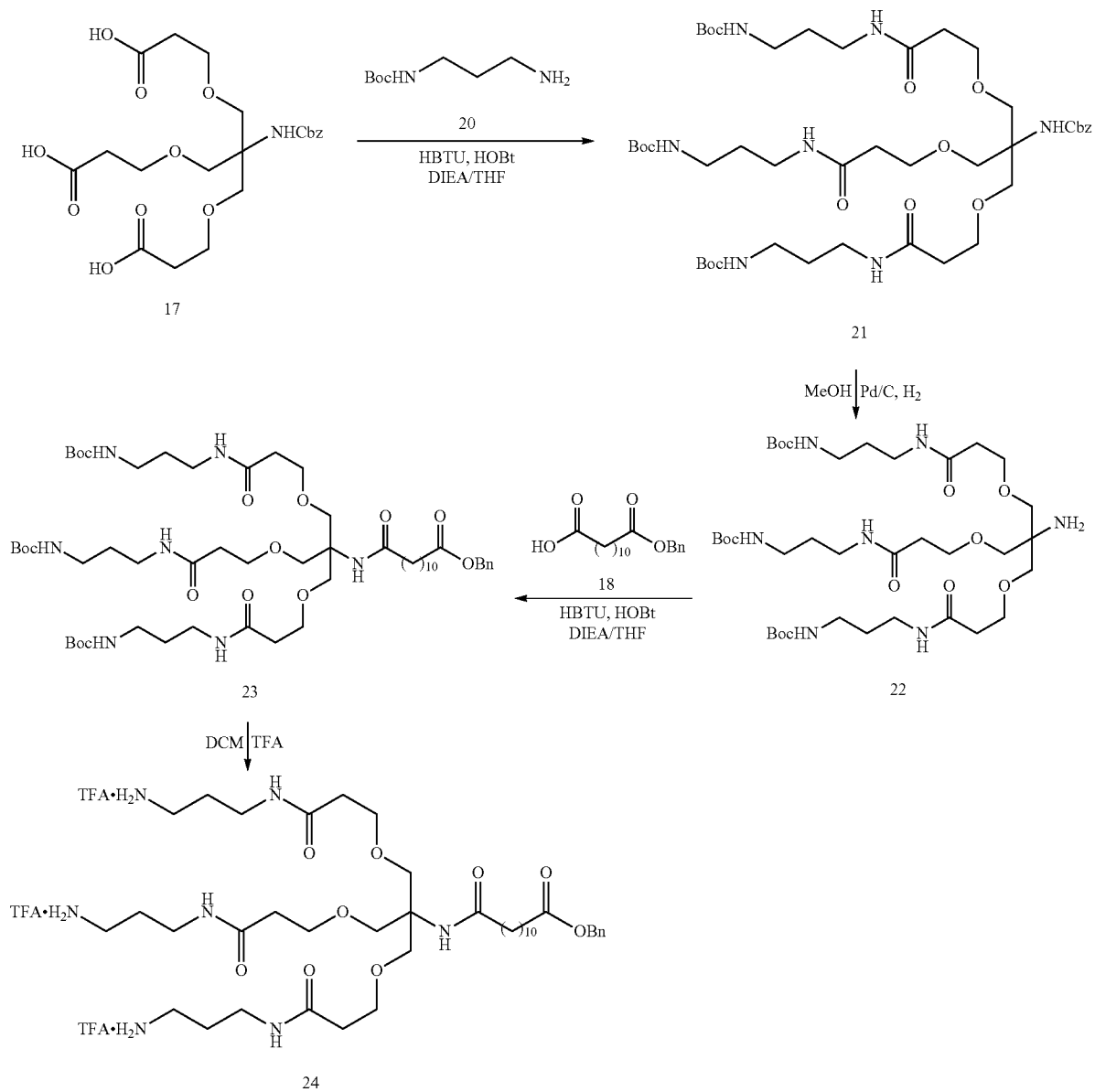

0° C.; 1-hydroxybenzotriazole hydrate (HOBt.H$_2$O, 351 g) and O-(Benzotriazol-1-yl)-N,N,N',N'-tetramethyluronium hexafluorophosphate (HBTU, 870 g) were added with stirring followed by drop-wise addition of DIEA (593 g). Temperature of the reaction was slowly brought to room temperature and continued stirring overnight. Water (3.6 L) was added to the reaction mixture, transferred to separatory funnel and the product was extracted into ethyl acetate (2×3.6 L). The organic layer was washed successively with 10% aqueous NaHCO$_3$ solution (1.8 L), water (1.8 L), 10% aqueous citric acid solution (3×4 L), water (1.8 L) and brine (1.8 L). The organic layer was dried over anhydrous sodium sulfate; solvents and volatiles were removed under reduced pressure to obtain the product 21 as pale yellow viscous liquid (690 g, 94%). $^1$H NMR (400 MHz, DMSO-D$_6$): δ 1.41 (s, 27H), 1.57-1.60 (t, 3H), 2.38-2.41 (t, 3H), 3.10-3.11 (m, 6H), 3.23-3.27 (m, 6H), 3.64-3.68 (m, 12H), 5.02 (s, 2H), 5.14 (m, 3H), 5.54 (s, 1H), 6.82 (s, 3H), 7.33 (S, 5H).

Step 1: Synthesis of Compound 21

Compound 17 (360 g) was dissolved in 1.8 L THF in a 10 L multi-neck RB flask under nitrogen atmosphere and a solution of N-(tert-butoxycarbonyl)-1,3-propanediamine (20, 426 g) in 1.8 L THF was added at ambient temperature. The reaction mixture was cooled over an ice-salt mixture to Step 2: Synthesis of Compound 22

Compound 21 (230 g) was dissolved in methanol (2.3 L) and charged into a hydrogenation vessel. This solution was degassed with nitrogen and 10% Pd—C (23 g, wet) was added and hydrogenated overnight at 40° C. for completion. After cooling to room temperature, the mixture was filtered through a pad of celite and washed with methanol (2×500 mL). Combined filtrate was evaporated under reduced pressure and the residue obtained was dried under high vacuum overnight to obtain the compound 22 (190 g, 96%) as pale yellow gum. $^1$H NMR (400 MHz, DMSO-D$_6$): δ 1.36 (s, 27H), 1.47-1.50 (m, 6H), 2.26-2.29 (m, 6H), 2.28-2.29 (m, 6H), 3.02-3.03 (m, 6H), 3.17 (m, 6H), 3.55-3.57 (m, 6H) 6.79 (m, 3H), 7.85 (m, 3H).

Step 3: Synthesis of Compound 23

A solution of compound 22 (860 g) and 18 (376 g) was prepared in THF (8.6 L) in a 10 L RB flask under nitrogen and the solution was cooled over an ice-salt bath. HOBt (179 g) and HBTU (445 g) were added to the reaction mixture with stirring followed by drop-wise addition of DIEA (300 g) over a period 30 min and slowly warmed the mixture to ambient temperature. The reaction mixture stirred overnight, mixed with cold water (8.6 L) and the product was extracted into ethyl acetate (2×8 L). The organic layer was washed successively with 10% aqueous NaHCO$_3$ solution (4.3 L), water (4.3 L) and 10% aq. citric acid solution (3×4 L), 10% aqueous sodium bicarbonate solution (4.3 L) and brine (4.3 L). The organic layer was dried over anhydrous sodium sulfate and solvents were removed under reduced pressure. The residue thus obtained was purified by silica gel chromatography using 4% methanol in dichloromethane as eluent to obtain the product 23 (710 g, 60%) as colorless gum. Compound 23 was characterized by NMR and mass spectroscopy before taking in to the next step. $^1$H NMR (400 MHz, DMSO-D$_6$): δ 1.25-1.29 (12H), 1.43 (s, 27H), 1.62-1.65 (m, 10H), 2.17 (m, 2H), 2.35 (m, 2H), 2.42 (t, 6H), 3.15-3.16 (m, 6H), 3.30 (q, 6H), 3.67-3.70 (m, 12H), 5.11 (s, 2H), 5.26 (m, 2H), 6.3 (s, 1H), 6.9 (s, 3H), 7334 (m, 5H).

Synthesis of Compound 24

Compound 23 (160 g) was dissolved in 800 mL dichloromethane in multi neck RB flask under nitrogen and cooled over an ice-water bath. A solution of 320 mL trifluoroacetic acid in 480 mL dichloromethane was added to the mixture and stirred overnight for complete deprotection of the N$^{Boc}$ amine. Solvents and volatiles were removed under reduced pressure and the residue was co-evaporated successively with toluene (6×500 mL) and dichloromethane (6×500 mL), and dried under high vacuum overnight to obtain the compound 24 as pale brown viscous liquid (166 g, quantitative). $^1$H NMR (400 MHz, DMSO-D$_6$): δ 1.23-1.27 (12H), 1.45 (t, 2H), 1.55 (t, 2H), 1.71 (t, 6H), 2.08 (t, 2H), 2.34 (s, 8H), 2.81 (d, 6H), 3.11-3.16 (q, 6H), 3.55-3.59 (m, 12H), 5.08 (s, 2H), 6.94 (s, 1H) 7.34 (m, 5H), 7.67-7.71 (s, 9H), 8.01-8.03 (s, 3H), 10.11 (b, 6H).

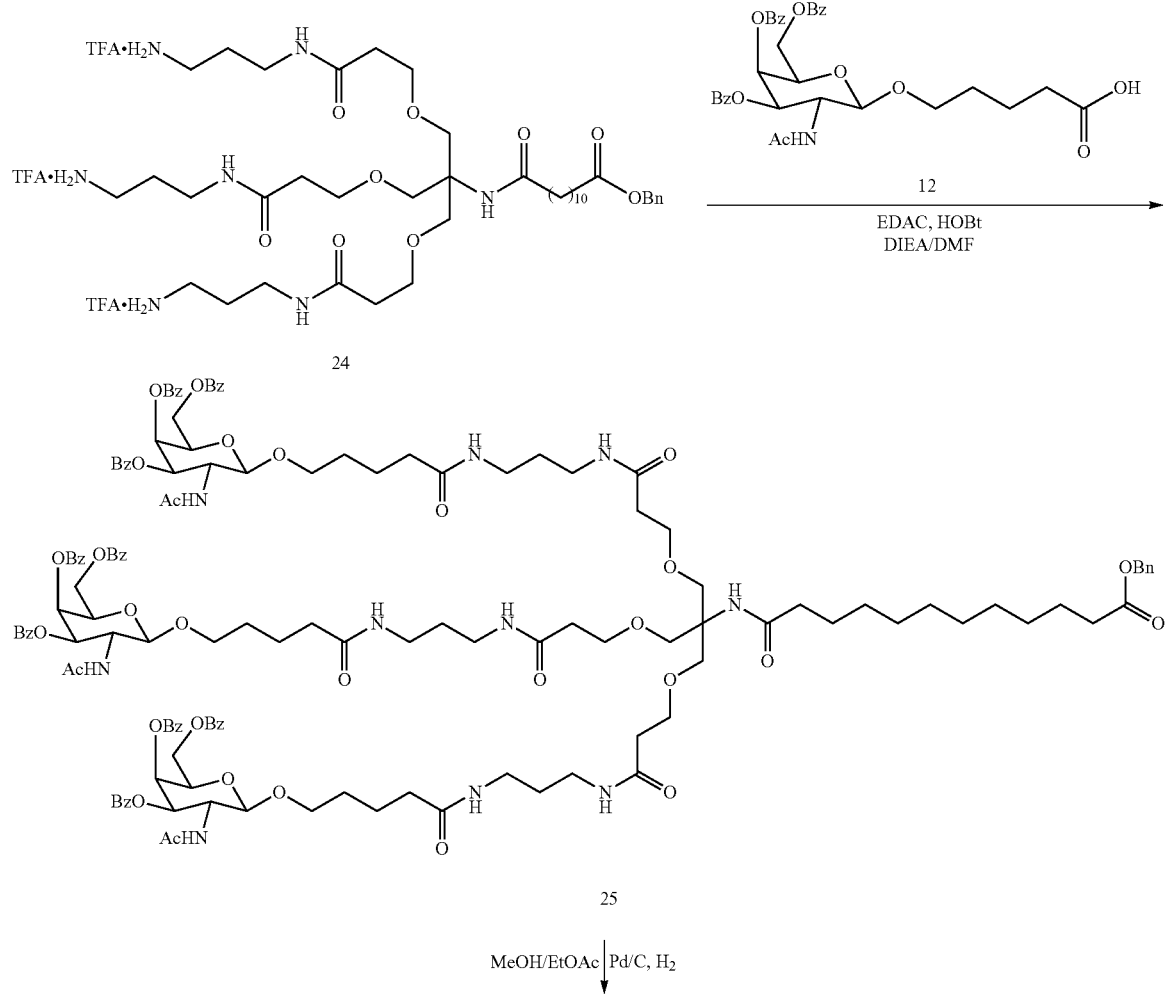

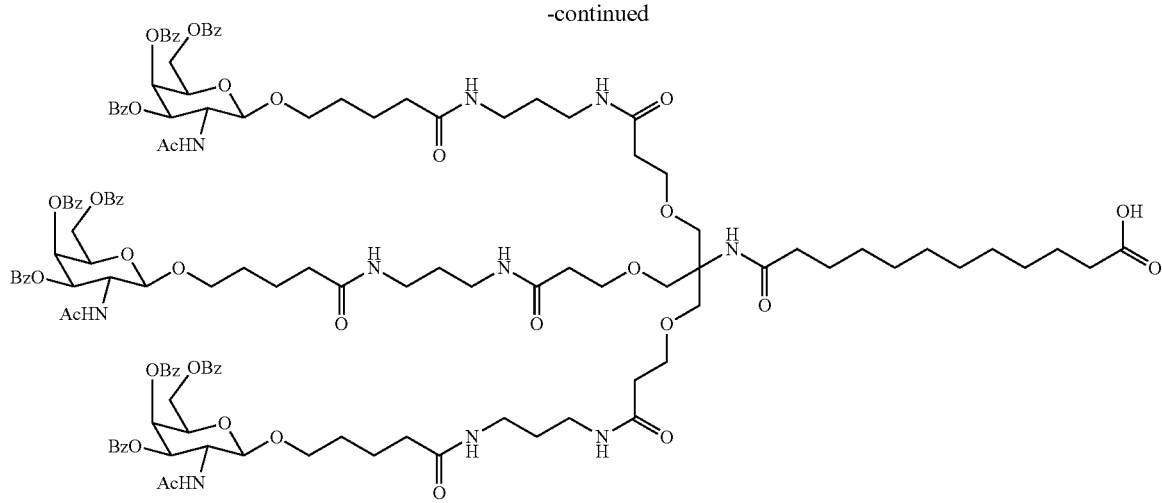

26

Step 1: Synthesis of Compound 25

The carboxylic acid 12 (57.50 g, 90.90 mmol), EDAC (35 g, 182 mmol) and HOBt (25 g, 182 mmol) were taken together in DMF (800 mL) under argon and the mixture was cooled over an ice-water mixture under stirring. DIEA (63 mL, 362 mmol) was added drop-wise to the mixture and stirred for 20 minutes. A solution of compound 24 (26.20 g, 22.70 mmol)) in DMF (200 mL) was added to the above mixture drop-wise. After addition, temperature of the reaction was slowly brought up to room temperature and stirred overnight. The reaction mixture was added to cold water (5 L) and allowed to settle the precipitate formed. Filtered and dissolved the precipitate in dichloromethane, washed successively with sodium bicarbonate solution, water and brine. Organic layer was dried over anhydrous sodium sulfate and solvents were evaporated under reduced pressure. The residue obtained was purified by silica gel column chromatography using 5-33% methanol in EtOAc as eluent to afford product 25 (54.60 g, 90%). $^1$H NMR (400 MHz, DMSO-$d_6$) δ 8.00 (d, J=9.2 Hz, 3H), 7.92 (t, J=6.7 Hz, 11H), 7.84 (t, J=5.7 Hz, 3H), 7.80-7.44 (m, 29H), 7.37 (dd, J=16.5, 8.6 Hz, 9H), 6.99 (s, 1H), 5.76 (d, J=3.5 Hz, 3H), 5.37 (dd, J=11.2, 3.3 Hz, 3H), 5.06 (s, 2H), 4.74 (d, J=8.5 Hz, 3H), 4.46 (d, J=8.0 Hz, 6H), 4.39-4.29 (m, 6H), 4.10-3.95 (m, 2H), 3.91-3.71 (m, 3H), 3.60-3.50 (m, 14H), 3.14-2.97 (m, 11H), 2.35-2.26 (m, 7H), 2.10-1.95 (m 7H), 1.70 (s, 9H), 1.60-1.45 (m, 20H), 1.26-1.08 (m, 12H). Mass calc. for $C_{143}H_{172}N_{10}O_{39}$: 2653.180; found: 2676.213 [M+Na$^+$, MALDI-TOF, matrix: 2-(4-hydroxyphenylazo) benzoic acid (HABA)].

Step 2: Synthesis of Compound 26

A solution of compound 25 (54.50 g, 20.54 mmol) in methanol/EtOAc (200 mL, 2:1) in a 2 L RB flask was degassed with hydrogen and Pd—C (5 g, 10%, wet degauss type) was added to the solution. The mixture was hydrogenated overnight under balloon pressure. The catalyst was filtered off through a small pad of celite and washed the celite bed with methanol (500 mL). Combined filtrate was evaporated under reduced pressure to afford the compound 26 (50.30 g, 96%) as off-white solid. $^1$H NMR (400 MHz, DMSO-$d_6$) δ 11.94 (s, 1H), 8.03-7.86 (m, 15H), 7.82 (t, J=5.8 Hz, 3H), 7.77-7.44 (m, 29H), 7.38 (t, J=7.7 Hz, 6H), 6.97 (s, 1H), 5.76 (d, J=3.3 Hz, 3H), 5.37 (dd, J=11.2, 3.3 Hz, 3H), 4.74 (d, J=8.5 Hz, 3H), 4.53-4.40 (m, 6H), 4.35-4.29 (m, 6H), 3.80 (dd, J=10.4, 5.3 Hz, 3H), 3.60-3.50 (m, 14H), 3.10-3.00 (m, 11H), 2.27 (t, J=6.5 Hz, 6H), 2.16 (t, J=7.4 Hz, 2H), 2.12-2.01 (m, 7H), 1.70 (s, 8H), 1.61-1.36 (m, 20H), 1.30-1.18 (m, 10H). Mass calc. for $C_{136}H_{166}N_{10}O_{39}$: 2563.130; found: 2586.150 [M+Na$^+$, MALDI-TOF, matrix: 2-(4-hydroxyphenylazo) benzoic acid (HABA)].

223 224
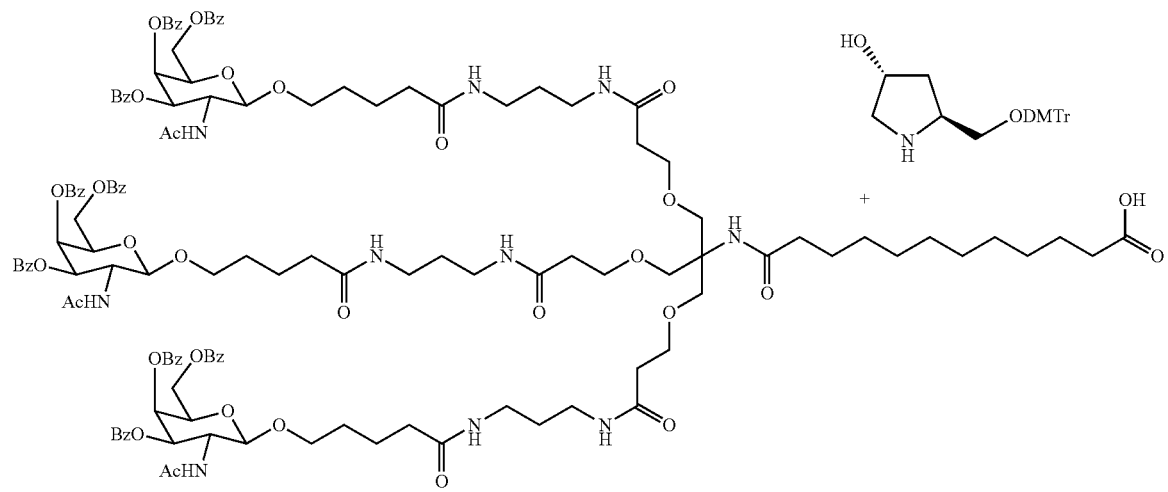
27 ↓ HBTU, DIEA/DCM
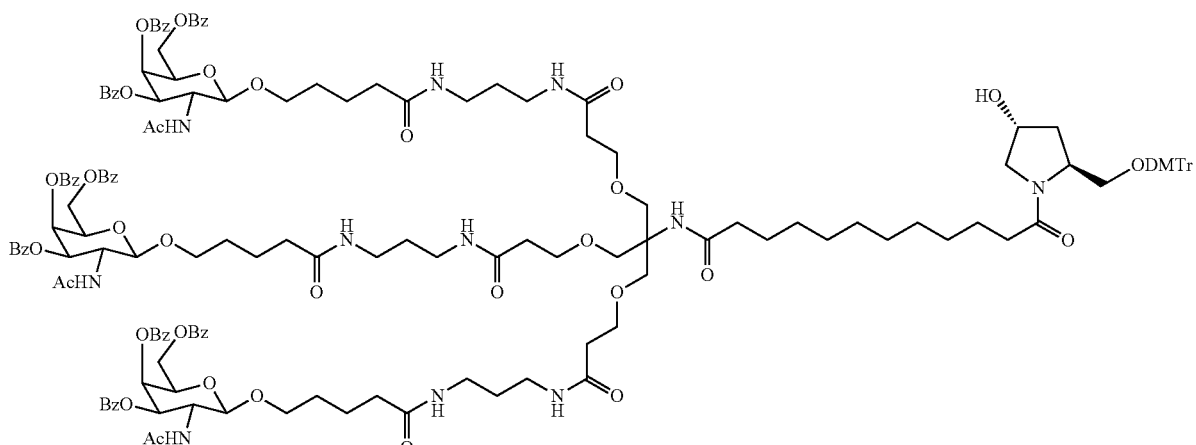
28 ↓ ETT, CH₃CN

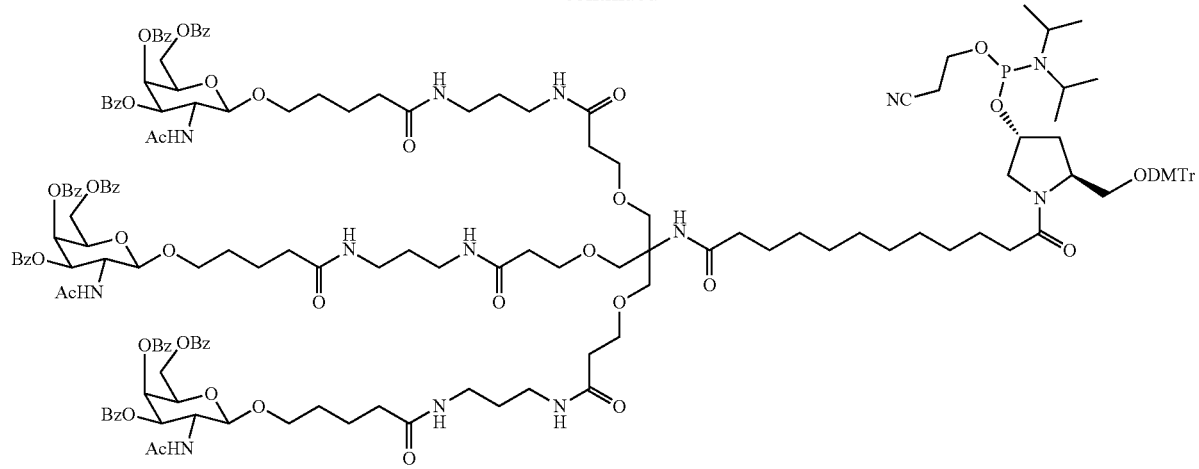

29

Step 1: Synthesis of Compound 29

To a solution of compound 27(43.00 g, 16.77 mmol) in dichloromethane (150 mL) were added HBTU (8.30 g, 1.3 eq.) and DIEA (8.80 mL, 3 eq.). The mixture stirred for 10 minutes at ambient temperature under argon. To this mixture a solution of amine (7.40 g, 1.05 eq) in dichloromethane was added and stirred overnight. TLC checked and mixture washed successively with water, bicarbonate and brine. Organic layer was dried over sodium sulfate and the crude product was purified by column chromatography using 3-15% Methanol in dichloromethane to get compound 28 as a an off-white solid (36.23 g, 74%). $^1$H NMR (400 MHz, DMSO-d$_6$) δ 8.11-7.78 (m, 18H), 7.78-7.12 (m, 43H), 6.97 (s, 1H), 6.90-6.84 (m, 4H), 5.75 (d, J=3.5 Hz, 3H), 5.36 (dd, J=11.1, 3.3 Hz, 3H), 4.93 (dd, J=32.6, 4.1 Hz, 1H), 4.73 (d, J=8.5 Hz, 3H), 4.55-4.20 (m, 13H), 4.14 (dd, J=8.1, 4.0 Hz, 1H), 3.85-3.74 (m, 3H), 3.71 (s, 5H), 3.55-3.48 (m, 15H), 3.31 (d, J=12.4 Hz, 2H), 3.08-2.98 (m, 14H), 2.27 (t, J=6.4 Hz, 6H), 2.18 (t, J=7.4 Hz, 2H), 2.04-1.98 (m, 9H), 1.70 (s, 8H), 1.62-1.32 (m, 20H), 1.32-1.00 (m, 14H). Mass calc. for $C_{62}H_{193}N_{11}O_{42}$: 2964.33; found: 2987.350 [M+Na$^+$, MALDI-TOF, matrix: 2-(4-hydroxyphenylazo) benzoic acid (HABA)].

Step 3: Synthesis of Compound 29

Compound 28 (5.18 g, 1.74 mmol) was dissolved in anhydrous acetonitrile (30 mL), and diamidite reagent (0.66 mL, 2.096 mmol) and ethyl thiotetrazole (0.225 g, 1.74 mmol) were added and stirred the mixture for 6 hrs at ambient temperature. The mixture was poured in to a cold dilute solution of sodium bicarbonate and extracted with dichloromethane. Solvents were removed and the conc. Solution was added to mixture of ether/hexanes (1:1) dropwise to precipitate the amidite. Filtered and dried the compound under vacuum to get compound 29 as a white solid (5.65 g, 95% yield). $^1$H NMR (400 MHz, DMSO-d6) δ 8.06-7.10 (m, 22H), 6.97 (s, 1H), 6.84 (dd, J=8.6, 2.9 Hz, 1H), 5.75 (d, J=3.1 Hz, 1H), 5.37 (dd, J=11.1, 3.1 Hz, 1H), 4.74 (d, J=8.5 Hz, 1H), 4.52-4.20 (m, 4H), 4.14 (d, J=11.5 Hz, 1H), 3.88-3.63 (m, 5H), 3.62-3.39 (m, 7H), 3.03 (s, 5H), 2.73 (t, J=6.0 Hz, 1H), 2.15-2.08 (m, 7H), 1.70 (s, 3H), 1.47 (d, J=30.5 Hz, 8H), 1.30-0.79 (m, 18H). $^{31}$P NMR (162 MHz, DMSO) δ 151.92, 151.70, 151.51, 151.18.

Example 21

Synthesis of Mono GalNAc Building Blocks for Oligonucleotide Conjugation

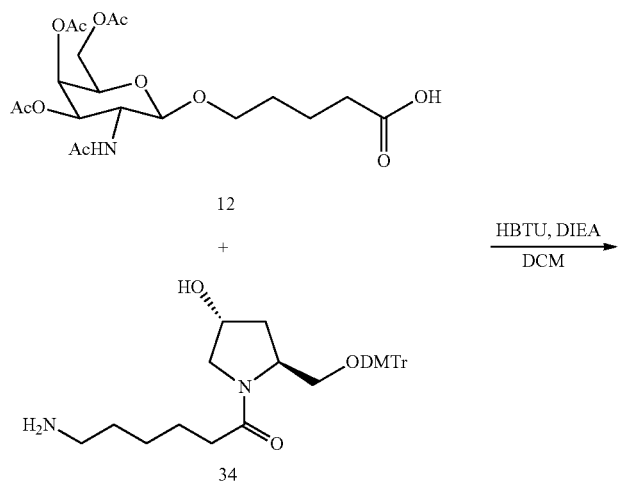

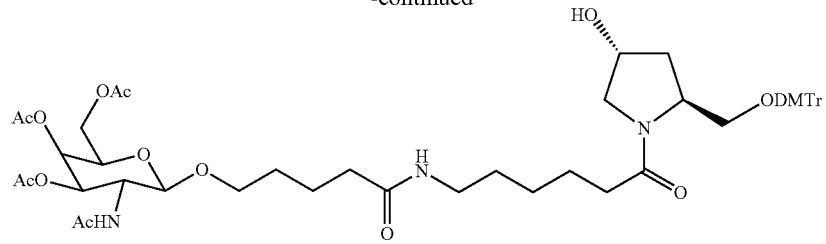

35

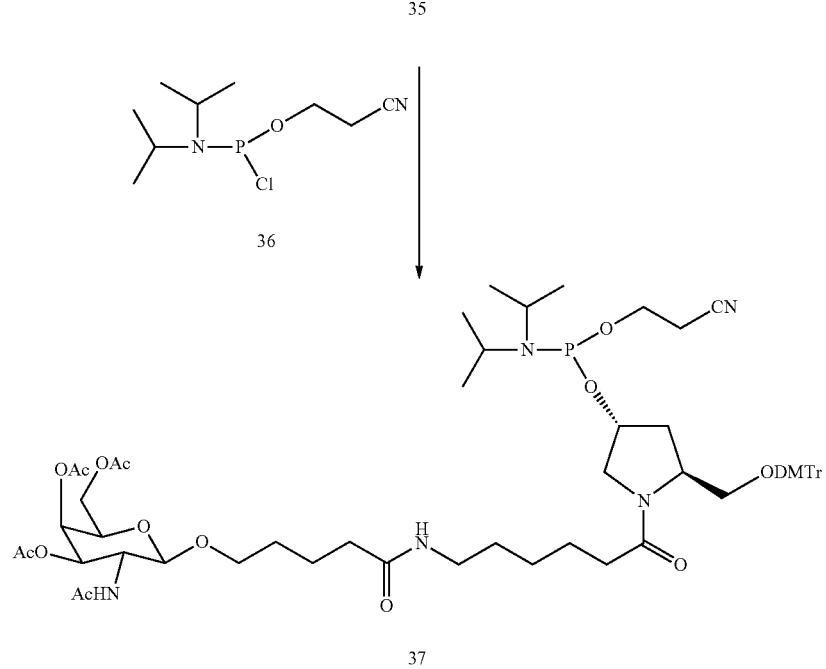

Step 1. Synthesis of 35

GalNAc acid 12 (8.39 g, 18.71 mmol) and amine 34 (10.00 g, 18.77 mmol) were taken together in dichloromethane. HBTU (10.68 g, 28.12 mmol) and DIEA (9.80 mL, 3 eq.) were added and stirred the mixture for 2 hrs at ambient temperature. TLC checked and the reaction mixture transferred to a separatory funnel and washed with water and brine. Organic layer was dried over sodium sulfate and removed the solvent. Crude product was purified by silica gel chromatography using dichloromethane and MeOH as solvents to get the compound 35 as a pale yellow fluffy solid (11.77 g, 63%). $^1$H NMR (400 MHz, DMSO) δ 7.80 (d, J=9.2 Hz, 1H), 7.69 (t, J=5.6 Hz, 1H), 7.39-7.09 (m, 9H), 6.86 (ddd, J=9.0, 5.4, 2.1 Hz, 4H), 5.20 (d, J=3.4 Hz, 1H), 5.03-4.83 (m, 2H), 4.47 (d, J=8.5 Hz, 1H), 4.41-4.07 (m, 2H), 4.04-3.95 (m, 3H), 3.86 (dt, J=11.2, 8.9 Hz, 1H), 3.79-3.68 (m, 6H), 3.68-3.36 (m, 3H), 3.21-2.88 (m, 5H), 2.26-2.14 (m, 2H), 2.09 (s, 3H), 2.02 (t, J=6.7 Hz, 2H), 1.98 (s, 3H), 1.87 (d, J=7.5 Hz, 3H), 1.76 (s, 3H), 1.53-1.29 (m, 7H).

Step 2. Synthesis of Compound 37

Hydroxy proline derivative 35 (6.00 g, 6.24 mmol) was dissolved in dichloromethane(100 mL) to that DIEA (2.20 mL, 3 eq) and amidite reagent 36 were added, the reaction mixture was stirred for 30 minutes and checked the TLC. It was transferred to a separatory funnel and washed with water and sodium bicarbonate solution. Organic layer was dried over sodium sulfate and the crude product was purified by silica gel chromatography using Dichloromethane and MeOH as eluent to get the compound 37 as white fluffy solid. $^1$H NMR (400 MHz, DMSO) δ 7.80 (d, J=9.2 Hz, 1H), 7.68 (s, 1H), 7.42-7.06 (m, 8H), 7.01-6.73 (m, 4H), 5.20 (d, J=3.3 Hz, 1H), 4.96 (dd, J=11.2, 3.3 Hz, 1H), 4.63 (d, J=4.7 Hz, 1H), 4.47 (d, J=8.5 Hz, 1H), 4.15 (s, 1H), 4.01 (s, 3H), 3.86 (d, J=11.0 Hz, 1H), 3.70 (d, J=16.5 Hz, 9H), 3.45 (ddd, J=37.0, 23.3, 16.4 Hz, 6H), 2.99 (dd, J=12.3, 6.4 Hz, 3H), 2.74 (dd, J=9.2, 5.8 Hz, 2H), 2.21 (s, 2H), 2.09 (s, 3H), 2.05-1.95 (m, 5H), 1.88 (s, 3H), 1.76 (s, 3H), 1.52-1.16 (m, 11H), 1.16-1.02 (m, 11H). $^{31}$P NMR δ=151.78, 151.61, 151.50, 151.30.

Example 22

Synthesis of Mono Amine Building Blocks for Post-Conjugation

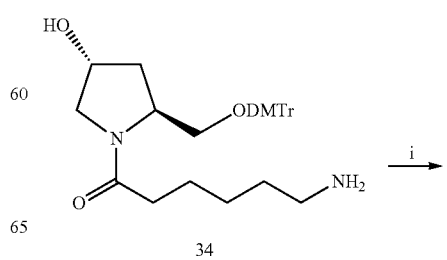

34

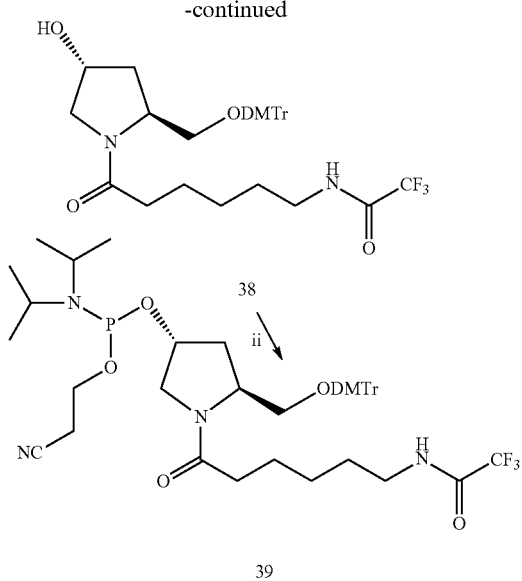

i) Ethyl Trifluroacetate, DIEA,DCM; ii) DIEA, DCM

Compound 38: Amine 34 (17.00 g, 31.90 mmol) was dissolved in dichloromethane (200 mL) under argon in an ice-water mixture for 10 minutes. Triethylamine (NEt$_3$, 8.60 mL, 64 mmol) and ethyl trifluoroacete (6.80 g, 48 mmol) were added to the above solution and slowly warmed mixture to ambient temperature. The reaction mixture stirred under argon at room temperature overnight. Completion of the reaction was confirmed by TLC (eluent: 5% MeOH in DCM, R$_f$=0.30). The mixture was transferred to a separatory funnel and washed successively with water (200 mL) and aq. sodium bicarbonate solution (100 mL) followed by standard work-up. The flash silica gel chromatographic purification of the residue using 50-100% ethyl acetate in hexanes containing 0.1% NEt$_3$ as eluent gave the trifluoroacetamide derivative 38 (18.10 g, 90%) as a pale yellow fluffy solid. $^1$H NMR (400 MHz, DMSO-d$_6$ mixture of rotamers: major to minor ratio ~7:3) δ 9.40 (t, J=5.4 Hz, 1H, NHC(O)CF$_3$), 7.41-7.13 (m, 9H, aromatic H), 6.93-6.86 (m, 4H, aromatic H), 4.99 (d, J=4.1 Hz, 0.7H, —CH(OH)), 4.90 (d, J=4.2 Hz, 0.3H, —CH(OH)), 4.44-4.38 (m, 0.7H, —CH(OH)—), 4.35-4.29 (m, 0.3H, —CH(OH)—), 4.20-4.12 (m, 1H), 3.73 (s, 6H, OCH$_3$), 3.58 (dd, J=10.6, 5.1 Hz, 0.7H), 3.46 (dd, J=11.9, 3.8 Hz, 0.3H), 3.33 (dd, J=10.6, 3.5 Hz, 0.7H), 3.26 (dd, J=12.1, 5.7 Hz, 0.3H), 3.21-3.05 (m, 4H), 3.05-2.97 (m, 1H), 2.11-1.78 (m, 3H), 1.59-1.23 (m, 6H). $^{13}$C NMR (126 MHz, DMSO-d$_6$) δ 170.8, 170.7, 158.0, 157.9, 156.2, 155.9, 144.9, 144.6, 135.8, 135.7, 135.5, 135.4, 129.5, 129.4, 127.7, 127.6, 127.5, 126.6, 126.4, 117.0, 114.7, 113.1, 113.0, 85.7, 85.0, 68.5, 67.4, 65.1, 63.3, 55.5, 55.0, 54.9, 53.3, 45.7, 37.9, 36.2, 33.9, 32.3, 28.05, 28.02, 25.8, 24.2, 23.9. $^{19}$F NMR (376 MHz, DMSO-d$_6$) δ −76.27, −77.13. HRMS (FAB) calc. for C$_{34}$H$_{40}$F$_3$N$_2$O$_6$: 629.2838; found 629.2828 (M+H).

Compound 39: To a solution of compound 38 (11.10 g, 17.66 mmol) in anhydrous DCM (100 mL), DIEA (7.6 mL, 44 mmol) was added followed by 2-cyanoethyl N,N-diisopropylchlorophosphoramidite (5.00 g, 21.20 mmol.) under argon and the reaction mixture was stirred at room temperature for 30 min. Completion of the reaction was confirmed by TLC (eluent: 5% MeOH in DCM R$_f$=0.35). The mixture was transferred to a separatory funnel and washed successively with water (150 mL) and aq. sodium bicarbonate solution (150 mL) followed by standard work-up. The flash silica gel chromatography purification of the residue using 20-50% ethyl acetate in hexanes containing 0.1% NEt$_3$ as eluent gave the phosphoramidite 39 (11.55 g, 79%) as a white fluffy solid. $^1$H NMR (400 MHz, DMSO-d$_6$, mixture of rotamers: major to minor ratio ~7:3) δ 9.39 (t, J=5.5 Hz, 1H, NHC(O)CF$_3$), 7.42-7.11 (m, 9H, aromatic H), 6.98-6.80 (m, 4H, aromatic H), 4.71-4.60 (m, 0.7H, —CH(OH)—), 4.59-4.48 (m, 0.3H, —CH(OH)—), 4.24-4.10 (m, 1H), 3.83-3.68 (m, 8H, —OCH$_3$), 3.65-3.38 (m, 4H), 3.38-3.10 (m, 3H), 3.09-3.95 (m, 1H), 2.80-2.70 (m, 2H), 2.35-2.06 (m, 3H), 2.05-1.89 (m, 1H), 1.64-1.37 (m, 4H), 1.35-1.23 (m, 2H), 1.23-1.02 (m, 12H). $^{31}$P NMR (162 MHz, DMSO-d$_6$) δ 147.01 (major), 146.75 (minor), 146.55 (minor), 146.18 (major).

Example 23

Synthesis of Triantennary GalNAc Acid (C12) NHS Ester

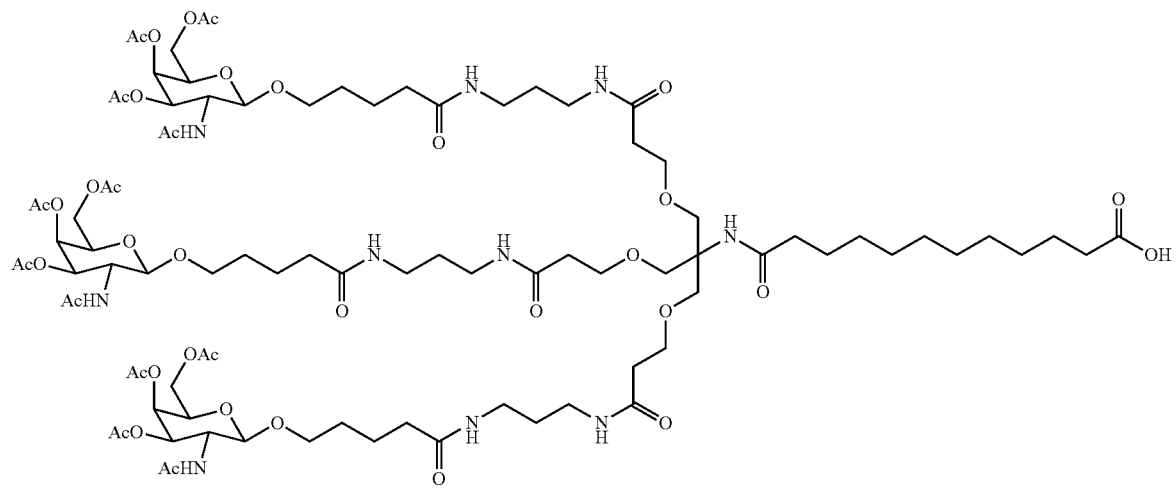

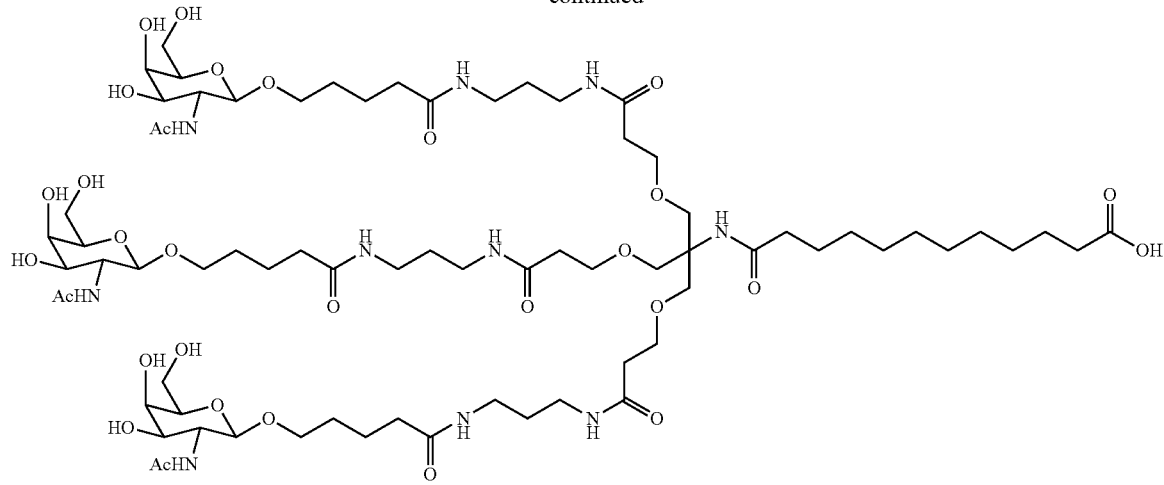

41

| DCC (2 eq), NHS (2 eq)
| DMF

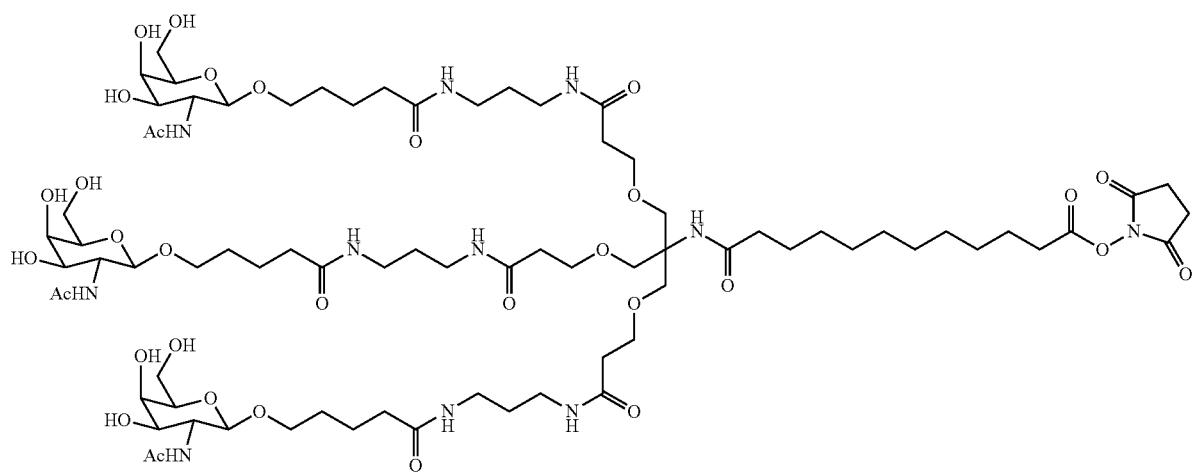

42

Synthesis of Compound 41. To a solution of the acid 40 (150 g, 74.8 mmol) in anhydrous methanol (1 L) a catalytic amount (0.5 g) of metallic sodium was added and the mixture was stirred at room temperature for 3 h. The progress of the reaction was monitored by checking the mass of the reaction. After the complete disappearance of all the mass spectral peaks corresponding to any acetylated product the reaction mixture was slowly acidified with acidic resin (Amberlite® IR120, Fluka Cat. #06428) until pH=7.4. The reaction mixture was filtered and the solid was washed with anhydrous MeOH (200 mL) and the combined organic layer was concentrated and dried to obtain the pure deprotected acid (122 g) as an off white solid in near quantitative yield. $^{1}$H NMR (400 MHz, DMSO-$d_6$): δ 7.88-7.64 (m, 9H, NH); 6.99 (s, 1H, NH); 5.25-4.45 (m, 9H, OH); 4.20 (d, J=8.4, 3H, sugar H4); 3.82-3.60 (m, 9H); 3.60-3.37 (m, 21H), 3.37-3.21 (m, 6H); 3.06-2.96 (m, 12H); 2.27 (t, J=6.3 Hz, 6H); 2.17-1.94 (m, 9H); 1.78 (s, 9H); 1.55-1.37 (m, 22H); 1.27-1.16 (bs, 12H). Mass calc. for $C_{73}H_{130}N_{10}O_{30}$: 1627.88; found: 1649.30 (M+Na+, MALDI-TOF, matrix: HABA).

Synthesis of Compound 42. To a solution of the acid 41 (120 g, 73 mmol) in anhydrous DMF (800 mL), DCC (30 g, 146 mmol) was added at room temperature with stirring followed by N-hydroxysuccinimide (16.8 g, 146 mmol). The reaction mixture was stirred for 42 h at room temperature during which the urea by-product precipitated. The reaction mixture was cooled in an ice bath and the precipitated urea was filtered off. The reaction mixture was concentrated to half the volume in a rotary evaporator. This solution was dropwise added to ethyl acetate (2 L) which was cooled in an ice-bath with vigorous stirring. The precipitated solid was filtered off and washed with ethyl acetate (2 L) and dried under vacuum to obtain the pure product as a white powder (107 g, 84%). 1H NMR (400 MHz, DMSO-d6) δ 7.95 (s, 1H, NH), 7.90-7.60 (m, 8H, NH), 6.98 (s, 1H, NH); 5.03-4.41 (m, 9H, OH); 4.20 (d, J=8.4 Hz, 3H), 3.74-3.56 (m, 9H), 3.56-3.24 (m, 24H), 3.02 (bs, 10H), 2.89 (s, 3H), 2.80 (s, 1H), 2.72 (s, 2H), 2.46 (s, 2H), 2.27 (t, J=6.6 Hz, 6H), 2.09-1.98 (m, 9H), 1.79 (s, 9H), 1.60-1.32 (m, 22H), 1.28-1.16 (m, 12H). Mass calc. for $C_{77}H_{133}N_{11}O_{32}$: 1724.96; found: 1746.4 (M+Na+, MALDI-TOF, matrix: HABA).

Example 24

Synthesis of GalNAc C5-NHS Ester

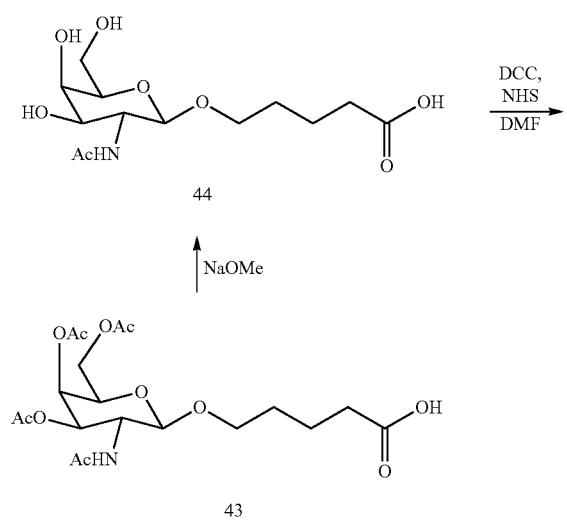

44

↑ NaOMe

43

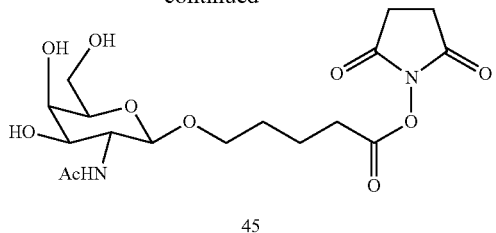

45

Step 1:

To a stirred solution of GalNAc acid peracetate 43 (100 g, 223.7 mmol) in MeOH (250 mL) was added pre-dissolved NaOMe (14.5 g, 269 mmol) in MeOH (500 mL). The above reaction mixture was stirred at room temperature overnight. Amberlite H+ resin was added and stirred for 30 min. to neutralize. Filtered off the resin followed by concentration of the solvent gave the foamy solid product 2 (75 g) which was used for the next step without purification.

Step 2:

To a stirred solution of 44 (25 g, 77.9 mmol) and NETS (17.9 g, 155.8 mmol) In DMF (250 mL) was added DCC (32.09 mg, 155.8 mmol) and stirred 14 h at room temperature. 1 L of ethyl acetate was added followed by filtration gave the product 45 (25 g, 77%). LCMS Calculated for $C_{17}H_{26}N_2O_{10}$: 418.399 (M+), Found: 419.0 (M++1).

Example 25

Synthesis Protocols of Oligonucleotides for some Exemplary Dual Targeting Multi-Targeted Molecules Comprising Two siRNAs

TABLE 1

Sequences of Single Strands Snthesized for Bis-siRNA's and Their Controls

| Target | Seq. ID | Strand (S/AS) | Sequence (5' to 3') | SEQ ID NO: |
|---|---|---|---|---|
| mTTR | A-128009.4 | S | asascaguGfuUfCfUfugcucuauaaL96 | 36 |
| mTTR | A-134468.1 | S | asascaguGfuUfCfUfugcucuausasaL96 | 37 |
| mTTR | A-128003.17 | AS | usUfsauaGfaGfCfaagaAfcAfcuguususu | 38 |
| FVII | A-134469.1 | S | csasggauCfaUfCfUfcaagucuuaaL96 | 39 |
| FVII | A-134470.1 | S | csasggauCfaUfCfUfcaagucuusasaL96 | 40 |
| FVII | A-126753.4 | AS | usUfsaagAfcuUfgagaUfgAfuccugsgsc | 41 |
| mTTR/FVII | A-134471.1 | S | asascaguGfuUfCfUfugcucuausasauuucsasggauCfaUfCfUfcaagucuuaaL96 | 42 |
| mTTR/FVII | A-134472.1 | S | asascaguGfuUfCfUfugcucuauaauuucsasggauCfaUfCfUfcaagucuuaaL96 | 43 |
| mTTR/FVII | A-134473.1 | S | asascaguGfuUfCfUfugcucuauaaQ50csasggauCfaUfCfUfcaagucuuaaL96 | 44 |
| FVII/mTTR | A-134474.1 | S | csasggauCfaUfCfUfcaagucuuaaQ50asascaguGfuUfCfUfugcucuauaaL96 | 45 |
| mTTR/FVII | A-134475.1 | S | asascaguGfuUfCfUfugcucuauaaQ50UfacsasggauucfaufcfufcaagucuuaaL96 | 46 |

TABLE 1-continued

Sequences of Single Strands Snthesized for Bis-siRNA's and Their Controls

| Target | Seq. ID | Strand (S/AS) | Sequence (5' to 3') | SEQ ID NO: |
|---|---|---|---|---|
| mTTR/ FVII | A-134476.1 | S | asascaguGfuUfCfUfugcucuauaaQ51csasggauCfaUfCfUfcaagucuuaaL96 | 47 |
| mTTR/ FVII | A-134477.1 | S | asascaguGfuUfCfUfugcucuauaaQ151csasggauCfaUfCfUfcaagucuusasa | 48 |
| mTTR | A-134478.1 | AS | usUfsauaGfaGfCfaagaAfcAfcuguususudCdAdCdAdGdGdC | 49 |
| FVII | A-134479.1 | S | csasggauCfaUfCfUfcaagucuusasa | 50 |
| FVII | A-134480.1 | AS | usUfsaagAfcuUfgagaUfgAfuccugsgscdCdTdGdTdGdAdA | 51 |
| mTTR | A-134481.1 | S | asascaguGfuUfCfUfugcucuausasadCdAdCdTdGdTdTdGdC | 52 |
| FVII | A-134482.1 | AS | usUfsaagAfcuUfgagaUfgAfuccugsgscdAdAdCdAdGdTdG | 53 |
| mTTR/ FVII | A-134483.1 | S | asascaguGfuUfCfUfugcucuausasadTdAdG(m5dC)csasggauCfaUfCfUfcaagucuuaaL96 | 54 |
| mTTR/ FVII | A-134484.1 | AS | usUfsaagAfcuUfgagaUfgAfuccugsgscdTdAusUfsauaGfaGfCfaagaAfcAfcuguususu | 55 |
| mTTR/ FVII | A-134485.1 | S | asascaguGfuUfCfUfugcucuausasadAdT(m5dC)dGcsasggauCfaUfCfUfcaagucuuaaL96 | 56 |
| mTTR/ FVII | A-134484.2 | AS | usUfsaagAfcuUfgagaUfgAfuccugsgscdTdAusUfsauaGfaGfCfaagaAfcAfcuguususu | 57 |

Oligonucleotide descriptions: The dual targeting multi-targeted molecules comprising two siRNAs (also referred to as bis-siRNAs) were conceived in three motifs. The most straightforward motif featured long sense (S) and anti-sense (AS) strands that partnered in a normal duplex and contained a short stretch of DNA on the AS strand for cleavage by nucleases within the cell to form the two active AS oligos. The second strategy featured a longer sense strand that can hybridize with two separate AS strands. Various spacers were used on the sense strand including a stretch of 2' OMe uridine (uuu), a $C_{12}$ linker (Q50), a disulfide bridge (Q51), and by moving the tri-GalNAc from the 3' end to the middle of the strand (Q151). The last motif featured four single strands, two of which contained DNA-based sticky ends. Two separate S and AS strands were annealed together, as each resulting duplex contained a single DNA sticky end overhang. The two duplexes were then connected through hybridization of the complementary sticky ends overhangs.

Standard coupling and oxidation: All of the above oligonucleotides were synthesized on the Applied Biosystems or MerMade synthesizers. They can be upscaled on the Äkta synthesizers for larger scale requests. Coupling of amidite was performed under standard synthesis conditions using 0.25 M 5-(ethylthio)-1H-tetrazole in acetonitrile for activation. Standard thiolation protocols with 3-(dimethylaminomethylene) amino-3H-1,2,4-dithiazole-5-thione (DDTT) were performed to convert the phosphite triester into a phosphorothioate linkage. Amidites were dissolved at 0.12-0.15 M in acetonitrile, with the exception of 2' OMe cytidine and uridine, which had 15% tetrahydrofuran or dimethylformamide as a co-solvent.

Synthesis Exceptions: Due to the large molecular weight of the Q151 monomer, special considerations needed to be undertaken for its coupling in strand A-134477.1. The phosphoramidite was dissolved at 0.07-0.09 M in acetonitrile. A double coupling was used with 0.6 M 5-(ethylthio)-1H-tetrazole for activation on the Applied Biosystems synthesizer. This was done to match the viscosities of the two solutions prior to mixing. After the first delivery of amidite, a 900 second hold was incurred, followed by a second delivery of amidite and activator and an additional 900 coupling hold. Subsequent amidite couplings proceeded under normal conditions.

Special care also needed to be used for the Q51 disulfide linker. Since the disulfide is sensitive to oxidation 10% tertbutyl hydroperoxide (TBHP) in acetonitrile (diluted from 70% aqueous TBHP) was used instead of the normal 0.02 M $I_2$ in THF/pyridine/$H_2O$ solution. This mild oxidation was used for the Q51 and all subsequent couplings.

Deprotection and cleavage: After synthesis the oligonucleotides were deprotected in a 4:1 mixture of aq. $NH_3$ and EtOH for 5 h at 60° C. or for 16 h at 35° C.

Purification: All of the oligonucleotides were purified to >85% purity using standard ion exchange chromatography methods and desalting procedures.

Figure 26:
FIG. 26 shows some exemplary linkers and monomers.
Figure 26:
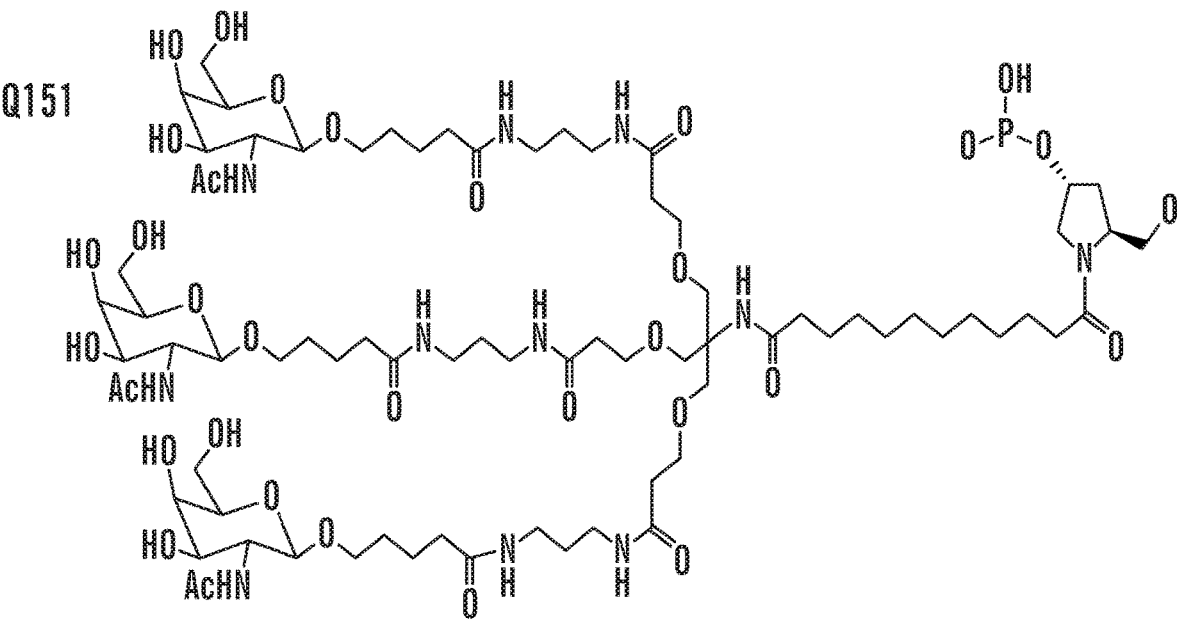
Figure 26:
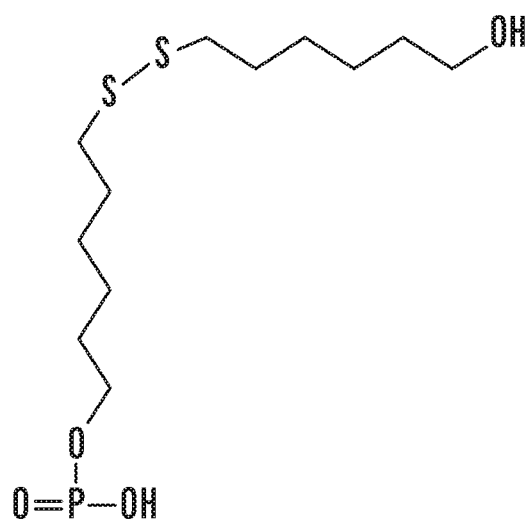
Figure 26:
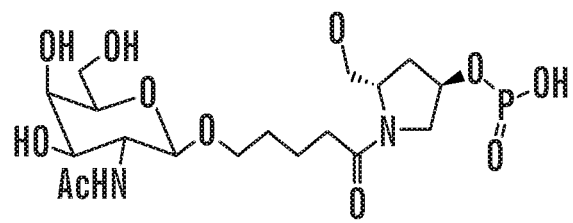

Structures of monomers Q50, Q51 and Q151 are shown in FIG. 26.

Source of reagents: Where the source of a reagent is not specifically given herein, such reagent can be obtained from any supplier of reagents for molecular biology at a quality/purity standard for application in molecular biology.

siRNA Synthesis: FVII and mTTR siRNA sequences were synthesized at 1 μmol scale on Mermade 192 synthesizer (BioAutomation) using the solid support mediated phosphoramidite chemistry. The solid support was controlled pore glass (500 Å) loaded with custom GalNAc ligand or universal solid support (AM biochemical). Ancillary synthesis reagents, 2'-F and 2'-O-Methyl RNA and deoxy phosphoramidites were obtained from Thermo-Fisher (Milwaukee, Wis.) and Hongene (China). Q50, Q51 and Q151 modification linkers (shown above) were introduced employing the corresponding phosphoramidites. Synthesis of 3' GalNAc conjugated single strands was performed on a GalNAc modified CPG support. Custom CPG universal solid support was used for the synthesis of antisense single strands. Coupling time for all phosphoramidites (100 mM in acetonitrile) was 5 min employing 5-Ethylthio-1H-tetrazole (ETT) as activator (0.6 M in acetonitrile). Phosphorothioate linkages were generated using a 50 mM solution of 3-((Dimethylamino-methylidene) amino)-3H-1,2,4-dithiazole-3-thione (DDTT, obtained from Chemgenes (Wilmington, Mass., USA) in anhydrous acetonitrile/pyridine (1:1 v/v). Oxidation time was 3 minutes. All sequences were synthesized with final removal of the DMT group ("DMT off").

Long strand designs and short strand designs were synthesized in a similar fashion, by adjusting the number of nucleotide synthesis steps. Linkers (Q50, Q51 and Q151) were coupled as standard phosphoramidites and the coupling was included as an additional nucleotide synthesis step.

Upon completion of the solid phase synthesis, oligoribonucleotides were cleaved from the solid support and deprotected in sealed 96 deep well plates using 200 µL Aqueous Methylamine reagent at 60° C. for 20 minutes. At the end of cleavage and deprotection step, the synthesis plate was allowed to come to room temperature and was precipitated by addition of 1 mL of acetontile:ethanol mixture (9:1). The plates were cooled at −80° C. for 2 hrs, and the superanatant was decanted carefully with the aid of a multichannel pipette. The oligonucleotide pellet was re-suspended in 20 mM NaOAc buffer and were desalted using a 5 mL HiTrap size exclusion column (GE Healthcare) on an AKTA Purifier System equipped with an A905 autosampler and a Frac 950 fraction collector. Desalted samples were collected in 96 well plates. Samples from each sequence were analyzed by LC-MS to confirm the identity, UV (260 nm) for quantification and a selected set of samples by IEX chromatography to determine purity.

For the multiplex constructs composed of 3 and less single strands, annealing of FVII and mTTR single strands was performed by mixing equimolar mixture of sense and antisense single strands. After combining the complementary single strands, the 96 well plate was sealed tightly and heated in an oven at 100° C. for 10 minutes and allowed to come slowly to room temperature over a period 2-3 hours. For the multiplex constructs composed of 4 or more single strands, individual reverse-complementary FVII and mTTR duplexes with long 3'-overhangs were prepared first, by mixing equimolar mixture of sense and antisense single strands in water, heating and cooling (as described above). Equimolar amounts of duplexes, having reverse-complementary 3'-overhangs were mixed together and the mixture was lyophilized from water until a dry powder was obtained. The multiplex constructs were then dissolved in sterile, endotoxin-free 1× PBS. The concentration of each multiplex was normalized to 300 µM in sterile, endotoxin-free 1× PBS.

In all cases, non-denaturing IEX-HPLC methods showed the presence of a single chromatogram peak, corresponding to the single entity multiplex construct.

TABLE 2

Some exemplary multi-targeted single entity conjugates and siRNAs used in this study and this is result of that follo

| Duplex ID | Sense ID | Sense (5' to 3') |
|---|---|---|
| AM-1 | A-134471 | asascaguGfuUfCfUfugcucuausasauuucsasgg auCfaUfCfUfcaagucuuaaL96 (SEQ ID NO: 42) |
| AM-2 | A-134472 | asascaguGfuUfCfUfugcucuauaauuucsasgga uCfaUfCfUfcaagucuuaaL96 (SEQ ID NO: 43) |
| AM-3 | A-134473 | asascaguGfuUfCfUfugcucuauaaQ50csasgga uCfaUfCfUfcaagucuuaaL96 (SEQ ID NO: 44) |
| AM-4 | A-134474 | csasggauCfaUfCfUfcaagucuuaaQ50asascag uGfuUfCfUfugcucuauaaL96 (SEQ ID NO: 45) |
| AM-5 | A-134475 | asascaguGfuUfCfUfugcucuauaaQ50Ufacsas ggauCfaUfCfUfcaagucuuaaL96 (SEQ ID NO: 46) |
| AM-6 | A-134476 | asascaguGfuUfCfUfugcucuauaaQ51csasgga uCfaUfCfUfcaagucuuaaL96 (SEQ ID NO: 47) |
| AM-7 | A-134477 | asascaguGfuUfCfUfugcucuauaaQ151csasgg auCfaUfCfUfcaagucuusasa (SEQ ID NO: 48) |
| AD-68267 | A-134483 | asascaguGfuUfCfUf fugcucuausasadTdAdG (m5dC)csasggauCfaUfCfUfcaagucuuaaL96 (SEQ ID NO: 54) |
| AD-68268 | A-134485 | asascaguGfuUfCfUfugcucuausasadAdT(m5dC) dGcsasggauCfaUfCfUfcaagucuuaaL96 (SEQ ID NO: 56) |
| AD-64228 | A-128009 | asascaguGfuUfCfUfugcucuauaaL96 (SEQ ID NO: 36) |

TABLE 2-continued

Some exemplary multi-targeted single entity conjugates
and siRNAs used in this study and this is result of that follo AD-68269  A-134469 csasggauCfaUfCfUfcaagucuuaaL96 (SEQ
                   ID NO: 39)

| Duplex ID | AS ID | Antisense (5' to 3') |
|---|---|---|
| AM-1 | A-128003 | usUfsauaGfaGfCfaagaAfcAfcuguususu (SEQ ID NO: 38) |
|  | A-126753 | usUfsaagAfcuUfgagaUfgAfuccugsgsc (SEQ IS NO: 41) |
| AM-2 | A-128003 | usUfsauaGfaGfCfaagaAfcAfcuguususu (SEQ ID NO: 38) |
|  | A-126753 | usUfsaagAfcuUfgagaUfgAfuccugsgsc (SEQ ID NO: 41) |
| AM-3 | A-128003 | usUfsauaGfaGfCfaagaAfcAfcuguususu (SEQ ID NO: 38) |
|  | A-126753 | usUfsaagAfcuUfgagaUfgAfuccugsgsc (SEQ ID NO: 41) |
| AM-4 | A-128003 | usUfsauaGfaGfCfaagaAfcAfcuguususu (SEQ ID NO: 38) |
|  | A-126753 | usUfsaagAfcuUfgagaUfgAfuccugsgsc (SEQ ID NO: 41) |
| AM-5 | A-128003 | usUfsauaGfaGfCfaagaAfcAfcuguususu (SEQ ID NO: 38) |
|  | A-126753 | usUfsaagAfcuUfgagaUfgAfuccugsgsc (SEQ ID NO: 41) |
| AM-6 | A-128003 | usUfsauaGfaGfCfaagaAfcAfcuguususu (SEQ ID NO: 38) |
|  | A-126753 | usUfsaagAfcuUfgagaUfgAfuccugsgsc (SEQ ID NO: 41) |
| AM-7 | A-128003 | usUfsauaGfaGfCfaagaAfcAfcuguususu (SEQ ID NO: 38) |
|  | A-126753 | usUfsaagAfcuUfgagaUfgAfuccugsgsc (SEQ ID NO: 41) |
| AD-68267 | A-134484 | usUfsaagAfcuUfgagaUfgAfuccugsgscdTdAusUfsauaGfaGfCfaag aAfcAfcuguususu (SEQ ID NO: 55) |
| AD-68268 | A-134484 | usUfsaagAfcuUfgagaUfgAfuccugsgscdTdAusUfsauaGfaGfCfaag aAfcAfcuguususu (SEQ ID NO: 55) |
| AD-64228 | A-128003 | usUfsauaGfaGfCfaagaAfcAfcuguususu (SEQ ID NO: 38) |
| AD-68269 | A-126753 | usUfsaagAfcuUfgagaUfgAfuccugsgsc (SEQ ID NO: 41) |

TABLE 3

Some more exemplary multi-targeted single entity conjugates and siRNAs used in this study

| Duplex ID | Sense ID | Sense (5' to 3') | AS ID | Antisense (5' to 3') | AS Target |
|---|---|---|---|---|---|
| AM-13 | A- | asascaguGfuUfCfUfugcucua uaaQ173Q173csasggauCfa UfCfUfcaagucuusasa (SEQ ID NO: 58) | A-128003 | usUfsauaGfaGfCfaagaAfcAfcuguususu (SEQ ID NO: 38) | mTTR |
|  |  |  | A-126753 | usUfsaagAfcuUfgagaUfgAfuccugsgsc (SEQ ID NO: 41) | FVII |
| AM-26 | A-128009 | asascaguGfuUfCfUfugcucua uaaL96 (SEQ ID NO: 36) | A- | usUfsauaGfaGfCfaagaAfcAfcuguususucacadGdGdC (SEQ ID NO: 59) | mTTR |
|  | A-134469 | csasggauCfaUfCfUfcaagucu uaaL96 (SEQ ID NO: 39) | A- | usUfsaagAfcuUfgagaUfgAfuccugsgsccugudGdAdA (SEQ ID NO: 60) | FVII |

In vitro free uptake and transfection of various exemplary multi-targeted molecules is summarized in Table 4.

TABLE 4

In vitro free uptake and transfection of some exemplary multi-targeted molecules

| Duplex ID | Free Uptake (IC$_{50}$ TTR/FVII) - nM | Transfection (IC$_{50}$ TTR/FVII) - nM |
|---|---|---|
| AM-1 | 0.3/2.5 | <0.002/<0.002 |
| AM-2 | 0.7/2.9 | <0.002/<0.002 |
| AM-3 | 0.9/1.4 | <0.002/<0.002 |
| AM-4 | 0.8/1.6 | 0.034/<0.002 |
| AM-5 | 0.7/1.5 | <0.002/<0.002 |
| AM-6 | 1.1/1.1 | <0.002/<0.002 |
| AM-7 | <0.45/0.9 | <0.002/<0.002 |
| AM-13 | N.A. | <0.002/<0.002 |
| AD-68267 | 0.6/2.5 | 5.8/19.3 |
| AD-68268 | <0.45/1.4 | 1.4/3.0 |

TABLE 4-continued

In vitro free uptake and transfection of some exemplary multi-targeted molecules

| Duplex ID | Free Uptake (IC$_{50}$ TTR/FVII) - nM | Transfection (IC$_{50}$ TTR/FVII) - nM |
|---|---|---|
| AM-26 | <0.45/<0.45 | 0.2/2.0 |
| mix AD-64228 AD-68269 | <0.45/<0.45 | <0.002/<0.002 |

Example 26

In Vivo Studies

In vivo studies: All animals were held in a pathogen-free environment, and all procedures involving animals were performed in accordance with local, state, and federal regulations as applicable and approved by the Institutional Animal Care and Use Committee (IACUC). Female C57BL/6 mice (7-8 weeks old) were obtained from Charles River Labs. The Bis-siRNA compounds (targeting FVII and TTR) were diluted to the appropriate concentrations in sterile PBS. Mice received either PBS or Bis-siRNA compounds via subcutaneous (s.c) injection at a volume of 10 mL/kg on Day 0. Blood samples were collected from animals by retro-orbital bleed at various time points (Day 0 [pre-dose], 7, 14, 21, and 28) and processed to serum (Microtainer Serum Separator Tubes; Becton Dickinson, Franklin Lakes, N.J., USA). Serum levels of Factor VII protein were determined by using an activity-based chromogenic assay (Biophen FVII, Aniara Corporation, Mason, Ohio). Serum levels of TTR protein were determined using a mouse TTR ELISA.

Mouse TTR Serum Protein Methods: TTR serum protein was quantified using a commercially available enzyme-linked immunosorbent assay, 41-ALBMS-E01 (ALPCO, Salem, N.H.), according to manufacturer's instructions. Briefly, serum samples were diluted 4000 fold in 1× ALPCO Kit Dilution Buffer. An 8-point mouse TTR standard curve was generated using 2.5× serial dilutions, ranging from 0 to 1000 ng/mL. Standards and samples (100 µL) were added to the plate and allowed to incubate for 30 minutes at room temperature. Plates were washed in 1× ALPCO Kit Wash Buffer and incubated for 20 minutes at room temperature with an affinity purified anti-Prealbumin antibody conjugated with horseradish peroxidase in a stabilizing buffer. After a wash in ALPCO Kit 1× Wash Buffer, plates were incubated for 10 minutes at room temperature in the dark with 3,3',5,5'-tetramethybenzidine (TMB) and hydrogen peroxide in citric acid buffer at pH 3.3. Reactions were quenched with 100 µL of 0.3 M sulfuric acid per well. Absorbance at 405 nm was read on a SpectraMax plate reader, and data were fit to a 4-parameter curve (y=(A−D)/(1+(x/C)^B)+D) as calculated in Softmax Pro Software to determine serum TTR protein levels expressed in µg/mL. Protein levels at each time point were normalized to the respective group average of vehicle control serum protein values. Results are shown in FIGS. 4-13.

Example 27

Duplex Analysis

Figure 14:
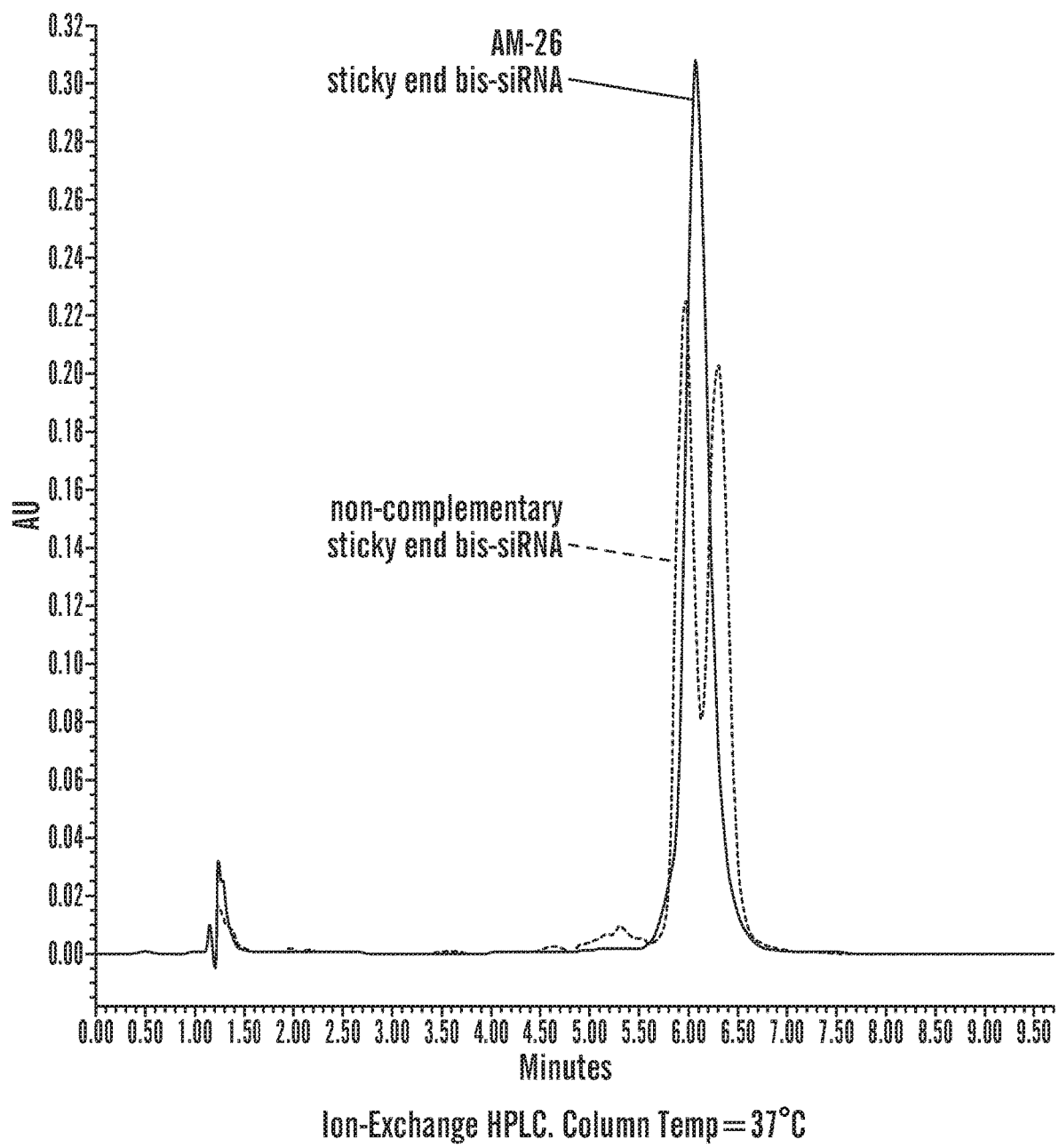
FIG. 14 shows duplex analysis and thermal melting profile from an embodiment of the multi-targeted single entity conjugates.
Figure 14:
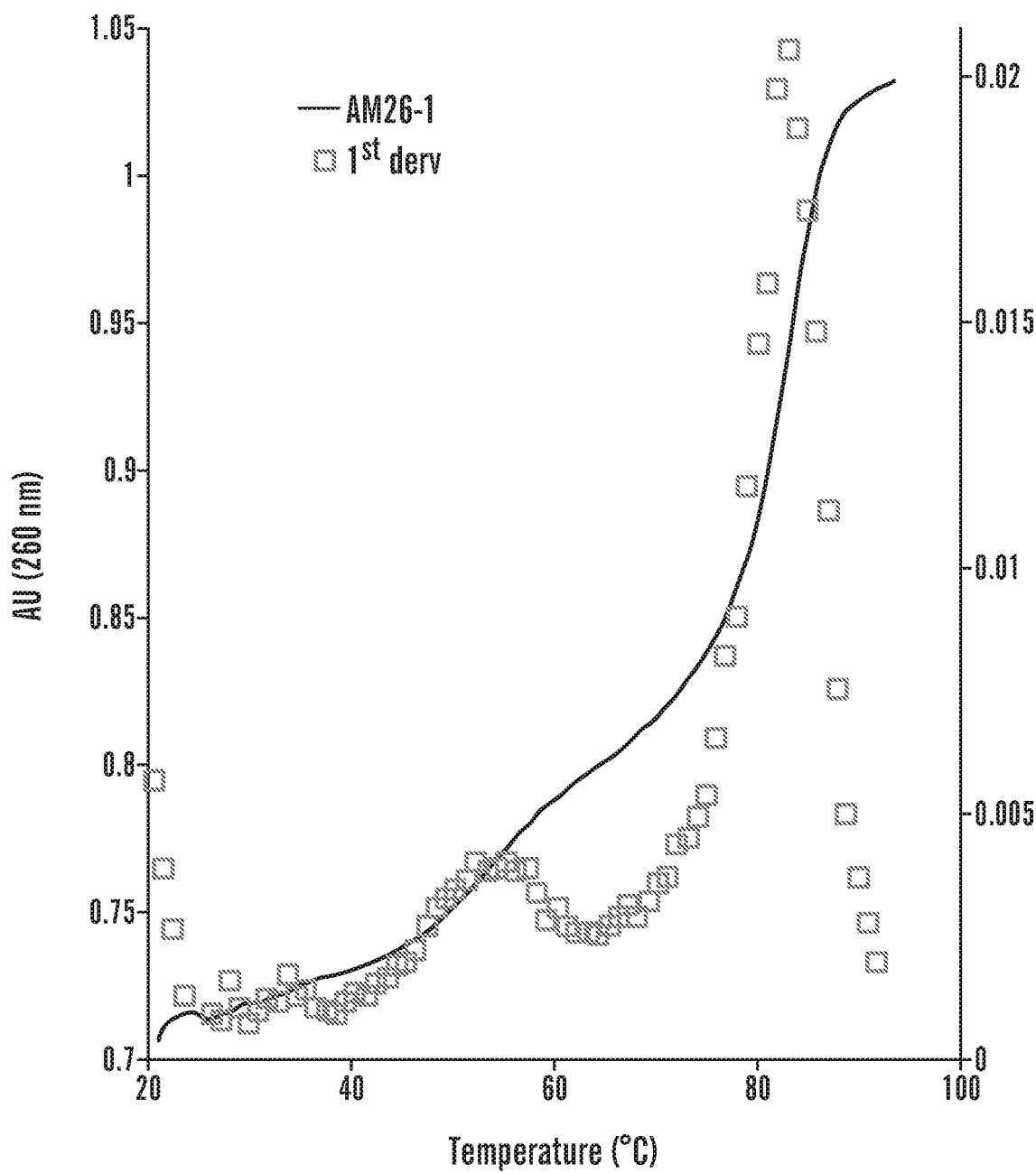
Figure 15:
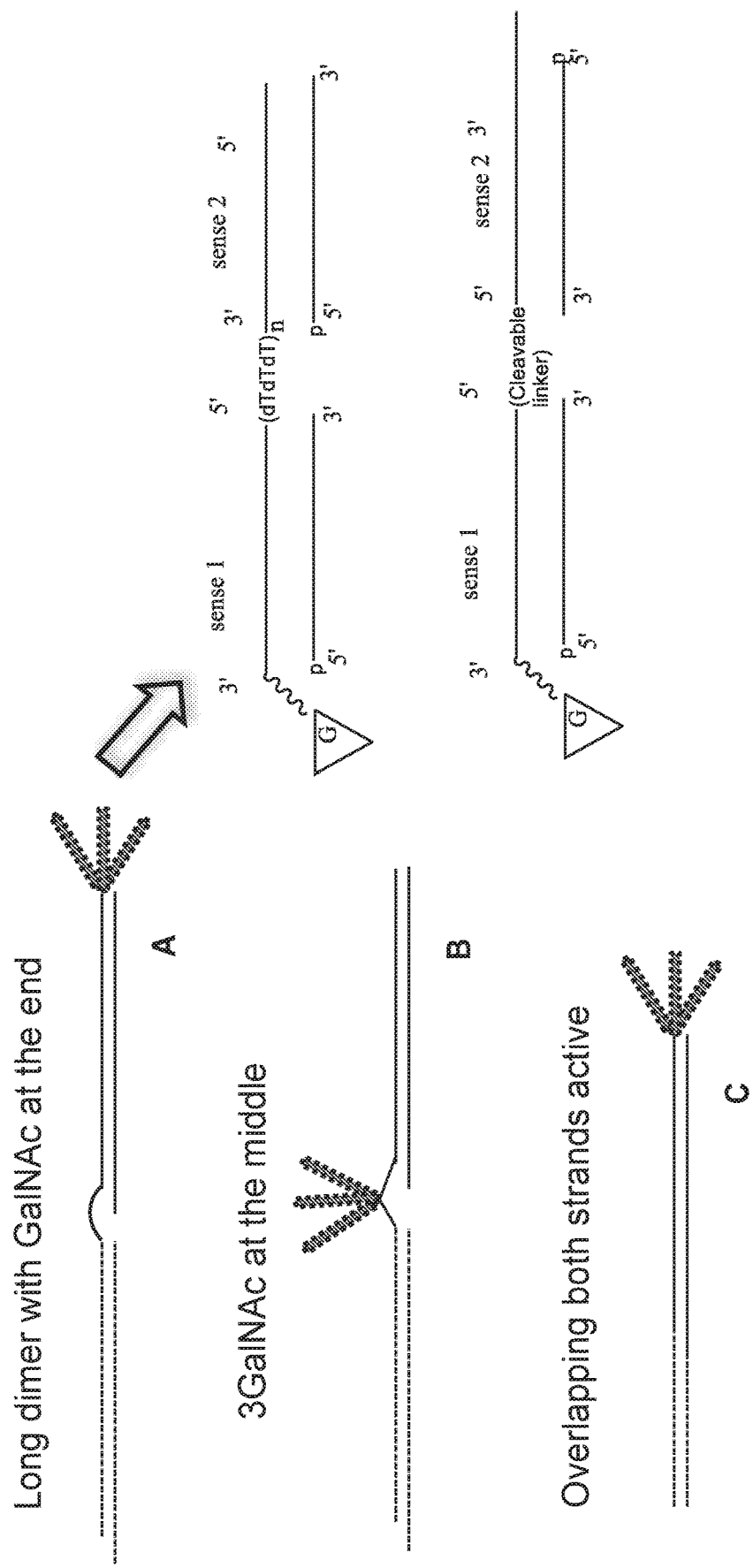
FIG. 15 is a schematic representation of three basic designs of some exemplary multi-targeted molecules.
Figure 16:
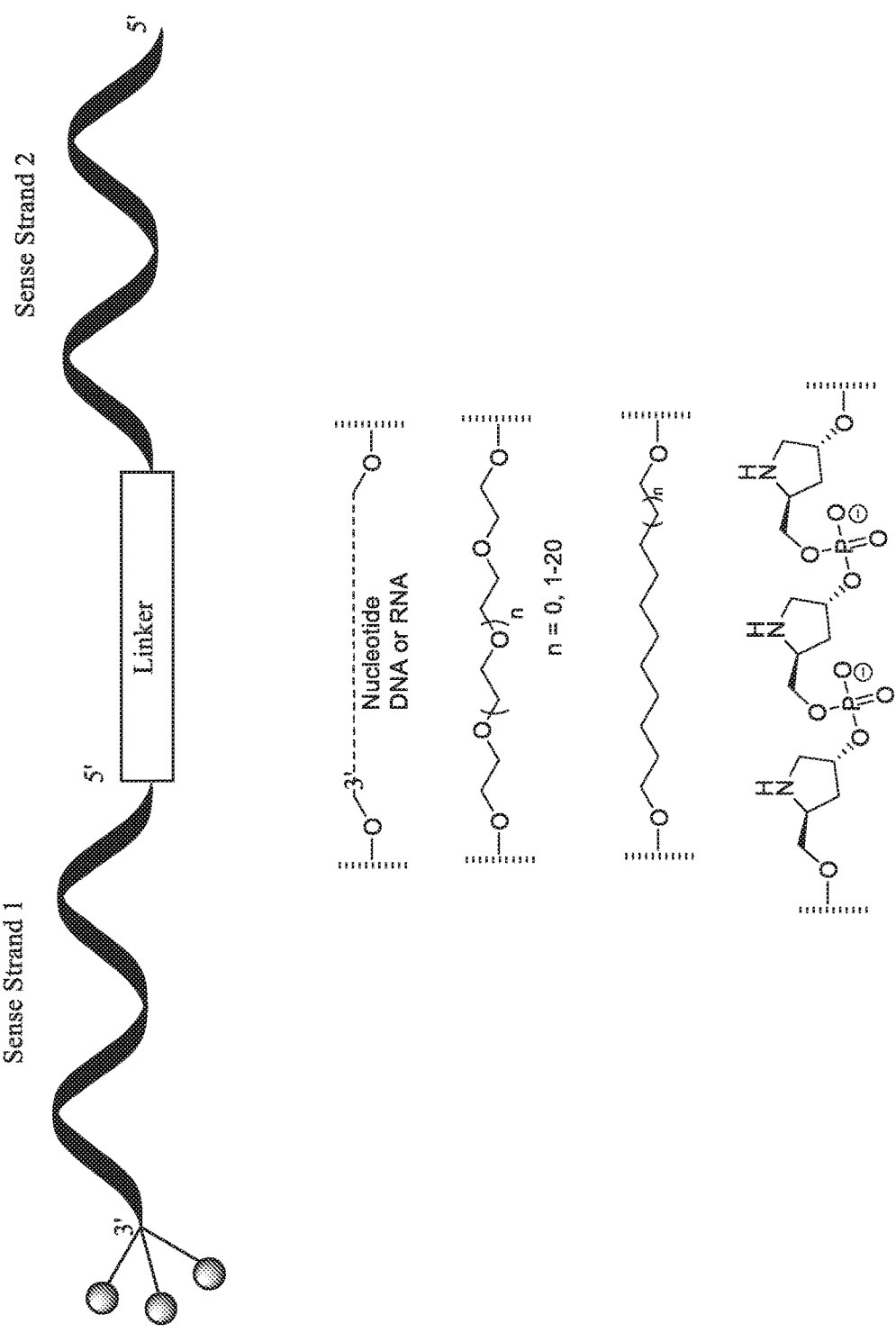
FIGS. 16 and 17 are schematic representations of multi-targeted molecule-GalNAc conjugates (e.g., bis(siRNA)-GalNac conjugates) according to some embodiments of the invention.
Figure 17:
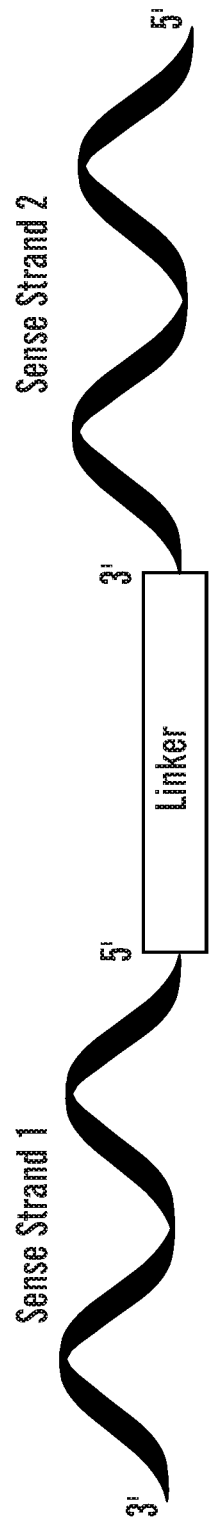
Figure 17:
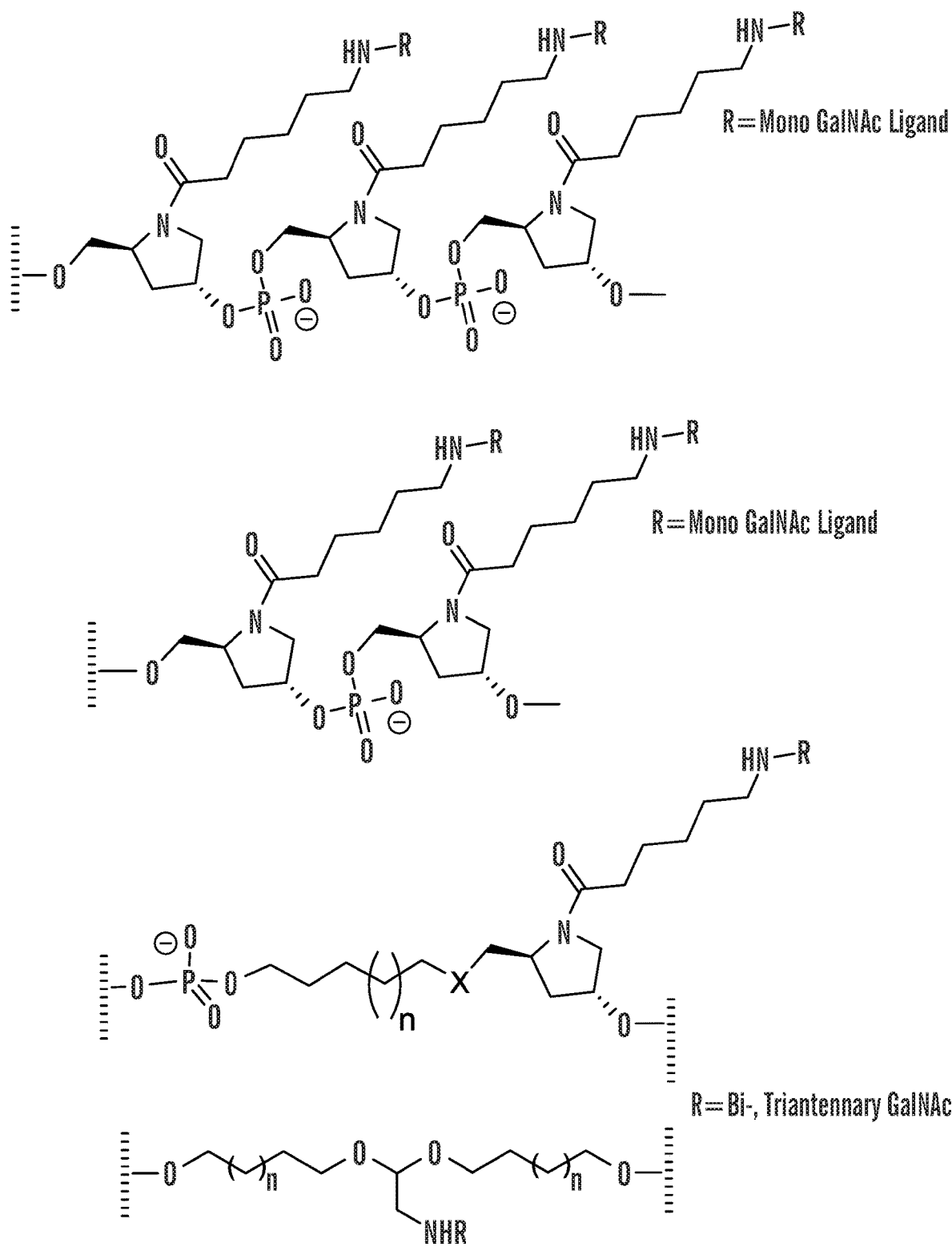
Figure 18:
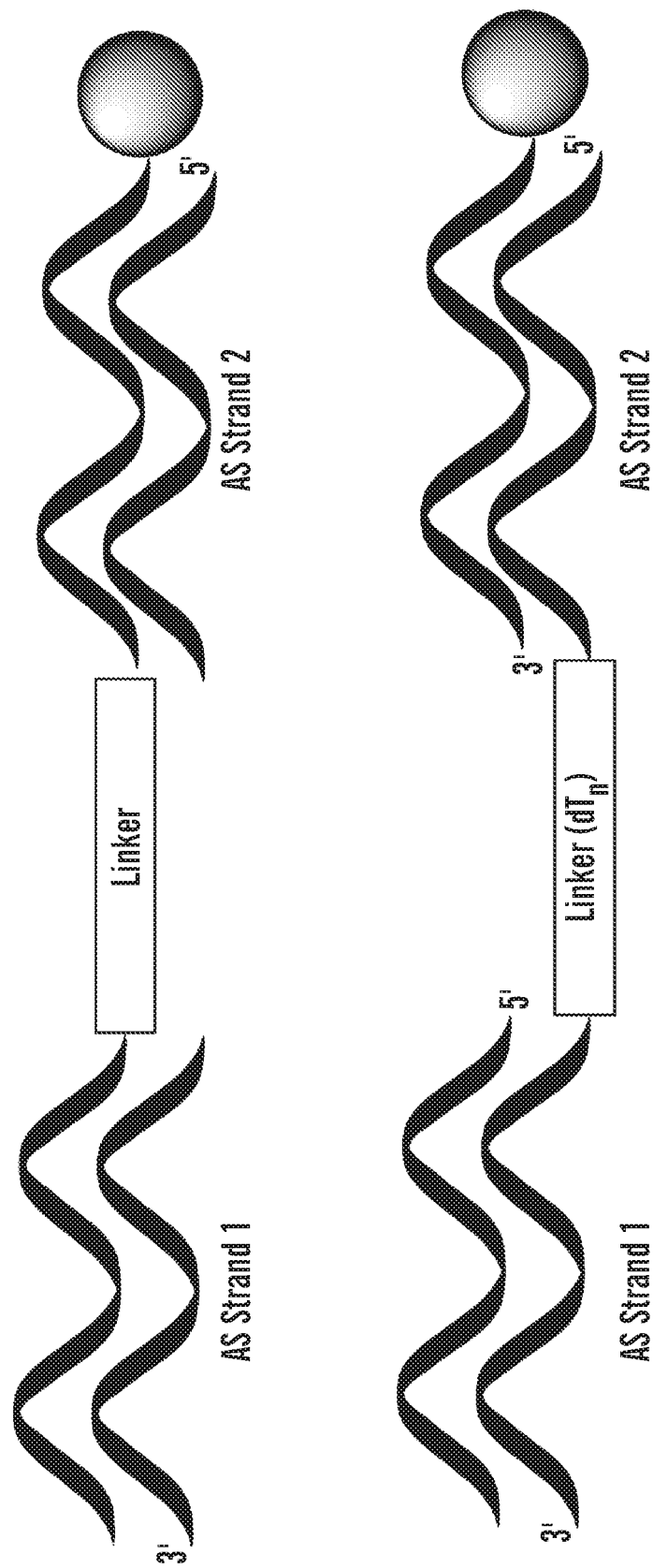
FIG. 18 shows schematic representation of some exemplary multi-targeted molecule designs according to some embodiments of the invention.
Figure 19:
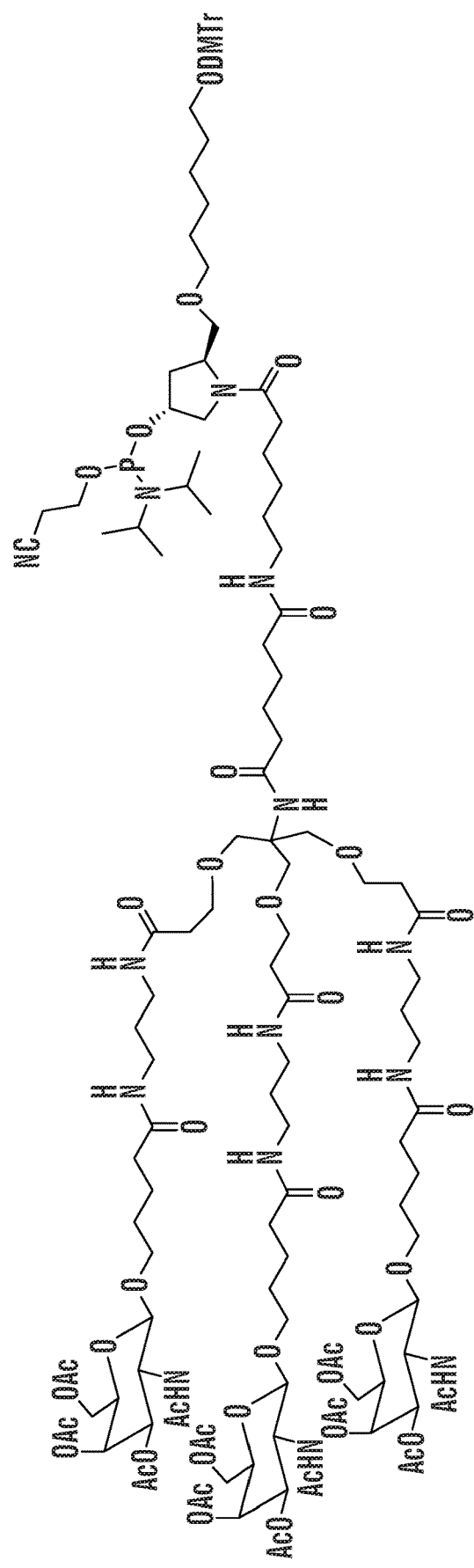
FIG. 19 shows some triantennary monomers for multi-targeted molecule designs.
Figure 19:
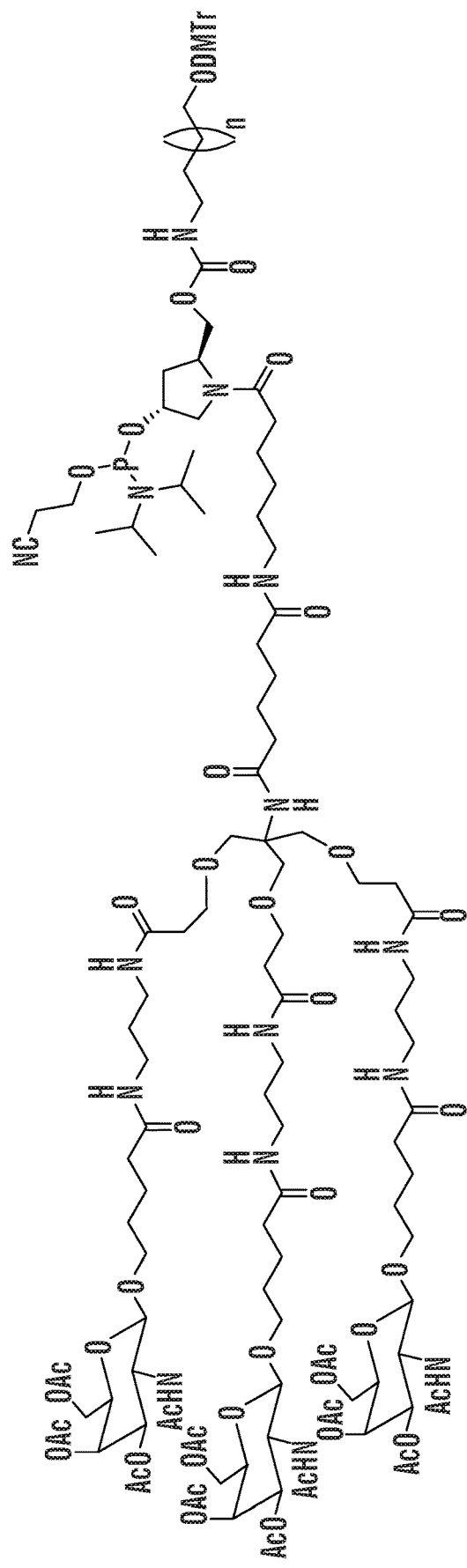
Figure 19:
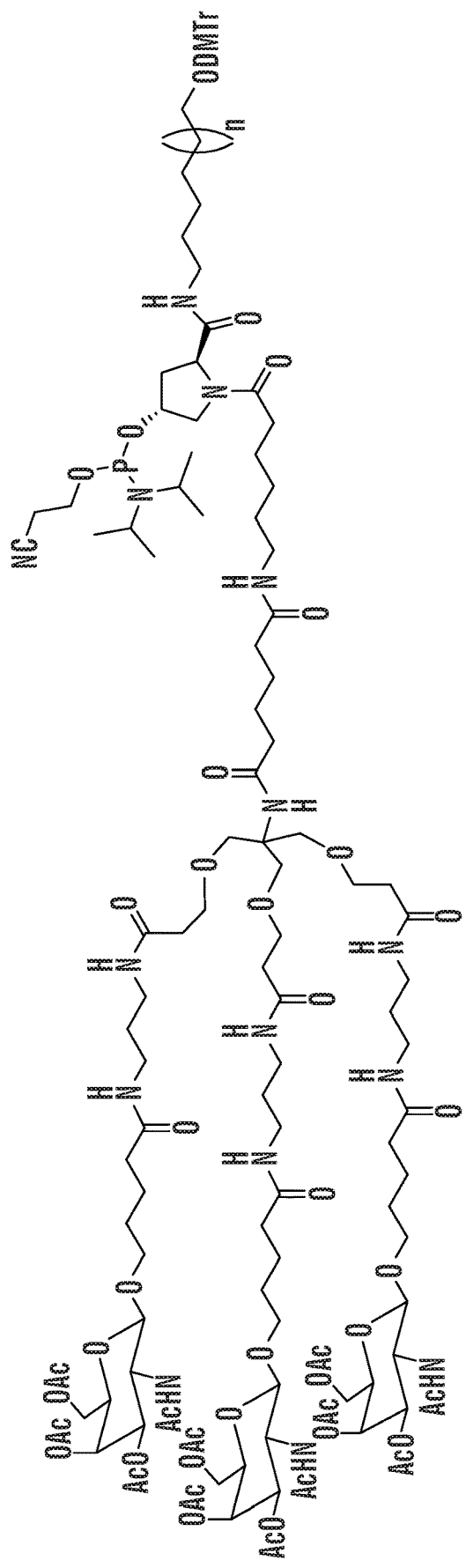
Figure 20:
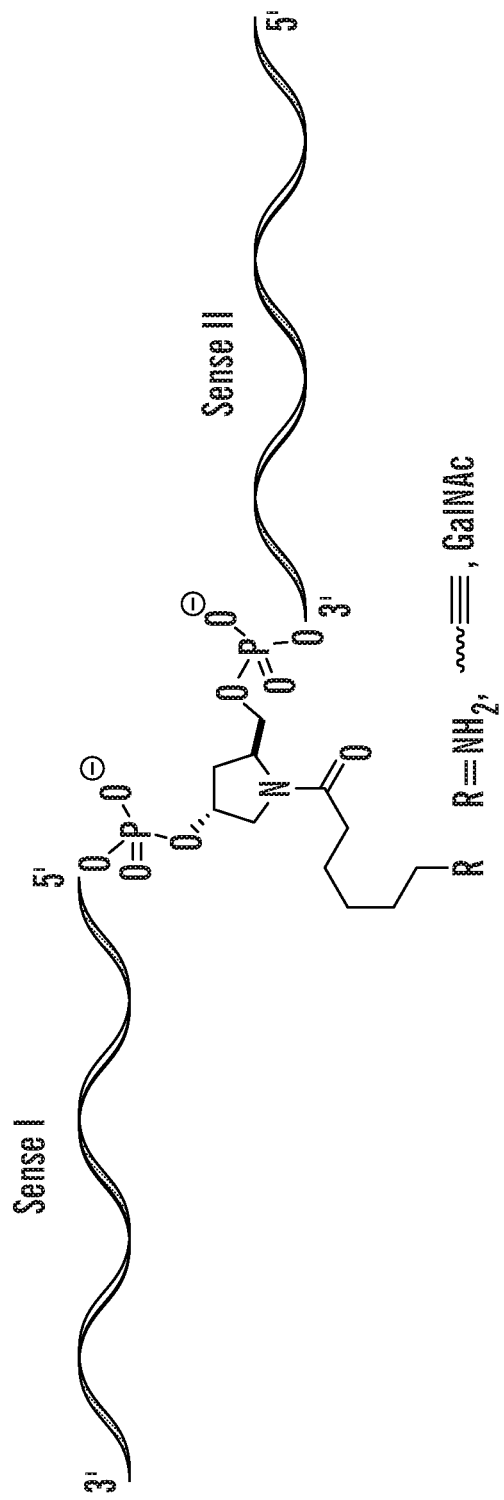
FIG. 20 shows a schematic representation of synthesis reagents of exemplary GalNAc conjugated multi-targeted molecules (e.g., bis(siRNA)-GalNAc conjugates).
Figure 20:
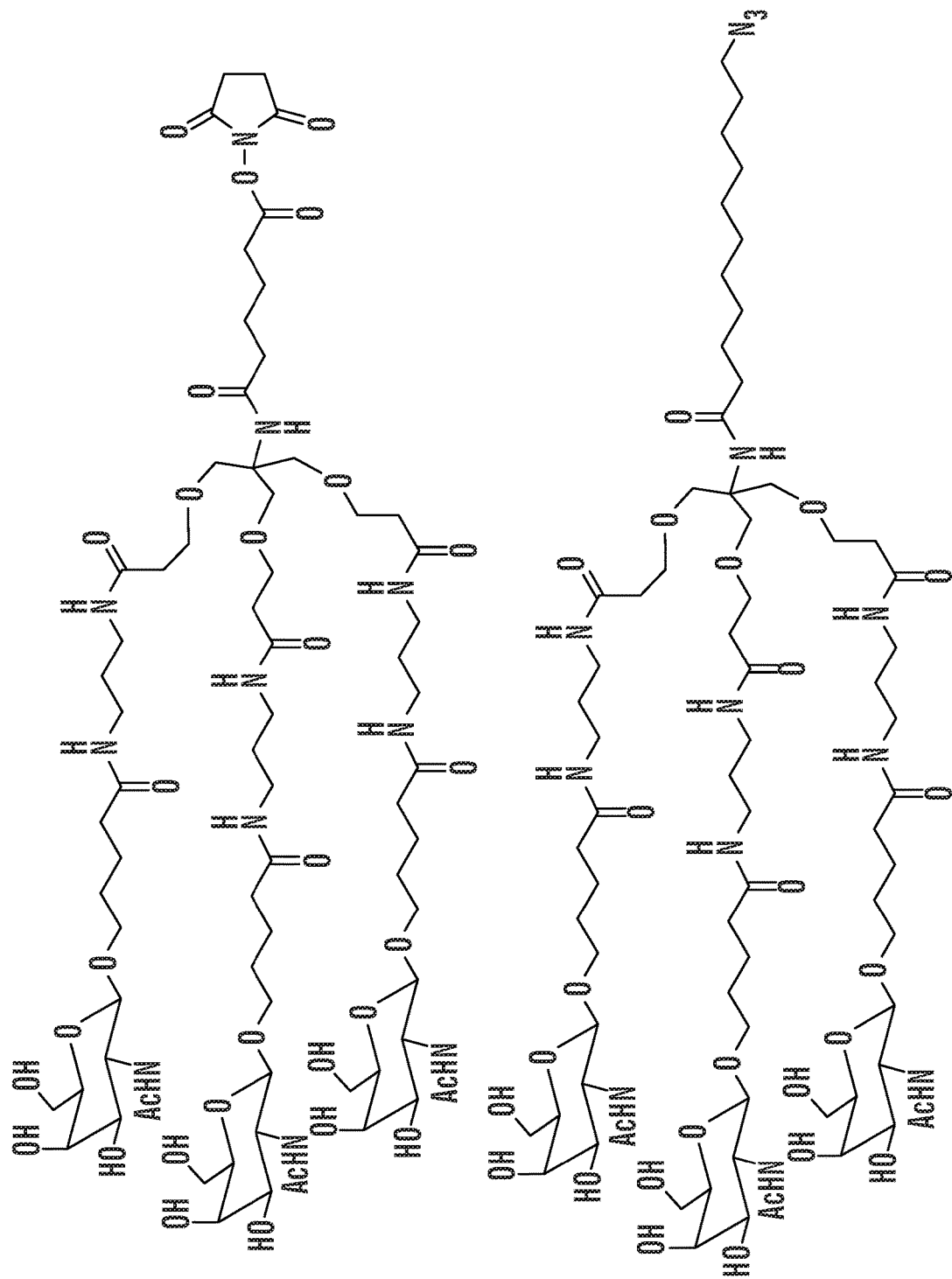
Figure 20:
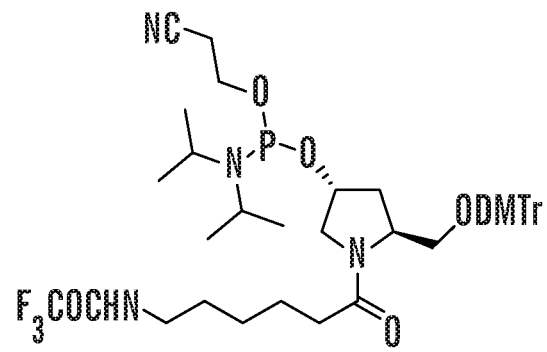
Figure 20:
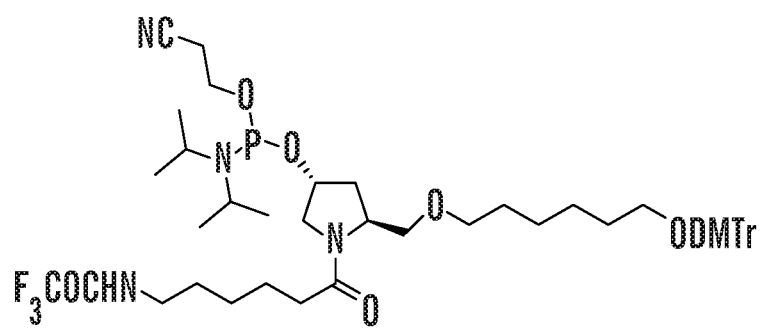
Figure 20:
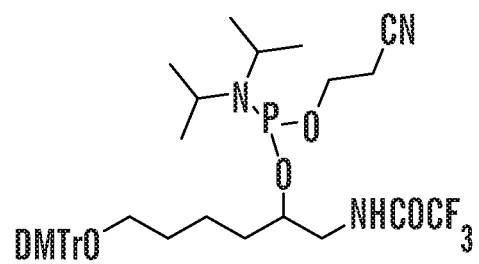
Figure 20:
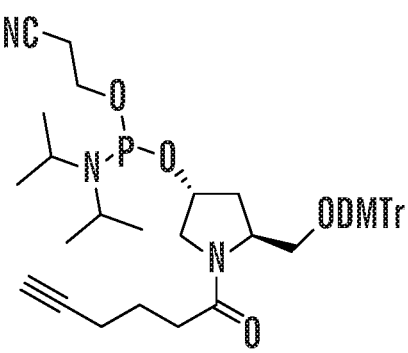
Figure 21:
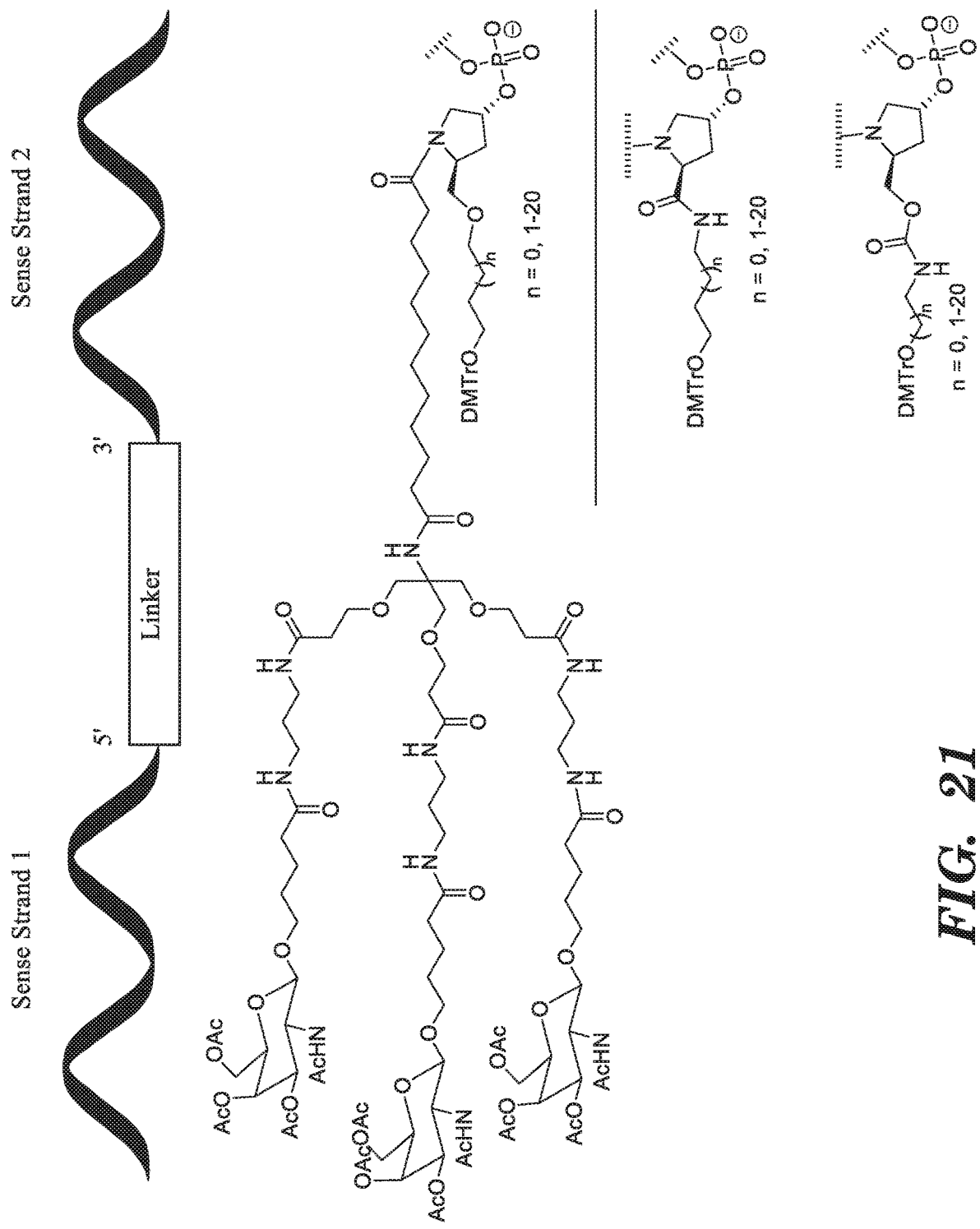
FIG. 21 shows some exemplary prolinol based linker molecules.
Figure 22:
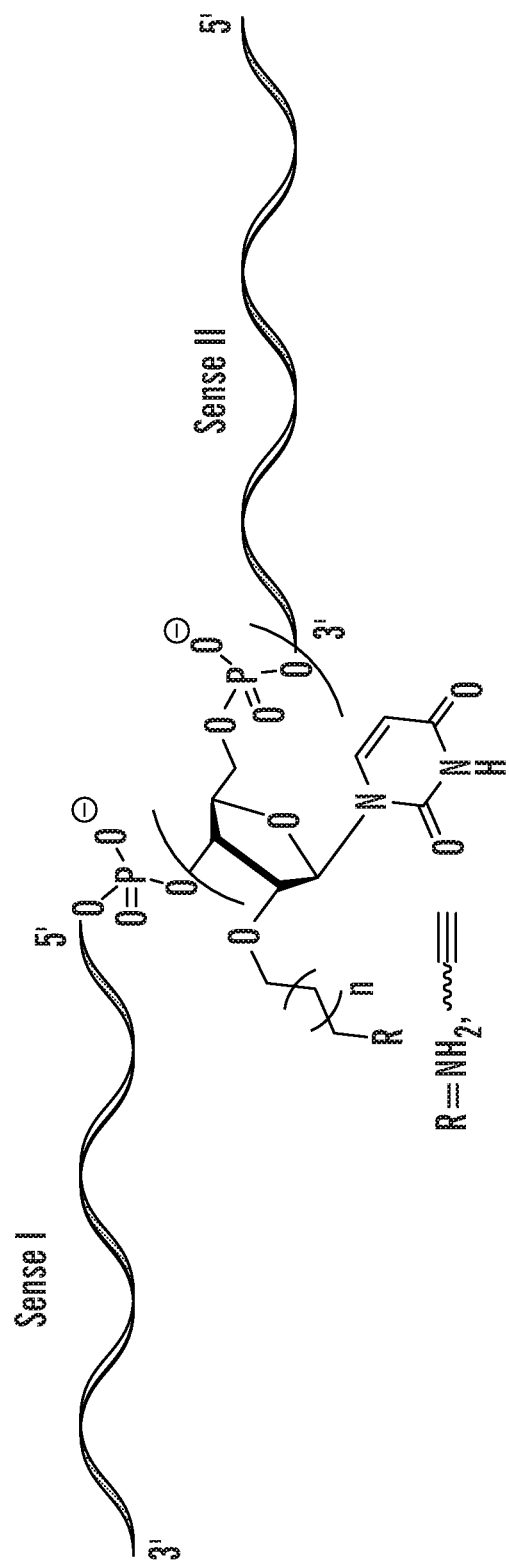
FIG. 22 shows an exemplary post-synthetic conjugation scheme.
Figure 22:
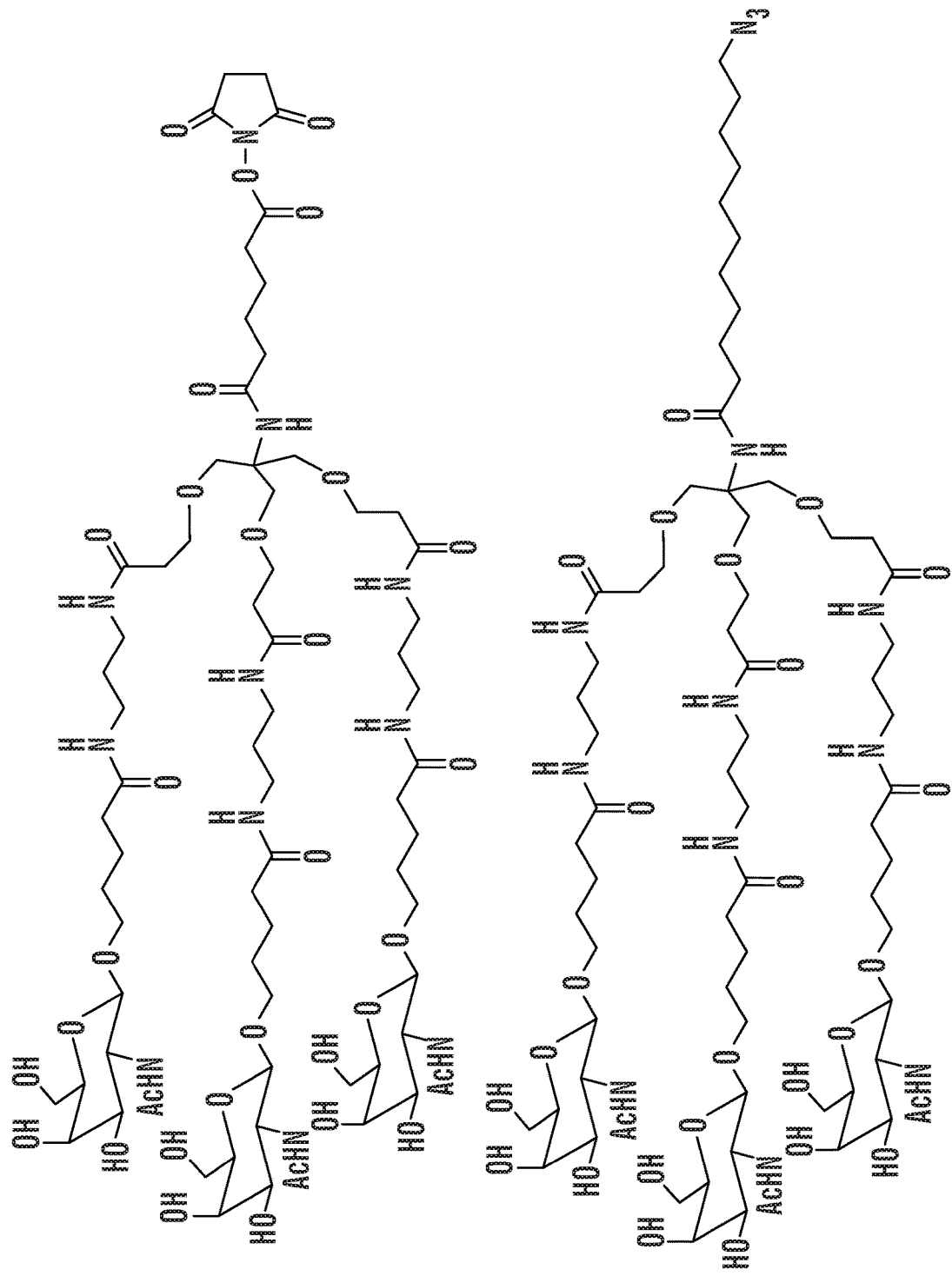
Figure 22:
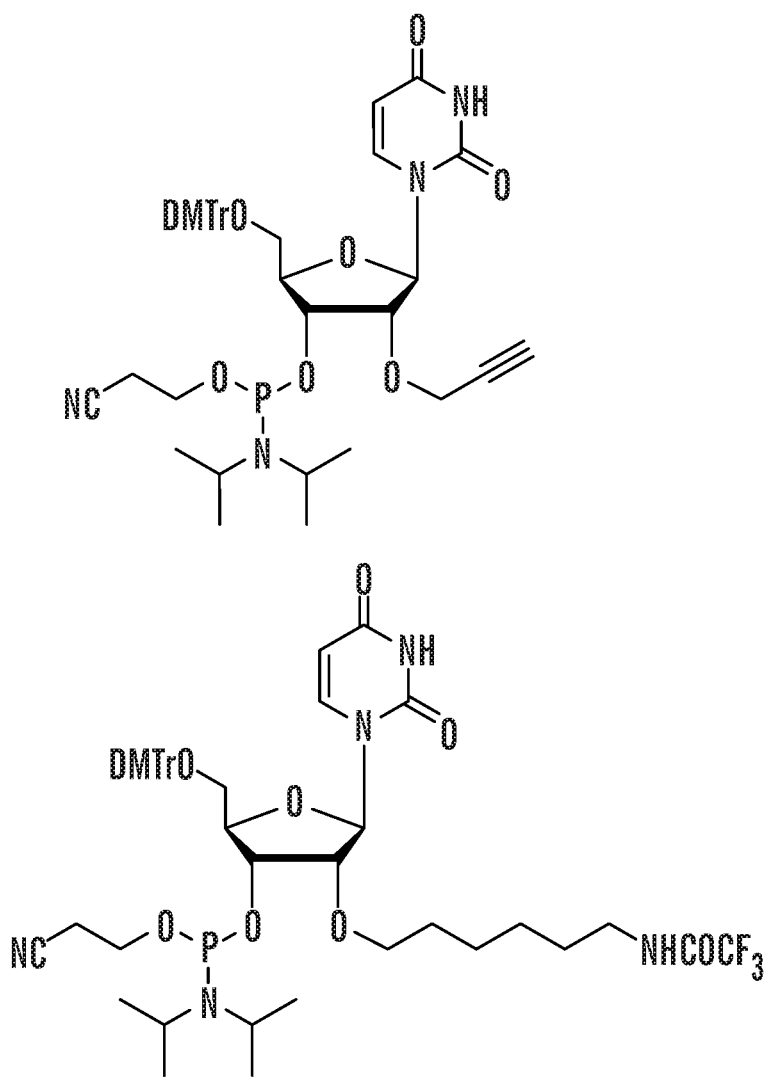
Figure 23:
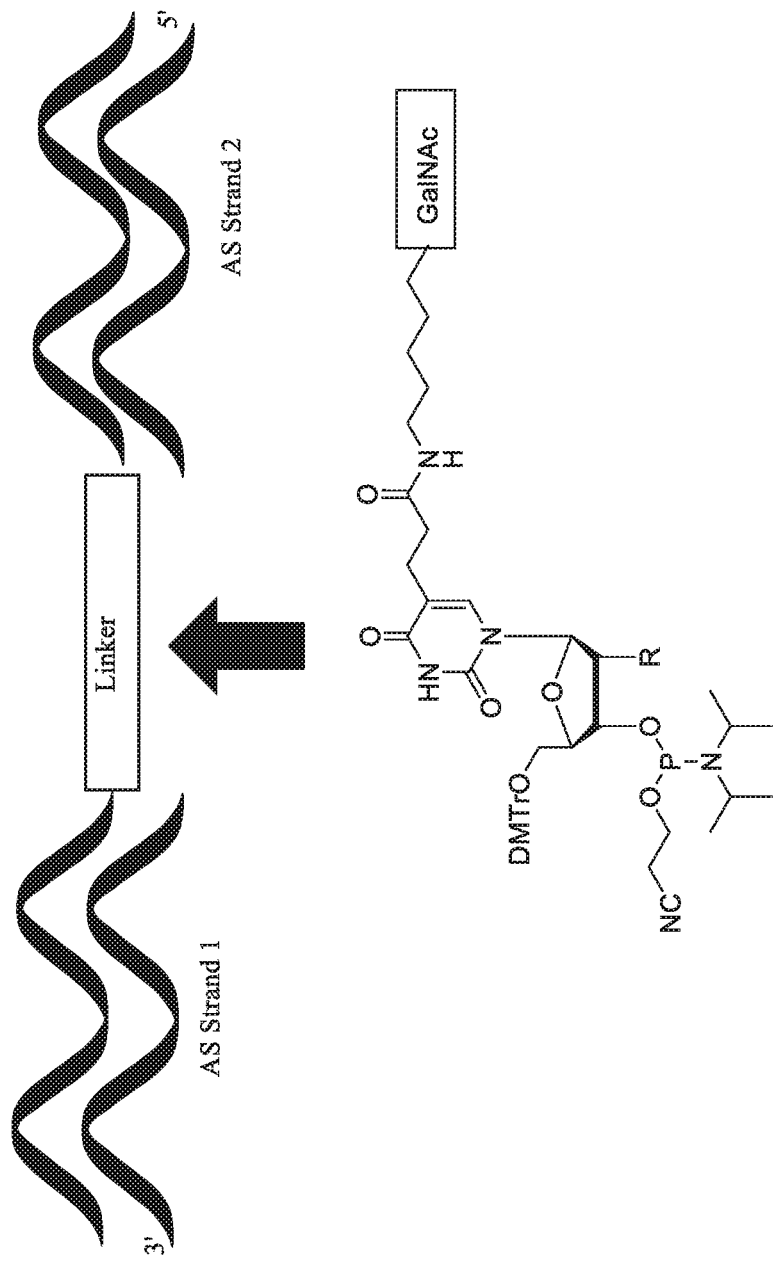
FIG. 23 shows an example of (1+1) or (1+1+1) type design at the bridge/linker.
Figure 24:
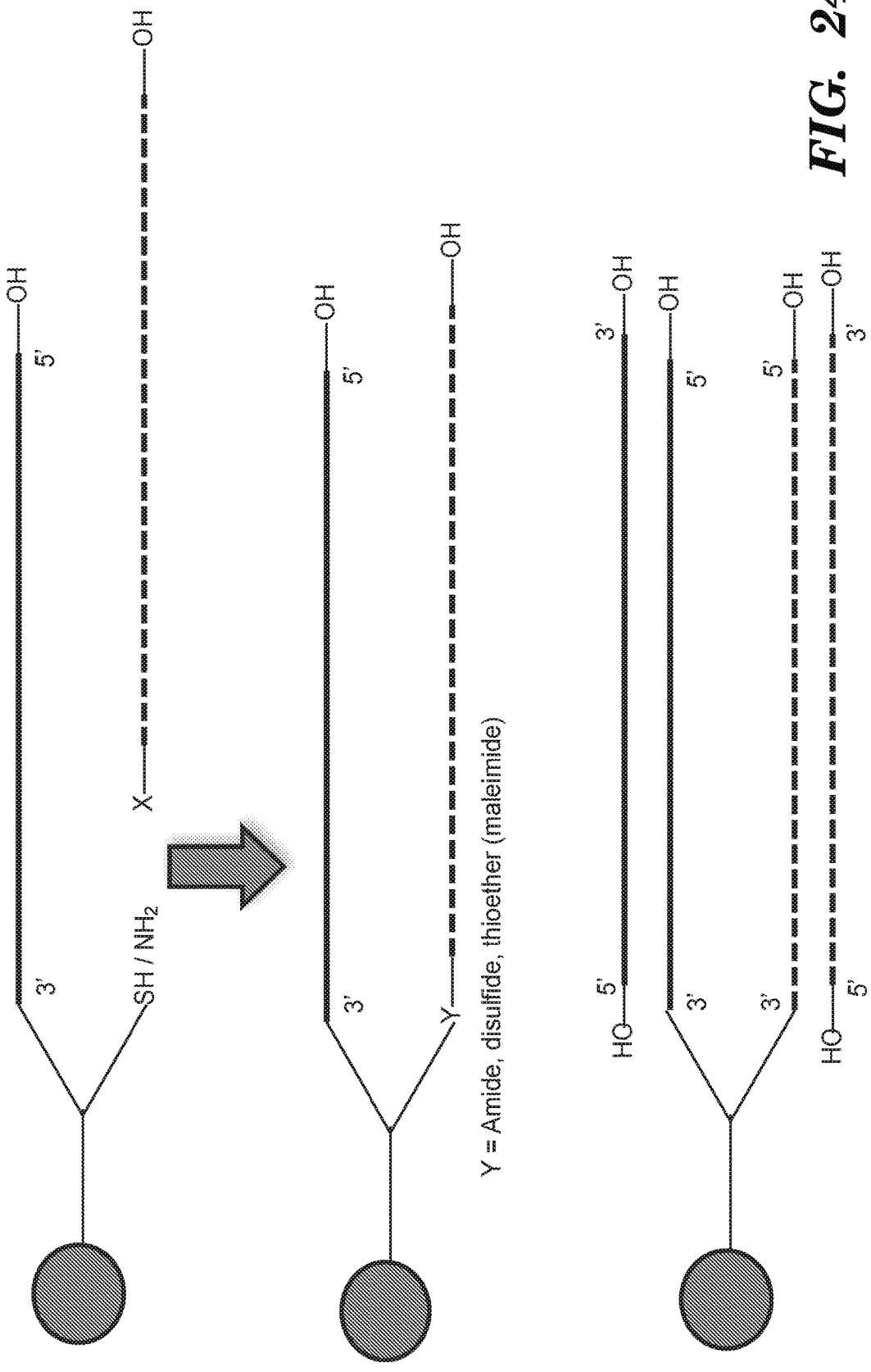
FIGS. 24 and 25 are schematic representations of bis(siRNA)-GalNAc orientations according to embodiments of the invention.
Figure 25:
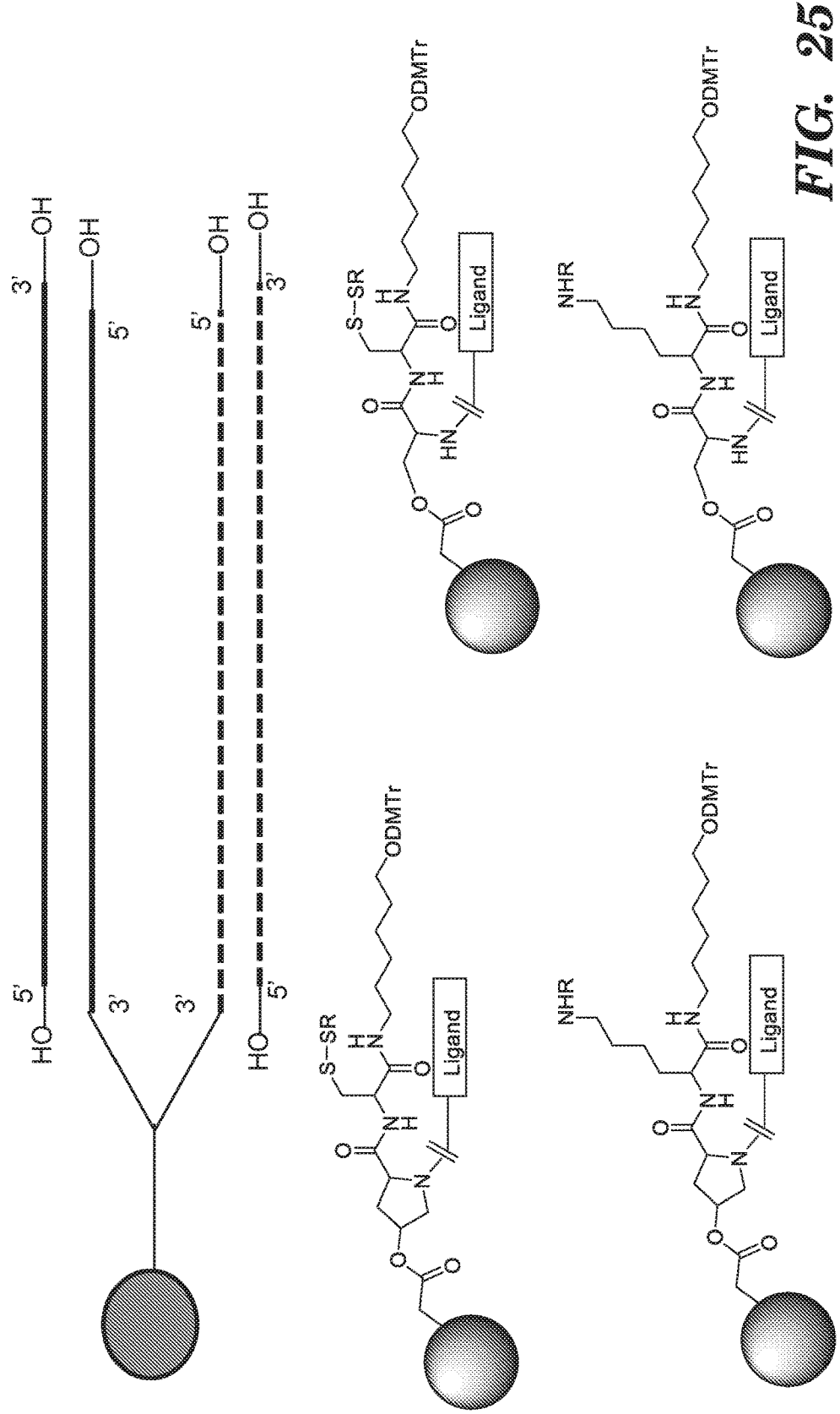

The two siRNAs with sticky ends were dissolved in nuclease-free water to a concentration of 1 mM. For the melting bis-siRNA duplexes, 20 µL of each duplex were mixed together, 100 µL of 10×PBS (pH 7.4, Ambion) were added, followed by 860 µL of nuclease-free water, resulting in 1 mL of stock duplex in 1×PBS. The stock bis-siRNA duplex was diluted ~8× with 1×PBS buffer, and the concentration was adjusted to AU at 260 nm of 0.5 ODU/mL (±5%) for each melting bis-siRNA duplex. Melting point temperature ($T_m$) was experimentally determined on a DU 800 Series UV/Vis Spectrophotometer (Beckman Coulter) equipped with the High-Performance Peltier Temperature Controller, the Micro Auto 6 $T_m$ Cell Holder (six 325 µL $T_m$ Microcells with Stopper) and the $T_m$ Analysis Software. Duplexes were analyzed in the six 325 µL-samples format with duplex denaturation and renaturation profiles measured within a temperature range from 20.0 to 80.0° C. with temperature ramping of 1.0° C./min. All $T_m$ values were calculated using the First Derivative method provided with the $T_m$ Analysis Software and average values from two separate experiments (independent duplex preparations), each one consisting of two independent $T_m$ measurements were calculated for each melting duplex. Average values were calculated using Microsoft Excel. Duplex analysis and thermal melting profile for duplex AM-26 are shown in FIG. 14. As can be seen, AM-26 appears as a single entity under these conditions. The non-complementary sticky end bis-siRNA in FIG. 14 have the same sense strands as the AM-26 duplex but have a stretch of 7 nucleotides (2'OMe RNA) at the antisense strand 3'-end of each siRNA duplex, such that they cannot form a duplex structure when mixed together. The stretch of 7 nucleotides at the antisense strand 3'-end of the first siRNA is does not hybridize with the stretch of 7 nucleotides at the antisense strand 3'-end of the second siRNA. In other words, they are fully mismatched. The antisense sequences of the non-complementary sticky end bis-siRNAs are 5'-usUfsauaGfaGfCfaagaAfcAfcuguususu-cacagcg-3' and 5'-usUfsaagAfcuUfgagaUfgAfuc-cugsgscgacacuu-3'.

Abbreviations used in describing the sequences, e.g., sequences described in Tables 1-3 are collected and described in Table 5 for convenience.

TABLE 5

Abbreviations of nucleotide monomers used in nucleic acid sequence representation.

| Abbreviation | Nucleotide(s) |
|---|---|
| A | Adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |

TABLE 5-continued

Abbreviations of nucleotide monomers used in nucleic acid sequence representation.

| Abbreviation | Nucleotide(s) |
| --- | --- |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| dT | 2'-deoxythymidine |
| dTs | 2'-deoxythymidine-3'-phosphorothioate |
| dU | 2'-deoxyuridine |
| dUs | 2'-deoxyuridine-3'-phosphorothioate |
| (m5dC) | 2'-deoxy-5-methylcytidine-3'-phosphate |
| s | phosphorothioate linkage |
| L96 | N-[tris(GalNAc-alkyl)-amidodecanoyl)]-4-hydroxyprolinol Hyp-(GalNAc-alkyl)3 |
| Q50 | —(CH$_2$)$_{12}$— (C12 linker) (See FIG. 26) |
| Q51 | —(CH$_2$)$_6$—S—S—(CH$_2$)$_6$— (C6—S—S—C6 linker) (See FIG. 26) |
| Q151 | tri-GalNAc (See FIG. 26) |
| Q173 | N-(GalNAc)-amidopentanoyl)-prolinol-4-phosphate (Hyp-C5-(GalNAc)) (See FIG. 26) |

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A multi-targeted molecule comprising a first double-stranded siRNA molecule and a second double-stranded siRNA molecule, wherein at least one ligand is conjugated with the multi-targeted molecule, and wherein the first and second siRNAs do not overlap with each other, and wherein:
   (i) the first and second siRNAs are connected together by a linker comprising the nucleotide sequence UUU;
   (ii) the sense strand of the first siRNA comprises a single-strand overhang at its 3'-end and the antisense strand of the second siRNA comprises a single-strand overhang at its 3'-end, wherein nucleic acid sequence of the single-strand overhang of the sense strand is substantially complementary to the nucleotide sequence of the single-strand overhang of the antisense strand, and wherein the two single-strand overhangs form a duplex; or
   (iii) the antisense strand of the first siRNA comprises a single-strand overhang at its 3'-end and the antisense strand of the second siRNA comprises a single-strand overhang at its 3'-end, wherein nucleic acid sequence of the single-strand overhang of the antisense strand is substantially complementary to the nucleotide sequence of the single-strand overhang of the antisense strand, and wherein the two single-strand overhangs form a duplex.

2. The multi-targeted molecule of claim 1, wherein the first and second siRNA are each conjugated with at least one ligand.

3. The multi-targeted molecule of claim 1, wherein said multi-targeted molecule inhibits gene expression of at least two target nucleic acids by at least 75% each relative to when the first and second siRNA are not connected together.

4. The multi-targeted molecule of claim 1, wherein the sense strand of the siRNAs comprises one block of two phosphorothioate internucleotide linkages and the antisense strand of the siRNAs comprises two blocks of two phosphorothioate internucleotide linkages.

5. The multi-targeted molecule of claim 1, wherein at least one of the first and second siRNA comprises a 3'-F modification at 5'-terminal of at least one strand.

6. The multi-targeted molecule of claim 1, wherein 3'-end of a sense strand of one siRNA is covalently linked to the 3'-end of an antisense strand of the other siRNA.

7. The multi-targeted molecule of claim 1, wherein 5'-end of a sense strand of one siRNA is covalently linked to the 5'-end of an antisense strand of the other siRNA.

8. The multi-targeted molecule of claim 1, wherein 3'-end of a sense strand of one siRNA is covalently linked to the 5'-end of an antisense strand of the other siRNA.

9. The multi-targeted molecule of claim 1, wherein 5'-end of a sense strand of one siRNA is covalently linked to the 3'-end of an antisense strand of the other siRNA.

10. The multi-targeted molecule of claim 1, wherein the length of the substantially complementary sequence is from 5 to 25 nucleotides.

11. The multi-targeted molecule of claim 1, wherein the first and second siRNA are each conjugated with at least one ligand.

12. The multi-targeted molecule of claim 1, wherein less than 5% of the duplex formed by the two single-strand overhangs is cleaved by a nuclease.

13. The multi-targeted molecule of claim 1, wherein at least 50% of the duplex formed by the two single-strand overhangs is cleaved by a nuclease.

* * * * *

SEQUENCE LISTING

```
<160> NUMBER OF SEQ ID NOS: 73

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ala Leu Glu Ala Leu Ala Glu Ala Leu Glu Ala Leu Ala Glu Ala
1               5                   10                  15

Leu Glu Ala Leu Ala Glu Ala Ala Ala Gly Gly Cys
            20                  25

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Gly Gly Cys
            20                  25                  30

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Leu Glu Ala Leu Ala Glu Ala Leu Glu Ala Leu Ala Glu Ala
```

-continued

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Leu Phe Glu Ala Ile Glu Gly Phe Ile Glu Asn Gly Trp Glu Gly
1               5                   10                  15

Met Ile Trp Asp Tyr Gly
            20

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 6
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Leu Phe Glu Ala Ile Glu Gly Phe Ile Glu Asn Gly Trp Glu Gly
1               5                   10                  15

Met Ile Asp Gly Trp Tyr Gly Cys Gly Leu Phe Glu Ala Ile Glu Gly
            20                  25                  30

Phe Ile Glu Asn Gly Trp Glu Gly Met Ile Asp Gly Trp Tyr Gly Cys
        35                  40                  45

<210> SEQ ID NO 7
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Leu Phe Glu Ala Ile Glu Gly Phe Ile Glu Asn Gly Trp Glu Gly
1               5                   10                  15

Met Ile Asp Gly Gly Cys Gly Leu Phe Glu Ala Ile Glu Gly Phe Ile
            20                  25                  30

Glu Asn Gly Trp Glu Gly Met Ile Asp Gly Gly Cys
        35                  40

<210> SEQ ID NO 8
<211> LENGTH: 35

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Leu Phe Gly Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Gly
            20                  25                  30

Gly Ser Cys
        35

<210> SEQ ID NO 9
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala Gly Gly
            20                  25                  30

Ser Cys

<210> SEQ ID NO 10
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Norleucine
<220> FEATURE:
<221> NAME/KEY: MOD_RES
<222> LOCATION: (38)..(38)
<223> OTHER INFORMATION: Norleucine

<400> SEQUENCE: 10

Gly Leu Phe Glu Ala Ile Glu Gly Phe Ile Glu Asn Gly Trp Glu Gly
1               5                   10                  15

Xaa Ile Asp Gly Lys Gly Leu Phe Glu Ala Ile Glu Gly Phe Ile Glu
            20                  25                  30

Asn Gly Trp Glu Gly Xaa Ile Asp Gly
        35                  40

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Phe Glu Ala Leu Leu Glu Leu Leu Glu Ser Leu Trp Glu Leu Leu
1               5                   10                  15

Leu Glu Ala
```

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Leu Phe Lys Ala Leu Leu Lys Leu Leu Lys Ser Leu Trp Lys Leu
1               5                   10                  15

Leu Leu Lys Ala
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Leu Phe Arg Ala Leu Leu Arg Leu Leu Arg Ser Leu Trp Arg Leu
1               5                   10                  15

Leu Leu Arg Ala
            20

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 15
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Leu Phe Phe Glu Ala Ile Ala Glu Phe Ile Glu Gly Gly Trp Glu
1               5                   10                  15

Gly Leu Ile Glu Gly Cys
            20

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
His His His His His Trp Tyr Gly
1               5
```

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Cys His Lys Lys Lys Lys Lys Lys His Cys
1               5                   10
```

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Arg Gln Ile Lys Ile Trp Phe Gln Asn Arg Arg Met Lys Trp Lys Lys
1               5                   10                  15
```

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Gly Arg Lys Lys Arg Arg Gln Arg Arg Arg Pro Pro Gln Cys
1               5                   10
```

<210> SEQ ID NO 21
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Gly Ala Leu Phe Leu Gly Trp Leu Gly Ala Ala Gly Ser Thr Met Gly
1               5                   10                  15

Ala Trp Ser Gln Pro Lys Lys Arg Lys Val
            20                  25
```

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Leu Ile Ile Leu Arg Arg Arg Ile Arg Lys Gln Ala His Ala His
1               5                   10                  15

Ser Lys

<210> SEQ ID NO 23
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Leu Ala Leu Lys Leu Ala Leu Lys Ala Leu Lys Ala Ala Leu Lys
1               5                   10                  15

Leu Ala

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Arg Arg Arg Arg Arg Arg Arg Arg
1               5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Phe Phe Lys Phe Phe Lys Phe Phe Lys
1               5                   10

```
<210> SEQ ID NO 27
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
            35

<210> SEQ ID NO 28
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
                20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
                20                  25                  30

<210> SEQ ID NO 30
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
                20                  25                  30

Lys Cys Cys Lys
            35

<210> SEQ ID NO 31
<211> LENGTH: 42
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 31

Arg Arg Arg Pro Arg Pro Tyr Leu Pro Arg Pro Arg Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
        35                  40

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Leu Pro Trp Lys Trp Pro Trp Trp Pro Trp Arg Arg
1               5                   10

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Ala Val Ala Leu Leu Pro Ala Val Leu Leu Ala Leu Leu Ala Pro
1               5                   10                  15

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Ala Leu Leu Pro Val Leu Leu Ala Ala Pro
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Lys Cys Arg Ile Val Val Ile Arg Val Cys Arg
1               5                   10

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 36
aacaguguuc uugcucuaua a                                          21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
aacaguguuc uugcucuaua a                                          21

<210> SEQ ID NO 38
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
uuauagagca agaacacugu uuu                                        23

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
caggaucauc ucaagucuua a                                          21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
caggaucauc ucaagucuua a                                          21

<210> SEQ ID NO 41
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
uuaagacuug agaugauccu ggc                                        23

<210> SEQ ID NO 42
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
aacaguguuc uugcucuaua auuucaggau caucucaagu cuuaa         45

<210> SEQ ID NO 43
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
aacaguguuc uugcucuaua auuucaggau caucucaagu cuuaa         45

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
aacaguguuc uugcucuaua a                                   21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
caggaucauc ucaagucuua a                                   21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
aacaguguuc uugcucuaua a                                   21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
aacaguguuc uugcucuaua a                                   21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
aacaguguuc uugcucuaua a                                         21

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
uuauagagca agaacacugu uuucacaggc                                30

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
caggaucauc ucaagucuua a                                         21

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
uuaagacuug agaugauccu ggcctgtgaa                                30

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
aacaguguuc uugcucuaua acactgttgc                                30

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
uuaagacuug agaugauccu ggcaacagtg                                30

```
<210> SEQ ID NO 54
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
aacaguguuc uugcucuaua atagccagga ucaucucaag ucuuaa            46

<210> SEQ ID NO 55
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 55
uuaagacuug agaugauccu ggctauuaua gagcaagaac acuguuuu          48

<210> SEQ ID NO 56
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 56
aacaguguuc uugcucuaua aatcgcagga ucaucucaag ucuuaa            46

<210> SEQ ID NO 57
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
uuaagacuug agaugauccu ggctauuaua gagcaagaac acuguuuu          48

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
aacaguguuc uugcucuaua a                                       21

<210> SEQ ID NO 59
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
uuauagagca agaacacugu uuucacaggc                                    30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
uuaagacuug agaugauccu ggccugugaa                                    30

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: This sequence may encompass 1-20 nucleotides,
      wherein some positions may be absent

<400> SEQUENCE: 61
tttttttttt tttttttttt                                               20

<210> SEQ ID NO 62
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
gccagguaag uau                                                      13

<210> SEQ ID NO 63
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ccagguaagu au                                                       12

<210> SEQ ID NO 64
<211> LENGTH: 11
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 64
cagguaagua u                                                            11

<210> SEQ ID NO 65
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
cagguaagua                                                              10

<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
caggaucauc ucaagucuua a                                                 21

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
aacaguguuc uugcucuaua a                                                 21

<210> SEQ ID NO 68
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
uacaggauca ucucaagucu uaa                                               23

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
caggaucauc ucaagucuua a                                                 21

<210> SEQ ID NO 70
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 70
caggaucauc ucaagucuua a                                              21

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
caggaucauc ucaagucuua a                                              21

<210> SEQ ID NO 72
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
uuauagagca agaacacugu uuucacagcg                                     30

<210> SEQ ID NO 73
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
uuaagacuug agaugauccu ggcgacacuu                                     30
```